US007968293B2

(12) United States Patent
Reipert et al.

(10) Patent No.: US 7,968,293 B2

(45) Date of Patent: Jun. 28, 2011

(54) IVIG MODULATION OF CHEMOKINES FOR TREATMENT OF MULTIPLE SCLEROSIS, ALZHEIMER'S DISEASE, AND PARKINSON'S DISEASE

(75) Inventors: Birgit Reipert, Deutsch Wagram (AT); Hartmut Ehrlich, Vienna (AT); Hans-Peter Schwarz, Vienna (AT); Irina Elovaara, Tampere (FI)

(73) Assignees: Baxter International Inc., Deerfield, IL (US); Baxter Healthcare S.A. (CH)

( * ) Notice: Subject to any disclaimer, the term of this patent is extended or adjusted under 35 U.S.C. 154(b) by 17 days.

(21) Appl. No.: 12/189,367

(22) Filed: Aug. 11, 2008

(65) Prior Publication Data

US 2009/0148463 A1 Jun. 11, 2009

Related U.S. Application Data

(60) Provisional application No. 60/955,610, filed on Aug. 13, 2007.

(51) Int. Cl.
*C12Q 1/68* (2006.01)
*G01N 33/50* (2006.01)

(52) U.S. Cl. ............................. 435/6; 435/7.1; 435/7.24

(58) Field of Classification Search ........................ None
See application file for complete search history.

(56) References Cited

U.S. PATENT DOCUMENTS

| | | | | |
|---|---|---|---|---|
| 2004/0014109 | A1 | 1/2004 | Pericak-Vance et al. | |
| 2004/0053251 | A1 | 3/2004 | Pericak-Vance et al. | |
| 2006/0003327 | A1* | 1/2006 | Achiron et al. | 435/6 |
| 2006/0183117 | A1 | 8/2006 | Pericak-Vance et al. | |
| 2006/0211060 | A1 | 9/2006 | Haley et al. | |
| 2008/0045582 | A1* | 2/2008 | Zineh et al. | 514/423 |
| 2010/0009377 | A1* | 1/2010 | Wohlgemuth et al. | 435/6 |
| 2010/0112568 | A1* | 5/2010 | Achiron et al. | 435/6 |

FOREIGN PATENT DOCUMENTS

| | | | |
|---|---|---|---|
| WO | WO 02/059604 | A2 | 8/2002 |
| WO | WO 02/059604 | A3 | 8/2002 |
| WO | WO 2005/027733 | A2 | 3/2005 |
| WO | WO 2005/027733 | A3 | 3/2005 |
| WO | WO 2005/067391 | A2 | 7/2005 |
| WO | WO 2005/067391 | A3 | 7/2005 |
| WO | WO 2006/077126 | A2 | 7/2006 |
| WO | WO 2006/077126 | A3 | 7/2006 |

OTHER PUBLICATIONS

Sapan CV et al. Antibody therapy (IVIG): evaluation of the use of genomics and proteomics for the study of immunomodulation therapeutics. Vox Sanguinis, Apr. 2007; 92:197-205.*

Andersson, U. et al., "Pooled Human IgG Modulates Cytokine Production in Lymphocytes and Monocytes," *Immunological Reviews*, 1994, vol. 139, pp. 21-42.

Basta, M. et al., "High Doses of Intravenous Ig Inhibit In Vitro Uptake of C4 Fragments Onto Sensitized Erythrocytes," *Blood*, Jan. 15, 1991, vol. 77, No. 2, pp. 376-380.

Bayary, J. et al., "Intravenous immunoglobulin in autoimmune disorders: an insight into the immunregulatory mechanisms," *International Immunopharmacology*, 2006, vol. 6, pp. 528-534.

Bayry, J. et al., "Mechanisms of action of intravenous immunoglobulin in autoimmune and inflammatory diseases," *Neurol. Sci.*, 2003, vol. 24, pp. S217-S221.

Bayry, J. et al., "Mechanisms of action of intravenous immunoglobulin in autoimmune and inflammatory disease," *Transfusion Clinique et Biologique*, 2003, vol. 10, pp. 165-169.

Calabresi, P.A. et al., "Diagnosis and Management of Multiple Sclerosis," *American Family Physician*, Nov. 15, 2004, vol. 70, No. 10, pp. 1935-1944.

Dalakas, M.C., "Intravenous Immune Globulin Therapy for Neurologic Diseases," *Annals of Internal Medicine*, May 1, 1997, vol. 126, No. 9, pp. 721-730.

Dudesek, A. et al., "Intravenouse immunoglobuline as therapeutic option in the treatment of multiple sclerosis,"*J. Neurol.*, 2006, vol. 253 (Suppl. 5), pp. V/50-V/58.

Hellings, N. et al., "Insights into the Immunopathogenesis of Multiple Sclerosis," *Immunologic Research*, 2002, vol. 1, pp. 27-51.

Huang, D. et al., "Chronic expression of monocyte chemoattractant protein-1 in the central nervous system causes delayed encephalopathy and impaired microglial function in mice," *The FASEB Journal*, May 2005, vol. 19, pp. 761-722.

Kazatchkine, M.D. et al., "Mechanism of action of intravenous immunoglobulin (IVIG)," *Multiple Sclerosis*, 2000, vol. 2 (Suppl. 2), pp. S24-526. or vol. 33, pp. 24-26.

Kim, Y.S. et al., "Microglia, major player in the brain inflammation: their roles in the pathogenesis of Parkinson's disease," *Experimental and Molecular Medicine*, Aug. 2006, vol. 38, No. 4, pp. 333-347.

Lewanska, M. et al., "No difference in efficacy of two different doses of intravenous immunoglobulins in MS: clinical and MRI assessment," *European Journal of Neurology*, 2002, vol. 9, pp. 565-572.

Samuelsson, A. et al., "Anti-inflammatory Activity of IVIG Mediated Through the Inhibitory Fc Receptor," *Science*, Jan. 19, 2001, vol. 291, pp. 484-486.

Sorensen, P.S. et al., "Intravenous immunoglobulin G for the treatment of relapsing-remitting multiple sclerosis: a meta-analysis," *European Journal of Neurology*, 2002, vol. 9, pp. 557-563.

Sørensen, P.S., "Treatment of multiple sclerosis with intravenous immunoglobulin: review of clinical trials," *Neurol. Sci.*, 2003, vol. 24, pp. S227-S230.

Sorenson, P.S. et al., "Intravenous immunoglobulin G reduces MRI activity in relapsing multiple sclerosis," *Neurology*, May 1998, vol. 50, pp. 1273-1281.

(Continued)

*Primary Examiner* — Daniel E Kolker
*Assistant Examiner* — Kimberly A. Ballard
(74) *Attorney, Agent, or Firm* — Morgan, Lewis & Bockius, LLC

(57) ABSTRACT

The present invention provides methods for providing a prognosis of treatment of diseases associated with inflammatory disease of the brain, including MS, e.g., relapsing-remitting multiple sclerosis (RRMS), Alzheimer's disease, and Parkinson's disease using molecular markers that are shown to be overexpressed or underexpressed in patients treated with intravenous immunoglobulins (IVIG). Also provided are methods to identify compounds that are useful for the treatment or prevention of MS, e.g., relapsing-remitting multiple sclerosis (RRMS), Alzheimer's disease, and Parkinson's disease.

13 Claims, 3 Drawing Sheets

OTHER PUBLICATIONS

Sospedra, M. et al., "Immunology of Multiple Sclerosis," *Annu. Rev. Immunol.*, 2005, vol. 23, pp. 683-747.

Stangel, M. et al., "Hochdosierte intravenöse Immunglobuline in der Behandlung der Multiples Sklerose," *Nervenarzt*, 2005, vol. 76, pp. 1267-1272.

Strasser-Fuchs, S. et al., "The Austrian Immunoglobulin in MS (AIMS) study: final analysis," *Multiple Sclerosis*, 2000, vol. 6 (Suppl. 2), pp. S9-S13.

Trebst, C. et al., "Promotion of Remyelination by Immunoglobulins: Implications for the Treatment of Multiple Sclerosis," *Current Pharmaceutical Design*, 2006, vol. 12, No. 2, pp. 241-249.

Wilms, H. et al., "Inflammation in Parkinson's Diseases and Other Neurodegenerative Disease: Cause and Therapeutic Implications," *Current Pharmaceutical Design*, 2007, vol. 13, No. 18, pp. 1925-1928.

Yamamoto, M. et al., "Overexpression of Monocyte Chemotactic Protein-1/CCLS2 in β-Amyloid Precursor Protein Transgenic Mice Show Accelerated Diffuse β-Amyloid Deposition," *American Journal of Pathology*, May 2005, vol. 166, No. 5, pp. 1475-1485.

Partial International Search Report mailed on Feb. 17, 2009, for International Application No. PCT/EP2008/006608, filed on Aug. 11, 2008, 3 pages.

* cited by examiner

Fig 2 A-B
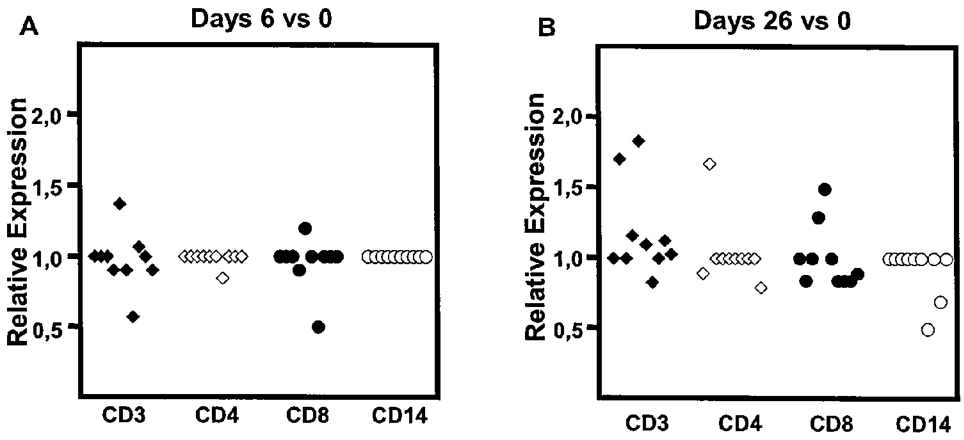

Fig 3 A-D
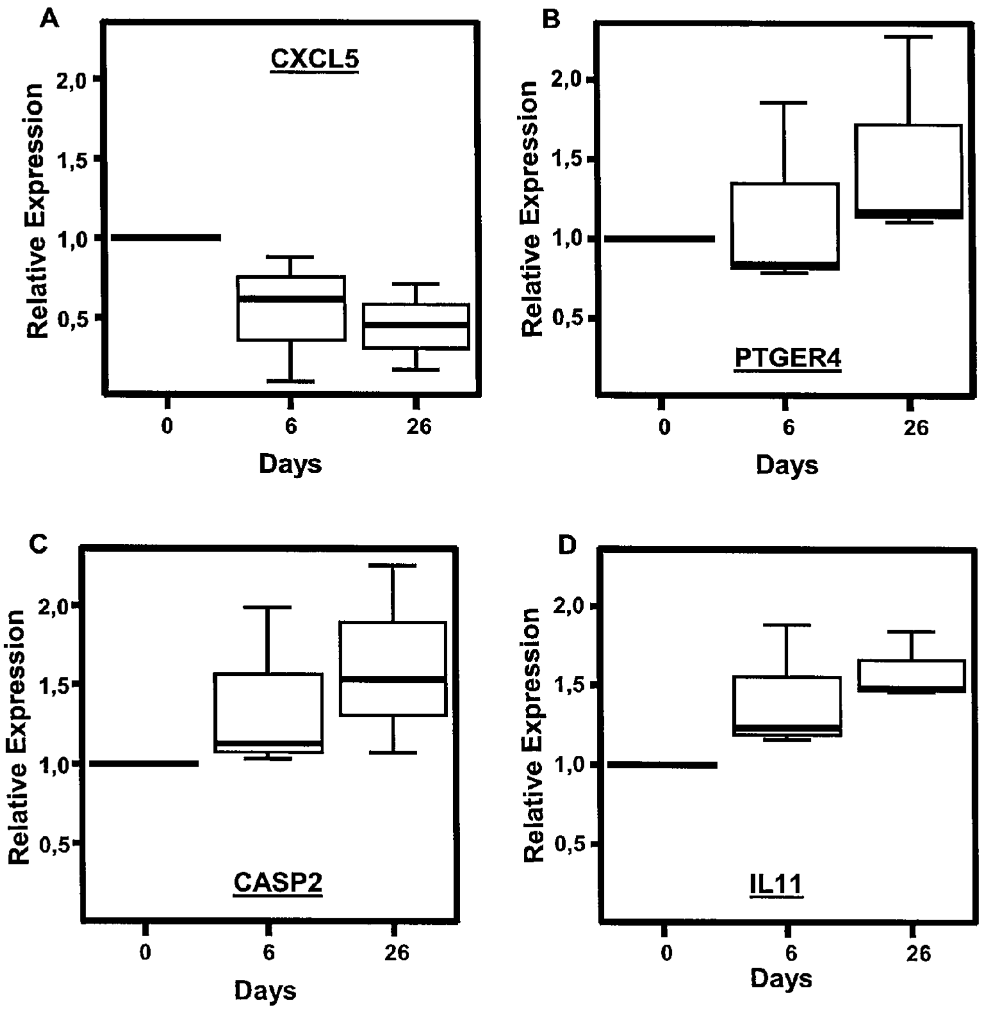

SEQUENCE LISTING

```
<160> NUMBER OF SEQ ID NOS: 84

<210> SEQ ID NO 1
<211> LENGTH: 3962
<212> TYPE: DNA
<213> ORGANISM: Homo sapiens
<220> FEATURE:
<223> OTHER INFORMATION: transcriptional regulating factor 1 (TRERF1)
      cDNA
<220> FEATURE:
<221> NAME/KEY: CDS
<222> LOCATION: (825)..(3731)
<223> OTHER INFORMATION: TRERF1

<400> SEQUENCE: 1

ctctgctcgc cccccatctc accccccaag cggatactgg tcttctcgtc ggattgccca     60

tgcacttgtt gcagaaacag ccaaggccct ggctgtggag aatgctgaag gaagaagacg    120
```

-continued

```
cagaagcagg acgaccctga aagattcagc ctcttcatcc tcaaacaggt cgcttctcgg    180
gagttcttgg tgttggaata ttttacagca aagcagtcga ccaggcctcc tcttcccacc    240
tgtccagcag catgaaagca gcatgattgg ccgaccgcag gagaagcccc cagaaccagg    300
cccccaactc agccatctgc ggaggtcaag gtgtgagcga cgtctcctca ccacagtgct    360
gtgtggtcta tacctcagcc agggagagga tgtgaaaccc cccgccctgc acatgagtgg    420
tacaggccaa caggaacacc tggctccagc cacgttcaca gacatgtcag ccgtggagta    480
gtgctgacac ttttctctca gcttctcagg gtttcagtcc ttttgggttt ggtttattta    540
ccttttttat ggttttgtgg ctggacgttc acaaccaagg cagacagcat gggtgaccag    600
caactgtaca agaccaacca tgtggcccat ggtagtgaga acctttteta ccaacagcca    660
ccacttggcg tccacagcgg gctgagccca ctgatggcta ccaatacacc tactcccagg    720
ccagcgagat ccggacccag aagcttacca gcggtgtctt acacaagctg gactctttca    780
cccaggtgtt tgccaaccaa aacctgcgaa ttcaggtcaa caatatggcc caggtgctgc    840
acactcagtc agcagtgatg gatggagccc ctgacagtgc tctccgccag ctgctgtctc    900
agaagcccat ggagccccca gcaccggcta tcccttcccg ctaccagcag gtgccccagc    960
agcctcaccc tggtttcact ggtgggctgt ccaaaccagc tcttcaggtc gggcagcacc   1020
ctacccaagg gcacctgtat tatgactacc agcagcctct ggctcaggtg ccagtgcagg   1080
gaggacagcc actgcaggcc ccacagatgc tgtcacagca catgcaacag atgcagcagc   1140
accagtatta cccaccgcag caacagcagc aagccgggca acagcgtatc tccatgcaag   1200
aaatacagac gcagccgcaa caaattcgcc catcacagcc acagccgccg ccacagcagc   1260
agcagccgca gcagctacag ctgcagcagc ggcagggttc aatgcagata cctcagtatt   1320
atcagcccca acccatgatg cagcacttgc aagagcagca gcagcaacag atgcacctgc   1380
agcctccttc ttatcacagg gaccctcacc agtatacccc agagcaggca cacactgtcc   1440
agctgattcc cctgggctcc atgtcccagt actactacca ggagccccag cagccctaca   1500
gccacccccct ttaccagcag agccacctgt cccagcacca gcagcgtgag gacagtcagc   1560
tgaagaccta ctctagtgac agacaggccc aggccatgct gagctcccat ggggacctgg   1620
ggcctcctga cacaggaatg ggagacccag cgagctcaga tctgacccgg gtcagcagca   1680
ccctccccca tcgcccctc ctatccccca gtgggatcca cctcaacaac atggggcctc    1740
agcatcagca gctgtctccc agtgccatgt ggccccagat gcacctacct gatgggagag   1800
cccagccagg gtcccctgag tcaagtggcc aacccaaagg agcgtttggg gagcagtttg   1860
atgccaagaa caagctgaca tgctccatct gcctgaagga gttcaagaac ctgcctgccc   1920
tgaatggcca catgcggtcc cacgggggaa tgagggcctc cccaacctc aaacaggaaa    1980
tccccaggaa gcatcagccg agtgtgccca aagccgagga gcccctcaag accgtgcagg   2040
agaagaaaaa gttccggcac cggtcggaac ctctcttcat cccgccgccg ccctcctaca   2100
acccgaaccc cgctgcctcc tactcgggcg ccaccctgta ccagagccag ctgcgctccc   2160
cgcgcgtcct cggggaccac ctgctcctgg accccaccca cgagctgccc ccttacacgc   2220
ccccacccat gctgagcccg gtgcgccagg gctcggggct cttcagcaat gtcctcatct   2280
ccggccacgg ccctggcgcc cacccgcagc tgcccctgac gcccctgacg cccacaccac   2340
gggtgctgct gtgtcgctcc aacagcatcg atggcagcaa cgtgacggtc accccagggc   2400
ctggagagca gactgtagat gttgaaccac gcatcaacat tggcttgaga ttccaagcag   2460
aaatccctga actccaagat atctctgccc tggcccagga cacacacaag gccacactgg   2520
```

```
tatggaagcc ctggccagaa ctagaaaacc atgacctcca gcaaagagtg gagaatcttc   2580

tgaatttgtg ctgttccagt gcattgccag gtggagggac caattctgaa tttgctttgc   2640

actctctgtt tgaggccaaa ggtgatgtga tggttgctct ggaaatgctg ctactgcgga   2700

agcctgtcag gttaaaatgt catcctttag caaattacca ctatgccggt tcggacaagt   2760

ggacctccct agaaagaaaa ctgtttaaca aagcactagc cacttacagc aaagacttta   2820

tttttgtaca gaagatggtg aagtccaaga cggtggctca gtgcgtggag tactactaca   2880

cgtggaaaaa gatcatgcgg ctggggcgga aacaccggac acgcctggca gaaatcatcg   2940

acgattgtgt gacaagtgaa gaagaagaag agttagagga ggaggaggag gaggacccgg   3000

aagaagatag gaaatccaca aaagaagaag agagtgaggt gccgaagtcc ccggagccac   3060

cacccgtccc cgtcctggct cccacggagg ggccgcccct gcaggccctg ggccagccct   3120

caggctcctt catctgtgaa atgcccaact gtggggctga ctgtagatgt catgtcactc   3180

cctttcttcc ccaggtgttc agctcccgac aggcactgaa tggccatgcc cgcatccacg   3240

ggggcaccaa ccaggtgacc aaggcccgag gtgccatccc ctctgggaag cagaagcctg   3300

gtggcaccca gagtgggtac tgttcggtaa agagctcacc ctctcacagc accaccagcg   3360

gcgagacaga ccccaccacc atcttcccct gcaaggagtg tggcaaagtc ttcttcaaga   3420

tcaaaagccg aaatgcacac atgaaaactc acaggcagca ggaggaacaa cagaggcaaa   3480

aggctcagaa ggcggctttt gcagctgaga tggcagccac gattgagagg actacggggc   3540

ccgtgggggc gccggggctg ctgcccctgg accagctgag tctgatcaaa cccatcaagg   3600

atgtggacat cctcgacgac gacgtcgtcc agcagttggg aggtgtcatg gaagaggctg   3660

aagttgtgga caccgatctt ctcttggatg atcaagattc agtcttgctt cagggtgacg   3720

cagaactata aagccctgtg tgtcacttag agacagtgaa aacccacggc ctccatcttc   3780

attaatcagg aaacctggac tgcctgcttg ttttgtaacc cttttaaact acctgtttta   3840

aaagtggtca ttttattcag gtttagaaaa aaaaatccta tttcttttcc ttttatttaa   3900

aaaaatttgt ttttgtgggg ggttgggggg aataaataat tggcacaact aaaaaaaaaa   3960

aa                                                                  3962
```

<210> SEQ ID NO 2
<211> LENGTH: 966
<212> TYPE: PRT
<213> ORGANISM: Homo sapiens
<220> FEATURE:
<223> OTHER INFORMATION: transcriptional regulating factor 1 (TRERF1)

<400> SEQUENCE: 2

```
Met Ala Gln Val Leu His Thr Gln Ser Ala Val Met Asp Gly Ala Pro
  1               5                  10                  15

Asp Ser Ala Leu Arg Gln Leu Leu Ser Gln Lys Pro Met Glu Pro Pro
             20                  25                  30

Ala Pro Ala Ile Pro Ser Arg Tyr Gln Gln Val Pro Gln Gln Pro His
         35                  40                  45

Pro Gly Phe Thr Gly Gly Leu Ser Lys Pro Ala Leu Gln Val Gly Gln
     50                  55                  60

His Pro Thr Gln Gly His Leu Tyr Tyr Asp Tyr Gln Gln Pro Leu Ala
 65                  70                  75                  80

Gln Val Pro Val Gln Gly Gly Gln Pro Leu Gln Ala Pro Gln Met Leu
                 85                  90                  95

Ser Gln His Met Gln Gln Met Gln Gln His Gln Tyr Tyr Pro Pro Gln
```

-continued

```
            100                 105                 110

Gln Gln Gln Gln Ala Gly Gln Gln Arg Ile Ser Met Gln Glu Ile Gln
        115                 120                 125

Thr Gln Pro Gln Gln Ile Arg Pro Ser Gln Pro Gln Pro Pro Pro Gln
    130                 135                 140

Gln Gln Gln Pro Gln Gln Leu Gln Leu Gln Gln Arg Gln Gly Ser Met
145                 150                 155                 160

Gln Ile Pro Gln Tyr Tyr Gln Pro Gln Pro Met Met Gln His Leu Gln
                165                 170                 175

Glu Gln Gln Gln Gln Gln Met His Leu Gln Pro Pro Ser Tyr His Arg
            180                 185                 190

Asp Pro His Gln Tyr Thr Pro Glu Gln Ala His Thr Val Gln Leu Ile
        195                 200                 205

Pro Leu Gly Ser Met Ser Gln Tyr Tyr Tyr Gln Glu Pro Gln Gln Pro
    210                 215                 220

Tyr Ser His Pro Leu Tyr Gln Gln Ser His Leu Ser Gln His Gln Gln
225                 230                 235                 240

Arg Glu Asp Ser Gln Leu Lys Thr Tyr Ser Ser Asp Arg Gln Ala Gln
                245                 250                 255

Ala Met Leu Ser Ser His Gly Asp Leu Gly Pro Pro Asp Thr Gly Met
            260                 265                 270

Gly Asp Pro Ala Ser Ser Asp Leu Thr Arg Val Ser Ser Thr Leu Pro
        275                 280                 285

His Arg Pro Leu Leu Ser Pro Ser Gly Ile His Leu Asn Asn Met Gly
    290                 295                 300

Pro Gln His Gln Gln Leu Ser Pro Ser Ala Met Trp Pro Gln Met His
305                 310                 315                 320

Leu Pro Asp Gly Arg Ala Gln Pro Gly Ser Pro Glu Ser Ser Gly Gln
                325                 330                 335

Pro Lys Gly Ala Phe Gly Glu Gln Phe Asp Ala Lys Asn Lys Leu Thr
            340                 345                 350

Cys Ser Ile Cys Leu Lys Glu Phe Lys Asn Leu Pro Ala Leu Asn Gly
        355                 360                 365

His Met Arg Ser His Gly Gly Met Arg Ala Ser Pro Asn Leu Lys Gln
    370                 375                 380

Glu Ile Pro Arg Lys His Gln Pro Ser Val Pro Lys Ala Glu Glu Pro
385                 390                 395                 400

Leu Lys Thr Val Gln Glu Lys Lys Lys Phe Arg His Arg Ser Glu Pro
                405                 410                 415

Leu Phe Ile Pro Pro Pro Pro Ser Tyr Asn Pro Asn Pro Ala Ala Ser
            420                 425                 430

Tyr Ser Gly Ala Thr Leu Tyr Gln Ser Gln Leu Arg Ser Pro Arg Val
        435                 440                 445

Leu Gly Asp His Leu Leu Leu Asp Pro Thr His Glu Leu Pro Pro Tyr
    450                 455                 460

Thr Pro Pro Pro Met Leu Ser Pro Val Arg Gln Gly Ser Gly Leu Phe
465                 470                 475                 480

Ser Asn Val Leu Ile Ser Gly His Gly Pro Gly Ala His Pro Gln Leu
                485                 490                 495

Pro Leu Thr Pro Leu Thr Pro Thr Pro Arg Val Leu Leu Cys Arg Ser
            500                 505                 510

Asn Ser Ile Asp Gly Ser Asn Val Thr Val Thr Pro Gly Pro Gly Glu
        515                 520                 525
```

-continued

```
Gln Thr Val Asp Val Glu Pro Arg Ile Asn Ile Gly Leu Arg Phe Gln
    530                 535                 540

Ala Glu Ile Pro Glu Leu Gln Asp Ile Ser Ala Leu Ala Gln Asp Thr
545                 550                 555                 560

His Lys Ala Thr Leu Val Trp Lys Pro Trp Pro Glu Leu Glu Asn His
                565                 570                 575

Asp Leu Gln Gln Arg Val Glu Asn Leu Leu Asn Leu Cys Cys Ser Ser
            580                 585                 590

Ala Leu Pro Gly Gly Gly Thr Asn Ser Glu Phe Ala Leu His Ser Leu
        595                 600                 605

Phe Glu Ala Lys Gly Asp Val Met Val Ala Leu Glu Met Leu Leu Leu
    610                 615                 620

Arg Lys Pro Val Arg Leu Lys Cys His Pro Leu Ala Asn Tyr His Tyr
625                 630                 635                 640

Ala Gly Ser Asp Lys Trp Thr Ser Leu Glu Arg Lys Leu Phe Asn Lys
                645                 650                 655

Ala Leu Ala Thr Tyr Ser Lys Asp Phe Ile Phe Val Gln Lys Met Val
            660                 665                 670

Lys Ser Lys Thr Val Ala Gln Cys Val Glu Tyr Tyr Tyr Thr Trp Lys
        675                 680                 685

Lys Ile Met Arg Gly Arg Lys His Arg Thr Arg Leu Ala Glu Ile Ile
    690                 695                 700

Asp Asp Cys Val Thr Ser Glu Glu Glu Glu Glu Leu Glu Glu Glu Glu
705                 710                 715                 720

Glu Glu Asp Pro Glu Glu Asp Arg Lys Ser Thr Lys Glu Glu Glu Ser
                725                 730                 735

Glu Val Pro Lys Ser Pro Glu Pro Pro Pro Val Pro Val Leu Ala Pro
            740                 745                 750

Thr Glu Gly Pro Pro Leu Gln Ala Leu Gly Gln Pro Ser Gly Ser Phe
        755                 760                 765

Ile Cys Glu Met Pro Asn Cys Gly Ala Asp Cys Arg Cys His Val Thr
    770                 775                 780

Pro Phe Leu Pro Gln Val Phe Ser Ser Arg Gln Ala Leu Asn Gly His
785                 790                 795                 800

Ala Arg Ile His Gly Gly Thr Asn Gln Val Thr Lys Ala Arg Gly Ala
                805                 810                 815

Ile Pro Ser Gly Lys Gln Lys Pro Gly Gly Thr Gln Ser Gly Tyr Cys
            820                 825                 830

Ser Val Lys Ser Ser Pro Ser His Ser Thr Thr Ser Gly Glu Asp Pro
        835                 840                 845

Thr Thr Ile Phe Pro Cys Lys Glu Cys Gly Lys Val Phe Phe Lys Ile
    850                 855                 860

Lys Ser Arg Asn Ala His Met Lys Thr His Arg Gln Gln Glu Glu Gln
865                 870                 875                 880

Gln Arg Gln Lys Ala Gln Lys Ala Ala Phe Ala Ala Glu Met Ala Ala
                885                 890                 895

Thr Ile Glu Arg Thr Thr Gly Pro Val Gly Ala Pro Gly Leu Leu Pro
            900                 905                 910

Leu Asp Gln Leu Ser Leu Ile Lys Pro Ile Lys Asp Val Asp Ile Leu
        915                 920                 925

Asp Asp Asp Val Val Gln Gln Leu Gly Gly Val Met Glu Glu Ala Glu
    930                 935                 940

Val Val Asp Thr Asp Leu Leu Leu Asp Asp Gln Asp Ser Val Leu Leu
945                 950                 955                 960
```

```
Gln Gly Asp Ala Glu Leu
                965


<210> SEQ ID NO 3
<211> LENGTH: 2138
<212> TYPE: DNA
<213> ORGANISM: Homo sapiens
<220> FEATURE:
<223> OTHER INFORMATION: chromosome 19 open reading frame 28 (C19orf28)
      cDNA
<220> FEATURE:
<221> NAME/KEY: CDS
<222> LOCATION: (171)..(1613)
<223> OTHER INFORMATION: C19orf28

<400> SEQUENCE: 3

tggggcggac gcggcggacg tgggtgaggg cgcggccgta agagagcggg acgcggggtg     60

cccggcgcgt ggtgggggtc cccggcgcct gccccccacgg cacccaagaa ggcctggcca   120

gggtaccctc cgcggagccc gggggtgggg ggcgcgggcc cggcgccgcg atgggcccgg   180

gacccccagc ggccggagcg gcgccgtccc cgcggccgct gtccctggtg gcgcggctga   240

gctacgccgt gggccacttc ctcaacgacc tgtgcgcgtc catgtggttc acctacctgc   300

tgctctacct gcactcggtg cgcgcctaca gctcccgcgg cgcggggctg ctgctgctgc   360

tgggccaggt ggccgacggg ctgtgcacac cgctcgtggg ctacgaggcc gaccgcgccg   420

ccagctgctg cgcccgctac ggcccgcgca aggcctggca cctggtcggc accgtctgcg   480

tcctgctgtc cttccccttc atcttcagcc cctgcctggg ctgtggggcg gccacgcccg   540

agtgggctgc cctcctctac tacggcccgt tcatcgtgat cttccagttt ggctgggcct   600

ccacacagat ctcccacctc agcctcatcc cggagctcgt caccaacgac catgagaagg   660

tggagctcac ggcactcagg tatgcgttca ccgtggtggc caacatcacc gtctacggcg   720

ccgcctggct cctgctgcac ctgcagggct cgtcgcgggt ggagcccacc caagacatca   780

gcatcagcga ccagctgggg ggccaggacg tgcccgtgtt ccggaacctg tccctgctgg   840

tggtgggtgt cggcgccgtg ttctcactgc tattccacct gggcacccgg gagaggcgcc   900

ggccgcatgc ggaggagcca ggcgagcaca ccccccctgtt ggcccctgcc acggcccagc   960

ccctgctgct ctggaagcac tggctccggg agccggcttt ctaccaggtg ggcatactgt  1020

acatgaccac caggctcatc gtgaacctgt cccagaccta catggccatg tacctcacct  1080

actcgctcca cctgcccaag aagttcatcg cgaccattcc cctggtgatg tacctcagcg  1140

gcttcttgtc ctccttcctc atgaagccca tcaacaagtg cattgggagg aacatgacct  1200

acttctcagg cctcctggtg atcctggcct ttgccgcctg ggtggcgctg gcggagggac  1260

tgggtgtggc cgtgtacgca gcggctgtgc tgctgggtgc tggctgtgcc accatcctcg  1320

tcacctcgct ggccatgacg gccgacctca tcggtcccca cacgaacagc ggagcgttcg  1380

tgtacggctc catgagcttc ttggataagg tggccaatgg gctggcagtc atggccatcc  1440

agagcctgca cccttgcccc tcagagctct gctgcagggc ctgcgtgagc ttttaccact  1500

gggcgatggt ggctgtgacg ggcggcgtgg gcgtggccgc tgccctgtgt ctctgtagcc  1560

tcctgctgtg gccgacccgc ctgcgacgct gggaccgtga tgcccggccc tgactcctga  1620

cagcctcctg cacctgtgca agggaactgt ggggacgcac gaggatgccc cccagggcct  1680

tggggaaaag cccccactgc cctcactct tctctggacc cccaccctcc atcctcaccc  1740

agctcccggg ggtggggtcg ggtgagggca gcagggatgc ccgccaggga cttgcaagga  1800

ccccctgggt tttgagggtg tcccattctc aactctaatc catcccagcc ctctggagga  1860
```

```
tttggggtgc ccctctcggc agggaacagg aagtaggaat cccagaaggg tctgggggaa   1920

ccctaaccct gagctcagtc cagttcaccc ctcacctcca gcctgggggt ctccagacac   1980

tgccagggcc ccctcaggac ggctggagcc tggaggagac agccacgggg tggtgggctg   2040

ggcctggacc ccaccgtggt gggcagcagg gctgcccggc aggcttggtg gactctgctg   2100

gcagcaaata aagagatgac ggcaaaaaaa aaaaaaaa                           2138


<210> SEQ ID NO 4
<211> LENGTH: 480
<212> TYPE: PRT
<213> ORGANISM: Homo sapiens
<220> FEATURE:
<223> OTHER INFORMATION: chromosome 19 open reading frame 28 (C19orf28)

<400> SEQUENCE: 4

Met Gly Pro Gly Pro Pro Ala Ala Gly Ala Ala Pro Ser Pro Arg Pro
  1               5                  10                  15

Leu Ser Leu Val Ala Arg Leu Ser Tyr Ala Val Gly His Phe Leu Asn
             20                  25                  30

Asp Leu Cys Ala Ser Met Trp Phe Thr Tyr Leu Leu Leu Tyr Leu His
         35                  40                  45

Ser Val Arg Ala Tyr Ser Ser Arg Gly Ala Gly Leu Leu Leu Leu Leu
     50                  55                  60

Gly Gln Val Ala Asp Gly Leu Cys Thr Pro Leu Val Gly Tyr Glu Ala
 65                  70                  75                  80

Asp Arg Ala Ala Ser Cys Cys Ala Arg Tyr Gly Pro Arg Lys Ala Trp
                 85                  90                  95

His Leu Val Gly Thr Val Cys Val Leu Leu Ser Phe Pro Phe Ile Phe
            100                 105                 110

Ser Pro Cys Leu Gly Cys Gly Ala Ala Thr Pro Glu Trp Ala Ala Leu
        115                 120                 125

Leu Tyr Tyr Gly Pro Phe Ile Val Ile Phe Gln Phe Gly Trp Ala Ser
    130                 135                 140

Thr Gln Ile Ser His Leu Ser Leu Ile Pro Glu Leu Val Thr Asn Asp
145                 150                 155                 160

His Glu Lys Val Glu Leu Thr Ala Leu Arg Tyr Ala Phe Thr Val Val
                165                 170                 175

Ala Asn Ile Thr Val Tyr Gly Ala Ala Trp Leu Leu Leu His Leu Gln
            180                 185                 190

Gly Ser Ser Arg Val Glu Pro Thr Gln Asp Ile Ser Ile Ser Asp Gln
        195                 200                 205

Leu Gly Gly Gln Asp Val Pro Val Phe Arg Asn Leu Ser Leu Leu Val
    210                 215                 220

Val Gly Val Gly Ala Val Phe Ser Leu Leu Phe His Leu Gly Thr Arg
225                 230                 235                 240

Glu Arg Arg Arg Pro His Ala Glu Glu Pro Gly Glu His Thr Pro Leu
                245                 250                 255

Leu Ala Pro Ala Thr Ala Gln Pro Leu Leu Leu Trp Lys His Trp Leu
            260                 265                 270

Arg Glu Pro Ala Phe Tyr Gln Val Gly Ile Leu Tyr Met Thr Thr Arg
        275                 280                 285

Leu Ile Val Asn Leu Ser Gln Thr Tyr Met Ala Met Tyr Leu Thr Tyr
    290                 295                 300

Ser Leu His Leu Pro Lys Lys Phe Ile Ala Thr Ile Pro Leu Val Met
305                 310                 315                 320
```

-continued

```
Tyr Leu Ser Gly Phe Leu Ser Ser Phe Leu Met Lys Pro Ile Asn Lys
                325                 330                 335

Cys Ile Gly Arg Asn Met Thr Tyr Phe Ser Gly Leu Leu Val Ile Leu
            340                 345                 350

Ala Phe Ala Ala Trp Val Ala Leu Ala Glu Gly Leu Gly Val Ala Val
        355                 360                 365

Tyr Ala Ala Ala Val Leu Leu Gly Ala Gly Cys Ala Thr Ile Leu Val
    370                 375                 380

Thr Ser Leu Ala Met Thr Ala Asp Leu Ile Gly Pro His Thr Asn Ser
385                 390                 395                 400

Gly Ala Phe Val Tyr Gly Ser Met Ser Phe Leu Asp Lys Val Ala Asn
                405                 410                 415

Gly Leu Ala Val Met Ala Ile Gln Ser Leu His Pro Cys Pro Ser Glu
            420                 425                 430

Leu Cys Cys Arg Ala Cys Val Ser Phe Tyr His Trp Ala Met Val Ala
        435                 440                 445

Val Thr Gly Gly Val Gly Val Ala Ala Ala Leu Cys Leu Cys Ser Leu
    450                 455                 460

Leu Leu Trp Pro Thr Arg Leu Arg Arg Trp Asp Arg Asp Ala Arg Pro
465                 470                 475                 480


<210> SEQ ID NO 5
<211> LENGTH: 1511
<212> TYPE: DNA
<213> ORGANISM: Homo sapiens
<220> FEATURE:
<223> OTHER INFORMATION: cyclin-dependent kinase inhibitor 1C (CDKN1C,
      p57, Kip2) cDNA
<220> FEATURE:
<221> NAME/KEY: CDS
<222> LOCATION: (261)..(1211)
<223> OTHER INFORMATION: CDKN1C

<400> SEQUENCE: 5

gaattccggg cacccctcga gcgagcgagc tagccagcag gcatcgaggg ggcgcggctg      60

ccgtccggac gagacaggcg aacccgacgc agaagagtcc accaccggac agtcaggtag     120

ccgccgcgtc cctcgcacac gcagagtcgg gcggcgcggg gtctcccttg cgcccggcct     180

ccgccctctc ctcctctcct ttccccttct tctcgctgtc ctctcctctc tcgctgcccg     240

cgtttgcgca gccccgggcc atgtccgacg cgtccctccg cagcacatcc acgatggagc     300

gtcttgtcgc ccgtgggacc ttcccagtac tagtgcgcac cagcgcctgc cgcagcctct     360

tcgggccggt ggaccacgag gagctgagcc gcgagctgca ggcccgcctg gccgagctga     420

acgccgagga ccagaaccgc tgggattacg acttccagca ggacatgccg ctgcggggcc     480

ctggacgcct gcagtggacc gaagtggaca gcgactcggt gcccgcgttc taccgcgaga     540

cggtgcaggt ggggcgctgc cgcctgctgc tggcgccgcg gcccgtcgcg gtcgcggtgg     600

ctgtcagccc gcccctcgag ccggccgctg agtccctcga cggcctcgag gaggcgccgg     660

agcagctgcc tagtgtcccg gtcccggccc cggcgtccac cccgcccccca gtcccggtcc     720

tggctccagc cccggccccg gctccggctc cggtcgcggc tccggtcgcg gctccggtcg     780

cggtcgcggt cctggccccg gccccggccc cggccccggc tccggctccg gccccggctc     840

cagtcgcggc cccggcccca gccccggccc cggccccggc cccggccccc gccccggccc     900

cggccccgga cgcggcgcct caagagagcg ccgagcaggg cgcgaaccag gggcagcgcg     960

gccaggagcc tctcgctgac cagctgcact cggggatttc gggacgtccc gcggccggca    1020
```

-continued

```
ccgcggccgc cagcgccaac ggcgcggcga tcaagaagct gtccgggcct ctgatctccg   1080

atttcttcgc caagcgcaag agatcagcgc ctgagaagtc gtcgggcgat gtccccgcgc   1140

cgtgtccctc tccaagcgcc gcccctggcg tgggctcggt ggagcagacc ccgcgcaaga   1200

ggctgcggtg agccaattta gagcccaaag agccccgagg gaacctgccg gggcagcgga   1260

cgttggaagg gcgctgggcc tcggctggga ccgttcatgt agcagcaacc ggcggcggct   1320

gccgcagagc agcgttcggt tttgttttta aattttgaaa actgtgcaat gtattaataa   1380

cgtcttttta tatctaaatg tattctgcac gagaaggtac actggtccca aagtgtaaag   1440

ctttaagagt catttatata aaatgtttaa tctctgctga aactcagtac aaaaaaaccg   1500

ggattccggc c                                                        1511
```

```
<210> SEQ ID NO 6
<211> LENGTH: 316
<212> TYPE: PRT
<213> ORGANISM: Homo sapiens
<220> FEATURE:
<223> OTHER INFORMATION: cyclin-dependent kinase inhibitor 1C (CDKN1C,
      p57, Kip2)

<400> SEQUENCE: 6

Met Ser Asp Ala Ser Leu Arg Ser Thr Ser Thr Met Glu Arg Leu Val
  1               5                  10                  15

Ala Arg Gly Thr Phe Pro Val Leu Val Arg Thr Ser Ala Cys Arg Ser
             20                  25                  30

Leu Phe Gly Pro Val Asp His Glu Glu Leu Ser Arg Glu Leu Gln Ala
         35                  40                  45

Arg Leu Ala Glu Leu Asn Ala Glu Asp Gln Asn Arg Trp Asp Tyr Asp
     50                  55                  60

Phe Gln Gln Asp Met Pro Leu Arg Gly Pro Gly Arg Leu Gln Trp Thr
 65                  70                  75                  80

Glu Val Asp Ser Asp Ser Val Pro Ala Phe Tyr Arg Glu Thr Val Gln
                 85                  90                  95

Val Gly Arg Cys Arg Leu Leu Leu Ala Pro Arg Pro Val Ala Val Ala
            100                 105                 110

Val Ala Val Ser Pro Pro Leu Glu Pro Ala Ala Glu Ser Leu Asp Gly
        115                 120                 125

Leu Glu Glu Ala Pro Glu Gln Leu Pro Ser Val Pro Val Pro Ala Pro
    130                 135                 140

Ala Ser Thr Pro Pro Pro Val Pro Val Leu Ala Pro Ala Pro Ala Pro
145                 150                 155                 160

Ala Pro Ala Pro Val Ala Ala Pro Val Ala Ala Pro Val Ala Val Ala
                165                 170                 175

Val Leu Ala Pro Ala Pro Ala Pro Ala Pro Ala Pro Ala Pro Ala Pro
            180                 185                 190

Ala Pro Val Ala Ala Pro Ala Pro Ala Pro Ala Pro Ala Pro Ala Pro
        195                 200                 205

Ala Pro Ala Pro Ala Pro Ala Pro Asp Ala Ala Pro Gln Glu Ser Ala
    210                 215                 220

Glu Gln Gly Ala Asn Gln Gly Gln Arg Gly Gln Glu Pro Leu Ala Asp
225                 230                 235                 240

Gln Leu His Ser Gly Ile Ser Gly Arg Pro Ala Ala Gly Thr Ala Ala
                245                 250                 255

Ala Ser Ala Asn Gly Ala Ala Ile Lys Lys Leu Ser Gly Pro Leu Ile
            260                 265                 270
```

-continued

```
Ser Asp Phe Phe Ala Lys Arg Lys Arg Ser Ala Pro Glu Lys Ser Ser
        275                 280                 285

Gly Asp Val Pro Ala Pro Cys Pro Ser Pro Ser Ala Ala Pro Gly Val
    290                 295                 300

Gly Ser Val Glu Gln Thr Pro Arg Lys Arg Leu Arg
305                 310                 315


<210> SEQ ID NO 7
<211> LENGTH: 7190
<212> TYPE: DNA
<213> ORGANISM: Homo sapiens
<220> FEATURE:
<223> OTHER INFORMATION: breast cancer 1, early onset (BRCA1) cDNA
<220> FEATURE:
<221> NAME/KEY: CDS
<222> LOCATION: (201)..(5792)
<223> OTHER INFORMATION: BRCA1

<400> SEQUENCE: 7

cttagcggta gccccttggt ttccgtggca acggaaaagc gcgggaatta cagataaatt      60

aaaactgcga ctgcgcggcg tgagctcgct gagacttcct ggacgggggga caggctgtgg    120

ggtttctcag ataactgggc ccctgcgctc aggaggcctt caccctctgc tctgggtaaa    180

gttcattgga acagaaagaa atggatttat tgctcttcgc gttgaagaag tacaaaatgt    240

cattaatgct atgcagaaaa tcttagagtg tcccatctgt ctggagttga tcaaggaacc    300

tgtctccaca aagtgtgacc acatattttg caaattttgc atgctgaaac ttctcaacca    360

gaagaaaggg ccttcacagt gtcctttatg taagaatgat ataaccaaaa ggagcctaca    420

agaaagtacg agatttagtc aacttgttga agagctattg aaaatcattt gtgcttttca    480

gcttgacaca ggtttggagt atgcaaacag ctataatttt gcaaaaaagg aaaataactc    540

tcctgaacat ctaaaagatg aagtttctat catccaaagt atgggctaca gaaaccgtgc    600

caaaagactt ctacagagtg aacccgaaaa tccttccttg caggaaacca gtctcagtgt    660

ccaactctct aaccttggaa ctgtgagaac tctgaggaca aagcagcgga tacaacctca    720

aaagacgtct gtctacattg aattgggatc tgattcttct gaagataccg ttaataaggc    780

aacttattgc agtgtgggag atcaagaatt gttacaaatc acccctcaag gaaccaggga    840

tgaaatcagt ttggattctg caaaaaaggc tgcttgtgaa ttttctgaga cggatgtaac    900

aaatactgaa catcatcaac ccagtaataa tgatttgaac accactgaga agcgtgcagc    960

tgagaggcat ccagaaaagt atcagggtag ttctgtttca aacttgcatg tggagccatg   1020

tggcacaaat actcatgcca gctcattaca gcatgagaac agcagtttat tactcactaa   1080

agacagaatg aatgtagaaa aggctgaatt ctgtaataaa agcaaacagc ctggcttagc   1140

aaggagccaa cataacagat gggctggaag taaggaaaca tgtaatgata ggcggactcc   1200

cagcacagaa aaaaaggtag atctgaatgc tgatcccctg tgtgagagaa aagaatggaa   1260

taagcagaaa ctgccatgct cagagaatcc tagagatact gaagatgttc cttggataac   1320

actaaatagc agcattcaga aagttaatga gtggttttcc agaagtgatg aactgttagg   1380

ttctgatgac tcacatgatg gggagtctga atcaaatgcc aaagtagctg atgtattgga   1440

cgttctaaat gaggtagatg aatattctgg ttcttcagag aaaatagact tactggccag   1500

tgatcctcat gaggctttaa tatgtaaaag tgaaagagtt cactccaaat cagtagagag   1560

taatattgaa gacaaaatat ttgggaaaac ctatcggaag aaggcaagcc tccccaactt   1620

aagccatgta actgaaaatc taattatagg agcatttgtt actgagccac agataataca   1680

agagcgtccc ctcacaaata aattaaagcg taaaaggaga cctacatcag gccttcatcc   1740
```

-continued

```
tgaggatttt atcaagaaag cagatttggc agttcaaaag actcctgaaa tgataaatca   1800
gggaactaac caaacggagc agaatggtca agtgatgaat attactaata gtggtcatga   1860
gaataaaaca aaaggtgatt ctattcagaa tgagaaaaat cctaacccaa tagaatcact   1920
cgaaaaagaa tctgctttca aaacgaaagc tgaacctata agcagcagta taagcaatat   1980
ggaactcgaa ttaaatatcc acaattcaaa agcacctaaa aagaataggc tgaggaggaa   2040
gtcttctacc aggcatattc atgcgcttga actagtagtc agtagaaatc taagcccacc   2100
taattgtact gaattgcaaa ttgatagttg ttctagcagt gaagagataa agaaaaaaaa   2160
gtacaaccaa atgccagtca ggcacagcag aaacctacaa ctcatggaag gtaaagaacc   2220
tgcaactgga gccaagaaga gtaacaagcc aaatgaacag acaagtaaaa gacatgacag   2280
cgatactttc ccagagctga agttaacaaa tgcacctggt tcttttacta agtgttcaaa   2340
taccagtgaa cttaaagaat ttgtcaatcc tagccttcca agagaagaaa aagaagagaa   2400
actagaaaca gttaaagtgt ctaataatgc tgaagacccc aaagatctca tgttaagtgg   2460
agaaagggtt ttgcaaactg aaagatctgt agagagtagc agtatttcat tggtacctgg   2520
tactgattat ggcactcagg aaagtatctc gttactggaa gttagcactc tagggaaggc   2580
aaaaacagaa ccaaataaat gtgtgagtca gtgtgcagca tttgaaaacc ccaagggact   2640
aattcatggt tgttccaaag ataatagaaa tgacacagaa ggctttaagt atccattggg   2700
acatgaagtt aaccacagtc gggaaacaag catagaaatg gaagaaagtg aacttgatgc   2760
tcagtatttg cagaatacat tcaaggtttc aaagcgccag tcatttgctc cgttttcaaa   2820
tccaggaaat gcagaagagg aatgtgcaac attctctgcc cactctgggt ccttaaagaa   2880
acaaagtcca aaagtcactt ttgaatgtga acaaaaggaa gaaaatcaag gaaagaatga   2940
gtctaatatc aagcctgtac agacagttaa tatcactgca ggctttcctg tggttggtca   3000
gaaagataag ccagttgata atgccaaatg tagtatcaaa ggaggctcta ggttttgtct   3060
atcatctcag ttcagaggca acgaaactgg actcattact ccaaataaac atggactttt   3120
acaaaaccca tatcgtatac caccactttt tcccatcaag tcatttgtta aaactaaatg   3180
taagaaaaat ctgctagagg aaaactttga ggaacattca atgtcacctg aaagagaaat   3240
gggaaatgag aacattccaa gtacagtgag cacaattagc cgtaataaca ttagagaaaa   3300
tgtttttaaa gaagccagct caagcaatat taatgaagta ggttccagta ctaatgaagt   3360
gggctccagt attaatgaaa taggttccag tgatgaaaac attcaagcag aactaggtag   3420
aaacagaggg ccaaaattga atgctatgct tagattaggg gttttgcaac ctgaggtcta   3480
taaacaaagt cttcctggaa gtaattgtaa gcatcctgaa ataaaaaagc aagaatatga   3540
agaagtagtt cagactgtta atacagattt ctctccatat ctgatttcag ataacttaga   3600
acagcctatg ggaagtagtc atgcatctca ggtttgttct gagacacctg atgacctgtt   3660
agatgatggt gaaataaagg aagatactag ttttgctgaa aatgacatta aggaaagttc   3720
tgctgttttt agcaaaagcg tccagaaagg agagcttagc aggagtccta gccctttcac   3780
ccatacacat ttggctcagg gttaccgaag aggggccaag aaattagagt cctcagaaga   3840
gaacttatct agtgaggatg aagagcttcc ctgcttccaa cacttgttat ttggtaaagt   3900
aaacaatata ccttctcagt ctactaggca tagcaccgtt gctaccgagt gtctgtctaa   3960
gaacacagag gagaatttat tatcattgaa gaatagctta aatgactgca gtaaccaggt   4020
aatattggca aaggcatctc aggaacatca ccttagtgag gaaacaaaat gttctgctag   4080
cttgttttct tcacagtgca gtgaattgga agacttgact gcaaatacaa acacccagga   4140
```

-continued

```
tcctttcttg attggttctt ccaaacaaat gaggcatcag tctgaaagcc agggagttgg   4200
tctgagtgac aaggaattgg tttcagatga tgaagaaaga ggaacgggct tggaagaaaa   4260
taatcaagaa gagcaaagca tggattcaaa cttaggtgaa gcagcatctg ggtgtgagag   4320
tgaaacaagc gtctctgaag actgctcagg gctatcctct cagagtgaca ttttaaccac   4380
tcagcagagg gataccatgc aacataacct gataaagctc cagcaggaaa tggctgaact   4440
agaagctgtg ttagaacagc atgggagcca gccttctaac agctaccctt ccatcataag   4500
tgactcttct gcccttgagg acctgcgaaa tccagaacaa agcacatcag aaaaagcagt   4560
attaacttca cagaaaagta gtgaataccc tataagccag aatccagaag gcctttctgc   4620
tgacaagttt gaggtgtctg cagatagttc taccagtaaa aataaagaac caggagtgga   4680
aaggtcatcc ccttctaaat gcccatcatt agatgatagg tggtacatgc acagttgctc   4740
tgggagtctt cagaatagaa actacccatc tcaagaggag ctcattaagg ttgttgatgt   4800
ggaggagcaa cagctggaag agtctgggcc acacgatttg acggaaacat cttacttgcc   4860
aaggcaagat ctagagggaa ccccttacct ggaatctgga atcagcctct tctctgatga   4920
ccctgaatct gatccttctg aagacagagc cccagagtca gctcgtgttg gcaacatacc   4980
atcttcaacc tctgcattga aagttcccca attgaaagtt gcagaatctg cccagagtcc   5040
agctgctgct catactactg atactgctgg gtataatgca atggaagaaa gtgtgagcag   5100
ggagaagcca gaattgacag cttcaacaga aagggtcaac aaaagaatgt ccatggtggt   5160
gtctggcctg accccagaag aatttatgct cgtgtacaag tttgccagaa aacaccacat   5220
cactttaact aatctaatta ctgaagagac tactcatgtt gttatgaaaa cagatgctga   5280
gtttgtgtgt gaacggacac tgaaatattt tctaggaatt gcgggaggaa aatgggtagt   5340
tagctatttc tgggtgaccc agtctattaa agaaagaaaa atgctgaatg agcatgattt   5400
tgaagtcaga ggagatgtgg tcaatggaag aaaccaccaa ggtccaaagc gagcaagaga   5460
atcccaggac agaaagatct tcagggggct agaaatctgt tgctatgggc ccttcaccaa   5520
catgcccaca gatcaactgg aatggatggt acagctgtgt ggtgcttctg tggtgaagga   5580
gctttcatca ttcacccttg gcacaggtgt ccacccaatt gtggttgtgc agccagatgc   5640
ctggacagag gacaatggct tccatgcaat tgggcagatg tgtgaggcac ctgtggtgac   5700
ccgagagtgg gtgttggaca gtgtagcact ctaccagtgc caggagctgg acacctacct   5760
gataccccag atcccccaca gccactactg actgcagcca gccacaggta cagagccaca   5820
ggaccccaag aatgagctta caaagtggcc tttccaggcc ctgggagctc ctctcactct   5880
tcagtccttc tactgtcctg gctactaaat attttatgta catcagcctg aaaaggactt   5940
ctggctatgc aagggtccct taaagatttt ctgcttgaag tctcccttgg aaatctgcca   6000
tgagcacaaa attatggtaa tttttcacct gagaagattt taaaaccatt taaacgccac   6060
caattgagca agatgctgat tcattattta tcagccctat tctttctatt caggctgttg   6120
ttggcttagg gctggaagca cagagtggct tggcctcaag agaatagctg gtttccctaa   6180
gtttacttct ctaaaaccct gtgttcacaa aggcagagag tcagaccctt caatggaagg   6240
agagtgcttg ggatcgatta tgtgacttaa agtcagaata gtccttgggc agttctcaaa   6300
tgttggagtg gaacattggg gaggaaattc tgaggcaggt attagaaatg aaaaggaaac   6360
ttgaaacctg ggcatggtgg ctcacgcctg taatcccagc actttgggag gccaaggtgg   6420
gcagatcact ggaggtcagg agttcgaaac cagcctggcc aacatggtga aaccccatct   6480
ctactaaaaa tacagaaatt agccggtcat ggtggtggac acctgtaatc ccagctactc   6540
```

```
aggtggctaa ggcaggagaa tcacttcagc ccgggaggtg gaggttgcag tgagccaaga   6600
tcataccacg gcactccagc ctgggtgaca gtgagactgt ggctcaaaaa aaaaaaaaaa   6660
aaaaggaaaa tgaaactaga agagatttct aaaagtctga gatatatttg ctagatttct   6720
aaagaatgtg ttctaaaaca gcagaagatt ttcaagaacc ggtttccaaa gacagtcttc   6780
taattcctca ttagtaataa gtaaaatgtt tattgttgta gctctggtat ataatccatt   6840
cctcttaaaa tataagacct ctggcatgaa tatttcatat ctataaaatg acagatccca   6900
ccaggaagga agctgttgct ttctttgagg tgattttttt cctttgctcc ctgttgctga   6960
aaccatacag cttcataaat aattttgctt gctgaaggaa gaaaaagtgt ttttcataaa   7020
cccattatcc aggactgttt atagctgttg gaaggactag gtcttcccta gcccccccag   7080
tgtgcaaggg cagtgaagac ttgattgtac aaaatacgtt ttgtaaatgt tgtgctgtta   7140
acactgcaaa taaacttggt agcaaacact tcaaaaaaaa aaaaaaaaaa              7190
```

```
<210> SEQ ID NO 8
<211> LENGTH: 1863
<212> TYPE: PRT
<213> ORGANISM: Homo sapiens
<220> FEATURE:
<223> OTHER INFORMATION: breast cancer 1, early onset (BRCA1)

<400> SEQUENCE: 8

Met Asp Leu Ser Ala Leu Arg Val Glu Glu Val Gln Asn Val Ile Asn
1               5                   10                  15

Ala Met Gln Lys Ile Leu Glu Cys Pro Ile Cys Leu Glu Leu Ile Lys
            20                  25                  30

Glu Pro Val Ser Thr Lys Cys Asp His Ile Phe Cys Lys Phe Cys Met
        35                  40                  45

Leu Lys Leu Leu Asn Gln Lys Lys Gly Pro Ser Gln Cys Pro Leu Cys
    50                  55                  60

Lys Asn Asp Ile Thr Lys Arg Ser Leu Gln Glu Ser Thr Arg Phe Ser
65                  70                  75                  80

Gln Leu Val Glu Glu Leu Leu Lys Ile Ile Cys Ala Phe Gln Leu Asp
                85                  90                  95

Thr Gly Leu Glu Tyr Ala Asn Ser Tyr Asn Phe Ala Lys Lys Glu Asn
            100                 105                 110

Asn Ser Pro Glu His Leu Lys Asp Glu Val Ser Ile Ile Gln Ser Met
        115                 120                 125

Gly Tyr Arg Asn Arg Ala Lys Arg Leu Leu Gln Ser Glu Pro Glu Asn
    130                 135                 140

Pro Ser Leu Gln Glu Thr Ser Leu Ser Val Gln Leu Ser Asn Leu Gly
145                 150                 155                 160

Thr Val Arg Thr Leu Arg Thr Lys Gln Arg Ile Gln Pro Gln Lys Thr
                165                 170                 175

Ser Val Tyr Ile Glu Leu Gly Ser Asp Ser Ser Glu Asp Thr Val Asn
            180                 185                 190

Lys Ala Thr Tyr Cys Ser Val Gly Asp Gln Glu Leu Leu Gln Ile Thr
        195                 200                 205

Pro Gln Gly Thr Arg Asp Glu Ile Ser Leu Asp Ser Ala Lys Lys Ala
    210                 215                 220

Ala Cys Glu Phe Ser Glu Thr Asp Val Thr Asn Thr Glu His His Gln
225                 230                 235                 240

Pro Ser Asn Asn Asp Leu Asn Thr Thr Glu Lys Arg Ala Ala Glu Arg
                245                 250                 255
```

-continued

```
His Pro Glu Lys Tyr Gln Gly Ser Ser Val Ser Asn Leu His Val Glu
            260                 265                 270

Pro Cys Gly Thr Asn Thr His Ala Ser Ser Leu Gln His Glu Asn Ser
        275                 280                 285

Ser Leu Leu Leu Thr Lys Asp Arg Met Asn Val Glu Lys Ala Glu Phe
    290                 295                 300

Cys Asn Lys Ser Lys Gln Pro Gly Leu Ala Arg Ser Gln His Asn Arg
305                 310                 315                 320

Trp Ala Gly Ser Lys Glu Thr Cys Asn Asp Arg Arg Thr Pro Ser Thr
                325                 330                 335

Glu Lys Lys Val Asp Leu Asn Ala Asp Pro Leu Cys Glu Arg Lys Glu
            340                 345                 350

Trp Asn Lys Gln Lys Leu Pro Cys Ser Glu Asn Pro Arg Asp Thr Glu
        355                 360                 365

Asp Val Pro Trp Ile Thr Leu Asn Ser Ser Ile Gln Lys Val Asn Glu
    370                 375                 380

Trp Phe Ser Arg Ser Asp Glu Leu Leu Gly Ser Asp Asp Ser His Asp
385                 390                 395                 400

Gly Glu Ser Glu Ser Asn Ala Lys Val Ala Asp Val Leu Asp Val Leu
                405                 410                 415

Asn Glu Val Asp Glu Tyr Ser Gly Ser Ser Glu Lys Ile Asp Leu Leu
            420                 425                 430

Ala Ser Asp Pro His Glu Ala Leu Ile Cys Lys Ser Glu Arg Val His
        435                 440                 445

Ser Lys Ser Val Glu Ser Asn Ile Glu Asp Lys Ile Phe Gly Lys Thr
    450                 455                 460

Tyr Arg Lys Lys Ala Ser Leu Pro Asn Leu Ser His Val Thr Glu Asn
465                 470                 475                 480

Leu Ile Ile Gly Ala Phe Val Thr Glu Pro Gln Ile Ile Gln Glu Arg
                485                 490                 495

Pro Leu Thr Asn Lys Leu Lys Arg Lys Arg Arg Pro Thr Ser Gly Leu
            500                 505                 510

His Pro Glu Asp Phe Ile Lys Lys Ala Asp Leu Ala Val Gln Lys Thr
        515                 520                 525

Pro Glu Met Ile Asn Gln Gly Thr Asn Gln Thr Glu Gln Asn Gly Gln
    530                 535                 540

Val Met Asn Ile Thr Asn Ser Gly His Glu Asn Lys Thr Lys Gly Asp
545                 550                 555                 560

Ser Ile Gln Asn Glu Lys Asn Pro Asn Pro Ile Glu Ser Leu Glu Lys
                565                 570                 575

Glu Ser Ala Phe Lys Thr Lys Ala Glu Pro Ile Ser Ser Ser Ile Ser
            580                 585                 590

Asn Met Glu Leu Glu Leu Asn Ile His Asn Ser Lys Ala Pro Lys Lys
        595                 600                 605

Asn Arg Leu Arg Arg Lys Ser Ser Thr Arg His Ile His Ala Leu Glu
    610                 615                 620

Leu Val Val Ser Arg Asn Leu Ser Pro Pro Asn Cys Thr Glu Leu Gln
625                 630                 635                 640

Ile Asp Ser Cys Ser Ser Ser Glu Glu Ile Lys Lys Lys Lys Tyr Asn
                645                 650                 655

Gln Met Pro Val Arg His Ser Arg Asn Leu Gln Leu Met Glu Gly Lys
            660                 665                 670

Glu Pro Ala Thr Gly Ala Lys Lys Ser Asn Lys Pro Asn Glu Gln Thr
```

-continued

```
        675                 680                 685

Ser Lys Arg His Asp Ser Asp Thr Phe Pro Glu Leu Lys Leu Thr Asn
    690                 695                 700

Ala Pro Gly Ser Phe Thr Lys Cys Ser Asn Thr Ser Glu Leu Lys Glu
705                 710                 715                 720

Phe Val Asn Pro Ser Leu Pro Arg Glu Glu Lys Glu Glu Lys Leu Glu
                725                 730                 735

Thr Val Lys Val Ser Asn Asn Ala Glu Asp Pro Lys Asp Leu Met Leu
            740                 745                 750

Ser Gly Glu Arg Val Leu Gln Thr Glu Arg Ser Val Glu Ser Ser Ser
        755                 760                 765

Ile Ser Leu Val Pro Gly Thr Asp Tyr Gly Thr Gln Glu Ser Ile Ser
    770                 775                 780

Leu Leu Glu Val Ser Thr Leu Gly Lys Ala Lys Thr Glu Pro Asn Lys
785                 790                 795                 800

Cys Val Ser Gln Cys Ala Ala Phe Glu Asn Pro Lys Gly Leu Ile His
                805                 810                 815

Gly Cys Ser Lys Asp Asn Arg Asn Asp Thr Glu Gly Phe Lys Tyr Pro
            820                 825                 830

Leu Gly His Glu Val Asn His Ser Arg Glu Thr Ser Ile Glu Met Glu
        835                 840                 845

Glu Ser Glu Leu Asp Ala Gln Tyr Leu Gln Asn Thr Phe Lys Val Ser
    850                 855                 860

Lys Arg Gln Ser Phe Ala Pro Phe Ser Asn Pro Gly Asn Ala Glu Glu
865                 870                 875                 880

Glu Cys Ala Thr Phe Ser Ala His Ser Gly Ser Leu Lys Lys Gln Ser
                885                 890                 895

Pro Lys Val Thr Phe Glu Cys Glu Gln Lys Glu Glu Asn Gln Gly Lys
            900                 905                 910

Asn Glu Ser Asn Ile Lys Pro Val Gln Thr Val Asn Ile Thr Ala Gly
        915                 920                 925

Phe Pro Val Val Gly Gln Lys Asp Lys Pro Val Asp Asn Ala Lys Cys
    930                 935                 940

Ser Ile Lys Gly Gly Ser Arg Phe Cys Leu Ser Ser Gln Phe Arg Gly
945                 950                 955                 960

Asn Glu Thr Gly Leu Ile Thr Pro Asn Lys His Gly Leu Leu Gln Asn
                965                 970                 975

Pro Tyr Arg Ile Pro Pro Leu Phe Pro Ile Lys Ser Phe Val Lys Thr
            980                 985                 990

Lys Cys Lys Lys Asn Leu Leu Glu Glu Asn Phe Glu Glu His Ser Met
        995                 1000                1005

Ser Pro Glu Arg Glu Met Gly Asn Glu Asn Ile Pro Ser Thr Val Ser
   1010                 1015                1020

Thr Ile Ser Arg Asn Asn Ile Arg Glu Asn Val Phe Lys Glu Ala Ser
1025                1030                1035                1040

Ser Ser Asn Ile Asn Glu Val Gly Ser Ser Thr Asn Glu Val Gly Ser
               1045                1050                1055

Ser Ile Asn Glu Ile Gly Ser Ser Asp Glu Asn Ile Gln Ala Glu Leu
           1060                1065                1070

Gly Arg Asn Arg Gly Pro Lys Leu Asn Ala Met Leu Arg Leu Gly Val
       1075                1080                1085

Leu Gln Pro Glu Val Tyr Lys Gln Ser Leu Pro Gly Ser Asn Cys Lys
   1090                1095                1100
```

```
His Pro Glu Ile Lys Lys Gln Glu Tyr Glu Glu Val Val Gln Thr Val
1105                1110                1115                1120

Asn Thr Asp Phe Ser Pro Tyr Leu Ile Ser Asp Asn Leu Glu Gln Pro
                1125                1130                1135

Met Gly Ser Ser His Ala Ser Gln Val Cys Ser Glu Thr Pro Asp Asp
            1140                1145                1150

Leu Leu Asp Asp Gly Glu Ile Lys Glu Asp Thr Ser Phe Ala Glu Asn
        1155                1160                1165

Asp Ile Lys Glu Ser Ser Ala Val Phe Ser Lys Ser Val Gln Lys Gly
    1170                1175                1180

Glu Leu Ser Arg Ser Pro Ser Pro Phe Thr His Thr His Leu Ala Gln
1185                1190                1195                1200

Gly Tyr Arg Arg Gly Ala Lys Lys Leu Glu Ser Ser Glu Glu Asn Leu
                1205                1210                1215

Ser Ser Glu Asp Glu Glu Leu Pro Cys Phe Gln His Leu Leu Phe Gly
            1220                1225                1230

Lys Val Asn Asn Ile Pro Ser Gln Ser Thr Arg His Ser Thr Val Ala
        1235                1240                1245

Thr Glu Cys Leu Ser Lys Asn Thr Glu Glu Asn Leu Leu Ser Leu Lys
    1250                1255                1260

Asn Ser Leu Asn Asp Cys Ser Asn Gln Val Ile Leu Ala Lys Ala Ser
1265                1270                1275                1280

Gln Glu His His Leu Ser Glu Glu Thr Lys Cys Ser Ala Ser Leu Phe
                1285                1290                1295

Ser Ser Gln Cys Ser Glu Leu Glu Asp Leu Thr Ala Asn Thr Asn Thr
            1300                1305                1310

Gln Asp Pro Phe Leu Ile Gly Ser Ser Lys Gln Met Arg His Gln Ser
        1315                1320                1325

Glu Ser Gln Gly Val Gly Leu Ser Asp Lys Glu Leu Val Ser Asp Asp
    1330                1335                1340

Glu Glu Arg Gly Thr Gly Leu Glu Glu Asn Asn Gln Glu Glu Gln Ser
1345                1350                1355                1360

Met Asp Ser Asn Leu Gly Glu Ala Ala Ser Gly Cys Glu Ser Glu Thr
                1365                1370                1375

Ser Val Ser Glu Asp Cys Ser Gly Leu Ser Ser Gln Ser Asp Ile Leu
            1380                1385                1390

Thr Thr Gln Gln Arg Asp Thr Met Gln His Asn Leu Ile Lys Leu Gln
        1395                1400                1405

Gln Glu Met Ala Glu Leu Glu Ala Val Leu Glu Gln His Gly Ser Gln
    1410                1415                1420

Pro Ser Asn Ser Tyr Pro Ser Ile Ile Ser Asp Ser Ser Ala Leu Glu
1425                1430                1435                1440

Asp Leu Arg Asn Pro Glu Gln Ser Thr Ser Glu Lys Ala Val Leu Thr
                1445                1450                1455

Ser Gln Lys Ser Ser Glu Tyr Pro Ile Ser Gln Asn Pro Glu Gly Leu
            1460                1465                1470

Ser Ala Asp Lys Phe Glu Val Ser Ala Asp Ser Ser Thr Ser Lys Asn
        1475                1480                1485

Lys Glu Pro Gly Val Glu Arg Ser Ser Pro Ser Lys Cys Pro Ser Leu
    1490                1495                1500

Asp Asp Arg Trp Tyr Met His Ser Cys Ser Gly Ser Leu Gln Asn Arg
1505                1510                1515                1520

Asn Tyr Pro Ser Gln Glu Glu Leu Ile Lys Val Val Asp Val Glu Glu
                1525                1530                1535
```

```
Gln Gln Leu Glu Glu Ser Gly Pro His Asp Leu Thr Glu Thr Ser Tyr
            1540                1545                1550

Leu Pro Arg Gln Asp Leu Glu Gly Thr Pro Tyr Leu Glu Ser Gly Ile
        1555                1560                1565

Ser Leu Phe Ser Asp Asp Pro Glu Ser Asp Pro Ser Glu Asp Arg Ala
    1570                1575                1580

Pro Glu Ser Ala Arg Val Gly Asn Ile Pro Ser Ser Thr Ser Ala Leu
1585                1590                1595                1600

Lys Val Pro Gln Leu Lys Val Ala Glu Ser Ala Gln Ser Pro Ala Ala
                1605                1610                1615

Ala His Thr Thr Asp Thr Ala Gly Tyr Asn Ala Met Glu Glu Ser Val
            1620                1625                1630

Ser Arg Glu Lys Pro Glu Leu Thr Ala Ser Thr Glu Arg Val Asn Lys
        1635                1640                1645

Arg Met Ser Met Val Val Ser Gly Leu Thr Pro Glu Glu Phe Met Leu
    1650                1655                1660

Val Tyr Lys Phe Ala Arg Lys His His Ile Thr Leu Thr Asn Leu Ile
1665                1670                1675                1680

Thr Glu Glu Thr Thr His Val Val Met Lys Thr Asp Ala Glu Phe Val
                1685                1690                1695

Cys Glu Arg Thr Leu Lys Tyr Phe Leu Gly Ile Ala Gly Gly Lys Trp
            1700                1705                1710

Val Val Ser Tyr Phe Trp Val Thr Gln Ser Ile Lys Glu Arg Lys Met
        1715                1720                1725

Leu Asn Glu His Asp Phe Glu Val Arg Gly Asp Val Val Asn Gly Arg
    1730                1735                1740

Asn His Gln Gly Pro Lys Arg Ala Arg Glu Ser Gln Asp Arg Lys Ile
1745                1750                1755                1760

Phe Arg Gly Leu Glu Ile Cys Cys Tyr Gly Pro Phe Thr Asn Met Pro
                1765                1770                1775

Thr Asp Gln Leu Glu Trp Met Val Gln Leu Cys Gly Ala Ser Val Val
            1780                1785                1790

Lys Glu Leu Ser Ser Phe Thr Leu Gly Thr Gly Val His Pro Ile Val
        1795                1800                1805

Val Val Gln Pro Asp Ala Trp Thr Glu Asp Asn Gly Phe His Ala Ile
    1810                1815                1820

Gly Gln Met Cys Glu Ala Pro Val Val Thr Arg Glu Trp Val Leu Asp
1825                1830                1835                1840

Ser Val Ala Leu Tyr Gln Cys Gln Glu Leu Asp Thr Tyr Leu Ile Pro
                1845                1850                1855

Gln Ile Pro His Ser His Tyr
            1860
```

<210> SEQ ID NO 9
<211> LENGTH: 5193
<212> TYPE: DNA
<213> ORGANISM: Homo sapiens
<220> FEATURE:
<223> OTHER INFORMATION: SH3-domain binding protein 4 (SH3BP4) cDNA
<220> FEATURE:
<221> NAME/KEY: CDS
<222> LOCATION: (394)..(3285)
<223> OTHER INFORMATION: SH3BP4

<400> SEQUENCE: 9

```
gggaccaccc tccgcccgcc gaggcggggg cccagcgcgc ccggcactct cggcggtccg      60
```

-continued

```
ggcccctcgc cactaccgcc gccgccgccg ccgtgagtcc cgcggagccg cgcgcgcccc    120
cggctgggcc gagccgctgg ccgacgagcg gagcctcagg agccggcggg gacgccatgc    180
gagccagcgt ctcccttctc tcctggacag aaggccgtgt cctgggactt ctctgatggc    240
gagaggctgc ggctgtacca ggaagaaaca tattgccgag tggatgccgc cgcgcagcgt    300
gtttgcttga ggcagaagct tcagcatctg ctgggataac tggaggaaga aatatgaagc    360
cttagcggct ttacccggga agcgagtttc gagatggcgg ctcagcggat ccgagcggcc    420
aactccaatg gcctccctcg ctgcaagtca gaggggaccc tgattgacct gagcgaaggg    480
ttttcagaga cgagctttaa tgacatcaaa gtgccttctc ccagtgcctt gctcgtagac    540
aaccccacac ctttcggaaa tgcaaaggaa gtgattgcga tcaaggacta ttgccccacc    600
aacttcacca cactgaagtt ctccaagggc gaccatctct acgtcttgga cacatctggc    660
ggtgagtggt ggtacgcaca caacaccacc gaaatgggct acatcccctc ctcctatgtg    720
cagcccttga actaccggaa ctcaacactg agtgacagcg gtatgattga taatcttcca    780
gacagcccag acgaggtagc caaggagctg gagctgctcg ggggatggac agatgacaaa    840
aaagtaccag gcagaatgta cagtaataac cctttctgga atggggtcca gaccaatcca    900
tttctgaatg ggaacgtgcc cgtcatgccc agcctggatg agctgaatcc caaaagtact    960
gtggatttgc tcctttttga cgcaggtaca tcctccttca ccgaatccag ctcagccacc   1020
acgaatagca ctggcaacat cttcgatgag cttccagtca caaacggact ccacgcagag   1080
ccgccggtca ggcgggacaa ccccttcttc agaagcaagc gctcctacag tctctcggaa   1140
ctctccgtcc tccaagccaa gtccgatgct cccacatcgt cgagtttctt caccggcttg   1200
aaatcacctg cccccgagca atttcagagc cgggaggatt ttcgaactgc ctggctaaac   1260
cacaggaagc tggcccggtc ttgccacgac ctggacttgc ttggccaaag ccctggttgg   1320
ggccagaccc aagccgtgga gacaaacatc gtgtgcaagc tggatagctc cgggggtgct   1380
gtccagcttc ctgacaccag catcagcatc cacgtgcccg agggccacgt cgcccctggg   1440
gagacccagc agatctccat gaaagccctg ctggaccccc cgctggagct caacagtgac   1500
aggtcctgca gcatcagccc tgtgctggag gtcaagctga gcaacctgga ggtgaaaacc   1560
tctatcatct tggagatgaa agtgtcagcc gagataaaaa atgacctttt tagcaaaagc   1620
acagtgggcc tccagtgcct gaggagcgac tcgaaggaag ggccatatgt ctccgtcccg   1680
ctcaactgca gctgtgggga cacggtccag gcacagctgc acaacctgga gccctgtatg   1740
tacgtggctg tcgtggccca tggcccaagc atcctctacc cttccaccgt gtgggacttc   1800
atcaataaaa aagtcacagt gggtctctac ggccctaaac acatccaccc atccttcaag   1860
acggtagtga ccatttttgg gcatgactgt gccccaaaga cgctcctggt cagcgaggtc   1920
acacgccagg cacccaaccc tgccccggtg gccctgcagc tgtgggggaa gcaccagttc   1980
gttttgtcca ggccccagga tctcaaggtc tgtatgtttt ccaatatgac gaattacgag   2040
gtcaaagcca gcgagcaggc caaagtggtg cgaggattcc agctgaagct gggcaaggtg   2100
agccgcctga tcttccccat cacctcccag aaccccaacg agctctctga cttcacgctg   2160
cgggttcagg tgaaggacga ccaggaggcc atcctcaccc agttttgtgt ccagactcct   2220
cagccacccc ctaaaagtgc catcaagcct tccgggcaaa ggaggtttct caagaagaac   2280
gaagtcggga aaatcatcct gtccccgttt gccaccacta caaagtaccc gactttccag   2340
gaccgcccgg tgtccagcct caagtttggt aagttgctca agactgtggt gcggcagaac   2400
aagaaccact acctgctgga gtacaagaag ggcgacggga tcgccctgct cagcgaggag   2460
```

-continued

```
cgggtcaggc tccggggcca gctgtggacc aaggagtggt acatcggcta ctaccagggc   2520
agggtgggcc tcgtgcacac caagaacgtg ctggtggtcg gcagggcccg gcccagcctg   2580
tgctcgggcc ccgagctgag cacctcggtg ctgctggagc agatcctgcg gccctgcaaa   2640
ttcctcacgt acatctatgc ctccgtgagg accctgctca tggagaacat cagcagctgg   2700
cgctccttcg ctgacgccct gggctacgtg aacctgccgc tcaccttttt ctgccgggca   2760
gagctggata gtgagcccga gcgggtggcg tccgtcctag aaaagctgaa ggaggactgt   2820
aacaacactg agaacaaaga acggaagtcc ttccagaagg agcttgtgat ggccctactg   2880
aagatggact gccagggcct ggtggtcaga ctcatccagg actttgtgct cctgaccacg   2940
gctgtagagg tggcccagcg ctggcgggag ctggctgaga agctggccaa ggtctccaag   3000
cagcagatgg acgcctacga gtctccccac cgggacagga acggggttgt ggacagcgag   3060
gccatgtgga agcctgcgta tgacttctta ctcacctgga gccatcagat cggggacagc   3120
taccgggatg tcatccagga gctgcacctg ggcctggaca agatgaaaaa ccccatcacc   3180
aagcgctgga agcacctcac tgggactctg atcttggtga actccctgga cgttctgaga   3240
gcagccgcct tcagccctgc ggaccaggac gacttcgtga tttgaatggg tcccctcccc   3300
tcctgctgct ctggagtgca agccctcttc tgccctgcgt gccctgctgt caccgcggag   3360
ctgaagaggg aggaaggggc ggctgctcag acagatttag ggcccgccag ctaggctaca   3420
cccatcatgc gccgccctcc tccatcgagg gagaggcctg aagggactgc ctactgcagc   3480
tcgttgccaa tcacatagct ttctatttgt taagtataaa tttaaattta aaatcacttt   3540
tttaacgaat gggggaaggg gatctatgag aaaggtggta tctaattttt ttatggacca   3600
taaaggttta aaagaaaata ggggcacagg ctgttgaggt ttttatgttg ttatagacct   3660
ttttaaatta tgttagagat gtatataggt atttaaaggt cactgggagc gtttctgatt   3720
cccggccaca ctttgcattt caacactcag cccggaaaga tgctcgttcg gttgttggac   3780
ctctttcact ccctgcgtgt aagaaggtga atcacgtggg aaaaagtggc ttttcagtaa   3840
acgggtacag ctcattcttt ctgagaaggc cccaggtcct gctccctcct cggatttgat   3900
tgtcttccgt gctttgcctc actcgtagta aatgaccatc catagaatat gtgaatcttt   3960
ggtgagcttc agtgggcaga gtgaagtccc gcattagcat ttaggtgccc tgagctgttt   4020
ctgccaatag attagaaagc agccatgagt tgacagtctt tagggcccct gccagtgtgc   4080
aattagtcat tgacaagaac aatgccattt gagagtgagg tggtccctgc tgctacgagg   4140
ccattgtact gtttttttcct tgaggtcaaa gcagtgcttc ccatagagtt tgctgcctct   4200
tctgtggaca ggaagaaaac ttcatgaccg aatcagagcc ttggtggcca ctgactctcg   4260
tgcttattgc agatgctgtg gttggcctca caagcaacgc cttatgctga tgtgcagagg   4320
tgccagctgc catttgccaa actctgcatt tcatttcatc taaggcttaa cccctcttcc   4380
ttcctggtgt acctgtgtct cctcggaagg aagtcatagt ttagatgaaa ccattttttg   4440
tacaatgtaa agatcatctg agcaagatga gcattttgta aaaatgaaaa tgtgactcac   4500
ataaaatcag gaacttgaca cagtgttgca ttaataactt tagggtgcag acatgctgtg   4560
tgaatctcac aatgcgtcgt agatgtcgcg tgttggaagg gagcaggagg aaggactgat   4620
actggcaaat cagtagagtg aggtgatcct tagcaacgtg ccaggacact tcctgtgtgc   4680
ctgcagttgt cagggaccat ttgggatccc gaatctcatt ctctaaaact gctttcttga   4740
aacatgttac ttccttagta taatcaatgt atactccctt actggcctga aacgttgtat   4800
agctacttat tcagatactg aagaccaacg gactgaaaaa aagaacaaac attagctatt   4860
```

-continued

```
ttatgctgca agaaccagga cacacaattc gccaatcatc ccaccatata accttcgatt   4920

gtgcttctca actccacccc ataatttctc ccagagacca tctatcacct tttccccaaa   4980

gaagaaacaa aaccagttgc accttaaacc atggatattt tttcctcagg ggctttaaat   5040

agtttcctat gcaacgtgtc ttgtagcaca aataaaattc tacaaaagtt gcagtaaatt   5100

ttatttggat attttaacct gttaagtgtg tgtgtgtttt ctgtacccaa ccagacttta   5160

aataaaaacaa acatgaaacc taaaaaaaaa aaa                              5193


<210> SEQ ID NO 10
<211> LENGTH: 963
<212> TYPE: PRT
<213> ORGANISM: Homo sapiens
<220> FEATURE:
<223> OTHER INFORMATION: SH3-domain binding protein 4 (SH3BP4)

<400> SEQUENCE: 10

Met Ala Ala Gln Arg Ile Arg Ala Ala Asn Ser Asn Gly Leu Pro Arg
1               5                   10                  15

Cys Lys Ser Glu Gly Thr Leu Ile Asp Leu Ser Glu Gly Phe Ser Glu
            20                  25                  30

Thr Ser Phe Asn Asp Ile Lys Val Pro Ser Pro Ser Ala Leu Leu Val
        35                  40                  45

Asp Asn Pro Thr Pro Phe Gly Asn Ala Lys Glu Val Ile Ala Ile Lys
    50                  55                  60

Asp Tyr Cys Pro Thr Asn Phe Thr Thr Leu Lys Phe Ser Lys Gly Asp
65                  70                  75                  80

His Leu Tyr Val Leu Asp Thr Ser Gly Gly Glu Trp Trp Tyr Ala His
                85                  90                  95

Asn Thr Thr Glu Met Gly Tyr Ile Pro Ser Ser Tyr Val Gln Pro Leu
            100                 105                 110

Asn Tyr Arg Asn Ser Thr Leu Ser Asp Ser Gly Met Ile Asp Asn Leu
        115                 120                 125

Pro Asp Ser Pro Asp Glu Val Ala Lys Glu Leu Glu Leu Leu Gly Gly
    130                 135                 140

Trp Thr Asp Asp Lys Lys Val Pro Gly Arg Met Tyr Ser Asn Asn Pro
145                 150                 155                 160

Phe Trp Asn Gly Val Gln Thr Asn Pro Phe Leu Asn Gly Asn Val Pro
                165                 170                 175

Val Met Pro Ser Leu Asp Glu Leu Asn Pro Lys Ser Thr Val Asp Leu
            180                 185                 190

Leu Leu Phe Asp Ala Gly Thr Ser Ser Phe Thr Glu Ser Ser Ser Ala
        195                 200                 205

Thr Thr Asn Ser Thr Gly Asn Ile Phe Asp Glu Leu Pro Val Thr Asn
    210                 215                 220

Gly Leu His Ala Glu Pro Pro Val Arg Arg Asp Asn Pro Phe Phe Arg
225                 230                 235                 240

Ser Lys Arg Ser Tyr Ser Leu Ser Glu Leu Ser Val Leu Gln Ala Lys
                245                 250                 255

Ser Asp Ala Pro Thr Ser Ser Ser Phe Phe Thr Gly Leu Lys Ser Pro
            260                 265                 270

Ala Pro Glu Gln Phe Gln Ser Arg Glu Asp Phe Arg Thr Ala Trp Leu
        275                 280                 285

Asn His Arg Lys Leu Ala Arg Ser Cys His Asp Leu Asp Leu Leu Gly
    290                 295                 300

Gln Ser Pro Gly Trp Gly Gln Thr Gln Ala Val Glu Thr Asn Ile Val
```

-continued

```
305                 310                 315                 320

Cys Lys Leu Asp Ser Ser Gly Gly Ala Val Gln Leu Pro Asp Thr Ser
                325                 330                 335

Ile Ser Ile His Val Pro Glu Gly His Val Ala Pro Gly Glu Thr Gln
            340                 345                 350

Gln Ile Ser Met Lys Ala Leu Leu Asp Pro Pro Leu Glu Leu Asn Ser
        355                 360                 365

Asp Arg Ser Cys Ser Ile Ser Pro Val Leu Glu Val Lys Leu Ser Asn
    370                 375                 380

Leu Glu Val Lys Thr Ser Ile Ile Leu Glu Met Lys Val Ser Ala Glu
385                 390                 395                 400

Ile Lys Asn Asp Leu Phe Ser Lys Ser Thr Val Gly Leu Gln Cys Leu
                405                 410                 415

Arg Ser Asp Ser Lys Glu Gly Pro Tyr Val Ser Val Pro Leu Asn Cys
            420                 425                 430

Ser Cys Gly Asp Thr Val Gln Ala Gln Leu His Asn Leu Glu Pro Cys
        435                 440                 445

Met Tyr Val Ala Val Val Ala His Gly Pro Ser Ile Leu Tyr Pro Ser
    450                 455                 460

Thr Val Trp Asp Phe Ile Asn Lys Lys Val Thr Val Gly Leu Tyr Gly
465                 470                 475                 480

Pro Lys His Ile His Pro Ser Phe Lys Thr Val Val Thr Ile Phe Gly
                485                 490                 495

His Asp Cys Ala Pro Lys Thr Leu Leu Val Ser Glu Val Thr Arg Gln
            500                 505                 510

Ala Pro Asn Pro Ala Pro Val Ala Leu Gln Leu Trp Gly Lys His Gln
        515                 520                 525

Phe Val Leu Ser Arg Pro Gln Asp Leu Lys Val Cys Met Phe Ser Asn
    530                 535                 540

Met Thr Asn Tyr Glu Val Lys Ala Ser Glu Gln Ala Lys Val Val Arg
545                 550                 555                 560

Gly Phe Gln Leu Lys Leu Gly Lys Val Ser Arg Leu Ile Phe Pro Ile
                565                 570                 575

Thr Ser Gln Asn Pro Asn Glu Leu Ser Asp Phe Thr Leu Arg Val Gln
            580                 585                 590

Val Lys Asp Asp Gln Glu Ala Ile Leu Thr Gln Phe Cys Val Gln Thr
        595                 600                 605

Pro Gln Pro Pro Pro Lys Ser Ala Ile Lys Pro Ser Gly Gln Arg Arg
    610                 615                 620

Phe Leu Lys Lys Asn Glu Val Gly Lys Ile Ile Leu Ser Pro Phe Ala
625                 630                 635                 640

Thr Thr Thr Lys Tyr Pro Thr Phe Gln Asp Arg Pro Val Ser Ser Leu
                645                 650                 655

Lys Phe Gly Lys Leu Leu Lys Thr Val Val Arg Gln Asn Lys Asn His
            660                 665                 670

Tyr Leu Leu Glu Tyr Lys Lys Gly Asp Gly Ile Ala Leu Leu Ser Glu
        675                 680                 685

Glu Arg Val Arg Leu Arg Gly Gln Leu Trp Thr Lys Glu Trp Tyr Ile
    690                 695                 700

Gly Tyr Tyr Gln Gly Arg Val Gly Leu Val His Thr Lys Asn Val Leu
705                 710                 715                 720

Val Val Gly Arg Ala Arg Pro Ser Leu Cys Ser Gly Pro Glu Leu Ser
                725                 730                 735
```

```
Thr Ser Val Leu Leu Glu Gln Ile Leu Arg Pro Cys Lys Phe Leu Thr
            740                 745                 750

Tyr Ile Tyr Ala Ser Val Arg Thr Leu Leu Met Glu Asn Ile Ser Ser
        755                 760                 765

Trp Arg Ser Phe Ala Asp Ala Leu Gly Tyr Val Asn Leu Pro Leu Thr
    770                 775                 780

Phe Phe Cys Arg Ala Glu Leu Asp Ser Glu Pro Glu Arg Val Ala Ser
785                 790                 795                 800

Val Leu Glu Lys Leu Lys Glu Asp Cys Asn Asn Thr Glu Asn Lys Glu
                805                 810                 815

Arg Lys Ser Phe Gln Lys Glu Leu Val Met Ala Leu Leu Lys Met Asp
            820                 825                 830

Cys Gln Gly Leu Val Val Arg Leu Ile Gln Asp Phe Val Leu Leu Thr
        835                 840                 845

Thr Ala Val Glu Val Ala Gln Arg Trp Arg Glu Leu Ala Glu Lys Leu
    850                 855                 860

Ala Lys Val Ser Lys Gln Gln Met Asp Ala Tyr Glu Ser Pro His Arg
865                 870                 875                 880

Asp Arg Asn Gly Val Val Asp Ser Glu Ala Met Trp Lys Pro Ala Tyr
                885                 890                 895

Asp Phe Leu Leu Thr Trp Ser His Gln Ile Gly Asp Ser Tyr Arg Asp
            900                 905                 910

Val Ile Gln Glu Leu His Leu Gly Leu Asp Lys Met Lys Asn Pro Ile
        915                 920                 925

Thr Lys Arg Trp Lys His Leu Thr Gly Thr Leu Ile Leu Val Asn Ser
    930                 935                 940

Leu Asp Val Leu Arg Ala Ala Ala Phe Ser Pro Ala Asp Gln Asp Asp
945                 950                 955                 960

Phe Val Ile


<210> SEQ ID NO 11
<211> LENGTH: 5490
<212> TYPE: DNA
<213> ORGANISM: Homo sapiens
<220> FEATURE:
<223> OTHER INFORMATION: collagen, type III, alpha 1 (Ehlers-Danlos
      syndrome type IV, autosomal dominant) (COL3A1)
      cDNA
<220> FEATURE:
<221> NAME/KEY: CDS
<222> LOCATION: (118)..(4518)
<223> OTHER INFORMATION: COL3A1

<400> SEQUENCE: 11

ggctgagttt tatgacgggc ccggtgctga agggcaggga acaacttgat ggtgctactt      60

tgaactgctt ttcttttctc ctttttgcac aaagagtctc atgtctgata tttagacatg     120

atgagctttg tgcaaaaggg gagctggcta cttctcgctc tgcttcatcc cactattatt     180

ttggcacaac aggaagctgt tgaaggagga tgttcccatc ttggtcagtc ctatgcggat     240

agagatgtct ggaagccaga accatgccaa atatgtgtct gtgactcagg atccgttctc     300

tgcgatgaca taatatgtga cgatcaagaa ttagactgcc ccaacccaga aattccattt     360

ggagaatgtt gtgcagtttg cccacagcct ccaactgctc ctactcgccc tcctaatggt     420

caaggacctc aaggccccaa gggagatcca ggccctcctg gtattcctgg gagaaatggt     480

gaccctggta ttccaggaca accagggtcc cctggttctc ctggcccccc tggaatctgt     540

gaatcatgcc ctactggtcc tcagaactat tctccccagt atgattcata tgatgtcaag     600
```

-continued

```
tctggagtag cagtaggagg actcgcaggc tatcctggac cagctggccc cccaggccct    660
cccggtcccc ctggtacatc tggtcatcct ggttcccctg gatctccagg ataccaagga    720
ccccctggtg aacctgggca agctggtcct tcaggccctc caggacctcc tggtgctata    780
ggtccatctg gtcctgctgg aaaagatgga gaatcaggta gacccggacg acctggagag    840
cgaggattgc ctggacctcc aggtatcaaa ggtccagctg ggatacctgg attccctggt    900
atgaaaggac acagaggctt cgatggacga aatggagaaa agggtgaaac aggtgctcct    960
ggattaaagg gtgaaaatgg tcttccaggc gaaaatggag ctcctggacc catgggtcca   1020
agaggggctc ctggtgagcg aggacggcca ggacttcctg ggctgcagg tgctcggggt   1080
aatgacggtg ctcgaggcag tgatggtcaa ccaggccctc ctggtcctcc tggaactgcc   1140
ggattccctg gatcccctgg tgctaagggt gaagttggac ctgcagggtc tcctggttca   1200
aatggtgccc ctggacaaag aggagaacct ggacctcagg gacacgctgg tgctcaaggt   1260
cctcctggcc ctcctgggat taatggtagt cctggtggta aaggcgaaat gggtcccgct   1320
ggcattcctg gagctcctgg actgatggga gcccggggtc ctccaggacc agccggtgct   1380
aatggtgctc ctggactgcg aggtggtgca ggtgagcctg gtaagaatgg tgccaaagga   1440
gagcccggac cacgtggtga acgcggtgag gctggtattc caggtgttcc aggagctaaa   1500
ggcgaagatg gcaaggatgg atcacctgga gaacctggtg caaatgggct tccaggagct   1560
gcaggagaaa ggggtgcccc tgggttccga ggacctgctg gaccaaatgg catcccagga   1620
gaaaagggtc ctgctggaga gcgtggtgct ccaggccctg cagggcccag aggagctgct   1680
ggagaacctg gcagagatgg cgtccctgga ggtccaggaa tgaggggcat gcccggaagt   1740
ccaggaggac caggaagtga tgggaaacca gggcctcccg gaagtcaagg agaaagtggt   1800
cgaccaggtc ctcctgggcc atctggtccc cgaggtcagc ctggtgtcat gggcttcccc   1860
ggtcctaaag gaaatgatgg tgctcctggt aagaatggag aacgaggtgg ccctggagga   1920
cctggccctc agggtcctcc tggaaagaat ggtgaaactg gacctcaggg acccccaggg   1980
cctactgggc ctggtggtga caaaggagac acaggacccc ctggtccaca aggattacaa   2040
ggcttgcctg gtacaggtgg tcctccagga gaaaatggaa aacctgggga accaggtcca   2100
aagggtgatg ccggtgcacc tggagctcca ggaggcaagg gtgatgctgg tgcccctggt   2160
gaacgtggac ctcctggatt ggcaggggcc ccaggactta gaggtggagc tggtccccct   2220
ggtcccgaag gaggaaaggg tgctgctggt cctcctgggc cacctggtgc tgctggtact   2280
cctggtctgc aaggaatgcc tggagaaaga ggaggtcttg gaagtcctgg tccaaagggt   2340
gacaagggtg aaccaggcgg tccaggtgct gatggtgtcc cagggaaaga tggcccaagg   2400
ggtcctactg gtcctattgg tcctcctggc ccagctggcc agcctggaga taagggtgaa   2460
ggtggtgccc ccggacttcc aggtatagct ggacctcgtg gtagccctgg tgagagaggt   2520
gaaactggcc ctccaggacc tgctggtttc cctggtgctc ctggacagaa tggtgaacct   2580
ggtggtaaag gagaaagagg ggctccgggt gagaaaggtg aaggaggccc tcctggagtt   2640
gcaggacccc ctggaggttc tggacctgct ggtcctcctg gtccccaagg tgtcaaaggt   2700
gaacgtggca gtcctggtgg acctggtgct gctggcttcc ctggtgctcg tggtcttcct   2760
ggtcctcctg gtagtaatgg taacccagga cccccaggtc ccagcggttc tccaggcaag   2820
gatgggcccc caggtcctgc gggtaacact ggtgctcctg gcagccctgg agtgtctgga   2880
ccaaaaggtg atgctggcca accaggagag aagggatcgc ctggtgccca gggcccacca   2940
ggagctccag gcccacttgg gattgctggg atcactggag cacggggtct tgcaggacca   3000
```

-continued

```
ccaggcatgc caggtcctag gggaagccct ggccctcagg gtgtcaaggg tgaaagtggg   3060
aaaccaggag ctaacggtct cagtggagaa cgtggtcccc ctggacccca gggtcttcct   3120
ggtctggctg gtacagctgg tgaacctgga agagatggaa accctggatc agatggtctt   3180
ccaggccgag atggatctcc tggtggcaag ggtgatcgtg gtgaaaatgg ctctcctggt   3240
gcccctggcg ctcctggtca tccaggccca cctggtcctg tcggtccagc tggaaagagt   3300
ggtgacagag gagaaagtgg ccctgctggc cctgctggtg ctcccggtcc tgctggttcc   3360
cgaggtgctc ctggtcctca aggcccacgt ggtgacaaag gtgaaacagg tgaacgtgga   3420
gctgctggca tcaaaggaca tcgaggattc cctggtaatc caggtgcccc aggttctcca   3480
ggccctgctg gtcagcaggg tgcaatcggc agtccaggac ctgcaggccc cagaggacct   3540
gttggaccca gtggacctcc tggcaaagat ggaaccagtg gacatccagg tcccattgga   3600
ccaccagggc ctcgaggtaa cagaggtgaa agaggatctg agggctcccc aggccaccca   3660
gggcaaccag gccctcctgg acctcctggt gcccctggtc cttgctgtgg tggtgttgga   3720
gccgctgcca ttgctgggat tggaggtgaa aaagctggcg gttttgcccc gtattatgga   3780
gatgaaccaa tggatttcaa aatcaacacc gatgagatta tgacttcact caagtctgtt   3840
aatggacaaa tagaaagcct cattagtcct gatggttctc gtaaaaaccc cgctagaaac   3900
tgcagagacc tgaaattctg ccatcctgaa ctcaagagtg gagaatactg ggttgaccct   3960
aaccaaggat gcaaattgga tgctatcaag gtattctgta atatggaaac tggggaaaca   4020
tgcataagtg ccaatccttt gaatgttcca cggaaacact ggtggacaga ttctagtgct   4080
gagaagaaac acgtttggtt tggagagtcc atggatggtg gttttcagtt tagctacggc   4140
aatcctgaac ttcctgaaga tgtccttgat gtgcagctgg cattccttcg acttctctcc   4200
agccgagctt cccagaacat cacatatcac tgcaaaaata gcattgcata catggatcag   4260
gccagtggaa atgtaaagaa ggccctgaag ctgatggggt caaatgaagg tgaattcaag   4320
gctgaaggaa atagcaaatt cacctacaca gttctggagg atggttgcac gaaacacact   4380
ggggaatgga gcaaaacagt ctttgaatat cgaacacgca aggctgtgag actacctatt   4440
gtagatattg caccctatga cattggtggt cctgatcaag aatttggtgt ggacgttggc   4500
cctgtttgct ttttataaac caaactctat ctgaaatccc aacaaaaaaa atttaactcc   4560
atatgtgttc ctcttgttct aatcttgtca accagtgcaa gtgaccgaca aaattccagt   4620
tatttatttc caaaatgttt ggaaacagta taatttgaca aagaaaaatg atacttctct   4680
ttttttgctg ttccaccaaa tacaattcaa atgcttttg ttttattttt ttaccaattc   4740
caatttcaaa atgtctcaat ggtgctataa taaataaact tcaacactct ttatgataac   4800
aacactgtgt tatattcttt gaatcctagc ccatctgcag agcaatgact gtgctcacca   4860
gtaaaagata acctttcttt ctgaaatagt caaatacgaa attagaaaag ccctccctat   4920
tttaactacc tcaactggtc agaaacacag attgtattct atgagtccca gaagatgaaa   4980
aaaattttat acgttgataa aacttataaa tttcattgat taatctcctg gaagattggt   5040
ttaaaaagaa aagtgtaatg caagaattta aagaaatatt tttaaagcca caattatttt   5100
aatattggat atcaactgct tgtaaaggtg ctcctctttt ttcttgtcat tgctggtcaa   5160
gattactaat atttgggaag gctttaaaga cgcatgttat ggtgctaatg tactttcact   5220
tttaaactct agatcagaat tgttgacttg cattcagaac ataaatgcac aaaatctgta   5280
catgtctccc atcagaaaga ttcattggca tgccacaggg gattctcctc cttcatcctg   5340
taaaggtcaa caataaaaac caaattatgg ggctgctttt gtcacactag catagagaat   5400
```

```
gtgttgaaat ttaactttgt aagcttgtat gtggttgttg atcttttttt tccttacaga   5460

cacccataat aaaatatcat attaaaattc                                     5490


<210> SEQ ID NO 12
<211> LENGTH: 1466
<212> TYPE: PRT
<213> ORGANISM: Homo sapiens
<220> FEATURE:
<223> OTHER INFORMATION: collagen, type III, alpha 1 (Ehlers-Danlos
      syndrome type IV, autosomal dominant) (COL3A1)

<400> SEQUENCE: 12

Met Met Ser Phe Val Gln Lys Gly Ser Trp Leu Leu Leu Ala Leu Leu
1               5                   10                  15

His Pro Thr Ile Ile Leu Ala Gln Gln Glu Ala Val Glu Gly Gly Cys
            20                  25                  30

Ser His Leu Gly Gln Ser Tyr Ala Asp Arg Asp Val Trp Lys Pro Glu
        35                  40                  45

Pro Cys Gln Ile Cys Val Cys Asp Ser Gly Ser Val Leu Cys Asp Asp
    50                  55                  60

Ile Ile Cys Asp Asp Gln Glu Leu Asp Cys Pro Asn Pro Glu Ile Pro
65                  70                  75                  80

Phe Gly Glu Cys Cys Ala Val Cys Pro Gln Pro Pro Thr Ala Pro Thr
                85                  90                  95

Arg Pro Pro Asn Gly Gln Gly Pro Gln Gly Pro Lys Gly Asp Pro Gly
            100                 105                 110

Pro Pro Gly Ile Pro Gly Arg Asn Gly Asp Pro Gly Ile Pro Gly Gln
        115                 120                 125

Pro Gly Ser Pro Gly Ser Pro Gly Pro Pro Gly Ile Cys Glu Ser Cys
    130                 135                 140

Pro Thr Gly Pro Gln Asn Tyr Ser Pro Gln Tyr Asp Ser Tyr Asp Val
145                 150                 155                 160

Lys Ser Gly Val Ala Val Gly Gly Leu Ala Gly Tyr Pro Gly Pro Ala
                165                 170                 175

Gly Pro Pro Gly Pro Pro Gly Pro Pro Gly Thr Ser Gly His Pro Gly
            180                 185                 190

Ser Pro Gly Ser Pro Gly Tyr Gln Gly Pro Pro Gly Glu Pro Gly Gln
        195                 200                 205

Ala Gly Pro Ser Gly Pro Pro Gly Pro Pro Gly Ala Ile Gly Pro Ser
    210                 215                 220

Gly Pro Ala Gly Lys Asp Gly Glu Ser Gly Arg Pro Gly Arg Pro Gly
225                 230                 235                 240

Glu Arg Gly Leu Pro Gly Pro Pro Gly Ile Lys Gly Pro Ala Gly Ile
                245                 250                 255

Pro Gly Phe Pro Gly Met Lys Gly His Arg Gly Phe Asp Gly Arg Asn
            260                 265                 270

Gly Glu Lys Gly Glu Thr Gly Ala Pro Gly Leu Lys Gly Glu Asn Gly
        275                 280                 285

Leu Pro Gly Glu Asn Gly Ala Pro Gly Pro Met Gly Pro Arg Gly Ala
    290                 295                 300

Pro Gly Glu Arg Gly Arg Pro Gly Leu Pro Gly Ala Ala Gly Ala Arg
305                 310                 315                 320

Gly Asn Asp Gly Ala Arg Gly Ser Asp Gly Gln Pro Gly Pro Pro Gly
                325                 330                 335

Pro Pro Gly Thr Ala Gly Phe Pro Gly Ser Pro Gly Ala Lys Gly Glu
            340                 345                 350
```

-continued

```
Val Gly Pro Ala Gly Ser Pro Gly Ser Asn Gly Ala Pro Gly Gln Arg
        355                 360                 365

Gly Glu Pro Gly Pro Gln Gly His Ala Gly Ala Gln Gly Pro Pro Gly
    370                 375                 380

Pro Pro Gly Ile Asn Gly Ser Pro Gly Gly Lys Gly Glu Met Gly Pro
385                 390                 395                 400

Ala Gly Ile Pro Gly Ala Pro Gly Leu Met Gly Ala Arg Gly Pro Pro
                405                 410                 415

Gly Pro Ala Gly Ala Asn Gly Ala Pro Gly Leu Arg Gly Gly Ala Gly
            420                 425                 430

Glu Pro Gly Lys Asn Gly Ala Lys Gly Glu Pro Gly Pro Arg Gly Glu
        435                 440                 445

Arg Gly Glu Ala Gly Ile Pro Gly Val Pro Gly Ala Lys Gly Glu Asp
    450                 455                 460

Gly Lys Asp Gly Ser Pro Gly Glu Pro Gly Ala Asn Gly Leu Pro Gly
465                 470                 475                 480

Ala Ala Gly Glu Arg Gly Ala Pro Gly Phe Arg Gly Pro Ala Gly Pro
                485                 490                 495

Asn Gly Ile Pro Gly Glu Lys Gly Pro Ala Gly Glu Arg Gly Ala Pro
            500                 505                 510

Gly Pro Ala Gly Pro Arg Gly Ala Ala Gly Glu Pro Gly Arg Asp Gly
        515                 520                 525

Val Pro Gly Gly Pro Gly Met Arg Gly Met Pro Gly Ser Pro Gly Gly
    530                 535                 540

Pro Gly Ser Asp Gly Lys Pro Gly Pro Pro Gly Ser Gln Gly Glu Ser
545                 550                 555                 560

Gly Arg Pro Gly Pro Pro Gly Pro Ser Gly Pro Arg Gly Gln Pro Gly
                565                 570                 575

Val Met Gly Phe Pro Gly Pro Lys Gly Asn Asp Gly Ala Pro Gly Lys
            580                 585                 590

Asn Gly Glu Arg Gly Gly Pro Gly Gly Pro Gly Pro Gln Gly Pro Pro
        595                 600                 605

Gly Lys Asn Gly Glu Thr Gly Pro Gln Gly Pro Pro Gly Pro Thr Gly
    610                 615                 620

Pro Gly Gly Asp Lys Gly Asp Thr Gly Pro Pro Gly Pro Gln Gly Leu
625                 630                 635                 640

Gln Gly Leu Pro Gly Thr Gly Gly Pro Pro Gly Glu Asn Gly Lys Pro
                645                 650                 655

Gly Glu Pro Gly Pro Lys Gly Asp Ala Gly Ala Pro Gly Ala Pro Gly
            660                 665                 670

Gly Lys Gly Asp Ala Gly Ala Pro Gly Glu Arg Gly Pro Pro Gly Leu
        675                 680                 685

Ala Gly Ala Pro Gly Leu Arg Gly Gly Ala Gly Pro Pro Gly Pro Glu
    690                 695                 700

Gly Gly Lys Gly Ala Ala Gly Pro Pro Gly Pro Pro Gly Ala Ala Gly
705                 710                 715                 720

Thr Pro Gly Leu Gln Gly Met Pro Gly Glu Arg Gly Gly Leu Gly Ser
                725                 730                 735

Pro Gly Pro Lys Gly Asp Lys Gly Glu Pro Gly Gly Pro Gly Ala Asp
            740                 745                 750

Gly Val Pro Gly Lys Asp Gly Pro Arg Gly Pro Thr Gly Pro Ile Gly
        755                 760                 765

Pro Pro Gly Pro Ala Gly Gln Pro Gly Asp Lys Gly Glu Gly Gly Ala
```

-continued

```
    770                 775                 780

Pro Gly Leu Pro Gly Ile Ala Gly Pro Arg Gly Ser Pro Gly Glu Arg
785                 790                 795                 800

Gly Glu Thr Gly Pro Pro Gly Pro Ala Gly Phe Pro Gly Ala Pro Gly
                805                 810                 815

Gln Asn Gly Glu Pro Gly Gly Lys Gly Glu Arg Gly Ala Pro Gly Glu
            820                 825                 830

Lys Gly Glu Gly Gly Pro Pro Gly Val Ala Gly Pro Pro Gly Gly Ser
        835                 840                 845

Gly Pro Ala Gly Pro Pro Gly Pro Gln Gly Val Lys Gly Glu Arg Gly
    850                 855                 860

Ser Pro Gly Gly Pro Gly Ala Ala Gly Phe Pro Gly Ala Arg Gly Leu
865                 870                 875                 880

Pro Gly Pro Pro Gly Ser Asn Gly Asn Pro Gly Pro Pro Gly Pro Ser
                885                 890                 895

Gly Ser Pro Gly Lys Asp Gly Pro Pro Gly Pro Ala Gly Asn Thr Gly
            900                 905                 910

Ala Pro Gly Ser Pro Gly Val Ser Gly Pro Lys Gly Asp Ala Gly Gln
        915                 920                 925

Pro Gly Glu Lys Gly Ser Pro Gly Ala Gln Gly Pro Pro Gly Ala Pro
    930                 935                 940

Gly Pro Leu Gly Ile Ala Gly Ile Thr Gly Ala Arg Gly Leu Ala Gly
945                 950                 955                 960

Pro Pro Gly Met Pro Gly Pro Arg Gly Ser Pro Gly Pro Gln Gly Val
                965                 970                 975

Lys Gly Glu Ser Gly Lys Pro Gly Ala Asn Gly Leu Ser Gly Glu Arg
            980                 985                 990

Gly Pro Pro Gly Pro Gln Gly Leu Pro Gly Leu Ala Gly Thr Ala Gly
        995                 1000                1005

Glu Pro Gly Arg Asp Gly Asn Pro Gly Ser Asp Gly Leu Pro Gly Arg
   1010                 1015                1020

Asp Gly Ser Pro Gly Gly Lys Gly Asp Arg Gly Glu Asn Gly Ser Pro
1025                1030                1035                1040

Gly Ala Pro Gly Ala Pro Gly His Pro Gly Pro Pro Gly Pro Val Gly
               1045                1050                1055

Pro Ala Gly Lys Ser Gly Asp Arg Gly Glu Ser Gly Pro Ala Gly Pro
           1060                1065                1070

Ala Gly Ala Pro Gly Pro Ala Gly Ser Arg Gly Ala Pro Gly Pro Gln
       1075                1080                1085

Gly Pro Arg Gly Asp Lys Gly Glu Thr Gly Glu Arg Gly Ala Ala Gly
   1090                1095                1100

Ile Lys Gly His Arg Gly Phe Pro Gly Asn Pro Gly Ala Pro Gly Ser
1105                1110                1115                1120

Pro Gly Pro Ala Gly Gln Gln Gly Ala Ile Gly Ser Pro Gly Pro Ala
               1125                1130                1135

Gly Pro Arg Gly Pro Val Gly Pro Ser Gly Pro Pro Gly Lys Asp Gly
           1140                1145                1150

Thr Ser Gly His Pro Gly Pro Ile Gly Pro Pro Gly Pro Arg Gly Asn
       1155                1160                1165

Arg Gly Glu Arg Gly Ser Glu Gly Ser Pro Gly His Pro Gly Gln Pro
   1170                1175                1180

Gly Pro Pro Gly Pro Pro Gly Ala Pro Gly Pro Cys Cys Gly Gly Val
1185                1190                1195                1200
```

```
Gly Ala Ala Ala Ile Ala Gly Ile Gly Gly Glu Lys Ala Gly Gly Phe
                1205                1210                1215

Ala Pro Tyr Tyr Gly Asp Glu Pro Met Asp Phe Lys Ile Asn Thr Asp
            1220                1225                1230

Glu Ile Met Thr Ser Leu Lys Ser Val Asn Gly Gln Ile Glu Ser Leu
        1235                1240                1245

Ile Ser Pro Asp Gly Ser Arg Lys Asn Pro Ala Arg Asn Cys Arg Asp
    1250                1255                1260

Leu Lys Phe Cys His Pro Glu Leu Lys Ser Gly Glu Tyr Trp Val Asp
1265                1270                1275                1280

Pro Asn Gln Gly Cys Lys Leu Asp Ala Ile Lys Val Phe Cys Asn Met
                1285                1290                1295

Glu Thr Gly Glu Thr Cys Ile Ser Ala Asn Pro Leu Asn Val Pro Arg
            1300                1305                1310

Lys His Trp Trp Thr Asp Ser Ser Ala Glu Lys Lys His Val Trp Phe
        1315                1320                1325

Gly Glu Ser Met Asp Gly Gly Phe Gln Phe Ser Tyr Gly Asn Pro Glu
    1330                1335                1340

Leu Pro Glu Asp Val Leu Asp Val Gln Leu Ala Phe Leu Arg Leu Leu
1345                1350                1355                1360

Ser Ser Arg Ala Ser Gln Asn Ile Thr Tyr His Cys Lys Asn Ser Ile
                1365                1370                1375

Ala Tyr Met Asp Gln Ala Ser Gly Asn Val Lys Lys Ala Leu Lys Leu
            1380                1385                1390

Met Gly Ser Asn Glu Gly Glu Phe Lys Ala Glu Gly Asn Ser Lys Phe
        1395                1400                1405

Thr Tyr Thr Val Leu Glu Asp Gly Cys Thr Lys His Thr Gly Glu Trp
    1410                1415                1420

Ser Lys Thr Val Phe Glu Tyr Arg Thr Arg Lys Ala Val Arg Leu Pro
1425                1430                1435                1440

Ile Val Asp Ile Ala Pro Tyr Asp Ile Gly Gly Pro Asp Gln Glu Phe
                1445                1450                1455

Gly Val Asp Val Gly Pro Val Cys Phe Leu
            1460                1465
```

<210> SEQ ID NO 13
<211> LENGTH: 3215
<212> TYPE: DNA
<213> ORGANISM: Homo sapiens
<220> FEATURE:
<223> OTHER INFORMATION: UDP-Gal:betaGlcNAc beta 1,3-
galactosyltransferase, polypeptide 2 (B3GALT2) cDNA
<220> FEATURE:
<221> NAME/KEY: CDS
<222> LOCATION: (696)..(1964)
<223> OTHER INFORMATION: B3GALT2

<400> SEQUENCE: 13

```
cctgtgcagc agctgaggaa ccgtggattt catattatag actaaaaccc cattaaaact     60

gctcaaaatc cttcctgcag ctgccaggca acaacgaaag aagagaggta aatcctattc    120

ttttccaata caactgaagc actacatttt agctctggct gctttacatt gcagctcagt    180

gttattagta gaaatatgga tactgagacg agaacacagc actgcattgt ccagccagga    240

aaaatagcag atgtaaaaag cttcaatgca tcaactgtcg ggaagagtca acagtgctac    300

aagcagaacg ggcaactaca gctcttttgt ttaacgaaag agagaatatg aaagaaaggg    360

aaaatttcag aagactagga cccatatgaa caaggagggt aactcgaaga caagcagaca    420
```

-continued

```
gatggacact ttggatactg tgaaaagcaa tcgcaggagg cagactgttg ggggatgtgc    480
gcatgttcga tagcatcttt tttgctgaag tgatggcgtg ccaaaagtat tttcagtggg    540
cataatcctc ttcacataaa tggcctgacc aaggagaatg actacaagag agacaatgtg    600
actgaattag aaaatgattg ccaaagaata gtattaagga gaagaaaaca tttttgtcac    660
caatctctca tataccacta ctggatattt acaacatgct tcagtggagg agaagacact    720
gctgctttgc aaagatgacc tggaatgcca aaaggtctct gttccgcact catcttattg    780
gagtactttc tctagtgttt ctttttgcta tgtttttgtt tttcaatcat catgactggc    840
tgccaggcag agctggattc aaagaaaacc ctgtgacata cactttccga ggatttcggt    900
caacaaaaag tgagacaaac cacagctccc ttcggaacat ttggaaagaa acagtccctc    960
aaaccctgag gcctcaaaca gcaactaact ctaataacac agacctgtca ccacaaggag   1020
ttacaggcct ggagaataca cttagtgcca atggaagtat ttacaatgaa aaaggtactg   1080
gacatccaaa ttcttaccat ttcaaatata ttattaatga gcctgaaaaa tgccaagaga   1140
aaagtccttt tttaatacta ctaatagctg cagagcctgg acaaatagaa gctagaagag   1200
ctattcggca aacttggggc aatgaaagtc tagcacctgg tattcaaatc acaagaatat   1260
ttttgttggg cttaagtatt aagctaaatg gctaccttca acgtgcaata ctggaagaaa   1320
gcagacaata tcatgatata attcaacagg aatacttaga tacgtactat aatttgacca   1380
ttaaaacact aatgggcatg aactgggttg caacatactg tccacatatt ccatatgtta   1440
tgaaaactga cagtgacatg tttgtcaaca ctgaatattt aatcaataag ttactgaagc   1500
cagatctgcc tcccagacat aactatttca ctggttacct aatgcgagga tatgcaccca   1560
atcgaaacaa agatagcaag tggtacatgc caccagacct ctacccaagt gagcgttatc   1620
ctgtcttctg ttctggaact ggttatgttt tttctggaga tctggcagaa aagattttta   1680
aagtttcttt aggtatccgc cgtttgcact tggaagatgt atatgtaggg atctgtcttg   1740
ccaagttgag aattgatcct gtaccccctc ccaatgagtt tgtgttcaat cactggcgag   1800
tctcttattc gagctgtaaa tacagccacc taattacctc tcatcagttc cagcctagtg   1860
aactgataaa atactggaac catttacaac aaaataagca caatgcctgt gccaacgcag   1920
caaaagaaaa ggcaggcagg tatcgccacc gtaaactaca ttagaaaaga caattttttt   1980
tcaatgtgca atttgtaaat attgctaaaa gcatgtatag ttaggaactg attacatccg   2040
taggacaagt tttagttaaa actcatcaca taaagaaatt caagaagtat ttttttaatt   2100
tctgaagaag ttaattctta aaactataac attatataac aaaaaaggtt tcccaaaaca   2160
atctatttaa aaaactgtat aaggagattc tgtgtattaa catgcaataa caagcatgca   2220
taaatcaatg gttcaagtct tctgttaggg ggccaataaa atgtatctgc atatgttttc   2280
cacataaatt ttaattcaag aaatgacagt caaaagatcc ttcattttag attaagcttt   2340
tcattttaat atataattta atgtaaataa aacatcacta tcaattttaa ggaaactttt   2400
taattgtgca aaggataaat tttttgacct attttagggt tctaaatgca ataagattta   2460
gttgagttat tccacaaaca cattataaag ttcagatgtt tcatcaatgc agttctcacg   2520
aaagtattta ctttttaaaa ataactgaga tattatttta aatttctttt attaatactt   2580
tcttttatta atatatgggg gaaaattatt ttgacatgac gtggtaaaat gtgaaaaact   2640
aatgtgtctc aggctcaagt ttttatagtt attaaatgtt tcaaaataga caagttttgt   2700
ttcctcattg atgttaagaa ccaaactcct atttcaatga gttattggat tagaccaatt   2760
actgcactct taaacagcac caccatttaa tttcatgtaa tatctaactt cgaatatatc   2820
```

-continued

```
tgtaaaggat aatcgaagca aaagtaatca cttaaaggca caaataggat gtactgttga   2880

aaaagataaa gagtgcaggt gcagtttcat tcaacacatt tttaagatgc atgtctgcca   2940

aaatgcaaca tacgggaagt ttatttcctg acagcaggtg tacacatgcc aacacttaat   3000

cattttatgg cacctatttc tttcttggag tgccaagttt gcaaacctgc agtttttaat   3060

ttggtagatg acaaatattc tgaatcacca attaaaaacc tttttgggag ggatggggaa   3120

aactacaaac gtttgacaaa cacaattcta ggatgaacaa tgtatacaat gcacttttat   3180

gaagttttta aaaataaagg aaaacaaaaa acttt                              3215


<210> SEQ ID NO 14
<211> LENGTH: 422
<212> TYPE: PRT
<213> ORGANISM: Homo sapiens
<220> FEATURE:
<223> OTHER INFORMATION: UDP-Gal:betaGlcNAc beta 1,3-
      galactosyltransferase, polypeptide 2 (B3GALT2)

<400> SEQUENCE: 14

Met Leu Gln Trp Arg Arg Arg His Cys Cys Phe Ala Lys Met Thr Trp
  1               5                  10                  15

Asn Ala Lys Arg Ser Leu Phe Arg Thr His Leu Ile Gly Val Leu Ser
             20                  25                  30

Leu Val Phe Leu Phe Ala Met Phe Leu Phe Phe Asn His His Asp Trp
         35                  40                  45

Leu Pro Gly Arg Ala Gly Phe Lys Glu Asn Pro Val Thr Tyr Thr Phe
     50                  55                  60

Arg Gly Phe Arg Ser Thr Lys Ser Glu Thr Asn His Ser Ser Leu Arg
 65                  70                  75                  80

Asn Ile Trp Lys Glu Thr Val Pro Gln Thr Leu Arg Pro Gln Thr Ala
                 85                  90                  95

Thr Asn Ser Asn Asn Thr Asp Leu Ser Pro Gln Gly Val Thr Gly Leu
            100                 105                 110

Glu Asn Thr Leu Ser Ala Asn Gly Ser Ile Tyr Asn Glu Lys Gly Thr
        115                 120                 125

Gly His Pro Asn Ser Tyr His Phe Lys Tyr Ile Ile Asn Glu Pro Glu
    130                 135                 140

Lys Cys Gln Glu Lys Ser Pro Phe Leu Ile Leu Leu Ile Ala Ala Glu
145                 150                 155                 160

Pro Gly Gln Ile Glu Ala Arg Arg Ala Ile Arg Gln Thr Trp Gly Asn
                165                 170                 175

Glu Ser Leu Ala Pro Gly Ile Gln Ile Thr Arg Ile Phe Leu Leu Gly
            180                 185                 190

Leu Ser Ile Lys Leu Asn Gly Tyr Leu Gln Arg Ala Ile Leu Glu Glu
        195                 200                 205

Ser Arg Gln Tyr His Asp Ile Ile Gln Gln Glu Tyr Leu Asp Thr Tyr
    210                 215                 220

Tyr Asn Leu Thr Ile Lys Thr Leu Met Gly Met Asn Trp Val Ala Thr
225                 230                 235                 240

Tyr Cys Pro His Ile Pro Tyr Val Met Lys Thr Asp Ser Asp Met Phe
                245                 250                 255

Val Asn Thr Glu Tyr Leu Ile Asn Lys Leu Leu Lys Pro Asp Leu Pro
            260                 265                 270

Pro Arg His Asn Tyr Phe Thr Gly Tyr Leu Met Arg Gly Tyr Ala Pro
        275                 280                 285

Asn Arg Asn Lys Asp Ser Lys Trp Tyr Met Pro Pro Asp Leu Tyr Pro
```

```
    290                 295                 300

Ser Glu Arg Tyr Pro Val Phe Cys Ser Gly Thr Gly Tyr Val Phe Ser
305                 310                 315                 320

Gly Asp Leu Ala Glu Lys Ile Phe Lys Val Ser Leu Gly Ile Arg Arg
                325                 330                 335

Leu His Leu Glu Asp Val Tyr Val Gly Ile Cys Leu Ala Lys Leu Arg
            340                 345                 350

Ile Asp Pro Val Pro Pro Pro Asn Glu Phe Val Phe Asn His Trp Arg
        355                 360                 365

Val Ser Tyr Ser Ser Cys Lys Tyr Ser His Leu Ile Thr Ser His Gln
    370                 375                 380

Phe Gln Pro Ser Glu Leu Ile Lys Tyr Trp Asn His Leu Gln Gln Asn
385                 390                 395                 400

Lys His Asn Ala Cys Ala Asn Ala Ala Lys Glu Lys Ala Gly Arg Tyr
                405                 410                 415

Arg His Arg Lys Leu His
            420


<210> SEQ ID NO 15
<211> LENGTH: 3489
<212> TYPE: DNA
<213> ORGANISM: Homo sapiens
<220> FEATURE:
<223> OTHER INFORMATION: glycosylphosphatidylinositol specific
      phospholipase D1 (GPLD1) cDNA
<220> FEATURE:
<221> NAME/KEY: CDS
<222> LOCATION: (112)..(2634)
<223> OTHER INFORMATION: GPLD1

<400> SEQUENCE: 15

gtgacctgct tagagagaag cggtgggtct gcacctggat tttggagtcc cagtgctgct      60

gcagctctga gcattcccac gtcaccagag aagccggtgg gcaatgagat catgtctgct     120

ttcaggttgt ggcctggcct gctgatcatg ttgggttctc tctgccatag aggttcaccg     180

tgtggccttt caacacacgt agaaatagga cacagagctc tggagtttct tcagcttcac     240

aatgggcgtg ttaactacag agagctgtta ctagaacacc aggatgcgta tcaggctgga     300

atcgtgtttc ctgattgttt ttaccctagc atctgcaaag gaggaaaatt ccatgatgtg     360

tctgagagca ctcactggac tccgtttctt aatgcaagcg ttcattatat ccgagagaac     420

tatccccttc cctgggagaa ggacacagag aaactggtag ctttcttgtt tggaattact     480

tctcacatgg cggcagatgt cagctggcat agtctgggcc ttgaacaagg attccttagg     540

accatgggag ctattgattt tcacggctcc tattcagagg ctcattcggc tggtgatttt     600

ggaggagatg tgttgagcca gtttgaattt aattttaatt accttgcacg acgctggtat     660

gtgccagtca aagatctact gggaatttat gagaaactgt atggtcgaaa agtcatcacc     720

gaaaatgtaa tcgttgattg ttcacatatc cagttcttag aaatgtatgg tgagatgcta     780

gctgtttcca agttatatcc cacttactct acaaagtccc cgtttttggt ggaacaattc     840

caagagtatt ttcttggagg actggatgat atggcatttt ggtccactaa tatttaccat     900

ctaacaagct tcatgttgga gaatgggacc agtgactgca acctgcctga gaaccctctg     960

ttcattgcat gtggcggcca gcaaaaccac acccagggct caaaaatgca gaaaaatgat    1020

tttcacagaa atttgactac atccctaact gaaagtgttg acaggaatat aaactatact    1080

gaaagaggag tgttctttag tgtaaattcc tggaccccgg attccatgtc ctttatctac    1140

aaggctttgg aaaggaacat aaggacaatg ttcataggtg gctctcagtt gtcacaaaag    1200
```

-continued

```
cacgtctcca gcccccttagc atcttacttc ttgtcatttc cttatgcgag gcttggctgg   1260
gcaatgacct cagctgacct caaccaggat gggcacggtg acctcgtggt gggcgcacca   1320
ggctacagcc gccccggcca catccacatc gggcgcgtgt acctcatcta cggcaatgac   1380
ctgggcctgc cacctgttga cctggacctg gacaaggagg cccacaggat ccttgaaggc   1440
ttccagccct caggtcggtt tggctcggcc ttggctgtgt tggactttaa cgtggacggc   1500
gtgcctgacc tggccgtggg agctccctcg gtgggctccg agcagctcac ctacaaaggt   1560
gccgtgtatg tctactttgg ttccaaacaa ggaggaatgt cttcttcccc taacatcacc   1620
atttcttgcc aggacatcta ctgtaacttg ggctggactc tcttggctgc agatgtgaat   1680
ggagacagtg aacccgatct ggtcatcggc tccccttttg caccaggtgg agggaagcag   1740
aagggaattg tggctgcgtt ttattctggc cccagcctga gcgacaaaga aaaactgaac   1800
gtggaggcag ccaactggac ggtgagaggc gaggaagact tctcctggtt tggatattcc   1860
cttcacggtg tcactgtgga caacagaacc ttgctgttgg ttgggagccc gacctggaag   1920
aatgccagca ggctgggcca tttgttacac atccgagatg agaaaaagag ccttgggagg   1980
gtgtatggct acttcccacc aaacggccaa agctggttta ccatttctgg agacaaggca   2040
atggggaaac tgggtacttc cctttccagt ggccacgtac tgatgaatgg gactctgaaa   2100
caagtgctgc tggttggagc ccctacgtac gatgacgtgt ctaaggtggc attcctgacc   2160
gtgaccctac accaaggcgg agccactcgc atgtacgcac tcacatctga cgcgcagcct   2220
ctgctgctca gcaccttcag cggagaccgc cgcttctccc gatttggtgg cgttctgcac   2280
ttgagtgacc tggatgatga tggcttagat gaaatcatca tggcagcccc cctgaggata   2340
gcagatgtaa cctctggact gattggggga gaagacggcc gagtatatgt atataatggc   2400
aaagagacca cccttggtga catgactggc aaatgcaaat catggataac tccatgtcca   2460
gaagaaaagg cccaatatgt attgatttct cctgaagcca gctcaaggtt tgggagctcc   2520
ctcatcaccg tgaggtccaa ggcaaagaac caagtcgtca ttgctgctgg aaggagttct   2580
ttgggagccc gactctccgg ggcacttcac gtctatagcc ttggctcaga ttgaagattt   2640
cactgcattt ccccactctg cccacctctc tcatgctgaa tcacatccat ggtgagcatt   2700
ttgatggaca aagtggcaca tccagtggag cggtggtaga tcctgataga catggggctc   2760
ctgggagtag agagacacac taacagccac accctctgga aatctgatac agtaaatata   2820
tgactgcacc agaaatatgt gaaatagcag acattctgct tactcatgtc tccttccaca   2880
gtttacttcc tcgctccctt tgcatctaaa cctttcttct ttcccaactt attgcctgta   2940
gtcagacctg ctgtacaacc tatttcctct tcctcttgaa tgtctttcca atggctggaa   3000
aggtccctct gtggttatct gttagaacag tctctgtaca caattcctcc taaaaacatc   3060
ctttttttaaa aaaagaattg ttcagccata aagaaagaac aagatcatgc cctttgcagg   3120
gacatggatg gagctggagg ccattatcct tcataaacta ttgcaggaac agaaaaccaa   3180
acactccata ttctcacttg taagtgggag ctaaatgaga acacgtggac acatagaggg   3240
aaacaacaca cactggggcc tatgagaggg cggaaggtgg gaggagggag agatcaggaa   3300
aaataactaa tggatactta gggtgatgaa ataatctgtg taacaaaccc ccatgacaca   3360
cctttatgta tgtaacaaac cagcacttcc tgcgcatgta cccctgaact taaaagttaa   3420
aaaaaagttg aacttaaaaa taacagattg gcccatgcca atcaaagtat aatagaaagc   3480
atagtatac                                                      3489
```

```
<210> SEQ ID NO 16
<211> LENGTH: 840
<212> TYPE: PRT
<213> ORGANISM: Homo sapiens
<220> FEATURE:
<223> OTHER INFORMATION: glycosylphosphatidylinositol specific
      phospholipase D1 (GPLD1)

<400> SEQUENCE: 16

Met Ser Ala Phe Arg Leu Trp Pro Gly Leu Leu Ile Met Leu Gly Ser
  1               5                  10                  15

Leu Cys His Arg Gly Ser Pro Cys Gly Leu Ser Thr His Val Glu Ile
             20                  25                  30

Gly His Arg Ala Leu Glu Phe Leu Gln Leu His Asn Gly Arg Val Asn
         35                  40                  45

Tyr Arg Glu Leu Leu Leu Glu His Gln Asp Ala Tyr Gln Ala Gly Ile
     50                  55                  60

Val Phe Pro Asp Cys Phe Tyr Pro Ser Ile Cys Lys Gly Gly Lys Phe
 65                  70                  75                  80

His Asp Val Ser Glu Ser Thr His Trp Thr Pro Phe Leu Asn Ala Ser
                 85                  90                  95

Val His Tyr Ile Arg Glu Asn Tyr Pro Leu Pro Trp Glu Lys Asp Thr
            100                 105                 110

Glu Lys Leu Val Ala Phe Leu Phe Gly Ile Thr Ser His Met Ala Ala
        115                 120                 125

Asp Val Ser Trp His Ser Leu Gly Leu Glu Gln Gly Phe Leu Arg Thr
    130                 135                 140

Met Gly Ala Ile Asp Phe His Gly Ser Tyr Ser Glu Ala His Ser Ala
145                 150                 155                 160

Gly Asp Phe Gly Gly Asp Val Leu Ser Gln Phe Glu Phe Asn Phe Asn
                165                 170                 175

Tyr Leu Ala Arg Arg Trp Tyr Val Pro Val Lys Asp Leu Leu Gly Ile
            180                 185                 190

Tyr Glu Lys Leu Tyr Gly Arg Lys Val Ile Thr Glu Asn Val Ile Val
        195                 200                 205

Asp Cys Ser His Ile Gln Phe Leu Glu Met Tyr Gly Glu Met Leu Ala
    210                 215                 220

Val Ser Lys Leu Tyr Pro Thr Tyr Ser Thr Lys Ser Pro Phe Leu Val
225                 230                 235                 240

Glu Gln Phe Gln Glu Tyr Phe Leu Gly Gly Leu Asp Asp Met Ala Phe
                245                 250                 255

Trp Ser Thr Asn Ile Tyr His Leu Thr Ser Phe Met Leu Glu Asn Gly
            260                 265                 270

Thr Ser Asp Cys Asn Leu Pro Glu Asn Pro Leu Phe Ile Ala Cys Gly
        275                 280                 285

Gly Gln Gln Asn His Thr Gln Gly Ser Lys Met Gln Lys Asn Asp Phe
    290                 295                 300

His Arg Asn Leu Thr Thr Ser Leu Thr Glu Ser Val Asp Arg Asn Ile
305                 310                 315                 320

Asn Tyr Thr Glu Arg Gly Val Phe Phe Ser Val Asn Ser Trp Thr Pro
                325                 330                 335

Asp Ser Met Ser Phe Ile Tyr Lys Ala Leu Glu Arg Asn Ile Arg Thr
            340                 345                 350

Met Phe Ile Gly Gly Ser Gln Leu Ser Gln Lys His Val Ser Ser Pro
        355                 360                 365

Leu Ala Ser Tyr Phe Leu Ser Phe Pro Tyr Ala Arg Leu Gly Trp Ala
```

-continued

```
    370                 375                 380

Met Thr Ser Ala Asp Leu Asn Gln Asp Gly His Gly Asp Leu Val Val
385                 390                 395                 400

Gly Ala Pro Gly Tyr Ser Arg Pro Gly His Ile His Ile Gly Arg Val
                405                 410                 415

Tyr Leu Ile Tyr Gly Asn Asp Leu Gly Leu Pro Pro Val Asp Leu Asp
            420                 425                 430

Leu Asp Lys Glu Ala His Arg Ile Leu Glu Gly Phe Gln Pro Ser Gly
        435                 440                 445

Arg Phe Gly Ser Ala Leu Ala Val Leu Asp Phe Asn Val Asp Gly Val
    450                 455                 460

Pro Asp Leu Ala Val Gly Ala Pro Ser Val Gly Ser Glu Gln Leu Thr
465                 470                 475                 480

Tyr Lys Gly Ala Val Tyr Val Tyr Phe Gly Ser Lys Gln Gly Gly Met
                485                 490                 495

Ser Ser Ser Pro Asn Ile Thr Ile Ser Cys Gln Asp Ile Tyr Cys Asn
            500                 505                 510

Leu Gly Trp Thr Leu Leu Ala Ala Asp Val Asn Gly Asp Ser Glu Pro
        515                 520                 525

Asp Leu Val Ile Gly Ser Pro Phe Ala Pro Gly Gly Gly Lys Gln Lys
    530                 535                 540

Gly Ile Val Ala Ala Phe Tyr Ser Gly Pro Ser Leu Ser Asp Lys Glu
545                 550                 555                 560

Lys Leu Asn Val Glu Ala Ala Asn Trp Thr Val Arg Gly Glu Glu Asp
                565                 570                 575

Phe Ser Trp Phe Gly Tyr Ser Leu His Gly Val Thr Val Asp Asn Arg
            580                 585                 590

Thr Leu Leu Leu Val Gly Ser Pro Thr Trp Lys Asn Ala Ser Arg Leu
        595                 600                 605

Gly His Leu Leu His Ile Arg Asp Glu Lys Lys Ser Leu Gly Arg Val
    610                 615                 620

Tyr Gly Tyr Phe Pro Pro Asn Gly Gln Ser Trp Phe Thr Ile Ser Gly
625                 630                 635                 640

Asp Lys Ala Met Gly Lys Leu Gly Thr Ser Leu Ser Ser Gly His Val
                645                 650                 655

Leu Met Asn Gly Thr Leu Lys Gln Val Leu Leu Val Gly Ala Pro Thr
            660                 665                 670

Tyr Asp Asp Val Ser Lys Val Ala Phe Leu Thr Val Thr Leu His Gln
        675                 680                 685

Gly Gly Ala Thr Arg Met Tyr Ala Leu Thr Ser Asp Ala Gln Pro Leu
    690                 695                 700

Leu Leu Ser Thr Phe Ser Gly Asp Arg Arg Phe Ser Arg Phe Gly Gly
705                 710                 715                 720

Val Leu His Leu Ser Asp Leu Asp Asp Asp Gly Leu Asp Glu Ile Ile
                725                 730                 735

Met Ala Ala Pro Leu Arg Ile Ala Asp Val Thr Ser Gly Leu Ile Gly
            740                 745                 750

Gly Glu Asp Gly Arg Val Tyr Val Tyr Asn Gly Lys Glu Thr Thr Leu
        755                 760                 765

Gly Asp Met Thr Gly Lys Cys Lys Ser Trp Ile Thr Pro Cys Pro Glu
    770                 775                 780

Glu Lys Ala Gln Tyr Val Leu Ile Ser Pro Glu Ala Ser Ser Arg Phe
785                 790                 795                 800
```

-continued

```
Gly Ser Ser Leu Ile Thr Val Arg Ser Lys Ala Lys Asn Gln Val Val
                805                 810                 815

Ile Ala Ala Gly Arg Ser Ser Leu Gly Ala Arg Leu Ser Gly Ala Leu
            820                 825                 830

His Val Tyr Ser Leu Gly Ser Asp
        835                 840


<210> SEQ ID NO 17
<211> LENGTH: 3882
<212> TYPE: DNA
<213> ORGANISM: Homo sapiens
<220> FEATURE:
<223> OTHER INFORMATION: myotubularin related protein 7 (MTMR7) cDNA
<220> FEATURE:
<221> NAME/KEY: CDS
<222> LOCATION: (36)..(2018)
<223> OTHER INFORMATION: MTMR7

<400> SEQUENCE: 17

gcgcccgccc gggaccctgc agacgtgggc cagccatgga gcacatccgc acgcccaagg     60

ttgaaaatgt ccgcttggta gatcgagtgt ctcctaaaaa agcagctcta ggtactttgt    120

atttgacggc tacccatgtc atattcgtgg aaaattcacc tgacgcaaga aaagaaacat    180

ggattcttca cagtcagatt tccaccattg agaaacaggc aacaaccgct accggatgcc    240

ctctgctgat tcgctgcaag aactttcaga taatacagct catcatacct caggaaagag    300

attgccacga cgtgtacatc tccctgatac gccttgcaag gccagtgaaa tatgaggagt    360

tatactgctt ttcattcaac cccatgctgg ataaagaaga aagagagcaa ggctgggtgc    420

tgatcgatct tagtgaagaa tacacgcgga tgggcctccc taatcattac tggcagctca    480

gcgatgtgaa tagagactac agagtctgtg actcttatcc tactgaactg tacgttccca    540

aatcggccac ggcacacatc atagtgggga gttccaaatt ccggagtaga cggcgatttc    600

ctgtcctttc ttactattat aaagataacc acgcctccat ctgccggagc agccagcccc    660

tgtccggctt cagtgcccgg tgcctggagg acgagcagat gctccaggcc attaggaaag    720

ccaatccagg aagtgacttc gtttatgtcg ttgacgcccg gcctaaactt aatgcaatgg    780

caaatcgtgc tgcagggaaa ggctatgaga atgaagacaa ttattccaat atcaagtttc    840

agtttatcgg gatagagaac atccatgtca tgaggaacag tctgcagaaa atgctggaag    900

tgtgtgaact taaatctccc tccatgagtg atttcctgtg ggtctggag aactctggct     960

ggttaaggca cattaaagcc ataatggatg caggaatctt cattgcaaag gcagtgtcag   1020

aggaaggggc aagtgtgctt gttcactgtt ctgatggctg ggacaggacc gctcaggtgt   1080

gctcggtggc aagcctgctg ctggaccctc actaccggac tctgaagggc ttcatggtat   1140

taattgaaaa ggactggatt tcctttggtc ataagtttaa tcaccgatat ggcaatctag   1200

atggtgaccc aaaagaaatc tctccagtta ttgaccagtt cattgagtgt gtttggcagt   1260

taatggaaca atttccctgt gcctttgagt tcaatgagag gtttttgatt cacattcaac   1320

atcacattta ttcctgccag tttggaaact tcctatgtaa cagccaaaag gagagacgag   1380

aactcaagat tcaagaaaga acatactcat tatgggctca cctgtggaag aatcgggccg   1440

actacctgaa tcctctgttt agagctgatc acagccagac tcagggaacc cttcatctcc   1500

ctacaacacc atgtaacttc atgtacaagt tttggagtgg aatgtataac cgctttgaaa   1560

aggggatgca gccccgacag tcagttacag attacctaat ggcagtgaag gaagaaactc   1620

agcagctaga ggaagaacta gaggccctgg aagaaaggct ggaaaaaatt caaaaggtcc   1680

agttaaattg cactaaggtg aagagtaagc aaagtgagcc cagcaagcac tcagggtttt   1740
```

```
ctacctcaga caacagcata gccaacactc cccaggatta cagtgggaat atgaaatcat   1800
ttccatcccg gagcccttca caaggcgatg aagattctgc tctgattcta acccaagaca   1860
atctgaaaag ttcagatcca gatctgtcag ccaacagtga ccaagagtcc ggggtggagg   1920
atttgagctg tcggtctcca agtggtggtg agcatgcacc gagtgaagat agtggcaagg   1980
accgggattc tgatgaagcc gtgtttctca ctgcctgaag tttccctttg gagttccaaa   2040
gtaaaggaca cataagcaac acttccaaaa acaagggaac aaggtggttt attgtaaaaa   2100
caggaaatgg tgcatgtcat tgagaactat tttaatgcag ctatgaaaag ggaaaaaagt   2160
gcccagttct tgatttctta gatactgaag aggacgtagt catttcattt atcaaatata   2220
aggaaaatta ttcaccattt tgaagctcac cctagactat gaaaattata ttcactgcag   2280
agcaattact tctgtcatta cctgaagtga tcagtatcta tcttccttgt catagcatgc   2340
atctctcaaa aagcctccac tcctttccct cacatctgtg atcatcatga ttcttttagt   2400
tcacttctag atgcatattt tgtgttttct aaagcatctg acattatcct cctttccgac   2460
cctcttatac atatttctaa aaacaggcac attggtgaga tgcacccttt ttagttaata   2520
gatgcattcc taaggagctt ttaattgctt atctttcagg cataatcatc actttaactt   2580
ttccttggag catatatttt gaattgtgag aataattttg ttgcttttct ctgagatcta   2640
tagtctgttt ctcctcatta tttaaaaatg ctaaaccttg tatctcactt tttctctaac   2700
actgatttaa tagctaacga ggtagaagca acattcattc tcctggtctt acatatgaat   2760
ttaagtatca gctttcttgt aataaccttt tattactgtt ctagagacta cactaccgac   2820
agtgtgggcc agccaccagc ctgatctcaa agtatcacat tataaagtta gtagataaaa   2880
catctgtgag tgaaaatcca gtttcaggaa ccagagaatt gggttgtcat gtctgtttaa   2940
tgaagggaat aggttttgta atctatcatt ttagaaatta tgtaactggc taatatggtt   3000
taattaacct tagtaacatc tcgtgaccac tgactgctga aagttctgaa aagaattttt   3060
gttttgttac actgcacatt taagggagag tccctcccct atcttatgag ttaaaaaaga   3120
cttcactagg tgacctaaat taaacttagt ggggaaaagt ggccatgttt ggacataaat   3180
aaatggtatt cacactgtat ggttttaata tattagtaca ttctagaatg taaaaggatt   3240
aaactttaca atttagatca atattttgaa tatgtgaaag gattaattta aactttacaa   3300
tttacatcaa tattttgaat atctgatttt ttttaatggg agaattatta catttcgctg   3360
aaatgaggac gagggcaaga aagcaacatt gctgatctct ctagtatgaa agatttggag   3420
ggagtgttgc aatatatata aatgaaaaca tttaattgtg ttcatcatat ttaaaaatat   3480
agaatatatt agagaactgt gatttaaaag tactgttaat gtaaaaaata aagcaagtgt   3540
aattaattct ttcagaatat aaaatttggg cattctctgc tgagcagttc ccaaattaag   3600
tacaaggaat gtttattcat tttctgcaat atactatatg taatagggaa taccttgcta   3660
aaataaaact taggatatag tggtaatggc tttcacattt ttataacata acataactca   3720
cttcacaacc ttcttggagc tgtccactct tagaaactct gttgcctaat attgaggatg   3780
tggctttaat ttcttccgtt tgacagtgta tgtctataaa aacaataaac atttttttaaa   3840
aaatgacaaa aaaaaaaaaa aaaaaaaaaa aaaaaaaaaa aa                      3882
```

<210> SEQ ID NO 18
<211> LENGTH: 660
<212> TYPE: PRT
<213> ORGANISM: Homo sapiens
<220> FEATURE:
<223> OTHER INFORMATION: myotubularin related protein 7 (MTMR7)

<400> SEQUENCE: 18

Met Glu His Ile Arg Thr Pro Lys Val Glu Asn Val Arg Leu Val Asp
1               5                   10                  15

Arg Val Ser Pro Lys Lys Ala Ala Leu Gly Thr Leu Tyr Leu Thr Ala
            20                  25                  30

Thr His Val Ile Phe Val Glu Asn Ser Pro Asp Ala Arg Lys Glu Thr
        35                  40                  45

Trp Ile Leu His Ser Gln Ile Ser Thr Ile Glu Lys Gln Ala Thr Thr
    50                  55                  60

Ala Thr Gly Cys Pro Leu Leu Ile Arg Cys Lys Asn Phe Gln Ile Ile
65                  70                  75                  80

Gln Leu Ile Ile Pro Gln Glu Arg Asp Cys His Asp Val Tyr Ile Ser
                85                  90                  95

Leu Ile Arg Leu Ala Arg Pro Val Lys Tyr Glu Glu Leu Tyr Cys Phe
            100                 105                 110

Ser Phe Asn Pro Met Leu Asp Lys Glu Glu Arg Glu Gln Gly Trp Val
        115                 120                 125

Leu Ile Asp Leu Ser Glu Glu Tyr Thr Arg Met Gly Leu Pro Asn His
    130                 135                 140

Tyr Trp Gln Leu Ser Asp Val Asn Arg Asp Tyr Arg Val Cys Asp Ser
145                 150                 155                 160

Tyr Pro Thr Glu Leu Tyr Val Pro Lys Ser Ala Thr Ala His Ile Ile
                165                 170                 175

Val Gly Ser Ser Lys Phe Arg Ser Arg Arg Arg Phe Pro Val Leu Ser
            180                 185                 190

Tyr Tyr Tyr Lys Asp Asn His Ala Ser Ile Cys Arg Ser Ser Gln Pro
        195                 200                 205

Leu Ser Gly Phe Ser Ala Arg Cys Leu Glu Asp Glu Gln Met Leu Gln
    210                 215                 220

Ala Ile Arg Lys Ala Asn Pro Gly Ser Asp Phe Val Tyr Val Val Asp
225                 230                 235                 240

Ala Arg Pro Lys Leu Asn Ala Met Ala Asn Arg Ala Ala Gly Lys Gly
                245                 250                 255

Tyr Glu Asn Glu Asp Asn Tyr Ser Asn Ile Lys Phe Gln Phe Ile Gly
            260                 265                 270

Ile Glu Asn Ile His Val Met Arg Asn Ser Leu Gln Lys Met Leu Glu
        275                 280                 285

Val Cys Glu Leu Lys Ser Pro Ser Met Ser Asp Phe Leu Trp Gly Leu
    290                 295                 300

Glu Asn Ser Gly Trp Leu Arg His Ile Lys Ala Ile Met Asp Ala Gly
305                 310                 315                 320

Ile Phe Ile Ala Lys Ala Val Ser Glu Glu Gly Ala Ser Val Leu Val
                325                 330                 335

His Cys Ser Asp Gly Trp Asp Arg Thr Ala Gln Val Cys Ser Val Ala
            340                 345                 350

Ser Leu Leu Leu Asp Pro His Tyr Arg Thr Leu Lys Gly Phe Met Val
        355                 360                 365

Leu Ile Glu Lys Asp Trp Ile Ser Phe Gly His Lys Phe Asn His Arg
    370                 375                 380

Tyr Gly Asn Leu Asp Gly Asp Pro Lys Glu Ile Ser Pro Val Ile Asp
385                 390                 395                 400

Gln Phe Ile Glu Cys Val Trp Gln Leu Met Glu Gln Phe Pro Cys Ala
                405                 410                 415

```
Phe Glu Phe Asn Glu Arg Phe Leu Ile His Ile Gln His His Ile Tyr
            420                 425                 430

Ser Cys Gln Phe Gly Asn Phe Leu Cys Asn Ser Gln Lys Glu Arg Arg
        435                 440                 445

Glu Leu Lys Ile Gln Glu Arg Thr Tyr Ser Leu Trp Ala His Leu Trp
    450                 455                 460

Lys Asn Arg Ala Asp Tyr Leu Asn Pro Leu Phe Arg Ala Asp His Ser
465                 470                 475                 480

Gln Thr Gln Gly Thr Leu His Leu Pro Thr Thr Pro Cys Asn Phe Met
                485                 490                 495

Tyr Lys Phe Trp Ser Gly Met Tyr Asn Arg Phe Glu Lys Gly Met Gln
            500                 505                 510

Pro Arg Gln Ser Val Thr Asp Tyr Leu Met Ala Val Lys Glu Glu Thr
        515                 520                 525

Gln Gln Leu Glu Glu Glu Leu Glu Ala Leu Glu Glu Arg Leu Glu Lys
    530                 535                 540

Ile Gln Lys Val Gln Leu Asn Cys Thr Lys Val Lys Ser Lys Gln Ser
545                 550                 555                 560

Glu Pro Ser Lys His Ser Gly Phe Ser Thr Ser Asp Asn Ser Ile Ala
                565                 570                 575

Asn Thr Pro Gln Asp Tyr Ser Gly Asn Met Lys Ser Phe Pro Ser Arg
            580                 585                 590

Ser Pro Ser Gln Gly Asp Glu Asp Ser Ala Leu Ile Leu Thr Gln Asp
        595                 600                 605

Asn Leu Lys Ser Ser Asp Pro Asp Leu Ser Ala Asn Ser Asp Gln Glu
    610                 615                 620

Ser Gly Val Glu Asp Leu Ser Cys Arg Ser Pro Ser Gly Gly Glu His
625                 630                 635                 640

Ala Pro Ser Glu Asp Ser Gly Lys Asp Arg Asp Ser Asp Glu Ala Val
                645                 650                 655

Phe Leu Thr Ala
            660


<210> SEQ ID NO 19
<211> LENGTH: 2299
<212> TYPE: DNA
<213> ORGANISM: Homo sapiens
<220> FEATURE:
<223> OTHER INFORMATION: transmembrane protein with EGF-like and two
      follistatin-like domains 1 (TMEFF1) cDNA
<220> FEATURE:
<221> NAME/KEY: CDS
<222> LOCATION: (110)..(1252)
<223> OTHER INFORMATION: TMEFF1

<400> SEQUENCE: 19

agcgggcggc tgctaggagg caccgaggca gcggcggggc tctgggcgcg cggctggatg      60

cccccggcct gcggctccct gcgcttcccg ccgtccaggg gcaccagtca tgggcgccgc     120

agccgctgag gcgccgctcc ggctgcctgc cgcgcctccg ctcgccttct gctgctacac     180

gtcggtgctt ctgctcttcg ccttctctct gccagggagc cgcgcgtcca accagccccc     240

gggtggtggc ggcggcagcg gcggggactg tcccggcggc aaaggcaaga gcatcaactg     300

ctcagaatta aatgtgaggg agtctgacgt aagagtttgt gatgagtcat catgtaaata     360

tggaggagtc tgtaaagaag atggagatgg tttgaaatgt gcatgccaat ttcagtgcca     420

tacaaattat attcctgtct gtggatcaaa tggggacact tatcaaaatg aatgctttct     480
```

-continued

```
cagaagggct gcttgtaagc accagaaaga gataacagta atagcaagag gaccatgcta    540

ctctgataat ggatctggat ctggagaagg agaagaggaa gggtcagggg cagaagttca    600

cagaaaacac tccaagtgtg gaccctgcaa atataaagct gagtgtgatg aagatgcaga    660

aaatgttggg tgtgtatgta atatagattg cagtggatac agttttaatc ctgtgtgtgc    720

ttctgatggg agttcctata acaatccctg ttttgttcga gaagcatctt gtataaagca    780

agaacaaatt gatataaggc atcttggtca ttgcacagat acagatgaca ctagtttgtt    840

gggaaagaaa gatgatggac tacaatatcg accagatgtg aaagatgcta gtgatcaaag    900

agaagatgtt tatattggaa accacatgcc ttgccctgaa aacctcaatg gttactgcat    960

ccatggaaaa tgtgaattca tctattctac tcagaaggct tcttgtagat gtgaatctgg   1020

ctacactgga cagcactgtg aaaagacaga ctttagtatt ctctatgtag tgccaagtag   1080

gcaaaagctc actcatgttc ttattgcagc aattattgga gctgtacaga ttgccatcat   1140

agtagcaatt gtaatgtgca taacaagaaa atgccccaaa aacaatagag gacgtcgaca   1200

gaagcaaaac ctaggtcatt ttacttcaga tacgtcatcc agaatggttt aaactgatga   1260

cttttatatg tacactgacc atgtgatgta catttattat gtcttttttt aaagaatgga   1320

aatatttatt tcagaggcct tatttttgga catttttagt gtagtactgt tggctcgtat   1380

ttagaatatt cagctacgac agttttggac tgtttagtag tctttgtttt atgtttttaa   1440

atacagaaat tgctttcaca aatttgtacc acatggtaat tctaagactt gttctttacc   1500

catggaatgt aatatttttg caaagatgga ctacttcaca aatggttata aagtcatatc   1560

cacttcttcc acaatgacca cagcaaatga ccaagcatga actaaaggta aagatgttta   1620

cagattactt ttcttacaaa aaaatctaga agacactgtg tttaaataga tatttaaatg   1680

tttttgagat ttagtaactg attttttaga cactgcctat cgcatgaact gtaaagctgt   1740

gtgtattagg tgtaaaatat ttataagata tatggactgg ggaatttgat tattcctccc   1800

tttgaaaaaa tagtcctaat aatttgaaca aatatgttag taatgatgga acagatcaat   1860

gaaaagtaga tatagatatt gtgaaaatag gctgtttaac aaacagattg gaataaagcc   1920

tattctacca gttaaactac tttaatacac attcattttt aaagaaaatg tttgttttaa   1980

cataaataaa caaatcgtat cagtgtttgt gaataaaata caaaaatgat tgttaatgat   2040

tggtgctctt aaagtgagct taaaatttat ccaagacgta tatccaaatt tgtcctgtag   2100

taatagatta atattcatag attgttggtg tttaaagatc tgaagtgtga gtagaatgta   2160

ttcagctgtt taacatgtag tttagatatt caaaagtatg catgtagaat ttaaagaata   2220

tgttaaaaat tattaatctt aatattttgt ttggaaaagc atgttataat ataatgtttt   2280

cacaaaaaaa aaaaaaaaa                                                2299
```

```
<210> SEQ ID NO 20
<211> LENGTH: 380
<212> TYPE: PRT
<213> ORGANISM: Homo sapiens
<220> FEATURE:
<223> OTHER INFORMATION: transmembrane protein with EGF-like and two
      follistatin-like domains 1 (TMEFF1)

<400> SEQUENCE: 20

Met Gly Ala Ala Ala Ala Glu Ala Pro Leu Arg Leu Pro Ala Ala Pro
  1               5                  10                  15

Pro Leu Ala Phe Cys Cys Tyr Thr Ser Val Leu Leu Leu Phe Ala Phe
             20                  25                  30

Ser Leu Pro Gly Ser Arg Ala Ser Asn Gln Pro Pro Gly Gly Gly Gly
```

```
        35                  40                  45

Gly Ser Gly Gly Asp Cys Pro Gly Gly Lys Gly Lys Ser Ile Asn Cys
    50                  55                  60

Ser Glu Leu Asn Val Arg Glu Ser Asp Val Arg Val Cys Asp Glu Ser
65                  70                  75                  80

Ser Cys Lys Tyr Gly Gly Val Cys Lys Glu Asp Gly Asp Gly Leu Lys
                85                  90                  95

Cys Ala Cys Gln Phe Gln Cys His Thr Asn Tyr Ile Pro Val Cys Gly
            100                 105                 110

Ser Asn Gly Asp Thr Tyr Gln Asn Glu Cys Phe Leu Arg Arg Ala Ala
        115                 120                 125

Cys Lys His Gln Lys Glu Ile Thr Val Ile Ala Arg Gly Pro Cys Tyr
    130                 135                 140

Ser Asp Asn Gly Ser Gly Ser Gly Glu Gly Glu Glu Glu Gly Ser Gly
145                 150                 155                 160

Ala Glu Val His Arg Lys His Ser Lys Cys Gly Pro Cys Lys Tyr Lys
                165                 170                 175

Ala Glu Cys Asp Glu Asp Ala Glu Asn Val Gly Cys Val Cys Asn Ile
            180                 185                 190

Asp Cys Ser Gly Tyr Ser Phe Asn Pro Val Cys Ala Ser Asp Gly Ser
        195                 200                 205

Ser Tyr Asn Asn Pro Cys Phe Val Arg Glu Ala Ser Cys Ile Lys Gln
    210                 215                 220

Glu Gln Ile Asp Ile Arg His Leu Gly His Cys Thr Asp Thr Asp Asp
225                 230                 235                 240

Thr Ser Leu Leu Gly Lys Lys Asp Asp Gly Leu Gln Tyr Arg Pro Asp
                245                 250                 255

Val Lys Asp Ala Ser Asp Gln Arg Glu Asp Val Tyr Ile Gly Asn His
            260                 265                 270

Met Pro Cys Pro Glu Asn Leu Asn Gly Tyr Cys Ile His Gly Lys Cys
        275                 280                 285

Glu Phe Ile Tyr Ser Thr Gln Lys Ala Ser Cys Arg Cys Glu Ser Gly
    290                 295                 300

Tyr Thr Gly Gln His Cys Glu Lys Thr Asp Phe Ser Ile Leu Tyr Val
305                 310                 315                 320

Val Pro Ser Arg Gln Lys Leu Thr His Val Leu Ile Ala Ala Ile Ile
                325                 330                 335

Gly Ala Val Gln Ile Ala Ile Ile Val Ala Ile Val Met Cys Ile Thr
            340                 345                 350

Arg Lys Cys Pro Lys Asn Asn Arg Gly Arg Arg Gln Lys Gln Asn Leu
        355                 360                 365

Gly His Phe Thr Ser Asp Thr Ser Ser Arg Met Val
    370                 375                 380


<210> SEQ ID NO 21
<211> LENGTH: 1550
<212> TYPE: DNA
<213> ORGANISM: Homo sapiens
<220> FEATURE:
<223> OTHER INFORMATION: NADH dehydrogenase (ubiquinone) 1 alpha
      subcomplex, 5, 13kDa (NDUFA5), nuclear gene
      encoding mitochondrial protein cDNA
<220> FEATURE:
<221> NAME/KEY: CDS
<222> LOCATION: (110)..(460)
<223> OTHER INFORMATION: NDUFA5

<400> SEQUENCE: 21
```

```
tggagctaag ctgtttccag ggtgacagag tggcgacctc ggtggtcgat tgagcaggtc     60

tgagaattgt tcccaaaggg ttgtgcgtca ccgagtcgtt ggcgctgtca tggcgggtgt    120

gctgaagaag accactggcc ttgtgggatt ggctgtgtgc aatactcctc acgagaggct    180

aagaatattg tacacaaaga ttcttgatgt tcttgaggaa atccctaaaa atgcagcata    240

tagaaagtat acagaacaga ttacaaatga gaagctggct atggttaaag cggaaccaga    300

tgttaaaaaa ttagaagacc aacttcaagg cggtcaatta gaagaggtga ttcttcaggc    360

tgaacatgaa ctaaatctgg caagaaaaat gagggaatgg aaactatggg agccattagt    420

ggaagagcct cctgccgatc agtggaaatg gccaatataa ttattaagtg actttggtgt    480

gttcatggga aactgatgta attaaatatt ctgttatatt aagagcgtgt tcttattact    540

gacattttgt aatcaagaaa agtgatatag aaaatatgta ggagactgtt aaaattggtg    600

attatggtaa tatggtcatg tgaatcaatt tttgatttat aaagtactca cacaagttgt    660

ttcaaagatg atatttctgt gaacagagag gccatgggaa gatttgaaaa ttattaaaga    720

aaaattccta cagattttca atgcagagac cataatcaaa aagtaaactt tctttagtag    780

tatgttcaat acatcattta attttttaag ttatcctgaa gaaggaaagg tccttaatta    840

ttatagtcta aacaaattta tagattactg tttgaagtaa ataatacgag tgaatatttt    900

caaatgtgat aaaatagcac aagtggctgg tgataaaatt tgaaattatg gttaacctca    960

gctgtgatct tatgtatgta aagtgaaatt taaatagata attataggtt gattacaaaa   1020

tccatagtgt cattttattt tagtcattat tgaattatac catttactct gttttcttat   1080

agtcttaatt ttattatatt ttgttgttac tgtattatat ttgaaaacct tcaaattaga   1140

atacattgta cagttaaaga aattgacttg gtacttaaaa gaaagatttc ccattgcata   1200

caggttattg gagaaatttt ccttttgttg catttgtgga agttagtttt ctggcccgtg   1260

gcctttaatt ttcttaatca acctaattac atcaggatag aggtagagtt tctgtaaaag   1320

aagagacatt aagagttcct gaaatttata tctggcatac cgataggctt atattcaaaa   1380

catcttagtc atacgaccat aaattaaaag tggagtcact aaatagtttg cagtacgttt   1440

ctaatataag tgtaggtggg tatcaaaaca agacaaatgc tgttcaggga aagaagttgg   1500

caagcttaag gttaaacaaa aataaaatta catgtgtttt cgccttccta               1550
```

```
<210> SEQ ID NO 22
<211> LENGTH: 116
<212> TYPE: PRT
<213> ORGANISM: Homo sapiens
<220> FEATURE:
<223> OTHER INFORMATION: NADH dehydrogenase (ubiquinone) 1 alpha
      subcomplex, 5, 13kDa (NDUFA5), nuclear gene
      encoding mitochondrial protein

<400> SEQUENCE: 22

Met Ala Gly Val Leu Lys Lys Thr Thr Gly Leu Val Gly Leu Ala Val
  1               5                  10                  15

Cys Asn Thr Pro His Glu Arg Leu Arg Ile Leu Tyr Thr Lys Ile Leu
             20                  25                  30

Asp Val Leu Glu Glu Ile Pro Lys Asn Ala Ala Tyr Arg Lys Tyr Thr
         35                  40                  45

Glu Gln Ile Thr Asn Glu Lys Leu Ala Met Val Lys Ala Glu Pro Asp
     50                  55                  60

Val Lys Lys Leu Glu Asp Gln Leu Gln Gly Gly Gln Leu Glu Glu Val
 65                  70                  75                  80
```

-continued

```
Ile Leu Gln Ala Glu His Glu Leu Asn Leu Ala Arg Lys Met Arg Glu
                 85                  90                  95

Trp Lys Leu Trp Glu Pro Leu Val Glu Glu Pro Pro Ala Asp Gln Trp
            100                 105                 110

Lys Trp Pro Ile
        115


<210> SEQ ID NO 23
<211> LENGTH: 14536
<212> TYPE: DNA
<213> ORGANISM: Homo sapiens
<220> FEATURE:
<223> OTHER INFORMATION: FAT tumor suppressor homolog 2 (Drosophila)
      (FAT2) cDNA
<220> FEATURE:
<221> NAME/KEY: CDS
<222> LOCATION: (14)..(13063)
<223> OTHER INFORMATION: FAT2

<400> SEQUENCE: 23

ggagttttcc accatgacta ttgccctgct gggttttgcc atattcttgc tccattgtgc     60

gacctgtgag aagcctctag aagggattct ctcctcctct gcttggcact tcacacactc    120

ccattacaat gccaccatct atgaaaattc ttctcccaag acctatgtgg agagcttcga    180

gaaaatgggc atctacctcg cggagccaca gtgggcagtg aggtaccgga tcatctctgg    240

ggatgtggcc aatgtattta aaactgagga gtatgtggtg ggcaacttct gcttcctaag    300

aataaggaca aagagcagca acacagctct tctgaacaga gaggtgcgag acagctacac    360

cctcatcatc caagccacag agaagacctt ggagttggaa gctttgaccc gtgtggtggt    420

ccacatcctg gaccagaatg acctgaagcc tctcttctct ccaccttcgt acagagtcac    480

catctctgag gacatgcccc tgaagagccc catctgcaag gtgactgcca cagatgctga    540

tctaggccag aatgctgagt tctattatgc ctttaacaca aggtcagaga tgtttgccat    600

ccatcccacc agcggtgtgg tcactgtggc tgggaagctt aacgtcacct ggcgaggaaa    660

gcatgagctc caggtgctag ctgtggaccg catgcggaaa atctctgagg gcaatgggtt    720

tggcagcctg gctgcacttg tggttcatgt ggagcctgcc ctcaggaagc ccccagccat    780

tgcttcggtg gtggtgactc caccagacag caatgatggt accacctatg ccactgtact    840

ggtcgatgca aatagctcag gagctgaagt ggagtcagtg gaagttgttg gtggtgaccc    900

tggaaagcac ttcaaagcca tcaagtctta tgcccggagc aatgagttca gtttggtgtc    960

tgtcaaagac atcaactgga tggagtacct tcatgggttc aacctcagcc tccaggccag   1020

gagtgggagc ggcccttatt tttattccca gatcaggggc tttcacctac caccttccaa   1080

actgtcttcc ctcaaattcg agaaggctgt ttacagagtg cagcttagtg agttttcccc   1140

tcctggcagc cgcgtggtga tggtgagagt caccccagcc ttccccaacc tgcagtatgt   1200

tctaaagcca tcttcagaga atgtaggatt taaacttaat gctcgaactg ggttgatcac   1260

caccacaaag ctcatggact tccacgacag agcccactat cagctacaca tcagaacctc   1320

accgggccag gcctccaccg tggtggtcat tgacattgtg gactgcaaca accatgcccc   1380

cctcttcaac aggtcttcct atgatggtac cttggatgag aacatccctc caggcaccag   1440

tgttttggct gtgactgcca ctgaccggga tcatggggaa aatggatatg tcacctattc   1500

cattgctgga ccaaaagctt tgccattttc tattgacccc tacctgggga tcatctccac   1560

ctccaaaccc atggactatg aactcatgaa aagaatttat accttccggg taagagcatc   1620

agactgggga tccccttttc gccgggagaa ggaagtgtcc atttttcttc agctcaggaa   1680
```

-continued

```
cttgaatgac aaccagccta tgtttgaaga agtcaactgt acagggtcta tccgccaaga   1740

ctggccagta gggaaatcga taatgactat gtcagccata gatgtggatg agcttcagaa   1800

cctaaaatac gagattgtat caggcaatga actagagtat tttgatctaa atcatttctc   1860

cggagtgata tccctcaaac gcccttttat caatcttact gctggtcaac ccaccagtta   1920

ttccctgaag attacagcct cagatggcaa aaactatgcc tcacccacaa ctttgaatat   1980

tactgtggtg aaggaccctc attttgaagt tcctgtaaca tgtgataaaa caggggtatt   2040

gacacaattc acaaagacta tcctccactt tattgggctt cagaaccagg agtccagtga   2100

tgaggaattc acttctttaa gcacatatca gattaatcat tacaccccac agtttgagga   2160

ccacttcccc caatccattg atgtccttga gagtgtccct atcaacaccc ccttggcccg   2220

cctagcagcc actgaccctg atgctggttt taatggcaaa ctggtctatg tgattgcaga   2280

tggcaatgag gagggctgct ttgacataga gctggagaca gggctgctca ctgtagctgc   2340

tcccttggac tatgaagcca ccaatttcta catcctcaat gtaacagtat atgacctggg   2400

cacaccccag aagtcctcct ggaagctgct gacagtgaat gtgaaagact ggaatgacaa   2460

cgcacccaga tttcctcccg gtgggtacca gttaaccatc tcggaggaca cagaagttgg   2520

aaccacaatt gcagagctga caaccaaaga tgctgactcg gaagacaatg gcagggttcg   2580

ctacaccctg ctaagtccca cagagaagtt ctccctccac cctctcactg gggaactggt   2640

tgttacagga cacctggacc gcgaatcaga gcctcggtac atactcaagg tggaggccag   2700

ggatcagccc agcaaaggcc accagctctt ctctgtcact gacctgataa tcacattgga   2760

ggatgtcaac gacaactctc cccagtgcat cacagaacac aacaggctga aggttccaga   2820

ggacctgccc cccgggactg tcttgacatt tctggatgcc tctgatcctg acctgggccc   2880

cgcaggtgaa gtgcgatatg ttctgatgga tggcgcccat gggaccttcc gggtggacct   2940

gatgacaggg gcgctcattc tggagagaga gctggacttt gagaggcgag ctgggtacaa   3000

tctgagcctg tgggccagtg atggtgggag gcccctagcc cgcaggactc tctgccatgt   3060

ggaggtgatc gtcctggatg tgaatgagaa tctccaccct ccccactttg cctccttcgt   3120

gcaccagggc caggtgcagg agaacagccc ctcgggaact caggtgattg tagtggctgc   3180

ccaggacgat gacagtggct tggatgggga gctccagtac ttcctgcgtg ctggcactgg   3240

actcgcagcc ttcagcatca accaagatac aggaatgatt cagactctgg cacccctgga   3300

ccgagaattt gcatcttact actggttgac ggtattagca gtggacaggg gttctgtgcc   3360

cctctcttct gtaactgaag tctacatcga ggttacggat gccaatgaca acccacccca   3420

gatgtcccaa gctgtgttct acccctccat ccaggaggat gctcccgtgg gcacctctgt   3480

gcttcaactg gatgcctggg acccagactc cagctccaaa gggaagctga ccttcaacat   3540

caccagtggg aactacatgg gattctttat gattcaccct gttacaggtc tcctatctac   3600

agcccagcag ctggacagag agaacaagga tgaacacatc ctggaggtga ctgtgctgga   3660

caatggggaa ccctcactga agtccacctc cagggtggtg gtaggcatct tggacgtcaa   3720

tgacaatcca cctatattct cccacaagct cttcaatgtc cgccttccag agaggctgag   3780

ccctgtgtcc cctgggcctg tgtacaggct ggtggcttca gacctggatg agggtcttaa   3840

tggcagagtc acctacagta tcgaggacag cgatgaggag gccttcagta tcgacctggt   3900

cacaggtgtg gtttcatcca gcagcacttt tacagctgga gagtacaaca tcctaacgat   3960

caaggcaaca gacagtgggc agccaccact ctcagccagt gtccggctac acattgagtg   4020

gatcccttgg ccccggccgt cctccatccc tctggccttt gatgagacct actacagctt   4080
```

-continued

```
tacggtcatg gagacggacc ctgtgaacca catggtgggg gtcatcagcg tagagggcag   4140
acccggactc ttctggttca acatctcagg tggggataag gacatggact ttgacattga   4200
gaagaccaca ggcagcatcg tcattgccag gcctcttgat accaggagaa ggtcgaacta   4260
taacttgact gttgaggtga cagatgggtc ccgcaccatt gccacacagg tccacatctt   4320
catgattgcc aacattaacc accatcggcc ccagtttctg gaaactcgtt atgaagtcag   4380
agttccccag gacaccgtgc caggggtaga gctcctgcga gtccaggcca tagatcaaga   4440
caagggcaaa agcctcatct ataccataca tggcagccaa gacccaggaa gtgccagcct   4500
cttccagctg gacccaagca gtggtgtcct ggtaacggtg ggaaaattgg acctcggctc   4560
ggggccctcc cagcacacac tgacagtcat ggtccgagac caggaaatac ctatcaagag   4620
gaacttcgtg tgggtgacca ttcatgtgga ggatggaaac ctccacccac cccgcttcac   4680
tcagctccat tatgaggcaa gtgttcctga caccatagcc cccggcacag agctgctgca   4740
ggtccgagcc atggatgctg accggggagt caatgctgag gtccactact ccctcctgaa   4800
agggaacagc gaaggtttct tcaacatcaa tgccctgcta ggcatcatta ctctagctca   4860
aaagcttgat caggcaaatc atgccccaca tactctgaca gtgaaggcag aagatcaagg   4920
ctccccacaa tggcatgacc tggctacagt gatcattcat gtctatccct cagataggag   4980
tgcccccatc ttttcaaaat ctgagtactt tgtagagatc cctgaatcaa tccctgttgg   5040
ttccccaatc ctccttgtct ctgctatgag cccctctgaa gttacctatg agttaagaga   5100
gggaaataag gatggagtct tctctatgaa ctcatattct ggccttattt ccacccagaa   5160
gaaattggac catgagaaaa tctcgtctta ccagctgaaa atccgaggca gcaatatggc   5220
aggtgcattt actgatgtca tggtggtggt tgacataatt gatgaaaatg acaatgctcc   5280
tatgttctta aagtcaactt ttgtgggcca aattagtgaa gcagctccac tgtatagcat   5340
gatcatggat aaaaacaaca accccttttgt gattcatgcc tctgacagtg acaaagaagc   5400
taattccttg ttggtctata aaattttgga gccggaggcc ttgaagtttt tcaaaattga   5460
tcccagcatg ggaaccctaa ccattgtatc agagatggat tatgagagca tgccctcttt   5520
ccaattctgt gtctatgtcc atgaccaagg aagccctgta ttatttgcac ccagacctgc   5580
ccaagtcatc attcatgtca gagatgtgaa tgattcccct cccagattct cagaacagat   5640
atatgaggta gcaatagtcg ggcctatcca tccaggcatg gagcttctca tggtgcgggc   5700
cagcgatgaa gactcagaag tcaattatag catcaaaact ggcaatgctg atgaagctgt   5760
taccatccat cctgtcactg gtagcatatc tgtgctgaat cctgctttcc tgggactctc   5820
tcggaagctc accatcaggg cttctgatgg cttgtatcaa gacactgcgc tggtaaaaat   5880
ttctttgacc caagtgcttg acaaaagctt gcagtttgat caggatgtct actgggcagc   5940
tgtgaaggag aacttgcagg acagaaaggc actggtgatt cttggtgccc agggcaatca   6000
tttgaatgac accctttcct actttctctt gaatggcaca gatatgtttc atatggtcca   6060
gtcagcaggt gtgttgcaga caagaggtgt ggcgtttgac cgggagcagc aggacactca   6120
tgagttggca gtggaagtga gggacaatcg gacacctcag cgggtggctc agggtttggt   6180
cagagtctct attgaggatg tcaatgacaa tccccccaaa tttaagcatc tgccctatta   6240
cacaatcatc caagatggca cagagccagg ggatgtcctc tttcaggtat ctgccactga   6300
tgaggacttg gggacaaatg ggctgttac atatgaattt gcagaagatt acacatattt   6360
ccgaattgac ccctatcttg ggacatatc actcaagaaa ccctttgatt atcaagcttt   6420
aaataaatat cacctcaaag tcattgctcg ggatggagga acgccatccc tccagagtga   6480
```

-continued

```
ggaagaggta cttgtcactg tgagaaataa atccaaccca ctgtttcaga gtccttatta   6540
caaagtcaga gtacctgaaa atatcaccct ctataccccca attctccaca cccaggcccg   6600
gagtccagag ggactccggc tcatctacaa cattgtggag gaagaaccct tgatgctgtt   6660
caccactgac ttcaagactg gtgtcctaac agtaacaggg cctttggact atgagtccaa   6720
gaccaaacat gtgttcacag tcagagccac ggatacagct ctggggtcat tttctgaagc   6780
cacagtggaa gtcctagtgg aggatgtcaa tgataaccct cccacttttt cccaattggt   6840
ctataccact tccatctcag aaggcttgcc tgctcagacc cctgtgatcc aactgttggc   6900
ttctgaccag gactcagggc ggaaccgtga cgtctcttat cagattgtgg aggatggctc   6960
agatgtttcc aagttcttcc agatcaatgg gagcacaggg gagatgtcca cagttcaaga   7020
actggattat gaagcccaac aacactttca tgtgaaagtc agggccatgg ataaaggaga   7080
tccccccactc actggtgaaa cccttgtggt tgtcaatgtg tctgatatca atgacaaccc   7140
cccagagttc agacaacctc aatatgaagc caatgtcagt gaactggcaa cctgtggaca   7200
cctggttctt aaagtccagg ctattgaccc tgacagcaga gacacctccc gcctggagta   7260
cctgattctt tctggcaatc aggacaggca cttcttcatt aacagctcat cgggaataat   7320
ttctatgttc aacctttgca aaaagcacct ggactcttct tacaatttga gggtaggtgc   7380
ttctgatgga gtcttccgag caactgtgcc tgtgtacatc aacactacaa atgccaacaa   7440
gtacagccca gagttccagc agcaccttta tgaggcagaa ttagcagaga atgcaatggt   7500
tggaaccaag gtgattgatt tgctagccat agacaaagat agtggtccct atggcactat   7560
agattatact atcatcaata aactagcaag tgagaagttc tccataaacc ccaatggcca   7620
gattgccact ctgcagaaac tggatcggga aaattcaaca gagagagtca ttgctattaa   7680
ggtcatggct cgggatggag gaggaagagt agccttctgc acggtgaaga tcatcctcac   7740
agatgaaaat gacaaccccc cacagttcaa agcatctgag tacacagtat ccattcaatc   7800
caatgtcagt aaagactctc cggttatcca ggtgttggcc tatgatgcag atgaaggtca   7860
gaacgcagat gtcacctact cagtgaaccc agaggaccta gttaaagatg tcattgaaat   7920
taacccagtc actggtgtgg tcaaggtgaa agacagcctg gtgggattgg aaaatcagac   7980
ccttgacttc ttcatcaaag cccaagatgg aggccctcct cactggaact ctctggtgcc   8040
agtacgactt caggtggttc ctaaaaaagt atccttaccg aaatttttctg aacctttgta   8100
tactttctct gcacctgaag accttccaga ggggtctgaa attgggattg ttaaagcagt   8160
ggcagctcaa gatccagtca tctacagtct agtgcggggc actacacctg agagcaacaa   8220
ggatggtgtc ttctccctag acccagacac aggggtcata aaggtgagga agcccatgga   8280
ccacgaatcc accaaattgt accagattga tgtgatggca cattgccttc agaacactga   8340
tgtggtgtcc ttggtctctg tcaacatcca agtgggagac gtcaatgaca ataggcctgt   8400
atttgaggct gatccatata aggctgtcct cactgagaat atgccagtgg ggacctcagt   8460
cattcaagtg actgccattg acaaggacac tgggagagat ggccaggtga gctacaggct   8520
gtctgcagac cctggtagca atgtccatga gctctttgcc attgacagtg agagtggttg   8580
gatcaccaca ctccaggaac ttgactgtga gacctgccag acttatcatt ttcatgtggt   8640
ggcctatgac cacggacaga ccatccagct atcctctcag gccctggttc aggtctccat   8700
tacagatgag aatgacaatg ctccccgatt tgcttctgaa gagtacagag gatctgtggt   8760
tgagaacagt gagcctggcg aactggtggc gactctaaag accctggatg ctgacatttc   8820
tgagcagaac aggcaggtca cctgctacat cacagaggga gaccccctgg gccagtttgg   8880
```

-continued

```
catcagccaa gttggagatg agtggaggat ttcctcaagg aagaccctgg accgcgagca   8940
tacagccaag tacttgctca gagtcacagc atctgatggc aagttccagg cttcggtcac   9000
tgtggagatc tttgtcctgg acgtcaatga taacagccca cagtgttcac agcttctcta   9060
tactggcaag gttcatgaag atgtatttcc aggacacttc attttgaagg tttctgccac   9120
agacttggac actgatacca atgctcagat cacatattct ctgcatggcc ctggggcgca   9180
tgaattcaag ctggatcctc atacagggga gctgaccaca ctcactgccc tagaccgaga   9240
aaggaaggat gtgttcaacc ttgttgccaa ggcgacggat ggaggtggcc gatcgtgcca   9300
ggcagacatc accctccatg tggaggatgt gaatgacaat gccccgcggt tcttccccag   9360
ccactgtgct gtggctgtct tcgacaacac cacagtgaag acccctgtgg ctgtagtatt   9420
tgcccgggat cccgaccaag gcgccaatgc ccaggtggtt tactctctgc cggattcagc   9480
cgaaggccac ttttccatcg acgccaccac gggggtgatc cgcctggaaa agccgctgca   9540
ggtcaggccc caggcaccac tggagctcac ggtccgtgcc tctgacctgg gcaccccaat   9600
accgctgtcc acgctgggca ccgtcacagt ctcggtggtg ggcctagaag actacctgcc   9660
cgtgttcctg aacaccgagc acagcgtgca ggtgcccgag gacgccccac ctggcacgga   9720
ggtgctgcag ctggccaccc tcactcgccc gggcgcagag aagaccggct accgcgtggt   9780
cagcgggaac gagcaaggca ggttccgcct ggatgctcgc acagggatcc tgtatgtcaa   9840
cgcaagcctg gactttgaga caagccccaa gtacttcctg tccattgagt gcagccggaa   9900
gagctcctct tccctcagtg acgtgaccac agtcatggtc aacatcactg atgtcaatga   9960
acaccggccc caattccccc aagatccata tagcacaagg gtcttagaga atgcccttgt  10020
gggtgacgtc atcctcacgg tatcagcgac tgatgaagat ggacccctaa atagtgacat  10080
tacctatagc ctcataggag ggaaccagct tgggcacttc accattcacc ccaaaaaggg  10140
ggagctacag gtggccaagg ccctggaccg ggaacaggcc tctagttatt ccctgaagct  10200
ccgagccaca gacagtgggc agcctccact gcatgaggac acagacatcg ctatccaagt  10260
ggctgatgtc aatgataacc caccgagatt cttccagctc aactacagca ccactgtcca  10320
ggagaactcc cccattggca gcaaagtcct gcagctgatc ctgagtgacc cagattctcc  10380
agagaatggc ccccccctact cgtttcgaat caccaagggg aacaacggct ctgccttccg  10440
agtgaccccg gatggatggc tggtgactgc tgagggccta agcaggaggg ctcaggaatg  10500
gtatcagctt cagatccagg cgtcagacag tggcatccct cccctctcgt ctttgacgtc  10560
tgtccgtgtc catgtcacag agcagagcca ctatgcacct tctgctctcc cactggagat  10620
cttcatcact gttggagagg atgagttcca gggtggcatg gtgggtaaga tccatgccac  10680
agaccgagac ccccaggaca cgctgaccta tagcctggca gaagaggaga ccctgggcag  10740
gcacttctca gtgggtgcgc ctgatggcaa gattatcgcc gcccagggcc tgcctcgtgg  10800
ccactactcg ttcaacgtca cggtcagcga tgggaccttc accacgactg ctggggtcca  10860
tgtgtacgtg tggcatgtgg ggcaggaggc tctgcagcag gccatgtgga tgggcttcta  10920
ccagctcacc cccgaggagc tggtgagtga ccactggcgg aacctgcaga ggttcctcag  10980
ccataagctg gacatcaaac gggctaacat tcacttggcc agcctccagc ctgcagaggc  11040
cgtggctggt gtggatgtgc tcctggtctt tgaggggcat tctggaacct tctacgagtt  11100
tcaggagcta gcatccatca tcactcactc agccaaggag atggagcatt cagtgggggt  11160
tcagatgcgg tcagctatgc ccatggtgcc ctgccagggg ccaacctgcc agggtcaaat  11220
ctgccataac acagtgcatc tggaccccaa ggttgggccc acgtacagca ccgccaggct  11280
```

-continued

```
cagcatccta accccgcggc accacctgca gaggagctgc tcctgcaatg gtactgctac  11340
aaggttcagt ggtcagagct atgtgcggta cagggcccca gcggctcgga actggcacat  11400
ccatttctat ctgaaaacac tccagccaca ggccattctt ctattcacca atgaaacagc  11460
gtccgtctcc ctgaagctgg ccagtggagt gccccagctg gaataccact gtctgggtgg  11520
tttctatgga aacctttcct cccagcgcca tgtgaatgac cacgagtggc actccatcct  11580
ggtggaggag atggacgctt ccattcgcct gatggttgac agcatgggca acacctccct  11640
tgtggtccca gagaactgcc gtggtctgag gcccgaaagg cacctcttgc tgggcggcct  11700
cattctgttg cattcttcct cgaatgtctc ccagggcttt gaaggctgcc tggatgctgt  11760
cgtggtcaac gaagaggctc tagatctgct ggcccctggc aagacggtgg caggcttgct  11820
ggagacacaa gccctcaccc agtgctgcct ccacagtgac tactgcagcc agaacacatg  11880
cctcaatggt gggaagtgct catggaccca tggggcaggc tatgtctgca aatgtccccc  11940
acagttctct gggaagcact gtgaacaagg aagggagaac tgtacttttg caccctgcct  12000
ggaaggtgga acttgcatcc tctcccccaa aggagcttcc tgtaactgcc ctcatcctta  12060
cacaggagac aggtgtgaaa tggaggcgag gggttgttca gaaggacact gcctagtcac  12120
tcccgagatc caaagggggg actgggggca gcaggagtta ctgatcatca cagtggccgt  12180
ggcgttcatt atcataagca ctgtcgggct tctcttctac tgccgccgtt gcaagtctca  12240
caagcctgtg gccatggagg acccagacct cctggccagg agtgttggtg ttgacaccca  12300
agccatgcct gccatcgagc tcaacccatt gagtgccagc tcctgcaaca acctcaacca  12360
accggaaccc agcaaggcct ctgttccaaa tgaactcgtc acatttggac ccaattctaa  12420
gcaacggcca gtggtctgca gtgtgccccc cagactcccg ccagctgcgg tcccttccca  12480
ctctgacaat gagcctgtca ttaagagaac ctggtccagc gaggagatgg tgtaccctgg  12540
cggagccatg gtctggcccc ctacttactc caggaacgaa cgctgggaat acccccactc  12600
cgaagtgact cagggccctc tgccgccctc ggctcaccgc cactcaaccc cagtcgtgat  12660
gccagagcct aatggcctct atgggggctt ccccttcccc ctggagatgg aaaacaagcg  12720
ggcacctctc ccaccccgtt acagcaacca gaacctggaa gatctgatgc cctctcggcc  12780
ccctagtccc cgggagcgcc tggttgcccc ctgtctcaat gagtacacgg ccatcagcta  12840
ctaccactcg cagttccggc agggaggggg agggccctgc ctggcagacg gggctacaa  12900
gggggtgggt atgcgcctca gccgagctgg gccctcttat gctgtctgtg aggtggaggg  12960
ggcacctctt gcaggccagg gccagccccg ggtgcccccc aactatgagg gctctgacat  13020
ggtggagagt gattatggca gctgtgagga ggtcatgttc tagcttccca ttcccagagc  13080
aaggcaggcg ggaggccaag gactggactt ggcttatttc ttcctgtctc gtagggggtg  13140
agttgagtgt ggctgggaga gtgggaggga agccctcagc ccaggctgtt gtcccttgaa  13200
atgtgctctt ccaatccccc acctagtccc tgagggtgga gggaagctga ggatagagct  13260
ccagaaacag cactagggtc ccaggagagg ggcatttcta gagcagtgac cctggaaaac  13320
caggaacaat tgactcctgg ggtgggcgac agacaggagg gctccctgat ctgccggctc  13380
tcagtccccg gggcaaagcc tgattgactg tgctggctca acttcaccaa gatgcattct  13440
catacctgcc cacagctcca ttttggaggc aggcaggttg gtgcctgaca gacaaccact  13500
acgcgggccg tacagaggag ctctagaggg ctgcgtggca tcctcctagg ggctgagagg  13560
tgagcagcag gggagcgggc acagtcccct ctgcccctgc ctcagtcgag cactcactgt  13620
gtctttgtca agtgtctgct ccacgtcagg cactgtgctt tgcaccgggg agaaaatggt  13680
```

-continued

```
gatggagggc aacaaggact ccgaggagca ccaccaggcc tcgggcccca gaggtcccgc  13740

tcctcagcct acacgcagag gaacgggccc acctcagagt cacaccactg gctgccagtc  13800

agggcctgcc aggagtctac acagctctga accttctttg ttaaagaatt cagacctcat  13860

ggaactctgg gttcttcatc ccaagtttcc caggcacttt tggccaaagg aaggaaggaa  13920

ctaattcttc attttaaaaa ttcttaggca ctttttgacc ttgctgtctg gatgagtttc  13980

ctcaatggga tttttcttcc ctagacacaa ggaagtctga actcctattt agggccggtt  14040

ggaagcaggg agctggaccg cagtgtccag gctggacacc tgccattgcc tcctctccac  14100

tgcagacgcc tgcccatcaa gtattacctg cagcgactca accctatgca tggagggtca  14160

atgtgggcac atgtctacac atgtgggtgc ccatggatag tacgtgtgta cacatgtgta  14220

gagtgtatgt agccaggagt ggtggggacc agaagcctct gtggcctttg gtgacctcac  14280

cactccctcc cacccagtcc ctccctctgg tccactgcct tttcatatgt gttgtttctg  14340

gagacagaag tcaaaaggaa gagcagtgga gccttgccca cagggctgct gcttcatgcg  14400

agagggagat gtgtgggcga gagccaattt gtgtgagtgg tttgtggctg tgtgtgtgac  14460

tgtgagtgtg agtgacagat acatagtttc attggtcatt ttttttttta acaataaagt  14520

atcttttttt actgtt                                                  14536


<210> SEQ ID NO 24
<211> LENGTH: 4349
<212> TYPE: PRT
<213> ORGANISM: Homo sapiens
<220> FEATURE:
<223> OTHER INFORMATION: FAT tumor suppressor homolog 2 (Drosophila)
      (FAT2)

<400> SEQUENCE: 24

Met Thr Ile Ala Leu Leu Gly Phe Ala Ile Phe Leu Leu His Cys Ala
  1               5                  10                  15

Thr Cys Glu Lys Pro Leu Glu Gly Ile Leu Ser Ser Ser Ala Trp His
             20                  25                  30

Phe Thr His Ser His Tyr Asn Ala Thr Ile Tyr Glu Asn Ser Ser Pro
         35                  40                  45

Lys Thr Tyr Val Glu Ser Phe Glu Lys Met Gly Ile Tyr Leu Ala Glu
     50                  55                  60

Pro Gln Trp Ala Val Arg Tyr Arg Ile Ile Ser Gly Asp Val Ala Asn
 65                  70                  75                  80

Val Phe Lys Thr Glu Glu Tyr Val Val Gly Asn Phe Cys Phe Leu Arg
                 85                  90                  95

Ile Arg Thr Lys Ser Ser Asn Thr Ala Leu Leu Asn Arg Glu Val Arg
            100                 105                 110

Asp Ser Tyr Thr Leu Ile Ile Gln Ala Thr Glu Lys Thr Leu Glu Leu
        115                 120                 125

Glu Ala Leu Thr Arg Val Val Val His Ile Leu Asp Gln Asn Asp Leu
    130                 135                 140

Lys Pro Leu Phe Ser Pro Pro Ser Tyr Arg Val Thr Ile Ser Glu Asp
145                 150                 155                 160

Met Pro Leu Lys Ser Pro Ile Cys Lys Val Thr Ala Thr Asp Ala Asp
                165                 170                 175

Leu Gly Gln Asn Ala Glu Phe Tyr Tyr Ala Phe Asn Thr Arg Ser Glu
            180                 185                 190

Met Phe Ala Ile His Pro Thr Ser Gly Val Val Thr Val Ala Gly Lys
        195                 200                 205
```

```
Leu Asn Val Thr Trp Arg Gly Lys His Glu Leu Gln Val Leu Ala Val
    210                 215                 220

Asp Arg Met Arg Lys Ile Ser Glu Gly Asn Gly Phe Gly Ser Leu Ala
225                 230                 235                 240

Ala Leu Val Val His Val Glu Pro Ala Leu Arg Lys Pro Pro Ala Ile
                245                 250                 255

Ala Ser Val Val Val Thr Pro Pro Asp Ser Asn Asp Gly Thr Thr Tyr
            260                 265                 270

Ala Thr Val Leu Val Asp Ala Asn Ser Ser Gly Ala Glu Val Glu Ser
        275                 280                 285

Val Glu Val Val Gly Gly Asp Pro Gly Lys His Phe Lys Ala Ile Lys
    290                 295                 300

Ser Tyr Ala Arg Ser Asn Glu Phe Ser Leu Val Ser Val Lys Asp Ile
305                 310                 315                 320

Asn Trp Met Glu Tyr Leu His Gly Phe Asn Leu Ser Leu Gln Ala Arg
                325                 330                 335

Ser Gly Ser Gly Pro Tyr Phe Tyr Ser Gln Ile Arg Gly Phe His Leu
            340                 345                 350

Pro Pro Ser Lys Leu Ser Ser Leu Lys Phe Glu Lys Ala Val Tyr Arg
        355                 360                 365

Val Gln Leu Ser Glu Phe Ser Pro Pro Gly Ser Arg Val Val Met Val
    370                 375                 380

Arg Val Thr Pro Ala Phe Pro Asn Leu Gln Tyr Val Leu Lys Pro Ser
385                 390                 395                 400

Ser Glu Asn Val Gly Phe Lys Leu Asn Ala Arg Thr Gly Leu Ile Thr
                405                 410                 415

Thr Thr Lys Leu Met Asp Phe His Asp Arg Ala His Tyr Gln Leu His
            420                 425                 430

Ile Arg Thr Ser Pro Gly Gln Ala Ser Thr Val Val Val Ile Asp Ile
        435                 440                 445

Val Asp Cys Asn Asn His Ala Pro Leu Phe Asn Arg Ser Ser Tyr Asp
    450                 455                 460

Gly Thr Leu Asp Glu Asn Ile Pro Pro Gly Thr Ser Val Leu Ala Val
465                 470                 475                 480

Thr Ala Thr Asp Arg Asp His Gly Glu Asn Gly Tyr Val Thr Tyr Ser
                485                 490                 495

Ile Ala Gly Pro Lys Ala Leu Pro Phe Ser Ile Asp Pro Tyr Leu Gly
            500                 505                 510

Ile Ile Ser Thr Ser Lys Pro Met Asp Tyr Glu Leu Met Lys Arg Ile
        515                 520                 525

Tyr Thr Phe Arg Val Arg Ala Ser Asp Trp Gly Ser Pro Phe Arg Arg
    530                 535                 540

Glu Lys Glu Val Ser Ile Phe Leu Gln Leu Arg Asn Leu Asn Asp Asn
545                 550                 555                 560

Gln Pro Met Phe Glu Glu Val Asn Cys Thr Gly Ser Ile Arg Gln Asp
                565                 570                 575

Trp Pro Val Gly Lys Ser Ile Met Thr Met Ser Ala Ile Asp Val Asp
            580                 585                 590

Glu Leu Gln Asn Leu Lys Tyr Glu Ile Val Ser Gly Asn Glu Leu Glu
        595                 600                 605

Tyr Phe Asp Leu Asn His Phe Ser Gly Val Ile Ser Leu Lys Arg Pro
    610                 615                 620

Phe Ile Asn Leu Thr Ala Gly Gln Pro Thr Ser Tyr Ser Leu Lys Ile
625                 630                 635                 640
```

```
Thr Ala Ser Asp Gly Lys Asn Tyr Ala Ser Pro Thr Thr Leu Asn Ile
                645                 650                 655

Thr Val Val Lys Asp Pro His Phe Glu Val Pro Val Thr Cys Asp Lys
            660                 665                 670

Thr Gly Val Leu Thr Gln Phe Thr Lys Thr Ile Leu His Phe Ile Gly
        675                 680                 685

Leu Gln Asn Gln Glu Ser Ser Asp Glu Glu Phe Thr Ser Leu Ser Thr
    690                 695                 700

Tyr Gln Ile Asn His Tyr Thr Pro Gln Phe Glu Asp His Phe Pro Gln
705                 710                 715                 720

Ser Ile Asp Val Leu Glu Ser Val Pro Ile Asn Thr Pro Leu Ala Arg
                725                 730                 735

Leu Ala Ala Thr Asp Pro Asp Ala Gly Phe Asn Gly Lys Leu Val Tyr
            740                 745                 750

Val Ile Ala Asp Gly Asn Glu Glu Gly Cys Phe Asp Ile Glu Leu Glu
        755                 760                 765

Thr Gly Leu Leu Thr Val Ala Ala Pro Leu Asp Tyr Glu Ala Thr Asn
    770                 775                 780

Phe Tyr Ile Leu Asn Val Thr Val Tyr Asp Leu Gly Thr Pro Gln Lys
785                 790                 795                 800

Ser Ser Trp Lys Leu Leu Thr Val Asn Val Lys Asp Trp Asn Asp Asn
                805                 810                 815

Ala Pro Arg Phe Pro Pro Gly Gly Tyr Gln Leu Thr Ile Ser Glu Asp
            820                 825                 830

Thr Glu Val Gly Thr Thr Ile Ala Glu Leu Thr Thr Lys Asp Ala Asp
        835                 840                 845

Ser Glu Asp Asn Gly Arg Val Arg Tyr Thr Leu Leu Ser Pro Thr Glu
    850                 855                 860

Lys Phe Ser Leu His Pro Leu Thr Gly Glu Leu Val Val Thr Gly His
865                 870                 875                 880

Leu Asp Arg Glu Ser Glu Pro Arg Tyr Ile Leu Lys Val Glu Ala Arg
                885                 890                 895

Asp Gln Pro Ser Lys Gly His Gln Leu Phe Ser Val Thr Asp Leu Ile
            900                 905                 910

Ile Thr Leu Glu Asp Val Asn Asp Asn Ser Pro Gln Cys Ile Thr Glu
        915                 920                 925

His Asn Arg Leu Lys Val Pro Glu Asp Leu Pro Pro Gly Thr Val Leu
    930                 935                 940

Thr Phe Leu Asp Ala Ser Asp Pro Asp Leu Gly Pro Ala Gly Glu Val
945                 950                 955                 960

Arg Tyr Val Leu Met Asp Gly Ala His Gly Thr Phe Arg Val Asp Leu
                965                 970                 975

Met Thr Gly Ala Leu Ile Leu Glu Arg Glu Leu Asp Phe Glu Arg Arg
            980                 985                 990

Ala Gly Tyr Asn Leu Ser Leu Trp Ala Ser Asp Gly Gly Arg Pro Leu
        995                 1000                1005

Ala Arg Arg Thr Leu Cys His Val Glu Val Ile Val Leu Asp Val Asn
   1010                 1015                1020

Glu Asn Leu His Pro Pro His Phe Ala Ser Phe Val His Gln Gly Gln
1025                1030                1035                1040

Val Gln Glu Asn Ser Pro Ser Gly Thr Gln Val Ile Val Val Ala Ala
                1045                1050                1055

Gln Asp Asp Asp Ser Gly Leu Asp Gly Glu Leu Gln Tyr Phe Leu Arg
```

```
            1060                1065                1070

Ala Gly Thr Gly Leu Ala Ala Phe Ser Ile Asn Gln Asp Thr Gly Met
        1075                1080                1085

Ile Gln Thr Leu Ala Pro Leu Asp Arg Glu Phe Ala Ser Tyr Tyr Trp
    1090                1095                1100

Leu Thr Val Leu Ala Val Asp Arg Gly Ser Val Pro Leu Ser Ser Val
1105                1110                1115                1120

Thr Glu Val Tyr Ile Glu Val Thr Asp Ala Asn Asp Asn Pro Pro Gln
                1125                1130                1135

Met Ser Gln Ala Val Phe Tyr Pro Ser Ile Gln Glu Asp Ala Pro Val
            1140                1145                1150

Gly Thr Ser Val Leu Gln Leu Asp Ala Trp Asp Pro Asp Ser Ser Ser
        1155                1160                1165

Lys Gly Lys Leu Thr Phe Asn Ile Thr Ser Gly Asn Tyr Met Gly Phe
    1170                1175                1180

Phe Met Ile His Pro Val Thr Gly Leu Leu Ser Thr Ala Gln Gln Leu
1185                1190                1195                1200

Asp Arg Glu Asn Lys Asp Glu His Ile Leu Glu Val Thr Val Leu Asp
                1205                1210                1215

Asn Gly Glu Pro Ser Leu Lys Ser Thr Ser Arg Val Val Val Gly Ile
            1220                1225                1230

Leu Asp Val Asn Asp Asn Pro Pro Ile Phe Ser His Lys Leu Phe Asn
        1235                1240                1245

Val Arg Leu Pro Glu Arg Leu Ser Pro Val Ser Pro Gly Pro Val Tyr
    1250                1255                1260

Arg Leu Val Ala Ser Asp Leu Asp Glu Gly Leu Asn Gly Arg Val Thr
1265                1270                1275                1280

Tyr Ser Ile Glu Asp Ser Asp Glu Glu Ala Phe Ser Ile Asp Leu Val
                1285                1290                1295

Thr Gly Val Val Ser Ser Ser Ser Thr Phe Thr Ala Gly Glu Tyr Asn
            1300                1305                1310

Ile Leu Thr Ile Lys Ala Thr Asp Ser Gly Gln Pro Pro Leu Ser Ala
        1315                1320                1325

Ser Val Arg Leu His Ile Glu Trp Ile Pro Trp Pro Arg Pro Ser Ser
    1330                1335                1340

Ile Pro Leu Ala Phe Asp Glu Thr Tyr Tyr Ser Phe Thr Val Met Glu
1345                1350                1355                1360

Thr Asp Pro Val Asn His Met Val Gly Val Ile Ser Val Glu Gly Arg
                1365                1370                1375

Pro Gly Leu Phe Trp Phe Asn Ile Ser Gly Gly Asp Lys Asp Met Asp
            1380                1385                1390

Phe Asp Ile Glu Lys Thr Thr Gly Ser Ile Val Ile Ala Arg Pro Leu
        1395                1400                1405

Asp Thr Arg Arg Arg Ser Asn Tyr Asn Leu Thr Val Glu Val Thr Asp
    1410                1415                1420

Gly Ser Arg Thr Ile Ala Thr Gln Val His Ile Phe Met Ile Ala Asn
1425                1430                1435                1440

Ile Asn His His Arg Pro Gln Phe Leu Glu Thr Arg Tyr Glu Val Arg
                1445                1450                1455

Val Pro Gln Asp Thr Val Pro Gly Val Glu Leu Leu Arg Val Gln Ala
            1460                1465                1470

Ile Asp Gln Asp Lys Gly Lys Ser Leu Ile Tyr Thr Ile His Gly Ser
        1475                1480                1485
```

```
Gln Asp Pro Gly Ser Ala Ser Leu Phe Gln Leu Asp Pro Ser Ser Gly
   1490                1495                1500

Val Leu Val Thr Val Gly Lys Leu Asp Leu Gly Ser Gly Pro Ser Gln
1505                1510                1515                1520

His Thr Leu Thr Val Met Val Arg Asp Gln Glu Ile Pro Ile Lys Arg
               1525                1530                1535

Asn Phe Val Trp Val Thr Ile His Val Glu Asp Gly Asn Leu His Pro
           1540                1545                1550

Pro Arg Phe Thr Gln Leu His Tyr Glu Ala Ser Val Pro Asp Thr Ile
       1555                1560                1565

Ala Pro Gly Thr Glu Leu Leu Gln Val Arg Ala Met Asp Ala Asp Arg
   1570                1575                1580

Gly Val Asn Ala Glu Val His Tyr Ser Leu Leu Lys Gly Asn Ser Glu
1585                1590                1595                1600

Gly Phe Phe Asn Ile Asn Ala Leu Leu Gly Ile Ile Thr Leu Ala Gln
               1605                1610                1615

Lys Leu Asp Gln Ala Asn His Ala Pro His Thr Leu Thr Val Lys Ala
           1620                1625                1630

Glu Asp Gln Gly Ser Pro Gln Trp His Asp Leu Ala Thr Val Ile Ile
       1635                1640                1645

His Val Tyr Pro Ser Asp Arg Ser Ala Pro Ile Phe Ser Lys Ser Glu
   1650                1655                1660

Tyr Phe Val Glu Ile Pro Glu Ser Ile Pro Val Gly Ser Pro Ile Leu
1665                1670                1675                1680

Leu Val Ser Ala Met Ser Pro Ser Glu Val Thr Tyr Glu Leu Arg Glu
               1685                1690                1695

Gly Asn Lys Asp Gly Val Phe Ser Met Asn Ser Tyr Ser Gly Leu Ile
           1700                1705                1710

Ser Thr Gln Lys Lys Leu Asp His Glu Lys Ile Ser Ser Tyr Gln Leu
       1715                1720                1725

Lys Ile Arg Gly Ser Asn Met Ala Gly Ala Phe Thr Asp Val Met Val
   1730                1735                1740

Val Val Asp Ile Ile Asp Glu Asn Asp Asn Ala Pro Met Phe Leu Lys
1745                1750                1755                1760

Ser Thr Phe Val Gly Gln Ile Ser Glu Ala Ala Pro Leu Tyr Ser Met
               1765                1770                1775

Ile Met Asp Lys Asn Asn Asn Pro Phe Val Ile His Ala Ser Asp Ser
           1780                1785                1790

Asp Lys Glu Ala Asn Ser Leu Leu Val Tyr Lys Ile Leu Glu Pro Glu
       1795                1800                1805

Ala Leu Lys Phe Phe Lys Ile Asp Pro Ser Met Gly Thr Leu Thr Ile
   1810                1815                1820

Val Ser Glu Met Asp Tyr Glu Ser Met Pro Ser Phe Gln Phe Cys Val
1825                1830                1835                1840

Tyr Val His Asp Gln Gly Ser Pro Val Leu Phe Ala Pro Arg Pro Ala
               1845                1850                1855

Gln Val Ile Ile His Val Arg Asp Val Asn Asp Ser Pro Pro Arg Phe
           1860                1865                1870

Ser Glu Gln Ile Tyr Glu Val Ala Ile Val Gly Pro Ile His Pro Gly
       1875                1880                1885

Met Glu Leu Leu Met Val Arg Ala Ser Asp Glu Asp Ser Glu Val Asn
   1890                1895                1900

Tyr Ser Ile Lys Thr Gly Asn Ala Asp Glu Ala Val Thr Ile His Pro
1905                1910                1915                1920
```

```
Val Thr Gly Ser Ile Ser Val Leu Asn Pro Ala Phe Leu Gly Leu Ser
                1925                1930                1935

Arg Lys Leu Thr Ile Arg Ala Ser Asp Gly Leu Tyr Gln Asp Thr Ala
            1940                1945                1950

Leu Val Lys Ile Ser Leu Thr Gln Val Leu Asp Lys Ser Leu Gln Phe
        1955                1960                1965

Asp Gln Asp Val Tyr Trp Ala Ala Val Lys Glu Asn Leu Gln Asp Arg
    1970                1975                1980

Lys Ala Leu Val Ile Leu Gly Ala Gln Gly Asn His Leu Asn Asp Thr
1985                1990                1995                2000

Leu Ser Tyr Phe Leu Leu Asn Gly Thr Asp Met Phe His Met Val Gln
                2005                2010                2015

Ser Ala Gly Val Leu Gln Thr Arg Gly Val Ala Phe Asp Arg Glu Gln
            2020                2025                2030

Gln Asp Thr His Glu Leu Ala Val Glu Val Arg Asp Asn Arg Thr Pro
        2035                2040                2045

Gln Arg Val Ala Gln Gly Leu Val Arg Val Ser Ile Glu Asp Val Asn
    2050                2055                2060

Asp Asn Pro Pro Lys Phe Lys His Leu Pro Tyr Tyr Thr Ile Ile Gln
2065                2070                2075                2080

Asp Gly Thr Glu Pro Gly Asp Val Leu Phe Gln Val Ser Ala Thr Asp
                2085                2090                2095

Glu Asp Leu Gly Thr Asn Gly Ala Val Thr Tyr Glu Phe Ala Glu Asp
            2100                2105                2110

Tyr Thr Tyr Phe Arg Ile Asp Pro Tyr Leu Gly Asp Ile Ser Leu Lys
        2115                2120                2125

Lys Pro Phe Asp Tyr Gln Ala Leu Asn Lys Tyr His Leu Lys Val Ile
    2130                2135                2140

Ala Arg Asp Gly Gly Thr Pro Ser Leu Gln Ser Glu Glu Glu Val Leu
2145                2150                2155                2160

Val Thr Val Arg Asn Lys Ser Asn Pro Leu Phe Gln Ser Pro Tyr Tyr
                2165                2170                2175

Lys Val Arg Val Pro Glu Asn Ile Thr Leu Tyr Thr Pro Ile Leu His
            2180                2185                2190

Thr Gln Ala Arg Ser Pro Glu Gly Leu Arg Leu Ile Tyr Asn Ile Val
        2195                2200                2205

Glu Glu Glu Pro Leu Met Leu Phe Thr Thr Asp Phe Lys Thr Gly Val
    2210                2215                2220

Leu Thr Val Thr Gly Pro Leu Asp Tyr Glu Ser Lys Thr Lys His Val
2225                2230                2235                2240

Phe Thr Val Arg Ala Thr Asp Thr Ala Leu Gly Ser Phe Ser Glu Ala
                2245                2250                2255

Thr Val Glu Val Leu Val Glu Asp Val Asn Asp Asn Pro Pro Thr Phe
            2260                2265                2270

Ser Gln Leu Val Tyr Thr Thr Ser Ile Ser Glu Gly Leu Pro Ala Gln
        2275                2280                2285

Thr Pro Val Ile Gln Leu Leu Ala Ser Asp Gln Asp Ser Gly Arg Asn
    2290                2295                2300

Arg Asp Val Ser Tyr Gln Ile Val Glu Asp Gly Ser Asp Val Ser Lys
2305                2310                2315                2320

Phe Phe Gln Ile Asn Gly Ser Thr Gly Glu Met Ser Thr Val Gln Glu
                2325                2330                2335

Leu Asp Tyr Glu Ala Gln Gln His Phe His Val Lys Val Arg Ala Met
```

```
        2340                2345                2350

Asp Lys Gly Asp Pro Pro Leu Thr Gly Glu Thr Leu Val Val Val Asn
     2355                2360                2365

Val Ser Asp Ile Asn Asp Asn Pro Pro Glu Phe Arg Gln Pro Gln Tyr
  2370                2375                2380

Glu Ala Asn Val Ser Glu Leu Ala Thr Cys Gly His Leu Val Leu Lys
2385                2390                2395                2400

Val Gln Ala Ile Asp Pro Asp Ser Arg Asp Thr Ser Arg Leu Glu Tyr
            2405                2410                2415

Leu Ile Leu Ser Gly Asn Gln Asp Arg His Phe Phe Ile Asn Ser Ser
        2420                2425                2430

Ser Gly Ile Ile Ser Met Phe Asn Leu Cys Lys Lys His Leu Asp Ser
     2435                2440                2445

Ser Tyr Asn Leu Arg Val Gly Ala Ser Asp Gly Val Phe Arg Ala Thr
  2450                2455                2460

Val Pro Val Tyr Ile Asn Thr Thr Asn Ala Asn Lys Tyr Ser Pro Glu
2465                2470                2475                2480

Phe Gln Gln His Leu Tyr Glu Ala Glu Leu Ala Glu Asn Ala Met Val
            2485                2490                2495

Gly Thr Lys Val Ile Asp Leu Leu Ala Ile Asp Lys Asp Ser Gly Pro
        2500                2505                2510

Tyr Gly Thr Ile Asp Tyr Thr Ile Ile Asn Lys Leu Ala Ser Glu Lys
     2515                2520                2525

Phe Ser Ile Asn Pro Asn Gly Gln Ile Ala Thr Leu Gln Lys Leu Asp
  2530                2535                2540

Arg Glu Asn Ser Thr Glu Arg Val Ile Ala Ile Lys Val Met Ala Arg
2545                2550                2555                2560

Asp Gly Gly Gly Arg Val Ala Phe Cys Thr Val Lys Ile Ile Leu Thr
            2565                2570                2575

Asp Glu Asn Asp Asn Pro Pro Gln Phe Lys Ala Ser Glu Tyr Thr Val
        2580                2585                2590

Ser Ile Gln Ser Asn Val Ser Lys Asp Ser Pro Val Ile Gln Val Leu
     2595                2600                2605

Ala Tyr Asp Ala Asp Glu Gly Gln Asn Ala Asp Val Thr Tyr Ser Val
  2610                2615                2620

Asn Pro Glu Asp Leu Val Lys Asp Val Ile Glu Ile Asn Pro Val Thr
2625                2630                2635                2640

Gly Val Val Lys Val Lys Asp Ser Leu Val Gly Leu Glu Asn Gln Thr
            2645                2650                2655

Leu Asp Phe Phe Ile Lys Ala Gln Asp Gly Gly Pro Pro His Trp Asn
        2660                2665                2670

Ser Leu Val Pro Val Arg Leu Gln Val Val Pro Lys Lys Val Ser Leu
     2675                2680                2685

Pro Lys Phe Ser Glu Pro Leu Tyr Thr Phe Ser Ala Pro Glu Asp Leu
  2690                2695                2700

Pro Glu Gly Ser Glu Ile Gly Ile Val Lys Ala Val Ala Ala Gln Asp
2705                2710                2715                2720

Pro Val Ile Tyr Ser Leu Val Arg Gly Thr Thr Pro Glu Ser Asn Lys
            2725                2730                2735

Asp Gly Val Phe Ser Leu Asp Pro Asp Thr Gly Val Ile Lys Val Arg
        2740                2745                2750

Lys Pro Met Asp His Glu Ser Thr Lys Leu Tyr Gln Ile Asp Val Met
     2755                2760                2765
```

-continued

```
Ala His Cys Leu Gln Asn Thr Asp Val Val Ser Leu Val Ser Val Asn
   2770                2775                2780

Ile Gln Val Gly Asp Val Asn Asp Asn Arg Pro Val Phe Glu Ala Asp
2785                2790                2795                2800

Pro Tyr Lys Ala Val Leu Thr Glu Asn Met Pro Val Gly Thr Ser Val
               2805                2810                2815

Ile Gln Val Thr Ala Ile Asp Lys Asp Thr Gly Arg Asp Gly Gln Val
           2820                2825                2830

Ser Tyr Arg Leu Ser Ala Asp Pro Gly Ser Asn Val His Glu Leu Phe
       2835                2840                2845

Ala Ile Asp Ser Glu Ser Gly Trp Ile Thr Thr Leu Gln Glu Leu Asp
   2850                2855                2860

Cys Glu Thr Cys Gln Thr Tyr His Phe His Val Val Ala Tyr Asp His
2865                2870                2875                2880

Gly Gln Thr Ile Gln Leu Ser Ser Gln Ala Leu Val Gln Val Ser Ile
               2885                2890                2895

Thr Asp Glu Asn Asp Asn Ala Pro Arg Phe Ala Ser Glu Glu Tyr Arg
           2900                2905                2910

Gly Ser Val Val Glu Asn Ser Glu Pro Gly Glu Leu Val Ala Thr Leu
       2915                2920                2925

Lys Thr Leu Asp Ala Asp Ile Ser Glu Gln Asn Arg Gln Val Thr Cys
   2930                2935                2940

Tyr Ile Thr Glu Gly Asp Pro Leu Gly Gln Phe Gly Ile Ser Gln Val
2945                2950                2955                2960

Gly Asp Glu Trp Arg Ile Ser Ser Arg Lys Thr Leu Asp Arg Glu His
               2965                2970                2975

Thr Ala Lys Tyr Leu Leu Arg Val Thr Ala Ser Asp Gly Lys Phe Gln
           2980                2985                2990

Ala Ser Val Thr Val Glu Ile Phe Val Leu Asp Val Asn Asp Asn Ser
       2995                3000                3005

Pro Gln Cys Ser Gln Leu Leu Tyr Thr Gly Lys Val His Glu Asp Val
   3010                3015                3020

Phe Pro Gly His Phe Ile Leu Lys Val Ser Ala Thr Asp Leu Asp Thr
3025                3030                3035                3040

Asp Thr Asn Ala Gln Ile Thr Tyr Ser Leu His Gly Pro Gly Ala His
               3045                3050                3055

Glu Phe Lys Leu Asp Pro His Thr Gly Glu Leu Thr Thr Leu Thr Ala
           3060                3065                3070

Leu Asp Arg Glu Arg Lys Asp Val Phe Asn Leu Val Ala Lys Ala Thr
       3075                3080                3085

Asp Gly Gly Gly Arg Ser Cys Gln Ala Asp Ile Thr Leu His Val Glu
   3090                3095                3100

Asp Val Asn Asp Asn Ala Pro Arg Phe Phe Pro Ser His Cys Ala Val
3105                3110                3115                3120

Ala Val Phe Asp Asn Thr Thr Val Lys Thr Pro Val Ala Val Val Phe
               3125                3130                3135

Ala Arg Asp Pro Asp Gln Gly Ala Asn Ala Gln Val Val Tyr Ser Leu
           3140                3145                3150

Pro Asp Ser Ala Glu Gly His Phe Ser Ile Asp Ala Thr Thr Gly Val
       3155                3160                3165

Ile Arg Leu Glu Lys Pro Leu Gln Val Arg Pro Gln Ala Pro Leu Glu
   3170                3175                3180

Leu Thr Val Arg Ala Ser Asp Leu Gly Thr Pro Ile Pro Leu Ser Thr
3185                3190                3195                3200
```

```
Leu Gly Thr Val Thr Val Ser Val Val Gly Leu Glu Asp Tyr Leu Pro
                3205                3210                3215

Val Phe Leu Asn Thr Glu His Ser Val Gln Val Pro Glu Asp Ala Pro
            3220                3225                3230

Pro Gly Thr Glu Val Leu Gln Leu Ala Thr Leu Thr Arg Pro Gly Ala
        3235                3240                3245

Glu Lys Thr Gly Tyr Arg Val Val Ser Gly Asn Glu Gln Gly Arg Phe
    3250                3255                3260

Arg Leu Asp Ala Arg Thr Gly Ile Leu Tyr Val Asn Ala Ser Leu Asp
3265                3270                3275                3280

Phe Glu Thr Ser Pro Lys Tyr Phe Leu Ser Ile Glu Cys Ser Arg Lys
                3285                3290                3295

Ser Ser Ser Ser Leu Ser Asp Val Thr Thr Val Met Val Asn Ile Thr
            3300                3305                3310

Asp Val Asn Glu His Arg Pro Gln Phe Pro Gln Asp Pro Tyr Ser Thr
        3315                3320                3325

Arg Val Leu Glu Asn Ala Leu Val Gly Asp Val Ile Leu Thr Val Ser
    3330                3335                3340

Ala Thr Asp Glu Asp Gly Pro Leu Asn Ser Asp Ile Thr Tyr Ser Leu
3345                3350                3355                3360

Ile Gly Gly Asn Gln Leu Gly His Phe Thr Ile His Pro Lys Lys Gly
                3365                3370                3375

Glu Leu Gln Val Ala Lys Ala Leu Asp Arg Glu Gln Ala Ser Ser Tyr
            3380                3385                3390

Ser Leu Lys Leu Arg Ala Thr Asp Ser Gly Gln Pro Pro Leu His Glu
        3395                3400                3405

Asp Thr Asp Ile Ala Ile Gln Val Ala Asp Val Asn Asp Asn Pro Pro
    3410                3415                3420

Arg Phe Phe Gln Leu Asn Tyr Ser Thr Thr Val Gln Glu Asn Ser Pro
3425                3430                3435                3440

Ile Gly Ser Lys Val Leu Gln Leu Ile Leu Ser Asp Pro Asp Ser Pro
                3445                3450                3455

Glu Asn Gly Pro Pro Tyr Ser Phe Arg Ile Thr Lys Gly Asn Asn Gly
            3460                3465                3470

Ser Ala Phe Arg Val Thr Pro Asp Gly Trp Leu Val Thr Ala Glu Gly
        3475                3480                3485

Leu Ser Arg Arg Ala Gln Glu Trp Tyr Gln Leu Gln Ile Gln Ala Ser
    3490                3495                3500

Asp Ser Gly Ile Pro Pro Leu Ser Ser Leu Thr Ser Val Arg Val His
3505                3510                3515                3520

Val Thr Glu Gln Ser His Tyr Ala Pro Ser Ala Leu Pro Leu Glu Ile
                3525                3530                3535

Phe Ile Thr Val Gly Glu Asp Glu Phe Gln Gly Gly Met Val Gly Lys
            3540                3545                3550

Ile His Ala Thr Asp Arg Asp Pro Gln Asp Thr Leu Thr Tyr Ser Leu
        3555                3560                3565

Ala Glu Glu Glu Thr Leu Gly Arg His Phe Ser Val Gly Ala Pro Asp
    3570                3575                3580

Gly Lys Ile Ile Ala Ala Gln Gly Leu Pro Arg Gly His Tyr Ser Phe
3585                3590                3595                3600

Asn Val Thr Val Ser Asp Gly Thr Phe Thr Thr Thr Ala Gly Val His
                3605                3610                3615

Val Tyr Val Trp His Val Gly Gln Glu Ala Leu Gln Gln Ala Met Trp
```

-continued

```
        3620                3625                3630

Met Gly Phe Tyr Gln Leu Thr Pro Glu Glu Leu Val Ser Asp His Trp
    3635                3640                3645

Arg Asn Leu Gln Arg Phe Leu Ser His Lys Leu Asp Ile Lys Arg Ala
  3650                3655                3660

Asn Ile His Leu Ala Ser Leu Gln Pro Ala Glu Ala Val Ala Gly Val
3665                3670                3675                3680

Asp Val Leu Leu Val Phe Glu Gly His Ser Gly Thr Phe Tyr Glu Phe
            3685                3690                3695

Gln Glu Leu Ala Ser Ile Ile Thr His Ser Ala Lys Glu Met Glu His
        3700                3705                3710

Ser Val Gly Val Gln Met Arg Ser Ala Met Pro Met Val Pro Cys Gln
    3715                3720                3725

Gly Pro Thr Cys Gln Gly Gln Ile Cys His Asn Thr Val His Leu Asp
  3730                3735                3740

Pro Lys Val Gly Pro Thr Tyr Ser Thr Ala Arg Leu Ser Ile Leu Thr
3745                3750                3755                3760

Pro Arg His His Leu Gln Arg Ser Cys Ser Cys Asn Gly Thr Ala Thr
            3765                3770                3775

Arg Phe Ser Gly Gln Ser Tyr Val Arg Tyr Arg Ala Pro Ala Ala Arg
        3780                3785                3790

Asn Trp His Ile His Phe Tyr Leu Lys Thr Leu Gln Pro Gln Ala Ile
    3795                3800                3805

Leu Leu Phe Thr Asn Glu Thr Ala Ser Val Ser Leu Lys Leu Ala Ser
  3810                3815                3820

Gly Val Pro Gln Leu Glu Tyr His Cys Leu Gly Gly Phe Tyr Gly Asn
3825                3830                3835                3840

Leu Ser Ser Gln Arg His Val Asn Asp His Glu Trp His Ser Ile Leu
            3845                3850                3855

Val Glu Glu Met Asp Ala Ser Ile Arg Leu Met Val Asp Ser Met Gly
        3860                3865                3870

Asn Thr Ser Leu Val Val Pro Glu Asn Cys Arg Gly Leu Arg Pro Glu
    3875                3880                3885

Arg His Leu Leu Leu Gly Gly Leu Ile Leu Leu His Ser Ser Ser Asn
  3890                3895                3900

Val Ser Gln Gly Phe Glu Gly Cys Leu Asp Ala Val Val Val Asn Glu
3905                3910                3915                3920

Glu Ala Leu Asp Leu Leu Ala Pro Gly Lys Thr Val Ala Gly Leu Leu
            3925                3930                3935

Glu Thr Gln Ala Leu Thr Gln Cys Cys Leu His Ser Asp Tyr Cys Ser
        3940                3945                3950

Gln Asn Thr Cys Leu Asn Gly Gly Lys Cys Ser Trp Thr His Gly Ala
    3955                3960                3965

Gly Tyr Val Cys Lys Cys Pro Pro Gln Phe Ser Gly Lys His Cys Glu
  3970                3975                3980

Gln Gly Arg Glu Asn Cys Thr Phe Ala Pro Cys Leu Glu Gly Gly Thr
3985                3990                3995                4000

Cys Ile Leu Ser Pro Lys Gly Ala Ser Cys Asn Cys Pro His Pro Tyr
            4005                4010                4015

Thr Gly Asp Arg Cys Glu Met Glu Ala Arg Gly Cys Ser Glu Gly His
        4020                4025                4030

Cys Leu Val Thr Pro Glu Ile Gln Arg Gly Asp Trp Gly Gln Gln Glu
    4035                4040                4045
```

-continued

```
Leu Leu Ile Ile Thr Val Ala Val Ala Phe Ile Ile Ile Ser Thr Val
   4050                4055                4060

Gly Leu Leu Phe Tyr Cys Arg Arg Cys Lys Ser His Lys Pro Val Ala
4065                4070                4075                4080

Met Glu Asp Pro Asp Leu Leu Ala Arg Ser Val Gly Val Asp Thr Gln
                4085                4090                4095

Ala Met Pro Ala Ile Glu Leu Asn Pro Leu Ser Ala Ser Ser Cys Asn
            4100                4105                4110

Asn Leu Asn Gln Pro Glu Pro Ser Lys Ala Ser Val Pro Asn Glu Leu
        4115                4120                4125

Val Thr Phe Gly Pro Asn Ser Lys Gln Arg Pro Val Val Cys Ser Val
   4130                4135                4140

Pro Pro Arg Leu Pro Pro Ala Ala Val Pro Ser His Ser Asp Asn Glu
4145                4150                4155                4160

Pro Val Ile Lys Arg Thr Trp Ser Ser Glu Glu Met Val Tyr Pro Gly
                4165                4170                4175

Gly Ala Met Val Trp Pro Pro Thr Tyr Ser Arg Asn Glu Arg Trp Glu
            4180                4185                4190

Tyr Pro His Ser Glu Val Thr Gln Gly Pro Leu Pro Pro Ser Ala His
        4195                4200                4205

Arg His Ser Thr Pro Val Val Met Pro Glu Pro Asn Gly Leu Tyr Gly
   4210                4215                4220

Gly Phe Pro Phe Pro Leu Glu Met Glu Asn Lys Arg Ala Pro Leu Pro
4225                4230                4235                4240

Pro Arg Tyr Ser Asn Gln Asn Leu Glu Asp Leu Met Pro Ser Arg Pro
                4245                4250                4255

Pro Ser Pro Arg Glu Arg Leu Val Ala Pro Cys Leu Asn Glu Tyr Thr
            4260                4265                4270

Ala Ile Ser Tyr Tyr His Ser Gln Phe Arg Gln Gly Gly Gly Gly Pro
        4275                4280                4285

Cys Leu Ala Asp Gly Gly Tyr Lys Gly Val Gly Met Arg Leu Ser Arg
   4290                4295                4300

Ala Gly Pro Ser Tyr Ala Val Cys Glu Val Glu Gly Ala Pro Leu Ala
4305                4310                4315                4320

Gly Gln Gly Gln Pro Arg Val Pro Pro Asn Tyr Glu Gly Ser Asp Met
                4325                4330                4335

Val Glu Ser Asp Tyr Gly Ser Cys Glu Glu Val Met Phe
            4340                4345
```

<210> SEQ ID NO 25
<211> LENGTH: 2475
<212> TYPE: DNA
<213> ORGANISM: Homo sapiens
<220> FEATURE:
<223> OTHER INFORMATION: chemokine (C-X-C motif) ligand 5 (CXCL5) cDNA
<220> FEATURE:
<221> NAME/KEY: CDS
<222> LOCATION: (119)..(463)
<223> OTHER INFORMATION: CXCL5

<400> SEQUENCE: 25

```
gtgcagaagg cacgaggaag ccacagtgct ccggatcctc caatcttcgc tcctccaatc      60

tccgctcctc cacccagttc aggaacccgc gaccgctcgc agcgctctct tgaccactat     120

gagcctcctg tccagccgcg cggcccgtgt ccccggtcct tcgagctcct tgtgcgcgct     180

gttggtgctg ctgctgctgc tgacgcagcc agggcccatc gccagcgctg gtcctgccgc     240

tgctgtgttg agagagctgc gttgcgtttg tttacagacc acgcaaggag ttcatcccaa     300
```

```
aatgatcagt aatctgcaag tgttcgccat aggcccacag tgctccaagg tggaagtggt    360
agcctccctg aagaacggga aggaaatttg tcttgatcca gaagcccctt ttctaaagaa    420
agtcatccag aaaattttgg acggtggaaa caaggaaaac tgattaagag aaatgagcac    480
gcatggaaaa gtttcccagt cttcagcaga gaagttttct ggaggtctct gaacccaggg    540
aagacaagaa ggaaagattt tgttgttgtt tgtttatttg tttttccagt agttagcttt    600
cttcctggat tcctcacttt gaagagtgtg aggaaaacct atgtttgccg cttaagcttt    660
cagctcagct aatgaagtgt ttagcatagt acctctgcta tttgctgtta ttttatctgc    720
tatgctattg aagttttggc aattgactat agtgtgagcc aggaatcact ggctgttaat    780
ctttcaaagt gtcttgaatt gtaggtgact attatatttc caagaaatat tccttaagat    840
attaactgag aaggctgtgg atttaatgtg gaaatgatgt ttcataagaa ttctgttgat    900
ggaaatacac tgttatcttc acttttataa gaaataggaa atattttaat gtttcttggg    960
gaatatgtta gagaatttcc ttactcttga ttgtgggata ctatttaatt atttcacttt   1020
agaaagctga gtgtttcaca ccttatctat gtagaatata tttccttatt cagaatttct   1080
aaaagtttaa gttctatgag ggctaatatc ttatcttcct ataattttag acattcttta   1140
tctttttagt atggcaaact gccatcattt acttttaaac tttgatttta tatgctattt   1200
attaagtatt ttattaggag taccataatt ctggtagcta aatatatatt ttagatagat   1260
gaagaagcta gaaaacaggc aaattcctga ctgctagttt atatagaaat gtattctttt   1320
agtttttaaa gtaaaggcaa acttaacaat gacttgtact ctgaaagttt tggaaacgta   1380
ttcaaacaat ttgaatataa atttatcatt tagttataaa aatatatagc gacatcctcg   1440
aggccctagc atttctcctt ggatagggga ccagagagag cttggaatgt taaaaacaaa   1500
acaaaacaaa aaaaaacaag gagaagttgt ccaagggatg tcaatttttt atccctctgt   1560
atgggttaga ttttccaaaa tcataatttg aagaaggcca gcatttatgg tagaatatat   1620
aattatatat aaggtggcca cgctggggca agttccctcc ccactcacag ctttggcccc   1680
tttcacagag tagaacctgg gttagaggat tgcagaagac gagcggcagc ggggagggca   1740
gggaagatgc ctgtcgggtt tttagcacag ttcatttcac tgggattttg aagcatttct   1800
gtctgaatgt aaagcctgtt ctagtcctgg tgggacacac tggggttggg ggtgggggaa   1860
gatgcggtaa tgaaaccggt tagtcagtgt tgtcttaata tccttgataa tgctgtaaag   1920
tttattttta caaatatttc tgtttaagct atttcacctt tgtttggaaa tccttccctt   1980
ttaaagagaa aatgtgacac ttgtgaaaag gcttgtagga aagctcctcc ctttttttct   2040
ttaaaccttt aaatgacaaa cctaggtaat taatggttgt gaatttctat ttttgctttg   2100
tttttaatga acatttgtct ttcagaatag gattctgtga taatatttaa atggcaaaaa   2160
caaaacataa ttttgtgcaa ttaacaaagc tactgcaaga aaaataaaac atttcttggt   2220
aaaaacgtat gtatttatat attatatatt tatatataat atatattata tatttagcat   2280
tgctgagctt tttagatgcc tattgtgtat cttttaaagg ttttgaccat tttgttatga   2340
gtaattacat atatattaca ttcactatat taaaattgta cttttttact atgtgtctca   2400
ttggttcata gtctttattt tgtcctttga ataaacatta aaagatttct aaacttcaaa   2460
aaaaaaaaaa aaaaa                                                    2475
```

<210> SEQ ID NO 26
<211> LENGTH: 114
<212> TYPE: PRT
<213> ORGANISM: Homo sapiens
<220> FEATURE:
<223> OTHER INFORMATION: chemokine (C-X-C motif) ligand 5 (CXCL5)

<400> SEQUENCE: 26

```
Met Ser Leu Leu Ser Ser Arg Ala Ala Arg Val Pro Gly Pro Ser Ser
  1               5                  10                  15

Ser Leu Cys Ala Leu Leu Val Leu Leu Leu Leu Leu Thr Gln Pro Gly
             20                  25                  30

Pro Ile Ala Ser Ala Gly Pro Ala Ala Ala Val Leu Arg Glu Leu Arg
         35                  40                  45

Cys Val Cys Leu Gln Thr Thr Gln Gly Val His Pro Lys Met Ile Ser
     50                  55                  60

Asn Leu Gln Val Phe Ala Ile Gly Pro Gln Cys Ser Lys Val Glu Val
 65                  70                  75                  80

Val Ala Ser Leu Lys Asn Gly Lys Glu Ile Cys Leu Asp Pro Glu Ala
                 85                  90                  95

Pro Phe Leu Lys Lys Val Ile Gln Lys Ile Leu Asp Gly Gly Asn Lys
            100                 105                 110

Glu Asn
```

<210> SEQ ID NO 27
<211> LENGTH: 1905
<212> TYPE: DNA
<213> ORGANISM: Homo sapiens
<220> FEATURE:
<223> OTHER INFORMATION: zinc finger protein 771 (ZNF771), mesenchymal stem cell protein DSC43 (LOC51333) cDNA
<220> FEATURE:
<221> NAME/KEY: CDS
<222> LOCATION: (25)..(852)
<223> OTHER INFORMATION: ZNF771

<400> SEQUENCE: 27

```
gaggtggtga aactcaagat ccccatggac aacaaggagg tcccgggcga ggcgcccgcg     60

ccgtccgccg acccggcgcg tccccacgcg tgccccgact gcggccgcgc cttcgcgcgc    120

cgctccacgc tggcgaagca cgcgcgcacg cacacgggcg aacggccctt cgggtgcacc    180

gagtgcgggc ggcgcttctc acagaagtcg gcgctgacca aacacggccg cacgcacacg    240

ggcgagcggc cctacgagtg ccccgagtgc gacaaacgct tctcggccgc ctcgaacctg    300

cggcagcacc gacggcggca cacgggcgag aagccgtacg catgcgcgca ctgcggccgc    360

cgcttcgcgc agagctccaa ctacgcacag cacctgcgcg tgcacacggg cgagaagccg    420

tacgcgtgcc cggactgcgg acgcgccttt ggcggcagct cgtgcctggc gcgccaccga    480

cgcacgcaca cgggcgagcg gccctacgct tgcgccgact gcggcacgcg cttcgctcag    540

agctcggcgc tggccaagca ccggcgcgtg cacacgggcg agaagccgca ccgctgcgct    600

gtgtgtggcc gtcgcttcgg ccaccgctcc aacctggcgg agcacgcgcg cacgcacaca    660

ggcgagcggc cctacccctg cgccgagtgc ggccgccgct tccgcctaag ctcgcacttc    720

attcgccacc gacgcgcgca catgcggcgc cgcctgtata tttgcgccgg ctgcggcagg    780

gacttcaagc tgccccctgg cgccacggcc gccactgcca ccgagcgttg cccggagtgt    840

gagggcagct gagtcccgca gggctgcgga ggggcgcgct ggggcttcga cctggctgca    900

ctaacccagg ctcctcctcg ccccggcctc cgggtctggg aaattgaggg gacggcaggc    960

ccggctgccc tggaactggg agacagggag aatcccctgc cggggtccct ggaaacagtg   1020

cccaccccac atcactacat tccctcggcc cgtgttagtg aataaagtat tatatcctca   1080

ccccacccgt gcctgtgagt gaggtgggtg ggagaggaag aaagttgggg ttctccaggc   1140
```

```
tcaggtgcca agtgagttgt caaggaacca aatggggatg taaacctaaa aggggttccc   1200

ggcacctcgg tttgtgttgg ttggaggtga tcgcacactt ggcccttggt tacgtcctca   1260

taaccttaga cctgaaaggg cccataaata tactatgttc acgatcagac acgcactgca   1320

ttcggcagag ctccagtgag caaggcacga ccctcagatc tcagtctagt gaaggagaga   1380

aaactgtaat aacactacgt taaaggtttt aactgctttg ttatgtaagc ttacccagcc   1440

cggcgcacag tgactcacgc ctgtaatccc agcactttgg gagggcgagg ctagcagatc   1500

acttgaggtt aggagttcga taccagcctg gccaacatgg tgaaacccgg tctctactaa   1560

aaatacaaaa attaactggg tgtggtggcg ggcgcctgta atcccagcta ctgagggggc   1620

tgaggcatga gaatcacttg aacctgggag acagaggttg caatgaaccg agatagtgcc   1680

attgcactcc ggcctgggca acagaggaag actgcctcaa acaaacaaaa aacaacaaac   1740

caaaccaaac caaaaaaatc tcaaagcgat tggacctagc agctcatgcc tgtaatctcc   1800

agcactttgg gaggcggagg caggaggatc tcttgaagtc aagagtttga gatcagcctg   1860

gagaacaaag tgagaccccc atctattaaa aaaaaaaaaa aaaaa                   1905


<210> SEQ ID NO 28
<211> LENGTH: 275
<212> TYPE: PRT
<213> ORGANISM: Homo sapiens
<220> FEATURE:
<223> OTHER INFORMATION: zinc finger protein 771 (ZNF771), mesenchymal
      stem cell protein DSC43 (LOC51333)

<400> SEQUENCE: 28

Met Asp Asn Lys Glu Val Pro Gly Glu Ala Pro Ala Pro Ser Ala Asp
1               5                   10                  15

Pro Ala Arg Pro His Ala Cys Pro Asp Cys Gly Arg Ala Phe Ala Arg
            20                  25                  30

Arg Ser Thr Leu Ala Lys His Ala Arg Thr His Thr Gly Glu Arg Pro
        35                  40                  45

Phe Gly Cys Thr Glu Cys Gly Arg Arg Phe Ser Gln Lys Ser Ala Leu
    50                  55                  60

Thr Lys His Gly Arg Thr His Thr Gly Glu Arg Pro Tyr Glu Cys Pro
65                  70                  75                  80

Glu Cys Asp Lys Arg Phe Ser Ala Ala Ser Asn Leu Arg Gln His Arg
                85                  90                  95

Arg Arg His Thr Gly Glu Lys Pro Tyr Ala Cys Ala His Cys Gly Arg
            100                 105                 110

Arg Phe Ala Gln Ser Ser Asn Tyr Ala Gln His Leu Arg Val His Thr
        115                 120                 125

Gly Glu Lys Pro Tyr Ala Cys Pro Asp Cys Gly Arg Ala Phe Gly Gly
    130                 135                 140

Ser Ser Cys Leu Ala Arg His Arg Arg Thr His Thr Gly Glu Arg Pro
145                 150                 155                 160

Tyr Ala Cys Ala Asp Cys Gly Thr Arg Phe Ala Gln Ser Ser Ala Leu
                165                 170                 175

Ala Lys His Arg Arg Val His Thr Gly Glu Lys Pro His Arg Cys Ala
            180                 185                 190

Val Cys Gly Arg Arg Phe Gly His Arg Ser Asn Leu Ala Glu His Ala
        195                 200                 205

Arg Thr His Thr Gly Glu Arg Pro Tyr Pro Cys Ala Glu Cys Gly Arg
    210                 215                 220
```

```
Arg Phe Arg Leu Ser Ser His Phe Ile Arg His Arg Arg Ala His Met
225                 230                 235                 240

Arg Arg Arg Leu Tyr Ile Cys Ala Gly Cys Gly Arg Asp Phe Lys Leu
                245                 250                 255

Pro Pro Gly Ala Thr Ala Ala Thr Ala Thr Glu Arg Cys Pro Glu Cys
            260                 265                 270

Glu Gly Ser
        275


<210> SEQ ID NO 29
<211> LENGTH: 2651
<212> TYPE: DNA
<213> ORGANISM: Homo sapiens
<220> FEATURE:
<223> OTHER INFORMATION: natriuretic peptide receptor C/guanylate
      cyclase C (atrionatriuretic peptide receptor C) (NPR3) cDNA
<220> FEATURE:
<221> NAME/KEY: CDS
<222> LOCATION: (219)..(1841)
<223> OTHER INFORMATION: NPR3

<400> SEQUENCE: 29

tctttttctt ttttttttaa gaaaaactag tgacattgca gagaaggacg cttcctctct     60

atcttttggc gcattagtga agggggtatt ctattttgtt aaagcgccca agggggcgca    120

gggaccttgg agagaagagt ggggaggaaa gaggaagggt gggtgggggg cagagggcga    180

gtcggcggcg gcgagggcaa gctctttctt gcggcacgat gccgtctctg ctggtgctca    240

ctttctcccc gtgcgtacta ctcggctggg cgttgctggc cggcggcacc ggtggcggtg    300

gcgttggcgg cggcggcggt ggcgcgggca taggcggcgg acgccaggag agagaggcgc    360

tgccgccaca gaagatcgag gtgctggtgt tactgcccca ggatgactcg tacttgtttt    420

cactcacccg ggtgcggccg gccatcgagt atgctctgcg cagcgtggag ggcaacggga    480

ctgggaggcg gcttctgccg ccgggcactc gcttccaggt ggcttacgag gattcagact    540

gtgggaaccg tgcgctcttc agcttggtgg accgcgtggc ggcggcgcgg ggcgccaagc    600

cagaccttat cctggggcca gtgtgcgagt atgcagcagc gccagtggcc cggcttgcat    660

cgcactggga cctgcccatg ctgtcggctg gggcgctggc cgctggcttc cagcacaagg    720

actctgagta ctcgcacctc acgcgcgtgg cgcccgccta cgccaagatg ggcgagatga    780

tgctcgccct gttccgccac caccactgga gccgcgctgc actggtctac agcgacgaca    840

agctggagcg gaactgctac ttcaccctcg agggggtcca cgaggtcttc caggaggagg    900

gtttgcacac gtccatctac agtttcgacg agaccaaaga cttggatctg gaagacatcg    960

tgcgcaatat ccaggccagt gagagagtgg tgatcatgtg tgcgagcagt gacaccatcc   1020

ggagcatcat gctggtggcg cacaggcatg gcatgaccag tggagactac gccttcttca   1080

acattgagct cttcaacagc tcttcctatg gagatggctc atggaagaga ggagacaaac   1140

acgactttga agctaagcaa gcatactcgt ccctccagac agtcactcta ctgaggacag   1200

tgaaacctga gtttgagaag ttttccatgg aggtgaaaag ttcagttgag aaacaagggc   1260

tcaatatgga ggattacgtt aacatgtttg ttgaaggatt ccacgatgcc atcctcctct   1320

acgtcttggc tctacatgaa gtactcagag ctggttacag caaaaaggat ggagggaaaa   1380

ttatacagca gacttggaac agaacatttg aaggtatcgc cgggcaggtg tccatagatg   1440

ccaacggaga ccgatatggg gatttctctg tgattgccat gactgatgtg gaggcgggca   1500

cccaggaggt tattggtgat tattttggaa aagaaggtcg ttttgaaatg cggccgaatg   1560

tcaaatatcc ttggggccct ttaaaactga gaatagatga aaaccgaatt gtagagcata   1620
```

```
caaacagctc tccctgcaaa tcatgtggcc tagaagaatc ggcagtgaca ggaattgtcg   1680

tgggggcttt actaggagct ggcttgctaa tggccttcta ctttttcagg aagaaataca   1740

gaataaccat tgagaggcga acccagcaag aagaaagtaa ccttggaaaa catcgggaat   1800

tacgggaaga ttccatcaga tcccattttt cagtagctta aaggaagccc cccacttttt   1860

tttttctgc ctgagattct ttaaggagat agacgggttg aaagacatca atgaaacaga    1920

aggggcgttc ttgaagaatt cataatttta agcagttagt aatttcattt taaaatttct   1980

gtagaagctc aggaattatg attaatcacc atctgcctcc aggcctttca tctcatgaca   2040

aacaaatata ataatgatat cgtgtcactc tgttaaatgt tcatactgtt tcaagcccat   2100

atgattagat ttatgttttt aaaatctgtt gtctccatat cttgatggct tttgggagca   2160

tttcacacaa ggatataaaa tgcggttttc ttaaatgaaa tgttttgtag ctagaataaa   2220

atcattttta caagtacagc attcttggaa agaatttaac acccaaaaag gggaaaatgt   2280

aatgaaaaat ctcaaggttg gaaatacagc cttactctct ctagagctgg aggacaggtt   2340

tgtggttgag gacttctctg tccgatgtct acattcaggt tctgacttca tatcttgaaa   2400

aaggatttcc tccctgtctt tttcagtgtc tcataaacgc tactctggat tgttgtaaat   2460

attagtgaga tgggaggatt tacagaagaa aagcaagtca aaaatatttc ctttttgatg   2520

taaaaaaaaa aagccctatt tcgcactaac attttatttt acaagtattt taatcttata   2580

ttttggtatt agaaaaattt gtctattttt tcattttgaa gattaaatgt tgcttacatt   2640

ttaaaaaaaa a                                                        2651
```

```
<210> SEQ ID NO 30
<211> LENGTH: 540
<212> TYPE: PRT
<213> ORGANISM: Homo sapiens
<220> FEATURE:
<223> OTHER INFORMATION: natriuretic peptide receptor C/guanylate
      cyclase C (atrionatriuretic peptide receptor C) (NPR3)

<400> SEQUENCE: 30

Met Pro Ser Leu Leu Val Leu Thr Phe Ser Pro Cys Val Leu Leu Gly
  1               5                  10                  15

Trp Ala Leu Leu Ala Gly Gly Thr Gly Gly Gly Gly Val Gly Gly Gly
             20                  25                  30

Gly Gly Gly Ala Gly Ile Gly Gly Gly Arg Gln Glu Arg Glu Ala Leu
         35                  40                  45

Pro Pro Gln Lys Ile Glu Val Leu Val Leu Leu Pro Gln Asp Asp Ser
     50                  55                  60

Tyr Leu Phe Ser Leu Thr Arg Val Arg Pro Ala Ile Glu Tyr Ala Leu
 65                  70                  75                  80

Arg Ser Val Glu Gly Asn Gly Thr Gly Arg Arg Leu Leu Pro Pro Gly
                 85                  90                  95

Thr Arg Phe Gln Val Ala Tyr Glu Asp Ser Asp Cys Gly Asn Arg Ala
            100                 105                 110

Leu Phe Ser Leu Val Asp Arg Val Ala Ala Ala Arg Gly Ala Lys Pro
        115                 120                 125

Asp Leu Ile Leu Gly Pro Val Cys Glu Tyr Ala Ala Ala Pro Val Ala
    130                 135                 140

Arg Leu Ala Ser His Trp Asp Leu Pro Met Leu Ser Ala Gly Ala Leu
145                 150                 155                 160

Ala Ala Gly Phe Gln His Lys Asp Ser Glu Tyr Ser His Leu Thr Arg
                165                 170                 175
```

-continued

```
Val Ala Pro Ala Tyr Ala Lys Met Gly Glu Met Met Leu Ala Leu Phe
            180                 185                 190

Arg His His His Trp Ser Arg Ala Ala Leu Val Tyr Ser Asp Asp Lys
        195                 200                 205

Leu Glu Arg Asn Cys Tyr Phe Thr Leu Glu Gly Val His Glu Val Phe
    210                 215                 220

Gln Glu Glu Gly Leu His Thr Ser Ile Tyr Ser Phe Asp Glu Thr Lys
225                 230                 235                 240

Asp Leu Asp Leu Glu Asp Ile Val Arg Asn Ile Gln Ala Ser Glu Arg
                245                 250                 255

Val Val Ile Met Cys Ala Ser Ser Asp Thr Ile Arg Ser Ile Met Leu
            260                 265                 270

Val Ala His Arg His Gly Met Thr Ser Gly Asp Tyr Ala Phe Phe Asn
        275                 280                 285

Ile Glu Leu Phe Asn Ser Ser Ser Tyr Gly Asp Gly Ser Trp Lys Arg
    290                 295                 300

Gly Asp Lys His Asp Phe Glu Ala Lys Gln Ala Tyr Ser Ser Leu Gln
305                 310                 315                 320

Thr Val Thr Leu Leu Arg Thr Val Lys Pro Glu Phe Glu Lys Phe Ser
                325                 330                 335

Met Glu Val Lys Ser Ser Val Glu Lys Gln Gly Leu Asn Met Glu Asp
            340                 345                 350

Tyr Val Asn Met Phe Val Glu Gly Phe His Asp Ala Ile Leu Leu Tyr
        355                 360                 365

Val Leu Ala Leu His Glu Val Leu Arg Ala Gly Tyr Ser Lys Lys Asp
    370                 375                 380

Gly Gly Lys Ile Ile Gln Gln Thr Trp Asn Arg Thr Phe Glu Gly Ile
385                 390                 395                 400

Ala Gly Gln Val Ser Ile Asp Ala Asn Gly Asp Arg Tyr Gly Asp Phe
                405                 410                 415

Ser Val Ile Ala Met Thr Asp Val Glu Ala Gly Thr Gln Glu Val Ile
            420                 425                 430

Gly Asp Tyr Phe Gly Lys Glu Gly Arg Phe Glu Met Arg Pro Asn Val
        435                 440                 445

Lys Tyr Pro Trp Gly Pro Leu Lys Leu Arg Ile Asp Glu Asn Arg Ile
    450                 455                 460

Val Glu His Thr Asn Ser Ser Pro Cys Lys Ser Cys Gly Leu Glu Glu
465                 470                 475                 480

Ser Ala Val Thr Gly Ile Val Val Gly Ala Leu Leu Gly Ala Gly Leu
                485                 490                 495

Leu Met Ala Phe Tyr Phe Phe Arg Lys Lys Tyr Arg Ile Thr Ile Glu
            500                 505                 510

Arg Arg Thr Gln Gln Glu Glu Ser Asn Leu Gly Lys His Arg Glu Leu
        515                 520                 525

Arg Glu Asp Ser Ile Arg Ser His Phe Ser Val Ala
    530                 535                 540
```

```
<210> SEQ ID NO 31
<211> LENGTH: 2984
<212> TYPE: DNA
<213> ORGANISM: Homo sapiens
<220> FEATURE:
<223> OTHER INFORMATION: early growth response 2 (Krox-20 homolog,
      Drosophila) (EGR2) cDNA
<220> FEATURE:
<221> NAME/KEY: CDS
```

-continued

<222> LOCATION: (339)..(1769)
<223> OTHER INFORMATION: EGR2

<400> SEQUENCE: 31
taactgagcg aggagcaatt gattaatagc tcggcgaggg gactcactga ctgttataat 60
aacactacac cagcaactcc tggcttccca gcagccggaa cacagacagg agagagtcag 120
tggcaaatag acatttttct tatttcttaa aaaacagcaa cttgtttgct acttttattt 180
ctgttgattt ttttttcttg gtgtgtgtgg tggttgtttt taagtgtgga gggcaaaagg 240
agataccatc ccaggctcag tccaacccct ctccaaaacg gcttttctga cactccaggt 300
agcgagggag ttgggtctcc aggttgtgcg aggagcaaat gatgaccgcc aaggccgtag 360
acaaaatccc agtaactctc agtggttttg tgcaccagct gtctgacaac atctacccgg 420
tggaggacct cgccgccacg tcggtgacca tctttcccaa tgccgaactg ggaggcccct 480
ttgaccagat gaacggagtg gccggagatg gcatgatcaa cattgacatg actggagaga 540
agaggtcgtt ggatctccca tatcccagca gctttgctcc cgtctctgca cctagaaacc 600
agaccttcac ttacatgggc aagttctcca ttgaccctca gtaccctggt gccagctgct 660
acccagaagg cataatcaat attgtgagtg caggcatctt gcaaggggtc acttccccag 720
cttcaaccac agcctcatcc agcgtcacct ctgcctcccc caacccactg gccacaggac 780
ccctgggtgt gtgcaccatg tcccagaccc agcctgacct ggaccacctg tactctccgc 840
caccgcctcc tcctccttat tctggctgtg caggagacct ctaccaggac ccttctgcgt 900
tcctgtcagc agccaccacc tccacctctt cctctctggc ctacccacca cctccttcct 960
atccatcccc caagccagcc acggacccag gtctcttccc aatgatccca gactatcctg 1020
gattctttcc atctcagtgc cagagagacc tacatggtac agctggccca gaccgtaagc 1080
cctttccctg cccactggac accctgcggg tgcccccctcc actcactcca ctctctacaa 1140
tccgtaactt taccctgggg ggccccagtg ctggggtgac cggaccaggg gccagtggag 1200
gcagcgaggg accccggctg cctggtagca gctcagcagc agcagcagcc gccgccgccg 1260
ccgcctataa cccacaccac ctgccactgc ggcccattct gaggcctcgc aagtacccca 1320
acagacccag caagacgccg gtgcacgaga ggccctaccc gtgcccagca gaaggctgcg 1380
accggcggtt ctcccgctct gacgagctga cacggcacat ccgaatccac actgggcata 1440
agcccttcca gtgtcggatc tgcatgcgca acttcagccg cagtgaccac ctcaccaccc 1500
atatccgcac ccacaccggt gagaagccct tcgcctgtga ctactgtggc cgaaagtttg 1560
cccggagtga tgagaggaag cgccacacca agatccacct gagacagaaa gagcggaaaa 1620
gcagtgcccc ctctgcatcg gtgccagccc cctctacagc ctcctgctct gggggcgtgc 1680
agcctggggg taccctgtgc agcagtaaca gcagcagtct tggcggaggg ccgctcgccc 1740
cttgctcctc tcggacccgg acaccttgag atgagactca ggctgataca ccagctccca 1800
aaggtcccgg aggccctttg tccactggag ctgcacaaca aacactacca ccctttcctg 1860
tccctctctc cctttgttgg gcaaagggct ttggtggagc tagcactgcc cccttttccac 1920 ctagaagcag gttcttccta aaacttagcc cattctagtc tctcttaggt gagttgacta 1980
tcaacccaag gcaaagggga ggctcagaag gaggtggtgt ggggatcccc tggccaagag 2040
ggctgaggtc tgaccctgct ttaaagggtt gtttgactag gttttgctac cccacttccc 2100
cttattttga cccatcacag gtttttgacc ctggatgtca gagttgatct aagacgtttt 2160
ctacaatagg ttgggagatg ctgatccctt caagtgggga cagcaaaaag acaagcaaaa 2220
ctgatgtgca ctttatggct tgggactgat ttgggggaca ttgtacagtg agtgaagtat 2280

```
agcctttatg ccacactctg tggccctaaa atggtgaatc agagcatatc tagttgtctc   2340

aacccttgaa gcaatatgta ttatatactc agagaacaga agtgcaatgt gatgggagga   2400

acgtagcaat atctgctcct tttcgagttg tttgagaaat gtaggctatt ttttcagtgt   2460

atatccactc agattttgtg tatttttgat gtacccacac tgttctctaa attctgaatc   2520

tttgggaaaa aatgtaaagc atttatgatc tcagaggtta acttatttaa gggggatgta   2580

catattctct gaaactagga tgcatgcaat tgtgttggaa gtgtccttgg tcgccttgtg   2640

tgatgtagac aaatgttaca aggctgcatg taaatgggtt gccttattat ggagaaaaaa   2700

atcactccct gagtttagta tggctgtata tttatgccta ttaatatttg gaattttttt   2760

tagaaagtat atttttgtat gctttgtttt gtgacttaaa agtgttacct ttgtagtcaa   2820

atttcagata agaatgtaca taatgttacc ggagctgatt tgtttggtca ttagctctta   2880

atagttgtga aaaaataaat ctattctaac gcaaaaccac taactgaagt tcagatataa   2940

tggatggttt gtgactatag tgtaaataaa tacttttcaa caat                    2984


<210> SEQ ID NO 32
<211> LENGTH: 476
<212> TYPE: PRT
<213> ORGANISM: Homo sapiens
<220> FEATURE:
<223> OTHER INFORMATION: early growth response 2 (Krox-20 homolog,
      Drosophila) (EGR2)

<400> SEQUENCE: 32

Met Met Thr Ala Lys Ala Val Asp Lys Ile Pro Val Thr Leu Ser Gly
  1               5                  10                  15

Phe Val His Gln Leu Ser Asp Asn Ile Tyr Pro Val Glu Asp Leu Ala
             20                  25                  30

Ala Thr Ser Val Thr Ile Phe Pro Asn Ala Glu Leu Gly Gly Pro Phe
         35                  40                  45

Asp Gln Met Asn Gly Val Ala Gly Asp Gly Met Ile Asn Ile Asp Met
     50                  55                  60

Thr Gly Glu Lys Arg Ser Leu Asp Leu Pro Tyr Pro Ser Ser Phe Ala
 65                  70                  75                  80

Pro Val Ser Ala Pro Arg Asn Gln Thr Phe Thr Tyr Met Gly Lys Phe
                 85                  90                  95

Ser Ile Asp Pro Gln Tyr Pro Gly Ala Ser Cys Tyr Pro Glu Gly Ile
            100                 105                 110

Ile Asn Ile Val Ser Ala Gly Ile Leu Gln Gly Val Thr Ser Pro Ala
        115                 120                 125

Ser Thr Thr Ala Ser Ser Ser Val Thr Ser Ala Ser Pro Asn Pro Leu
    130                 135                 140

Ala Thr Gly Pro Leu Gly Val Cys Thr Met Ser Gln Thr Gln Pro Asp
145                 150                 155                 160

Leu Asp His Leu Tyr Ser Pro Pro Pro Pro Pro Pro Pro Tyr Ser Gly
                165                 170                 175

Cys Ala Gly Asp Leu Tyr Gln Asp Pro Ser Ala Phe Leu Ser Ala Ala
            180                 185                 190

Thr Thr Ser Thr Ser Ser Ser Leu Ala Tyr Pro Pro Pro Pro Ser Tyr
        195                 200                 205

Pro Ser Pro Lys Pro Ala Thr Asp Pro Gly Leu Phe Pro Met Ile Pro
    210                 215                 220

Asp Tyr Pro Gly Phe Phe Pro Ser Gln Cys Gln Arg Asp Leu His Gly
225                 230                 235                 240
```

```
Thr Ala Gly Pro Asp Arg Lys Pro Phe Pro Cys Pro Leu Asp Thr Leu
                245                 250                 255

Arg Val Pro Pro Pro Leu Thr Pro Leu Ser Thr Ile Arg Asn Phe Thr
            260                 265                 270

Leu Gly Gly Pro Ser Ala Gly Val Thr Gly Pro Gly Ala Ser Gly Gly
        275                 280                 285

Ser Glu Gly Pro Arg Leu Pro Gly Ser Ser Ser Ala Ala Ala Ala Ala
    290                 295                 300

Ala Ala Ala Ala Ala Tyr Asn Pro His His Leu Pro Leu Arg Pro Ile
305                 310                 315                 320

Leu Arg Pro Arg Lys Tyr Pro Asn Arg Pro Ser Lys Thr Pro Val His
                325                 330                 335

Glu Arg Pro Tyr Pro Cys Pro Ala Glu Gly Cys Asp Arg Arg Phe Ser
            340                 345                 350

Arg Ser Asp Glu Leu Thr Arg His Ile Arg Ile His Thr Gly His Lys
        355                 360                 365

Pro Phe Gln Cys Arg Ile Cys Met Arg Asn Phe Ser Arg Ser Asp His
    370                 375                 380

Leu Thr Thr His Ile Arg Thr His Thr Gly Glu Lys Pro Phe Ala Cys
385                 390                 395                 400

Asp Tyr Cys Gly Arg Lys Phe Ala Arg Ser Asp Glu Arg Lys Arg His
                405                 410                 415

Thr Lys Ile His Leu Arg Gln Lys Glu Arg Lys Ser Ser Ala Pro Ser
            420                 425                 430

Ala Ser Val Pro Ala Pro Ser Thr Ala Ser Cys Ser Gly Gly Val Gln
        435                 440                 445

Pro Gly Gly Thr Leu Cys Ser Ser Asn Ser Ser Ser Leu Gly Gly Gly
    450                 455                 460

Pro Leu Ala Pro Cys Ser Ser Arg Thr Arg Thr Pro
465                 470                 475


<210> SEQ ID NO 33
<211> LENGTH: 1725
<212> TYPE: DNA
<213> ORGANISM: Homo sapiens
<220> FEATURE:
<223> OTHER INFORMATION: leukocyte immunoglobulin-like receptor,
      subfamily A (with TM domain), member 4 (LILRA4), immunoglobulin-
      like transcript 7 (ILT7) cDNA
<220> FEATURE:
<221> NAME/KEY: CDS
<222> LOCATION: (58)..(1557)
<223> OTHER INFORMATION: LILRA4

<400> SEQUENCE: 33

ctacgggcac cgtggccaca cctgcctgca cagccagggc caggaggagg agatgccatg      60

accctcattc tcacaagcct gctcttcttt gggctgagcc tgggccccag gacccgggtg     120

caggcagaaa acctacccaa acccatcctg tgggccgagc caggtcccgt gatcacctgg     180

cataaccccg tgaccatctg gtgtcagggc accctggagg cccaggggta ccgtctggat     240

aaagagggaa actcaatgtc gaggcacata ttaaaaacac tggagtctga aaacaaggtc     300

aaactctcca tcccatccat gatgtgggaa catgcagggc gatatcactg ttactatcag     360

agccctgcag gctggtcaga gcccagcgac cccctggagc tggtggtgac agcctacagc     420

agacccaccc tgtccgcact gccaagccct gtggtgacct caggagtgaa cgtgaccctc     480

cggtgtgcct cacggctggg actgggcagg ttcactctga ttgaggaagg agaccacagg     540
```

```
ctctcctgga ccctgaactc acaccaacac aaccatggaa agttccaggc cctgttcccc    600

atgggccccc tgaccttcag caacaggggt acattcagat gctacggcta tgaaaacaac    660

accccatacg tgtggtcgga acccagtgac cccctgcagc tactggtgtc aggcgtgtct    720

aggaagccct ccctcctgac cctgcagggc cctgtcgtga cccccggaga gaatctgacc    780

ctccagtgtg gctctgatgt cggctacatc agatacactc tgtacaagga gggggccgat    840

ggcctccccc agcgccctgg ccggcagccc caggctgggc tctcccaggc caacttcacc    900

ctgagccctg tgagccgctc ctacgggggc cagtacagat gctacggcgc acacaacgtc    960

tcctccgagt ggtcggcccc cagtgacccc ctggacatcc tgatcgcagg acagatctct   1020

gacagaccct ccctctcagt gcagccgggc cccacggtga cctcaggaga gaaggtgacc   1080

ctgctgtgtc agtcatggga cccgatgttc actttccttc tgaccaagga gggggcagcc   1140

catcccccgt tgcgtctgag atcaatgtac ggagctcata agtaccaggc tgaattcccc   1200

atgagtcctg tgacctcagc ccacgcgggg acctacaggt gctacggctc acgcagctcc   1260

aacccctacc tgctgtctca ccccagtgag cccctggagc tcgtggtctc aggagcaact   1320

gagaccctca atccagcaca aaagaagtca gattccaaga ctgccccaca cctccaggat   1380

tacacagtgg agaatctcat ccgcatgggt gtggctggct tggtcctgct gttcctcggg   1440

attctgttat ttgaggctca gcacagccag agaagccccc caaggtgcag ccaggaggca   1500

aacagcagaa aggacaatgc acccttcaga gtggtggagc cttgggaaca gatctgatga   1560

tctgaggagg ttctggaaga ctggggcagc agttggggaa gtgtctgctg agaatatcaa   1620

ggggaagaag catgggtcag gtgcaggaag atgtctgggt gtctgtagaa gatgcttcct   1680

ccattaaact gtggtgcttt cctcctcaaa aaaaaaaaaa aaaaa                  1725
```

```
<210> SEQ ID NO 34
<211> LENGTH: 499
<212> TYPE: PRT
<213> ORGANISM: Homo sapiens
<220> FEATURE:
<223> OTHER INFORMATION: leukocyte immunoglobulin-like receptor,
      subfamily A (with TM domain), member 4 (LILRA4), immunoglobulin-
      like transcript 7 (ILT7)

<400> SEQUENCE: 34

Met Thr Leu Ile Leu Thr Ser Leu Leu Phe Phe Gly Leu Ser Leu Gly
  1               5                  10                  15

Pro Arg Thr Arg Val Gln Ala Glu Asn Leu Pro Lys Pro Ile Leu Trp
             20                  25                  30

Ala Glu Pro Gly Pro Val Ile Thr Trp His Asn Pro Val Thr Ile Trp
         35                  40                  45

Cys Gln Gly Thr Leu Glu Ala Gln Gly Tyr Arg Leu Asp Lys Glu Gly
     50                  55                  60

Asn Ser Met Ser Arg His Ile Leu Lys Thr Leu Glu Ser Glu Asn Lys
 65                  70                  75                  80

Val Lys Leu Ser Ile Pro Ser Met Met Trp Glu His Ala Gly Arg Tyr
                 85                  90                  95

His Cys Tyr Tyr Gln Ser Pro Ala Gly Trp Ser Glu Pro Ser Asp Pro
            100                 105                 110

Leu Glu Leu Val Val Thr Ala Tyr Ser Arg Pro Thr Leu Ser Ala Leu
        115                 120                 125

Pro Ser Pro Val Val Thr Ser Gly Val Asn Val Thr Leu Arg Cys Ala
    130                 135                 140

Ser Arg Leu Gly Leu Gly Arg Phe Thr Leu Ile Glu Glu Gly Asp His
```

-continued

```
145                 150                 155                 160

Arg Leu Ser Trp Thr Leu Asn Ser His Gln His Asn His Gly Lys Phe
                165                 170                 175

Gln Ala Leu Phe Pro Met Gly Pro Leu Thr Phe Ser Asn Arg Gly Thr
            180                 185                 190

Phe Arg Cys Tyr Gly Tyr Glu Asn Asn Thr Pro Tyr Val Trp Ser Glu
        195                 200                 205

Pro Ser Asp Pro Leu Gln Leu Leu Val Ser Gly Val Ser Arg Lys Pro
    210                 215                 220

Ser Leu Leu Thr Leu Gln Gly Pro Val Val Thr Pro Gly Glu Asn Leu
225                 230                 235                 240

Thr Leu Gln Cys Gly Ser Asp Val Gly Tyr Ile Arg Tyr Thr Leu Tyr
                245                 250                 255

Lys Glu Gly Ala Asp Gly Leu Pro Gln Arg Pro Gly Arg Gln Pro Gln
            260                 265                 270

Ala Gly Leu Ser Gln Ala Asn Phe Thr Leu Ser Pro Val Ser Arg Ser
        275                 280                 285

Tyr Gly Gly Gln Tyr Arg Cys Tyr Gly Ala His Asn Val Ser Ser Glu
    290                 295                 300

Trp Ser Ala Pro Ser Asp Pro Leu Asp Ile Leu Ile Ala Gly Gln Ile
305                 310                 315                 320

Ser Asp Arg Pro Ser Leu Ser Val Gln Pro Gly Pro Thr Val Thr Ser
                325                 330                 335

Gly Glu Lys Val Thr Leu Leu Cys Gln Ser Trp Asp Pro Met Phe Thr
            340                 345                 350

Phe Leu Leu Thr Lys Glu Gly Ala Ala His Pro Pro Leu Arg Leu Arg
        355                 360                 365

Ser Met Tyr Gly Ala His Lys Tyr Gln Ala Glu Phe Pro Met Ser Pro
    370                 375                 380

Val Thr Ser Ala His Ala Gly Thr Tyr Arg Cys Tyr Gly Ser Arg Ser
385                 390                 395                 400

Ser Asn Pro Tyr Leu Leu Ser His Pro Ser Glu Pro Leu Glu Leu Val
                405                 410                 415

Val Ser Gly Ala Thr Glu Thr Leu Asn Pro Ala Gln Lys Lys Ser Asp
            420                 425                 430

Ser Lys Thr Ala Pro His Leu Gln Asp Tyr Thr Val Glu Asn Leu Ile
        435                 440                 445

Arg Met Gly Val Ala Gly Leu Val Leu Leu Phe Leu Gly Ile Leu Leu
    450                 455                 460

Phe Glu Ala Gln His Ser Gln Arg Ser Pro Pro Arg Cys Ser Gln Glu
465                 470                 475                 480

Ala Asn Ser Arg Lys Asp Asn Ala Pro Phe Arg Val Val Glu Pro Trp
                485                 490                 495

Glu Gln Ile
```

<210> SEQ ID NO 35
<211> LENGTH: 837
<212> TYPE: DNA
<213> ORGANISM: Homo sapiens
<220> FEATURE:
<223> OTHER INFORMATION: prostaglandin D2 synthase 21kDa (brain)
(PTGDS) cDNA
<220> FEATURE:
<221> NAME/KEY: CDS
<222> LOCATION: (76)..(648)
<223> OTHER INFORMATION: PTGDS

<400> SEQUENCE: 35

```
gctcctcctg cacacctccc tcgctctccc acaccactgg caccaggccc cggacacccg     60
ctctgctgca ggagaatggc tactcatcac acgctgtgga tgggactggc cctgctgggg    120
gtgctgggcg acctgcaggc agcaccggag gcccaggtct ccgtgcagcc caacttccag    180
caggacaagt tcctggggcg ctggttcagc gcgggcctcg cctccaactc gagctggctc    240
cgggagaaga aggcggcgtt gtccatgtgc aagtctgtgg tggcccctgc cacggatggt    300
ggcctcaacc tgacctccac cttcctcagg aaaaaccagt gtgagacccg aaccatgctg    360
ctgcagcccg cggggtccct cggctcctac agctaccgga gtccccactg ggcagcacc     420
tactccgtgt cagtggtgga gaccgactac gaccagtacg cgctgctgta cagccagggc    480
agcaagggcc ctggcgagga cttccgcatg gccaccctct acagccgaac ccagaccccc    540
agggctgagt taaaggagaa attcaccgcc ttctgcaagg cccagggctt cacagaggat    600
accattgtct tcctgcccca aaccgataag tgcatgacgg aacaatagga ctccccaggg    660
ctgaagctgg gatcccggcc agccaggtga cccccacgct ctggatgtct ctgctctgtt    720
ccttccccga gcccctgccc cggctccccg ccaaagcaac cctgcccact caggcttcat    780
cctgcacaat aaactccgga agcaagtcag taaaaaaaaa aaaaaaaaaa aaaaaaa       837
```

<210> SEQ ID NO 36
<211> LENGTH: 190
<212> TYPE: PRT
<213> ORGANISM: Homo sapiens
<220> FEATURE:
<223> OTHER INFORMATION: prostaglandin D2 synthase 21kDa (brain) (PTGDS)

<400> SEQUENCE: 36

```
Met Ala Thr His His Thr Leu Trp Met Gly Leu Ala Leu Leu Gly Val
1               5                   10                  15

Leu Gly Asp Leu Gln Ala Ala Pro Glu Ala Gln Val Ser Val Gln Pro
            20                  25                  30

Asn Phe Gln Gln Asp Lys Phe Leu Gly Arg Trp Phe Ser Ala Gly Leu
        35                  40                  45

Ala Ser Asn Ser Ser Trp Leu Arg Glu Lys Lys Ala Ala Leu Ser Met
    50                  55                  60

Cys Lys Ser Val Val Ala Pro Ala Thr Asp Gly Gly Leu Asn Leu Thr
65                  70                  75                  80

Ser Thr Phe Leu Arg Lys Asn Gln Cys Glu Thr Arg Thr Met Leu Leu
                85                  90                  95

Gln Pro Ala Gly Ser Leu Gly Ser Tyr Ser Tyr Arg Ser Pro His Trp
            100                 105                 110

Gly Ser Thr Tyr Ser Val Ser Val Val Glu Thr Asp Tyr Asp Gln Tyr
        115                 120                 125

Ala Leu Leu Tyr Ser Gln Gly Ser Lys Gly Pro Gly Glu Asp Phe Arg
    130                 135                 140

Met Ala Thr Leu Tyr Ser Arg Thr Gln Thr Pro Arg Ala Glu Leu Lys
145                 150                 155                 160

Glu Lys Phe Thr Ala Phe Cys Lys Ala Gln Gly Phe Thr Glu Asp Thr
                165                 170                 175

Ile Val Phe Leu Pro Gln Thr Asp Lys Cys Met Thr Glu Gln
            180                 185                 190
```

<210> SEQ ID NO 37
<211> LENGTH: 3213

<212> TYPE: DNA
<213> ORGANISM: Homo sapiens
<220> FEATURE:
<223> OTHER INFORMATION: periostin, osteoblast specific factor (POSTN) cDNA
<220> FEATURE:
<221> NAME/KEY: CDS
<222> LOCATION: (12)..(2522)
<223> OTHER INFORMATION: POSTN

<400> SEQUENCE: 37

```
agagactcaa gatgattccc tttttaccca tgttttctct actattgctg cttattgtta     60

accctataaa cgccaacaat cattatgaca agatcttggc tcatagtcgt atcaggggtc    120

gggaccaagg cccaaatgtc tgtgcccttc aacagatttt gggcaccaaa aagaaatact    180

tcagcacttg taagaactgg tataaaaagt ccatctgtgg acagaaaacg actgttttat    240

atgaatgttg ccctggttat atgagaatgg aaggaatgaa aggctgccca gcagttttgc    300

ccattgacca tgtttatggc actctgggca tcgtgggagc caccacaacg cagcgctatt    360

ctgacgcctc aaaactgagg gaggagatcg agggaaaggg atccttcact tactttgcac    420

cgagtaatga ggcttgggac aacttggatt ctgatatccg tagaggtttg gagagcaacg    480

tgaatgttga attactgaat gctttacata gtcacatgat taataagaga atgttgacca    540

aggacttaaa aaatggcatg attattcctt caatgtataa caatttgggg cttttcatta    600

accattatcc taatggggtt gtcactgtta attgtgctcg aatcatccat gggaaccaga    660

ttgcaacaaa tggtgttgtc catgtcattg accgtgtgct tacacaaatt ggtacctcaa    720

ttcaagactt cattgaagca gaagatgacc tttcatcttt tagagcagct gccatcacat    780

cggacatatt ggaggccctt ggaagagacg gtcacttcac actctttgct cccaccaatg    840

aggcttttga gaaacttcca cgaggtgtcc tagaaaggtt catgggagac aaagtggctt    900

ccgaagctct tatgaagtac cacatcttaa atactctcca gtgttctgag tctattatgg    960

gaggagcagt ctttgagacg ctggaaggaa atacaattga gataggatgt gacggtgaca   1020

gtataacagt aaatggaatc aaaatggtga acaaaaagga tattgtgaca aataatggtg   1080

tgatccattt gattgatcag gtcctaattc ctgattctgc caaacaagtt attgagctgg   1140

ctggaaaaca gcaaaccacc ttcacggatc ttgtggccca attaggcttg gcatctgctc   1200

tgaggccaga tggagaatac actttgctgg cacctgtgaa taatgcattt tctgatgata   1260

ctctcagcat ggttcagcgc ctccttaaat taattctgca gaatcacata ttgaaagtaa   1320

aagttggcct taatgagctt tacaacgggc aaatactgga aaccatcgga ggcaaacagc   1380

tcagagtctt cgtatatcgt acagctgtct gcattgaaaa ttcatgcatg gagaaaggga   1440

gtaagcaagg gagaaacggt gcgattcaca tattccgcga gatcatcaag ccagcagaga   1500

aatccctcca tgaaaagtta aaacaagata agcgctttag caccttcctc agcctacttg   1560

aagctgcaga cttgaaagag ctcctgacac aacctggaga ctggacatta tttgtgccaa   1620

ccaatgatgc ttttaaggga atgactagtg aagaaaaaga aattctgata cgggacaaaa   1680

atgctcttca aaacatcatt ctttatcacc tgacaccagg agttttcatt ggaaaaggat   1740

ttgaacctgg tgttactaac attttaaaga ccacacaagg aagcaaaatc tttctgaaag   1800

aagtaaatga tacacttctg gtgaatgaat tgaaatcaaa agaatctgac atcatgacaa   1860

caaatggtgt aattcatgtt gtagataaac tcctctatcc agcagacaca cctgttggaa   1920

atgatcaact gctggaaata cttaataaat taatcaaata catccaaatt aagtttgttc   1980

gtggtagcac cttcaaagaa atccccgtga ctgtctatac aactaaaatt ataaccaaag   2040
```

-continued

```
ttgtggaacc aaaaattaaa gtgattgaag gcagtcttca gcctattatc aaaactgaag   2100

gacccacact aacaaaagtc aaaattgaag gtgaacctga attcagactg attaaagaag   2160

gtgaaacaat aactgaagtg atccatggag agccaattat taaaaaatac accaaaatca   2220

ttgatggagt gcctgtggaa ataactgaaa aagagacacg agaagaacga atcattacag   2280

gtcctgaaat aaaatacact aggatttcta ctggaggtgg agaaacagaa gaaactctga   2340

agaaattgtt acaagaagag gtcaccaagg tcaccaaatt cattgaaggt ggtgatggtc   2400

atttatttga agatgaagaa attaaaagac tgcttcaggg agacacaccc gtgaggaagt   2460

tgcaagccaa caaaaaagtt caaggttcta gaagacgatt aagggaaggt cgttctcagt   2520

gaaaatccaa aaaccagaaa aaaatgttta tacaacccta agtcaataac ctgaccttag   2580

aaaattgtga gagccaagtt gacttcagga actgaaacat cagcacaaag aagcaatcat   2640

caaataattc tgaacacaaa tttaatattt ttttttctga atgagaaaca tgagggaaat   2700

tgtggagtta gcctcctgtg gtaaaggaat tgaagaaaat ataacacctt acaccctttt   2760

tcatcttgac attaaaagtt ctggctaact ttggaatcca ttagagaaaa atccttgtca   2820

ccagattcat tacaattcaa atcgaagagt tgtgaactgt tatcccattg aaaagaccga   2880

gccttgtatg tatgttatgg atacataaaa tgcacgcaag ccattatctc tccatgggaa   2940

gctaagttat aaaaataggt gcttggtgta caaaactttt tatatcaaaa ggctttgcac   3000

atttctatat gagtgggttt actggtaaat tatgttattt tttacaacta attttgtact   3060

ctcagaatgt ttgtcatatg cttcttgcaa tgcatatttt ttaatctcaa acgtttcaat   3120

aaaaccattt ttcagatata aagagaatta cttcaaattg agtaattcag aaaaactcaa   3180

gatttaagtt aaaaagtggt ttggacttgg gaa                                3213
```

```
<210> SEQ ID NO 38
<211> LENGTH: 836
<212> TYPE: PRT
<213> ORGANISM: Homo sapiens
<220> FEATURE:
<223> OTHER INFORMATION: periostin, osteoblast specific factor (POSTN)

<400> SEQUENCE: 38

Met Ile Pro Phe Leu Pro Met Phe Ser Leu Leu Leu Leu Leu Ile Val
 1               5                  10                  15

Asn Pro Ile Asn Ala Asn Asn His Tyr Asp Lys Ile Leu Ala His Ser
            20                  25                  30

Arg Ile Arg Gly Arg Asp Gln Gly Pro Asn Val Cys Ala Leu Gln Gln
        35                  40                  45

Ile Leu Gly Thr Lys Lys Lys Tyr Phe Ser Thr Cys Lys Asn Trp Tyr
    50                  55                  60

Lys Lys Ser Ile Cys Gly Gln Lys Thr Thr Val Leu Tyr Glu Cys Cys
65                  70                  75                  80

Pro Gly Tyr Met Arg Met Glu Gly Met Lys Gly Cys Pro Ala Val Leu
                85                  90                  95

Pro Ile Asp His Val Tyr Gly Thr Leu Gly Ile Val Gly Ala Thr Thr
            100                 105                 110

Thr Gln Arg Tyr Ser Asp Ala Ser Lys Leu Arg Glu Glu Ile Glu Gly
        115                 120                 125

Lys Gly Ser Phe Thr Tyr Phe Ala Pro Ser Asn Glu Ala Trp Asp Asn
    130                 135                 140

Leu Asp Ser Asp Ile Arg Arg Gly Leu Glu Ser Asn Val Asn Val Glu
145                 150                 155                 160
```

-continued

```
Leu Leu Asn Ala Leu His Ser His Met Ile Asn Lys Arg Met Leu Thr
                165                 170                 175

Lys Asp Leu Lys Asn Gly Met Ile Ile Pro Ser Met Tyr Asn Asn Leu
            180                 185                 190

Gly Leu Phe Ile Asn His Tyr Pro Asn Gly Val Val Thr Val Asn Cys
        195                 200                 205

Ala Arg Ile Ile His Gly Asn Gln Ile Ala Thr Asn Gly Val Val His
    210                 215                 220

Val Ile Asp Arg Val Leu Thr Gln Ile Gly Thr Ser Ile Gln Asp Phe
225                 230                 235                 240

Ile Glu Ala Glu Asp Asp Leu Ser Ser Phe Arg Ala Ala Ala Ile Thr
                245                 250                 255

Ser Asp Ile Leu Glu Ala Leu Gly Arg Asp Gly His Phe Thr Leu Phe
            260                 265                 270

Ala Pro Thr Asn Glu Ala Phe Glu Lys Leu Pro Arg Gly Val Leu Glu
        275                 280                 285

Arg Phe Met Gly Asp Lys Val Ala Ser Glu Ala Leu Met Lys Tyr His
    290                 295                 300

Ile Leu Asn Thr Leu Gln Cys Ser Glu Ser Ile Met Gly Gly Ala Val
305                 310                 315                 320

Phe Glu Thr Leu Glu Gly Asn Thr Ile Glu Ile Gly Cys Asp Gly Asp
                325                 330                 335

Ser Ile Thr Val Asn Gly Ile Lys Met Val Asn Lys Lys Asp Ile Val
            340                 345                 350

Thr Asn Asn Gly Val Ile His Leu Ile Asp Gln Val Leu Ile Pro Asp
        355                 360                 365

Ser Ala Lys Gln Val Ile Glu Leu Ala Gly Lys Gln Gln Thr Thr Phe
    370                 375                 380

Thr Asp Leu Val Ala Gln Leu Gly Leu Ala Ser Ala Leu Arg Pro Asp
385                 390                 395                 400

Gly Glu Tyr Thr Leu Leu Ala Pro Val Asn Asn Ala Phe Ser Asp Asp
                405                 410                 415

Thr Leu Ser Met Val Gln Arg Leu Leu Lys Leu Ile Leu Gln Asn His
            420                 425                 430

Ile Leu Lys Val Lys Val Gly Leu Asn Glu Leu Tyr Asn Gly Gln Ile
        435                 440                 445

Leu Glu Thr Ile Gly Gly Lys Gln Leu Arg Val Phe Val Tyr Arg Thr
    450                 455                 460

Ala Val Cys Ile Glu Asn Ser Cys Met Glu Lys Gly Ser Lys Gln Gly
465                 470                 475                 480

Arg Asn Gly Ala Ile His Ile Phe Arg Glu Ile Ile Lys Pro Ala Glu
                485                 490                 495

Lys Ser Leu His Glu Lys Leu Lys Gln Asp Lys Arg Phe Ser Thr Phe
            500                 505                 510

Leu Ser Leu Leu Glu Ala Ala Asp Leu Lys Glu Leu Leu Thr Gln Pro
        515                 520                 525

Gly Asp Trp Thr Leu Phe Val Pro Thr Asn Asp Ala Phe Lys Gly Met
    530                 535                 540

Thr Ser Glu Glu Lys Glu Ile Leu Ile Arg Asp Lys Asn Ala Leu Gln
545                 550                 555                 560

Asn Ile Ile Leu Tyr His Leu Thr Pro Gly Val Phe Ile Gly Lys Gly
                565                 570                 575

Phe Glu Pro Gly Val Thr Asn Ile Leu Lys Thr Thr Gln Gly Ser Lys
            580                 585                 590
```

Ile Phe Leu Lys Glu Val Asn Asp Thr Leu Leu Val Asn Glu Leu Lys
595 600 605

Ser Lys Glu Ser Asp Ile Met Thr Thr Asn Gly Val Ile His Val Val
610 615 620

Asp Lys Leu Leu Tyr Pro Ala Asp Thr Pro Val Gly Asn Asp Gln Leu
625 630 635 640

Leu Glu Ile Leu Asn Lys Leu Ile Lys Tyr Ile Gln Ile Lys Phe Val
645 650 655

Arg Gly Ser Thr Phe Lys Glu Ile Pro Val Thr Val Tyr Thr Thr Lys
660 665 670

Ile Ile Thr Lys Val Val Glu Pro Lys Ile Lys Val Ile Glu Gly Ser
675 680 685

Leu Gln Pro Ile Ile Lys Thr Glu Gly Pro Thr Leu Thr Lys Val Lys
690 695 700

Ile Glu Gly Glu Pro Glu Phe Arg Leu Ile Lys Glu Gly Glu Thr Ile
705 710 715 720

Thr Glu Val Ile His Gly Glu Pro Ile Ile Lys Lys Tyr Thr Lys Ile
725 730 735

Ile Asp Gly Val Pro Val Glu Ile Thr Glu Lys Glu Thr Arg Glu Glu
740 745 750

Arg Ile Ile Thr Gly Pro Glu Ile Lys Tyr Thr Arg Ile Ser Thr Gly
755 760 765

Gly Gly Glu Thr Glu Glu Thr Leu Lys Lys Leu Leu Gln Glu Glu Val
770 775 780

Thr Lys Val Thr Lys Phe Ile Glu Gly Gly Asp Gly His Leu Phe Glu
785 790 795 800

Asp Glu Glu Ile Lys Arg Leu Leu Gln Gly Asp Thr Pro Val Arg Lys
805 810 815

Leu Gln Ala Asn Lys Lys Val Gln Gly Ser Arg Arg Arg Leu Arg Glu
820 825 830

Gly Arg Ser Gln
835

<210> SEQ ID NO 39
<211> LENGTH: 5855
<212> TYPE: DNA
<213> ORGANISM: Homo sapiens
<220> FEATURE:
<223> OTHER INFORMATION: wingless-type MMTV integration site family, member 5A (WNT5A) cDNA
<220> FEATURE:
<221> NAME/KEY: CDS
<222> LOCATION: (319)..(1461)
<223> OTHER INFORMATION: WNT5A

<400> SEQUENCE: 39
agttgcctgc gcgccctcgc cggaccggcg gctccctagt tgcgccccga ccaggccctg 60
cccttgctgc cggctcgcgc gcgtccgcgc cccctccatt cctgggcgca tcccagctct 120
gccccaactc gggagtccag gcccgggcgc cagtgcccgc ttcagctccg gttcactgcg 180
cccgccggac gcgcgccgga ggactccgca gccctgctcc tgaccgtccc cccaggctta 240
acccggtcgc tccgctcgga ttcctcggct gcgctcgctc gggtggcgac ttcctccccg 300
cgccccctcc ccctcgccat gaagaagtcc attggaatat taagcccagg agttgctttg 360
gggatggctg gaagtgcaat gtcttccaag ttcttcctag tggctttggc catatttttc 420
tccttcgccc aggttgtaat tgaagccaat tcttggtggt cgctaggtat gaataaccct 480

-continued

```
gttcagatgt cagaagtata tattatagga gcacagcctc tctgcagcca actggcagga    540
ctttctcaag gacagaagaa actgtgccac ttgtatcagg accacatgca gtacatcgga    600
gaaggcgcga agacaggcat caaagaatgc cagtatcaat tccgacatcg aaggtggaac    660
tgcagcactg tggataacac ctctgttttt ggcagggtga tgcagatagg cagccgcgag    720
acggccttca catacgcggt gagcgcagca ggggtggtga acgccatgag ccgggcgtgc    780
cgcgagggcg agctgtccac ctgcggctgc agccgcgccg cgcgccccaa ggacctgccg    840
cgggactggc tctggggcgg ctgcggcgac aacatcgact atggctaccg ctttgccaag    900
gagttcgtgg acgcccgcga gcgggagcgc atccacgcca agggctccta cgagagtgct    960
cgcatcctca tgaacctgca caacaacgag gccggccgca ggacggtgta caacctggct   1020
gatgtggcct gcaagtgcca tggggtgtcc ggctcatgta gcctgaagac atgctggctg   1080
cagctggcag acttccgcaa ggtgggtgat gccctgaagg agaagtacga cagcgcggcg   1140
gccatgcggc tcaacagccg ggcaagttg gtacaggtca acagccgctt caactcgccc    1200
accacacaag acctggtcta catcgacccc agccctgact actgcgtgcg caatgagagc   1260
accggctcgc tgggcacgca gggccgcctg tgcaacaaga cgtcggaggg catggatggc   1320
tgcgagctca tgtgctgcgg ccgtggctac gaccagttca agaccgtgca gacggagcgc   1380
tgccactgca agttccactg gtgctgctac gtcaagtgca agaagtgcac ggagatcgtg   1440
gaccagtttg tgtgcaagta gtgggtgcca cccagcactc agccccgctc ccaggacccg   1500
cttatttata gaaagtacag tgattctggt ttttggtttt tagaaatatt ttttattttt   1560
ccccaagaat tgcaaccgga accatttttt ttcctgttac catctaagaa ctctgtggtt   1620
tattattaat attataatta ttatttggca ataatggggg tgggaaccaa gaaaaatatt   1680
tattttgtgg atctttgaaa aggtaataca agacttcttt tgatagtata gaatgaaggg   1740
gaaataacac ataccctaac ttagctgtgt ggacatggta cacatccaga aggtaaagaa   1800
atacattttc tttttctcaa atatgccatc atatgggatg ggtaggttcc agttgaaaga   1860
gggtggtaga aatctattca caattcagct tctatgacca aaatgagttg taaattctct   1920
ggtgcaagat aaaaggtctt gggaaaacaa aacaaaacaa aacaaacctc ccttccccag   1980
cagggctgct agcttgcttt ctgcattttc aaaatgataa tttacaatgg aaggacaaga   2040
atgtcatatt ctcaaggaaa aaaggtatat cacatgtctc attctcctca aatattccat   2100
ttgcagacag accgtcatat tctaatagct catgaaattt gggcagcagg gaggaaagtc   2160
cccagaaatt aaaaaattta aaactcttat gtcaagatgt tgatttgaag ctgttataag   2220
aattaggatt ccagattgta aaaagatccc caaatgattc tggacactag attttttttgt  2280
ttggggaggt tggcttgaac ataaatgaaa atatcctgtt attttcttag ggatacttgg   2340
ttagtaaatt ataatagtaa aaataataca tgaatcccat tcacaggttc tcagcccaag   2400
caacaaggta attgcgtgcc attcagcact gcaccagagc agacaaccta tttgaggaaa   2460
aacagtgaaa tccaccttcc tcttcacact gagccctctc tgattcctcc gtgttgtgat   2520
gtgatgctgg ccacgtttcc aaacggcagc tccactgggt cccctttggt tgtaggacag   2580
gaaatgaaac attaggagct ctgcttggaa aacagttcac tacttaggga tttttgtttc   2640
ctaaaacttt tattttgagg agcagtagtt ttctatgttt taatgacaga acttggctaa   2700
tggaattcac agaggtgttg cagcgtatca ctgttatgat cctgtgttta gattatccac   2760
tcatgcttct cctattgtac tgcaggtgta ccttaaaact gttcccagtg tacttgaaca   2820
gttgcattta taagggggga aatgtggttt aatggtgcct gatatctcaa agtcttttgt   2880
```

-continued

```
acataacata tatatatata tacatatata taaatataaa tataaatata tctcattgca   2940
gccagtgatt tagatttaca gtttactctg ggttatttc tctgtctaga gcattgttgt   3000
ccttcactgc agtccagttg ggattattcc aaaagttttt tgagtcttga gcttgggctg   3060
tggccctgct gtgatcatac cttgagcacg acgaagcaac cttgtttctg aggaagcttg   3120
agttctgact cactgaaatg cgtgttgggt tgaagatatc ttttttcttt tctgcctcac   3180
ccctttgtct ccaacctcca tttctgttca ctttgtggag agggcattac ttgttcgtta   3240
tagacatgga cgttaagaga tattcaaaac tcagaagcat cagcaatgtt tctcttttct   3300
tagttcattc tgcagaatgg aaacccatgc ctattagaaa tgacagtact tattaattga   3360
gtccctaagg aatattcagc ccactacata gatagctttt tttttttttt ttttaataag   3420
gacacctctt tccaaacagt gccatcaaat atgttcttat ctcagactta cgttgtttta   3480
aaagtttgga aagatacaca tctttcatac ccccttagg caggttggct ttcatatcac   3540
ctcagccaac tgtggctctt aatttattgc ataatgatat tcacatcccc tcagttgcag   3600
tgaattgtga gcaaaagatc ttgaaagcaa aaagcactaa ttagtttaaa atgtcacttt   3660
tttggttttt attatacaaa aaccatgaag tacttttttt atttgctaaa tcagattgtt   3720
cctttttagt gactcatgtt tatgaagaga gttgagttta acaatcctag cttttaaaag   3780
aaactattta atgtaaaata ttctacatgt cattcagata ttatgtatat cttctagcct   3840
ttattctgta cttttaatgt acatatttct gtcttgcgtg atttgtatat ttcactggtt   3900
taaaaaacaa acatcgaaag gcttatgcca aatggaagat agaatataaa ataaaacgtt   3960
acttgtatat tggtaagtgg tttcaattgt ccttcagata attcatgtgg agatttttgg   4020
agaaaccatg acggatagtt taggatgact acatgtcaaa gtaataaaag agtggtgaat   4080
tttaccaaaa ccaagctatt tggaagcttc aaaaggtttc tatatgtaat ggaacaaaag   4140
gggaattctc ttttcctata tatgttcctt acaaaaaaaa aaaaaaaaga aatcaagcag   4200
atggcttaaa gctggttata ggattgctca cattctttta gcattatgca tgtaacttaa   4260
ttgttttaga gcgtgttgct gttgtaacat cccagagaag aatgaaaagg cacatgcttt   4320
tatccgtgac cagattttta gtccaaaaaa atgtattttt ttgtgtgttt accactgcaa   4380
ctattgcacc tctctatttg aatttactgt ggaccatgtg tggtgtctct atgccctttg   4440
aaagcagttt ttataaaaag aaagcccggg tctgcagaga atgaaaactg gttggaaact   4500
aaaggttcat tgtgttaagt gcaattaata caagttattg tgcttttcaa aaatgtacac   4560
ggaaatctgg acagtgctgc acagattgat acattagcct ttgctttttc tctttccgga   4620
taaccttgta acatattgaa accttttaag gatgccaaga atgcattatt ccacaaaaaa   4680
acagcagacc aacatataga gtgtttaaaa tagcatttct gggcaaattc aaactcttgt   4740
ggttctagga ctcacatctg tttcagtttt tcctcagttg tatattgacc agtgttcttt   4800
attgcaaaaa catataccccg atttagcagt gtcagcgtat tttttcttct catcctggag   4860
cgtattcaag atcttcccaa tacaagaaaa ttaataaaaa atttatatat aggcagcagc   4920
aaaagagcca tgttcaaaat agtcattatg ggctcaaata gaaagaagac ttttaagttt   4980
taatccagtt tatctgttga gttctgtgag ctactgacct cctgagactg gcactgtgta   5040
agttttagtt gcctacccta gctcttttct cgtacaattt tgccaatacc aagtttcaat   5100
ttgtttttac aaaacattat tcaagccact agaattatca aatatgacgc tatagcagag   5160
taaatactct gaataagaga ccggtactag ctaactccaa gagatcgtta gcagcatcag   5220
tccacaaaca cttagtggcc cacaatatat agagagatag aaaaggtagt tataacttga   5280
```

-continued

```
agcatgtatt taatgcaaat aggcacgaag gcacaggtct aaaatactac attgtcactg   5340

taagctatac ttttaaaata tttatttttt ttaaagtatt ttctagtctt ttctctctct   5400

gtggaatggt gaaagagaga tgccgtgttt tgaaagtaag atgatgaaat gaatttttaa   5460

ttcaagaaac attcagaaac ataggaatta aaacttagag aaatgatcta atttccctgt   5520

tcacacaaac tttacacttt aatctgatga ttggatattt tattttagtg aaacatcatc   5580

ttgttagcta actttaaaaa atggatgtag aatgattaaa ggttggtatg attttttttt   5640

aatgtatcag tttgaaccta gaatattgaa ttaaaatgct gtctcagtat tttaaaagca   5700

aaaaaggaat ggaggaaaat tgcatcttag accatttta tatgcagtgt acaatttgct   5760

gggctagaaa tgagataaag attatttatt tttgttcata tcttgtactt ttctattaaa   5820

atcattttat gaaatccaaa aaaaaaaaaa aaaaa                              5855


<210> SEQ ID NO 40
<211> LENGTH: 380
<212> TYPE: PRT
<213> ORGANISM: Homo sapiens
<220> FEATURE:
<223> OTHER INFORMATION: wingless-type MMTV integration site family,
      member 5A (WNT5A)

<400> SEQUENCE: 40

Met Lys Lys Ser Ile Gly Ile Leu Ser Pro Gly Val Ala Leu Gly Met
  1               5                  10                  15

Ala Gly Ser Ala Met Ser Ser Lys Phe Phe Leu Val Ala Leu Ala Ile
             20                  25                  30

Phe Phe Ser Phe Ala Gln Val Val Ile Glu Ala Asn Ser Trp Trp Ser
         35                  40                  45

Leu Gly Met Asn Asn Pro Val Gln Met Ser Glu Val Tyr Ile Ile Gly
     50                  55                  60

Ala Gln Pro Leu Cys Ser Gln Leu Ala Gly Leu Ser Gln Gly Gln Lys
 65                  70                  75                  80

Lys Leu Cys His Leu Tyr Gln Asp His Met Gln Tyr Ile Gly Glu Gly
                 85                  90                  95

Ala Lys Thr Gly Ile Lys Glu Cys Gln Tyr Gln Phe Arg His Arg Arg
            100                 105                 110

Trp Asn Cys Ser Thr Val Asp Asn Thr Ser Val Phe Gly Arg Val Met
        115                 120                 125

Gln Ile Gly Ser Arg Glu Thr Ala Phe Thr Tyr Ala Val Ser Ala Ala
    130                 135                 140

Gly Val Val Asn Ala Met Ser Arg Ala Cys Arg Glu Gly Glu Leu Ser
145                 150                 155                 160

Thr Cys Gly Cys Ser Arg Ala Ala Arg Pro Lys Asp Leu Pro Arg Asp
                165                 170                 175

Trp Leu Trp Gly Gly Cys Gly Asp Asn Ile Asp Tyr Gly Tyr Arg Phe
            180                 185                 190

Ala Lys Glu Phe Val Asp Ala Arg Glu Arg Glu Arg Ile His Ala Lys
        195                 200                 205

Gly Ser Tyr Glu Ser Ala Arg Ile Leu Met Asn Leu His Asn Asn Glu
    210                 215                 220

Ala Gly Arg Arg Thr Val Tyr Asn Leu Ala Asp Val Ala Cys Lys Cys
225                 230                 235                 240

His Gly Val Ser Gly Ser Cys Ser Leu Lys Thr Cys Trp Leu Gln Leu
                245                 250                 255

Ala Asp Phe Arg Lys Val Gly Asp Ala Leu Lys Glu Lys Tyr Asp Ser
```

```
            260                 265                 270

Ala Ala Ala Met Arg Leu Asn Ser Arg Gly Lys Leu Val Gln Val Asn
        275                 280                 285

Ser Arg Phe Asn Ser Pro Thr Thr Gln Asp Leu Val Tyr Ile Asp Pro
    290                 295                 300

Ser Pro Asp Tyr Cys Val Arg Asn Glu Ser Thr Gly Ser Leu Gly Thr
305                 310                 315                 320

Gln Gly Arg Leu Cys Asn Lys Thr Ser Glu Gly Met Asp Gly Cys Glu
                325                 330                 335

Leu Met Cys Cys Gly Arg Gly Tyr Asp Gln Phe Lys Thr Val Gln Thr
            340                 345                 350

Glu Arg Cys His Cys Lys Phe His Trp Cys Cys Tyr Val Lys Cys Lys
        355                 360                 365

Lys Cys Thr Glu Ile Val Asp Gln Phe Val Cys Lys
    370                 375                 380


<210> SEQ ID NO 41

<400> SEQUENCE: 41

000


<210> SEQ ID NO 42

<400> SEQUENCE: 42

000


<210> SEQ ID NO 43
<211> LENGTH: 487
<212> TYPE: DNA
<213> ORGANISM: Homo sapiens
<220> FEATURE:
<223> OTHER INFORMATION: defensin, alpha 3, neutrophil-specific (DEFA3)
      cDNA
<220> FEATURE:
<221> NAME/KEY: CDS
<222> LOCATION: (86)..(370)
<223> OTHER INFORMATION: DEFA3

<400> SEQUENCE: 43

ccttgctata gaagacctgg gacagaggac tgctgtctgc cctctctggt caccctgcct      60

agctagagga tctgtgaccc cagccatgag gaccctcgcc atccttgctg ccattctcct     120

ggtggccctg caggcccagg ctgagccact ccaggcaaga gctgatgagg ttgctgcagc     180

cccggagcag attgcagcgg acatcccaga agtggttgtt tcccttgcat gggacgaaag     240

cttggctcca aagcatccag gctcaaggaa aaacatggac tgctattgca gaataccagc     300

gtgcattgca ggagaacgtc gctatggaac ctgcatctac cagggaagac tctgggcatt     360

ctgctgctga gcttgcagaa aaagaaaaat gagctcaaaa tttgctttga gagctacagg     420

gaattgctat tactcctgta ccttctgctc aatttccttt cctcatctca aataaatgcc     480

ttgttac                                                               487


<210> SEQ ID NO 44
<211> LENGTH: 91
<212> TYPE: PRT
<213> ORGANISM: Homo sapiens
<220> FEATURE:
<223> OTHER INFORMATION: defensin, alpha 3, neutrophil-specific
      (DEFA3)

<400> SEQUENCE: 44
```

-continued

```
Met Arg Thr Leu Ala Ile Leu Ala Ala Ile Leu Leu Val Ala Leu Gln
  1               5                  10                  15

Ala Gln Ala Glu Pro Leu Gln Ala Arg Ala Asp Glu Val Ala Ala Ala
             20                  25                  30

Pro Glu Gln Ile Ala Ala Asp Ile Pro Glu Val Val Val Ser Leu Ala
         35                  40                  45

Trp Asp Glu Ser Leu Ala Pro Lys His Pro Gly Ser Arg Lys Asn Met
     50                  55                  60

Asp Cys Tyr Cys Arg Ile Pro Ala Cys Ile Ala Gly Glu Arg Arg Tyr
 65                  70                  75                  80

Gly Thr Cys Ile Tyr Gln Gly Arg Leu Trp Ala
                 85                  90


<210> SEQ ID NO 45
<211> LENGTH: 1262
<212> TYPE: DNA
<213> ORGANISM: Homo sapiens
<220> FEATURE:
<223> OTHER INFORMATION: POU domain, class 1, transcription factor 1
      (POU1F1), growth hormone factor 1 (GHF-1),
      pituitary-specific transcription factor 1 (Pit1)
      cDNA
<220> FEATURE:
<221> NAME/KEY: CDS
<222> LOCATION: (86)..(370)
<223> OTHER INFORMATION: DEFA3

<400> SEQUENCE: 45

ctcagagcct tcctgatgta tatatgcagg tagtgagaat tgaatcggcc ctttgagaca     60

gtaatataat aaaactctga tttggggagc agcggttctc cttatttttc tactctcttg    120

tgggaatgag ttgccaagct tttacttcgg ctgatacctt tatacctctg aattctgacg    180

cctctgcaac tctgcctctg ataatgcatc acagtgctgc cgagtgtcta ccagtctcca    240

accatgccac caatgtgatg tctacagcaa caggacttca ttattctgtt ccttcctgtc    300

attatggaaa ccagccatca acctatggag tgatggcagg tagtttaacc ccttgtcttt    360

ataaatttcc tgaccacacc ttgagtcatg gatttcctcc tatacaccag cctcttctgg    420

cagaggaccc cacagctgct gatttcaagc aggaactcag gcggaaaagt aaattggtgg    480

aagagccaat agacatggat tctccagaaa tcagagaact tgaaaagttt gccaatgaat    540

ttaaagtgag acgaattaaa ttaggataca cccagacaaa tgttggggag gccctggcag    600

ctgtgcatgg ctctgaattc agtcaaacaa caatctgccg atttgaaaat ctgcagctca    660

gctttaaaaa tgcatgcaaa ctgaaagcaa tattatccaa atggctggag gaagctgagc    720

aagtaggagc tttgtacaat gaaaaagtgg gagcaaatga aaggaaaaga aaacgaagaa    780

caactataag cattgctgct aaagatgctc tggagagaca ctttggagaa cagaataaac    840

cttcttctca agagatcatg aggatggctg aagaactgaa tctggagaaa gaagtagtaa    900

gagtttggtt ttgcaaccgg aggcagagag aaaaacgggt gaaaacaagt ctgaatcaga    960

gtttattttc tatttctaag gaacatcttg agtgcagata agatttttct attgtataat   1020

agcctttttc tcccgtttca ttcctttctc ttcctcaaca aaaacagaaa ttacttggtt   1080

gacttaaaat cattttatat caatagcttt tacagaagct ttacttttcc actttttttt   1140

aaaaaaaaga aaccaacaat ttaaattata ttgatgttat ttacttaaaa taattattct   1200

cagaagccac attatctatt ttaagccaaa tatattaaca gtaataaaat gatctctctg   1260

tc                                                                  1262
```

<210> SEQ ID NO 46
<211> LENGTH: 291
<212> TYPE: PRT
<213> ORGANISM: Homo sapiens
<220> FEATURE:
<223> OTHER INFORMATION: POU domain, class 1, transcription factor 1 (POU1F1), growth hormone factor 1 (GHF-1), pituitary-specific transcription factor 1 (Pit1)

<400> SEQUENCE: 46

```
Met Ser Cys Gln Ala Phe Thr Ser Ala Asp Thr Phe Ile Pro Leu Asn
  1               5                  10                  15

Ser Asp Ala Ser Ala Thr Leu Pro Leu Ile Met His His Ser Ala Ala
             20                  25                  30

Glu Cys Leu Pro Val Ser Asn His Ala Thr Asn Val Met Ser Thr Ala
         35                  40                  45

Thr Gly Leu His Tyr Ser Val Pro Ser Cys His Tyr Gly Asn Gln Pro
     50                  55                  60

Ser Thr Tyr Gly Val Met Ala Gly Ser Leu Thr Pro Cys Leu Tyr Lys
 65                  70                  75                  80

Phe Pro Asp His Thr Leu Ser His Gly Phe Pro Pro Ile His Gln Pro
                 85                  90                  95

Leu Leu Ala Glu Asp Pro Thr Ala Ala Asp Phe Lys Gln Glu Leu Arg
            100                 105                 110

Arg Lys Ser Lys Leu Val Glu Glu Pro Ile Asp Met Asp Ser Pro Glu
        115                 120                 125

Ile Arg Glu Leu Glu Lys Phe Ala Asn Glu Phe Lys Val Arg Arg Ile
    130                 135                 140

Lys Leu Gly Tyr Thr Gln Thr Asn Val Gly Glu Ala Leu Ala Ala Val
145                 150                 155                 160

His Gly Ser Glu Phe Ser Gln Thr Thr Ile Cys Arg Phe Glu Asn Leu
                165                 170                 175

Gln Leu Ser Phe Lys Asn Ala Cys Lys Leu Lys Ala Ile Leu Ser Lys
            180                 185                 190

Trp Leu Glu Glu Ala Glu Gln Val Gly Ala Leu Tyr Asn Glu Lys Val
        195                 200                 205

Gly Ala Asn Glu Arg Lys Arg Lys Arg Arg Thr Thr Ile Ser Ile Ala
    210                 215                 220

Ala Lys Asp Ala Leu Glu Arg His Phe Gly Glu Gln Asn Lys Pro Ser
225                 230                 235                 240

Ser Gln Glu Ile Met Arg Met Ala Glu Glu Leu Asn Leu Glu Lys Glu
                245                 250                 255

Val Val Arg Val Trp Phe Cys Asn Arg Arg Gln Arg Glu Lys Arg Val
            260                 265                 270

Lys Thr Ser Leu Asn Gln Ser Leu Phe Ser Ile Ser Lys Glu His Leu
        275                 280                 285

Glu Cys Arg
    290
```

<210> SEQ ID NO 47
<211> LENGTH: 3842
<212> TYPE: DNA
<213> ORGANISM: Homo sapiens
<220> FEATURE:
<223> OTHER INFORMATION: cadherin 13, H-cadherin (heart) (CDH13) cDNA
<220> FEATURE:
<221> NAME/KEY: CDS
<222> LOCATION: (121)..(2262)
<223> OTHER INFORMATION: CDH13

<400> SEQUENCE: 47
gggaagttgg ctggctggcg aggcagagcc tctcctcaaa gcctggctcc cacggaaaat 60
atgctcagtg cagccgcgtg catgaatgaa aacgccgccg ggcgcttcta gtcggacaaa 120
atgcagccga gaactccgct cgttctgtgc gttctcctgt cccaggtgct gctgctaaca 180
tctgcagaag atttggactg cactcctgga tttcagcaga aagtgttcca tatcaatcag 240
ccagctgaat tcattgagga ccagtcaatt ctaaacttga ccttcagtga ctgtaaggga 300
aacgacaagc tacgctatga ggtctcgagc ccatacttca aggtgaacag cgatggcggc 360
ttagttgctc tgagaaacat aactgcagtg ggcaaaactc tgttcgtcca tgcacggacc 420
ccccatgcgg aagatatggc agaactcgtg attgtcgggg ggaaagacat ccagggctcc 480
ttgcaggata tatttaaatt tgcaagaact tctcctgtcc caagacaaaa gaggtccatt 540
gtggtatctc ccattttaat tccagagaat cagagacagc ctttcccaag agatgttggc 600
aaggtagtcg atagtgacag gccagaaagg tccaagttcc ggctcactgg aaagggagtg 660
gatcaagagc ctaaaggaat tttcagaatc aatgagaaca cagggagcgt ctccgtgaca 720
cggaccttgg acagagaagt aatcgctgtt tatcaactat ttgtggagac cactgatgtc 780
aatggcaaaa ctctcgaggg gccggtgcct ctggaagtca ttgtgattga tcagaatgac 840
aaccgaccga tctttcggga aggcccctac atcggccacg tcatggaagg gtcacccaca 900
ggcaccacag tgatgcggat gacagccttt gatgcagatg acccagccac cgataatgcc 960
ctcctgcggt ataatatccg tcagcagacg cctgacaagc catctcccaa catgttctac 1020
atcgatcctg agaaaggaga cattgtcact gttgtgtcac ctgcgctgct ggaccgagag 1080
actctggaaa atcccaagta tgaactgatc atcgaggctc aagatatggc tggactggat 1140
gttggattaa caggcacggc cacagccacg atcatgatcg atgacaaaaa tgatcactca 1200
ccaaaattca ccaagaaaga gtttcaagcc acagtcgagg aaggagctgt gggagttatt 1260
gtcaatttga cagttgaaga taaggatgac cccaccacag gtgcatggag ggctgcctac 1320
accatcatca acggaaaccc cgggcagagc tttgaaatcc acaccaaccc tcaaaccaac 1380
gaagggatgc tttctgttgt caaaccattg gactatgaaa tttctgcctt ccacaccctg 1440
ctgatcaaag tggaaaatga agacccactc gtacccgacg tctcctacgg ccccagctcc 1500
acagccaccg tccacatcac tgtcctggat gtcaacgagg gcccagtctt ctacccagac 1560
cccatgatgg tgaccaggca ggaggacctc tctgtgggca gcgtgctgct gacagtgaat 1620
gccacggacc ccgactccct gcagcatcaa accatcaggt attctgttta caaggaccca 1680
gcaggttggc tgaatattaa ccccatcaat gggactgttg acaccacagc tgtgctggac 1740
cgtgagtccc catttgtcga caacagcgtg tacactgctc tcttcctggc aattgacagt 1800
ggcaaccctc ccgctacggg cactgggact ttgctgataa ccctggagga cgtgaatgac 1860
aatgccccgt tcatttaccc cacagtagct gaagtctgtg atgatgccaa aaacctcagt 1920
gtagtcattt tgggagcatc agataaggat cttcacccga atacagatcc tttcaaattt 1980
gaaatccaca aacaagctgt tcctgataaa gtctggaaga tctccaagat caacaataca 2040
cacgccctgg taagccttct tcaaaatctg aacaaagcaa actacaacct gcccatcatg 2100
gtgacagatt cagggaaacc acccatgacg aatatcacag atctcagggt acaagtgtgc 2160
tcctgcagga attccaaagt ggactgcaac gcggcagggg ccctgcgctt cagcctgccc 2220
tcagtcctgc tcctcagcct cttcagctta gcttgtctgt gagaactcct gacgtctgaa 2280
gcttgactcc caagtttcca tagcaacagg aaaaaaaaaa atctatccaa atctgaagat 2340

```
tgcggtttac agctatcgaa cttcacaact aggcctcaat tgttccggtt ttttattttc   2400

tttacaattt cacttagtct gtacttcatc attttgacag catcttcctc cctcctttaa   2460

ttaatggaat cttctgaatt ttccctgaat gtttaaagat catgacatat gacttgatct   2520

tctgggagca ggaacaatga ctactttttc tggtgtgtta acatgtcgct agccagtgct   2580

ccaggcaccc agctttgtct gtgggttagt attggtgtat gtatgagtat ctgtatgtat   2640

atatacacgg tatttataga gagagactat cctggagaag cctcgttttg atgccattct   2700

tccttgcaag gttaagcaag gtgggtggaa actaagacac ctgaaccctc cagggcctcc   2760

cgcatcaagg tcagcatgag gacagaccac agagctgtca cttttgctcc gaagctactt   2820

ctccactgtc ccgttcagtc tgaatgctgc cacaaccagc caggcaggtc cacagagagg   2880

gagagcagag aaagaagtcc tttctcttta ttgagttcga ggactacaac caatttacac   2940

tgccatctga tgccgtgatc ctgagccaag gaggtgagga gcagagcagg caatttcacc   3000

accaaatgcc aagaaaaggg ctgacatttt ctttcatggg caccaacctg catttgtatg   3060

tgtcccgaat ccacagtcgt actgattcta atggggacac agatcatggt agagaatctc   3120

tccctcctca gtaaatgtac aactgcacct gtcatcatgg aggtcataca tgcatacaaa   3180

gaggtgtaca ggtaccatct tgtatacaca tatataccca catgtacaga catacattta   3240

tgcacattca cgctgtttgt ttcatatata caggcataaa atagagtaaa tacaggtagt   3300

tttaaaagta cccttttgtg tgaattgact accgttgttt gcaaacccga aaataaaaga   3360

cgttcattat gtatgaaaag taactgattt gtattctgtg agcatgtaaa agcggaaagt   3420

tagtgcttgt tctaagatta ccttcttgtt gataaaccat aaatgaatca tcaaagctca   3480

caccaaattt ttctatcaaa taaaactagt gacagcttgt ggctttttat tagagctcgc   3540

cacgaactag ggtaaggtga gtgtcttagc atattttaat gcagttgctt actaaaggtt   3600

ttaaccgcac atgcacacac acacgctttc ttatgcaatc tatgtttgca cttgtgcttt   3660

cagttagcct tctgtaggaa gtagaagtca tatgttgtct ttgttgtagt gaaattatac   3720

agatagagtt ccatatattg tatttgtttc aatggtaaat ccttttggaa catatagaat   3780

gcagagattt ttttttccat taaaataaat gggtattggt ggttaaaaaa aaaaaaaaaa   3840

aa                                                                  3842
```

```
<210> SEQ ID NO 48
<211> LENGTH: 713
<212> TYPE: PRT
<213> ORGANISM: Homo sapiens
<220> FEATURE:
<223> OTHER INFORMATION: cadherin 13, H-cadherin (heart) (CDH13)

<400> SEQUENCE: 48

Met Gln Pro Arg Thr Pro Leu Val Leu Cys Val Leu Leu Ser Gln Val
1               5                   10                  15

Leu Leu Leu Thr Ser Ala Glu Asp Leu Asp Cys Thr Pro Gly Phe Gln
            20                  25                  30

Gln Lys Val Phe His Ile Asn Gln Pro Ala Glu Phe Ile Glu Asp Gln
        35                  40                  45

Ser Ile Leu Asn Leu Thr Phe Ser Asp Cys Lys Gly Asn Asp Lys Leu
    50                  55                  60

Arg Tyr Glu Val Ser Ser Pro Tyr Phe Lys Val Asn Ser Asp Gly Gly
65                  70                  75                  80

Leu Val Ala Leu Arg Asn Ile Thr Ala Val Gly Lys Thr Leu Phe Val
                85                  90                  95
```

```
His Ala Arg Thr Pro His Ala Glu Asp Met Ala Glu Leu Val Ile Val
            100                 105                 110

Gly Gly Lys Asp Ile Gln Gly Ser Leu Gln Asp Ile Phe Lys Phe Ala
        115                 120                 125

Arg Thr Ser Pro Val Pro Arg Gln Lys Arg Ser Ile Val Val Ser Pro
    130                 135                 140

Ile Leu Ile Pro Glu Asn Gln Arg Gln Pro Phe Pro Arg Asp Val Gly
145                 150                 155                 160

Lys Val Val Asp Ser Asp Arg Pro Glu Arg Ser Lys Phe Arg Leu Thr
                165                 170                 175

Gly Lys Gly Val Asp Gln Glu Pro Lys Gly Ile Phe Arg Ile Asn Glu
            180                 185                 190

Asn Thr Gly Ser Val Ser Val Thr Arg Thr Leu Asp Arg Glu Val Ile
        195                 200                 205

Ala Val Tyr Gln Leu Phe Val Glu Thr Thr Asp Val Asn Gly Lys Thr
    210                 215                 220

Leu Glu Gly Pro Val Pro Leu Glu Val Ile Val Ile Asp Gln Asn Asp
225                 230                 235                 240

Asn Arg Pro Ile Phe Arg Glu Gly Pro Tyr Ile Gly His Val Met Glu
                245                 250                 255

Gly Ser Pro Thr Gly Thr Thr Val Met Arg Met Thr Ala Phe Asp Ala
            260                 265                 270

Asp Asp Pro Ala Thr Asp Asn Ala Leu Leu Arg Tyr Asn Ile Arg Gln
        275                 280                 285

Gln Thr Pro Asp Lys Pro Ser Pro Asn Met Phe Tyr Ile Asp Pro Glu
    290                 295                 300

Lys Gly Asp Ile Val Thr Val Val Ser Pro Ala Leu Leu Asp Arg Glu
305                 310                 315                 320

Thr Leu Glu Asn Pro Lys Tyr Glu Leu Ile Ile Glu Ala Gln Asp Met
                325                 330                 335

Ala Gly Leu Asp Val Gly Leu Thr Gly Thr Ala Thr Ala Thr Ile Met
            340                 345                 350

Ile Asp Asp Lys Asn Asp His Ser Pro Lys Phe Thr Lys Lys Glu Phe
        355                 360                 365

Gln Ala Thr Val Glu Glu Gly Ala Val Gly Val Ile Val Asn Leu Thr
    370                 375                 380

Val Glu Asp Lys Asp Asp Pro Thr Thr Gly Ala Trp Arg Ala Ala Tyr
385                 390                 395                 400

Thr Ile Ile Asn Gly Asn Pro Gly Gln Ser Phe Glu Ile His Thr Asn
                405                 410                 415

Pro Gln Thr Asn Glu Gly Met Leu Ser Val Val Lys Pro Leu Asp Tyr
            420                 425                 430

Glu Ile Ser Ala Phe His Thr Leu Leu Ile Lys Val Glu Asn Glu Asp
        435                 440                 445

Pro Leu Val Pro Asp Val Ser Tyr Gly Pro Ser Ser Thr Ala Thr Val
    450                 455                 460

His Ile Thr Val Leu Asp Val Asn Glu Gly Pro Val Phe Tyr Pro Asp
465                 470                 475                 480

Pro Met Met Val Thr Arg Gln Glu Asp Leu Ser Val Gly Ser Val Leu
                485                 490                 495

Leu Thr Val Asn Ala Thr Asp Pro Asp Ser Leu Gln His Gln Thr Ile
            500                 505                 510

Arg Tyr Ser Val Tyr Lys Asp Pro Ala Gly Trp Leu Asn Ile Asn Pro
```

-continued

```
        515                 520                 525

Ile Asn Gly Thr Val Asp Thr Thr Ala Val Leu Asp Arg Glu Ser Pro
    530                 535                 540

Phe Val Asp Asn Ser Val Tyr Thr Ala Leu Phe Leu Ala Ile Asp Ser
545                 550                 555                 560

Gly Asn Pro Pro Ala Thr Gly Thr Gly Thr Leu Leu Ile Thr Leu Glu
                565                 570                 575

Asp Val Asn Asp Asn Ala Pro Phe Ile Tyr Pro Thr Val Ala Glu Val
            580                 585                 590

Cys Asp Asp Ala Lys Asn Leu Ser Val Val Ile Leu Gly Ala Ser Asp
        595                 600                 605

Lys Asp Leu His Pro Asn Thr Asp Pro Phe Lys Phe Glu Ile His Lys
    610                 615                 620

Gln Ala Val Pro Asp Lys Val Trp Lys Ile Ser Lys Ile Asn Asn Thr
625                 630                 635                 640

His Ala Leu Val Ser Leu Leu Gln Asn Leu Asn Lys Ala Asn Tyr Asn
                645                 650                 655

Leu Pro Ile Met Val Thr Asp Ser Gly Lys Pro Pro Met Thr Asn Ile
            660                 665                 670

Thr Asp Leu Arg Val Gln Val Cys Ser Cys Arg Asn Ser Lys Val Asp
        675                 680                 685

Cys Asn Ala Ala Gly Ala Leu Arg Phe Ser Leu Pro Ser Val Leu Leu
    690                 695                 700

Leu Ser Leu Phe Ser Leu Ala Cys Leu
705                 710


<210> SEQ ID NO 49
<211> LENGTH: 5158
<212> TYPE: DNA
<213> ORGANISM: Homo sapiens
<220> FEATURE:
<223> OTHER INFORMATION: tripartite motif-containing 58 (TRIM58) cDNA
<220> FEATURE:
<221> NAME/KEY: CDS
<222> LOCATION: (49)..(1509)
<223> OTHER INFORMATION: TRIM58

<400> SEQUENCE: 49

gggagacggt gcgggcggcc gggagcgcag ccctccggga ggcgggtcat ggcctgggcg      60

ccgcccgggg agcggctgcg cgaggatgcg cggtgcccgg tgtgcctgga tttcctgcag     120

gagccggtca gcgtggactg cggccacagc ttctgcctca ggtgcatctc cgagttctgc     180

gagaagtcgg acggcgcgca gggcggcgtc tacgcctgtc cgcagtgccg gggccccttc     240

cggccctcgg gctttcgccc caaccggcag ctggcgggcc tggtggagag cgtgcggcgg     300

ctggggttgg gcgcggggcc cggggcgcgg cgatgcgcgc ggcacggcga ggacctgagc     360

cgcttctgcg aggaggacga ggcggcgctg tgctgggtgt gcgacgccgg ccccgagcac     420

aggacgcacc gcacggcgcc gctgcaggag gccgccggca gctaccaggt aaagctccag     480

atggctctgg aacttatgag gaaagagttg gaggacgcct tgactcagga ggccaacgtg     540

gggaaaaaga ctgtcatttg gaaggagaaa gtggaaatgc agaggcagcg cttcagattg     600

gagtttgaga agcatcgtgg ctttctggcc caggaggagc aacggcagct gaggcggctg     660

gaggcggagg agcgagcgac gctgcagaga ctgcgggaga gcaagagccg gctggtccag     720

cagagcaagg ccctgaagga gctggcggat gagctgcagg agaggtgcca gcgcccggcc     780

ctgggtctgc tggagggtgt gagaggagtc ctgagcagaa gtaaggctgt cacaaggctg     840
```

-continued

```
gaagcagaga acatccccat ggaactgaag acagcatgct gcatccctgg gaggagggag    900
ctcttaagga agttccaagt ggatgtaaag ctggatcccg ccacggcgca cccgagtctg    960
ctcttgaccg ccgacctgcg cagtgtgcag gatggagaac catggaggga tgtccccaac   1020
aaccctgagc gatttgacac atggccctgc atcctgggtt tgcagagctt ctcatcaggg   1080
aggcattact gggaggttct ggtgggagaa ggagcagagt ggggtttagg ggtctgtcaa   1140
gacacactgc caagaaaggg ggaaaccacg ccatctcctg agaatggggt ctgggccctg   1200
tggctgctga aagggaatga gtacatggtc cttgcctccc catcagtgcc tcttctccaa   1260
ctggaaagtc ctcgctgcat tgggattttc ttggactatg aagccggtga aatttcattc   1320
tacaatgtca cagatggatc ttatatctac acattcaacc aactcttctc tggtcttctt   1380
cggccttact ttttcatctg tgatgcaact cctcttatct tgccacccac aacaatagca   1440
gggtcaggaa attgggcatc cagggatcat ttagatcctg cttctgatgt aagagatgat   1500
catctctaaa attctgttcc caagatgcag tcctagcgta gcgaacgttc ctggagtggg   1560
gtgaaggata tcaatatact aagttttaac agatacccca tttaggtcag cacttgattc   1620
gttgttgctg tgaaatatgt ccatgggaca aaagagggaa tatgaaatat ttgcatatgg   1680
gaagattata gagcataata attttgtaaa tggagcaatc tcaacctcta tttctagatc   1740
acattttctt gatgtcttcc ttcaaattaa tgaccttgga ttacataagg atttctatgc   1800
attcattata atttgttatt cctttcaata tccttgtatt tcaaatcttc catataagaa   1860
ttagacatgg caattcttaa attgattcag aatggtctga tactattcca gtatcacctc   1920
cttaattctg tttctcctcg ttttcctgat tttccttctc attctctcct tccccgctct   1980
gtctctctct ccctgtcact ctctctctct tgttccttat tttttgtttc ttacctctta   2040
ctgtttaacc tgttgcttcc ttctggatta atacatttag agccattcct ttatatggtc   2100
acatttccta tgactttact caattacttt taaaatcctt tctattctga gactaatttt   2160
taagaattac aaagctcatt cttctgaatc taatatcact aactcctaga ctttttccgt   2220
tttctttgga tacactttaa gtaggaattt atcagaattt tcattcaact cgttctttaa   2280
tgcagatatt tactagttat aagaccttaa ggctgggtgc agtggctcac gcctgtaatc   2340
ccagcacttt gggaggctga ggcgggtgga tcacaagctc aggagttcaa gaccagcctg   2400
gccaacatgg tgaaaccctg tctctactaa aaaaaaaaaa aaaatagaaa aattagctgg   2460
gcatggtggc aggagcctgt aatcccagct attctggagg tggagacagg agaattgctt   2520
gaaccctgga ggcggaggtt gcagtgagcc aatatctcac cactgtactc cagcccagtg   2580
cgagactcca tctcaaaaaa gaaaaaagac ctcaaacaac acttctctct ctcttttagc   2640
tgcttgttat ggttcctata catggaacaa ttatactggc ctcactgtgt tatggtaaat   2700
atttaaggtc atatttgata ttgctggttt gaattcagct tttccattta aatacattat   2760
aatgatgatg atgaaatcat gataatattt aacttatttt taaagtatat tctgtacctt   2820
tccaacaaaa aggttaaaag tcattgaagg ctaaccttac tgccttcttt gtatcactgt   2880
cttctaaata attattatgt ctgggtacag tggctcacgc ctgtaatccc agcactttgg   2940
gaggccgagg tgggcagatc acgaggtcag gagattgaga ccatcctggc taacacagtg   3000
aaaccccgtc tctactaaaa atacaaaaag aaattagctg ggcgtggtgg tgggtgcctg   3060
ttgtcccagc tacttgggag gctgaggcag gagaatggca tgaacccagg aggcagagct   3120
tgtagtgagc cgagatcgcg ccactgcact ccagccgggg caacagagca agactccatc   3180
tcaaaaataa ataaataaat aaataaataa ataaataaat aaataaatat tacacaaatg   3240
```

```
ctaaaatgtt taaatggtaa atgcttcaat gctaaccaaa tattaattaa tggcaaatta   3300

tttaacatta tctgataata atctgcagaa ggtttaattt tcctcctcaa tttgaagttc   3360

aagatgtttt tctcttccag ggagattttt tcgactgaca tctttaactt accttccaat   3420

catattacta acgtagcctt cttcctagat tttttaattg tttgatcatg agcgaacact   3480

tctactctct gtgatagatt tgcaaacaga ggaaataacg catcctcgtg tccctcttct   3540

tggtgttcca caggccatgt gtgccctagc cctcgttcat gcaaggtctg tgtagggaag   3600

gtggacttca gctcagcaac agcatccctt cccacaggga tcaggtgggt ggcttgagat   3660

accccttcca tggggcacca cccattcagt gagacgggga agccctgggt gggagggaga   3720

acacctccac atgtcttcta ctctctccat aggatggaat gagtgtccca gtcccaggag   3780

tatccatttc ccactgtgta gcccagtact ctggtctcac tgtctctgct gaatcctgtc   3840

tcactgtgca tattattgtg gtttatatca gtcagtaaac caatgtgagt cttcatctct   3900

tgcattctta ggttcatagt tttgtgtgtc tcctgtaatg actcttctct ttccctttcc   3960

aactcctgaa agattgccac tatttcctct ggaactttgt ttcgttacca gcaaaatcct   4020

cgacatccat acccgtttcc tggctttccc tctcctttcc tctgaatggt agtcttttat   4080

attcagctgt ccacttgaca tcaaaataga catttgaac tcaatttgcc taaaacttac   4140

ccacaaattt ctccccaagt ctctccctaa ctgcaacaac aaaaaccaca ggcttctccc   4200

tgtcactgga tggcaactcc attcttttga ttgcttaagc caggcatccg attgagtact   4260

ttcttgattt ctccagccca catccagtcc atcggcaagc cctgttggtc ctaccttcag   4320

aatatgtccg gggttcagtt gtcctggcca ccctgctgct gtaaccatgg tcagaactcc   4380

atcctgcccc tctggattat gactttcgtt tcctcacagt ggtcctgctt gggctctagg   4440

cccttccact cccattctct ctacagcagc tgggctgatt cctttagcac ccaaggatat   4500

gttggcatca cagtgactta gataccatca caaagacctc ccattcaact tagagtgaaa   4560

gtcagaatcc tcacagtgaa tccccaggcc ctagaggatg tgaaccccca ggccctagag   4620

gatctgaacc cccatccctc ctctgattat ctctcccacc cccacttccc tttgcattct   4680

gctccagctg ccctggcctc atggctgggt ttccaccaaa gcaggcactt cccatcacag   4740

ggccatttcc ccgcctgtgg cttctgcttg acattccctt ttccctgata tccccttgac   4800

tcattattcc ctttcttcct taactcttct gagatccagc ttctcagtga taccacacag   4860

ccctactccc cccagagccc atctagagct cacctttcca gtcgcccttg ccaggctcag   4920

tggaggctct ttgttcccca tacagtacgt gtcgtcgtac tatattgtta ggcttattta   4980

atttatgtat gttttgcctt tttgtgctaa atgtaaacac cacaagggga ggtatctttg   5040

tctgttgaca atgatacatt caatgtttct caagcacccc caatgctggt ttgtatgtgg   5100

ttatcattca atctgtattt gttgaatgaa taaatgattg actatgtgga gagcaaaa     5158
```

<210> SEQ ID NO 50
<211> LENGTH: 486
<212> TYPE: PRT
<213> ORGANISM: Homo sapiens
<220> FEATURE:
<223> OTHER INFORMATION: tripartite motif-containing 58 (TRIM58)

<400> SEQUENCE: 50

```
Met Ala Trp Ala Pro Pro Gly Glu Arg Leu Arg Glu Asp Ala Arg Cys
  1               5                  10                  15

Pro Val Cys Leu Asp Phe Leu Gln Glu Pro Val Ser Val Asp Cys Gly
             20                  25                  30
```

```
His Ser Phe Cys Leu Arg Cys Ile Ser Glu Phe Cys Glu Lys Ser Asp
        35                  40                  45

Gly Ala Gln Gly Gly Val Tyr Ala Cys Pro Gln Cys Arg Gly Pro Phe
    50                  55                  60

Arg Pro Ser Gly Phe Arg Pro Asn Arg Gln Leu Ala Gly Leu Val Glu
65                  70                  75                  80

Ser Val Arg Arg Leu Gly Leu Gly Ala Gly Pro Gly Ala Arg Arg Cys
                85                  90                  95

Ala Arg His Gly Glu Asp Leu Ser Arg Phe Cys Glu Glu Asp Glu Ala
            100                 105                 110

Ala Leu Cys Trp Val Cys Asp Ala Gly Pro Glu His Arg Thr His Arg
        115                 120                 125

Thr Ala Pro Leu Gln Glu Ala Ala Gly Ser Tyr Gln Val Lys Leu Gln
    130                 135                 140

Met Ala Leu Glu Leu Met Arg Lys Glu Leu Glu Asp Ala Leu Thr Gln
145                 150                 155                 160

Glu Ala Asn Val Gly Lys Lys Thr Val Ile Trp Lys Glu Lys Val Glu
                165                 170                 175

Met Gln Arg Gln Arg Phe Arg Leu Glu Phe Glu Lys His Arg Gly Phe
            180                 185                 190

Leu Ala Gln Glu Glu Gln Arg Gln Leu Arg Arg Leu Glu Ala Glu Glu
        195                 200                 205

Arg Ala Thr Leu Gln Arg Leu Arg Glu Ser Lys Ser Arg Leu Val Gln
    210                 215                 220

Gln Ser Lys Ala Leu Lys Glu Leu Ala Asp Glu Leu Gln Glu Arg Cys
225                 230                 235                 240

Gln Arg Pro Ala Leu Gly Leu Leu Glu Gly Val Arg Gly Val Leu Ser
                245                 250                 255

Arg Ser Lys Ala Val Thr Arg Leu Glu Ala Glu Asn Ile Pro Met Glu
            260                 265                 270

Leu Lys Thr Ala Cys Cys Ile Pro Gly Arg Arg Glu Leu Leu Arg Lys
        275                 280                 285

Phe Gln Val Asp Val Lys Leu Asp Pro Ala Thr Ala His Pro Ser Leu
    290                 295                 300

Leu Leu Thr Ala Asp Leu Arg Ser Val Gln Asp Gly Glu Pro Trp Arg
305                 310                 315                 320

Asp Val Pro Asn Asn Pro Glu Arg Phe Asp Thr Trp Pro Cys Ile Leu
                325                 330                 335

Gly Leu Gln Ser Phe Ser Ser Gly Arg His Tyr Trp Glu Val Leu Val
            340                 345                 350

Gly Glu Gly Ala Glu Trp Gly Leu Gly Val Cys Gln Asp Thr Leu Pro
        355                 360                 365

Arg Lys Gly Glu Thr Thr Pro Ser Pro Glu Asn Gly Val Trp Ala Leu
    370                 375                 380

Trp Leu Leu Lys Gly Asn Glu Tyr Met Val Leu Ala Ser Pro Ser Val
385                 390                 395                 400

Pro Leu Leu Gln Leu Glu Ser Pro Arg Cys Ile Gly Ile Phe Leu Asp
                405                 410                 415

Tyr Glu Ala Gly Glu Ile Ser Phe Tyr Asn Val Thr Asp Gly Ser Tyr
            420                 425                 430

Ile Tyr Thr Phe Asn Gln Leu Phe Ser Gly Leu Leu Arg Pro Tyr Phe
        435                 440                 445

Phe Ile Cys Asp Ala Thr Pro Leu Ile Leu Pro Pro Thr Thr Ile Ala
    450                 455                 460
```

```
Gly Ser Gly Asn Trp Ala Ser Arg Asp His Leu Asp Pro Ala Ser Asp
465                 470                 475                 480

Val Arg Asp Asp His Leu
                485


<210> SEQ ID NO 51
<211> LENGTH: 3194
<212> TYPE: DNA
<213> ORGANISM: Homo sapiens
<220> FEATURE:
<223> OTHER INFORMATION: Zwilch, kinetochore associated, homolog
      (Drosophila) (ZWILCH, FLJ10036) cDNA
<220> FEATURE:
<221> NAME/KEY: CDS
<222> LOCATION: (247)..(1509)
<223> OTHER INFORMATION: ZWILCH

<400> SEQUENCE: 51

agtcgaggta tcttctcccc aaccactgct cttattttaa ttattgcaga cggaagttga     60

agactattga catagtaaat agctctgggt ggcttgaaac gaaagtttaa ctttgcggac    120

aaacaggact tattgtaggg ggtggtcaaa atagtcccgg cggggcgggg ccatgacccc    180

tgacgtcgcc ggtccggcgc gcagttcagt ttggcggttc cggtaccgct ctcacattgg    240

ggcgggatgt gggagcggct gaactgcgca gcagaggact tttattctcg tctccttcag    300

aaatttaatg aagaaaagaa aggaatccgt aaagacccat ttctctatga ggctgatgtc    360

caagtgcagt tgatcagcaa aggccaacca aaccctttga aaaatattct aaatgaaaat    420

gacatagtat tcatagtgga aaaagtgcct ttagaaaagg aagaaacaag tcatattgaa    480

gaacttcaat ctgaagaaac tgccatatct gatttctcta ctggcgaaaa tgttggacca    540

cttgctttac cagttgggaa ggcaaggcag ttaattggac tttacaccat ggctcacaat    600

cctaatatga cccatttgaa gattaatctg ccagttactg cccttcctcc cctttgggta    660

agatgtgaca gttcagatcc tgaaggtact tgttggctag gagctgagct tatcacaaca    720

aacaacagca ttacaggaat tgtcttatat gtggtcagtt gtaaagctga taaaaattat    780

tctgtaaatc ttgaaaacct aaaaaattta cacaagaaaa gacatcactt gtctactgta    840

acatccaaag gctttgccca gtatgagctc tttaagtcct ctgccttgga tgatacaatc    900

acagcatcac aaactgcgat cgctttggat atttcctgga gtcctgtgga tgagattctt    960

caaatccctc cactctcttc aactgcaact ctgaatatta aagtggaatc aggagagccc   1020

agaggtcctt tgaatcatct ctacagagaa ctgaaatttc ttcttgtttt ggctgatggt   1080

ttgaggactg gtgtcactga atggctcgag cccctggaag caaaatctgc tgttgaactt   1140

gttcaggaat ttctgaatga cttaaataag ctggatggat ttggtgattc tacaaaaaaa   1200

gacactgagg ttgagacctt gaagcatgac actgctgcag tcgatcgttc cgtcaagcgt   1260

cttttcaaag ttcggagtga tcttgatttt gctgagcaac tgtggtgcaa aatgagcagt   1320

agtgtgattt cataccaaga cttggtgaag tgtttcacat tgatcatcca gagtctacaa   1380

cgtggtgata tacagccatg gctccatagt ggaagtaaca gtttactaag taagctcatt   1440

catcagtctt atcatggaac catggacaca gtttctctca gtgggactat tccagttcaa   1500

atgcttttgg aaattggttt ggacaaacta aagaaagatt atatcagttt tttcataggt   1560

caggaacttg catctttgaa tcatttggaa tacttcattg ctccatcagt agatatacaa   1620

gaacaggttt atcgtgtcca aaaactccac catattctag aaatattagt cagttgcatg   1680

cctttcatta aatctcaaca tgaactcctc ttttctttaa cacagatctg cataaagtat   1740
```

-continued

```
tacaaacaaa atcctcttga tgagcaacac atttttcagc tgccagtcag accaactgct   1800
gtaaagaact tatatcaaag tgagaagcca cagaaatgga gagtggaaat atatagtggt   1860
caaaagaaga ttaagacagt ttggcaactg agtgacagct cacccataga ccatctgaat   1920
tttcacaaac ctgatttttc ggaattaaca ctaaacggta gcctggaaga aaggatattc   1980
tttactaaca tggttacctg cagccaggtg catttcaagt gaagtgtgct gatgaagtcc   2040
tctataagca caagccaaaa agagaaagag aaaaaaaggt aattattgta gaacctgaaa   2100
acagcaatgt atggaaaccc tcaaagcaga aaagggagga agatcctgaa gattctctta   2160
tgaagctcca aaattgataa tcctgtctca gctctgcctc ctcaggagga gcattagtag   2220
aacagcagtg atgaggacac agagggagca gacagtgggt accacgatct ccgtaaccat   2280
ttgcatgtga cttagcaagg gctctgaaat gacaaagaga acgagcacca caaatgagaa   2340
caggatcatt ttagtaaata cagctttatc ccaaaagctt taactgtatt gggaaaactt   2400
aaaaaatagc atcctcaaat tttctgattc ttatttgcca tgaaatagaa cttagtaaat   2460
taaatgttat ttgaaaatgt tataagagct ttgtaaatat ttcagaaaat atgggataaa   2520
tgcctgaatt tggttcttct acaggtgcta taataaagtc catctctcaa tacttatact   2580
ttctaaattc atctcagaat attagcagcc atattccaca gttcctataa tttttactgg   2640
gggggatttg tgataggaaa gtccttggga aacatttcca atctttcaaa atattattgt   2700
gtatcttaag aagtatagga acttgtatgt tgaaatgttg tatggtagtt cttgtatagt   2760
taaataataa tctttttaag agttaatgat aagcatatgt tatgtgcatt attaataaaa   2820
tagtggccac ttaggtaata cccactttta tcttgtgtgc tgggtactct ggttactgag   2880
ataaataagg cactggacat cctcacgtgg agttcacagg ctcatcagtg aattctgtac   2940
cacatttcaa ccttgtttat tttagtttaa tggaatatac attcttagta ttgcctgatt   3000
atttaaattt gttgaggggg attgcatgtt gctttattgg cctgtaaaaa tagctagttt   3060
ggtaagattt ggtctcgcac cttccatctt tgctaccaca ttaaagatga gcttgttaaa   3120
aaggaaagca tatttctctg attgccctta tggagaaata aagataaaat tcaaagaaac   3180
aaaaaaaaaa aaaa                                                     3194
```

<210> SEQ ID NO 52
<211> LENGTH: 591
<212> TYPE: PRT
<213> ORGANISM: Homo sapiens
<220> FEATURE:
<223> OTHER INFORMATION: Zwilch, kinetochore associated, homolog (Drosophila) (ZWILCH, FLJ10036)

<400> SEQUENCE: 52

```
Met Trp Glu Arg Leu Asn Cys Ala Ala Glu Asp Phe Tyr Ser Arg Leu
  1               5                  10                  15

Leu Gln Lys Phe Asn Glu Glu Lys Lys Gly Ile Arg Lys Asp Pro Phe
             20                  25                  30

Leu Tyr Glu Ala Asp Val Gln Val Gln Leu Ile Ser Lys Gly Gln Pro
         35                  40                  45

Asn Pro Leu Lys Asn Ile Leu Asn Glu Asn Asp Ile Val Phe Ile Val
     50                  55                  60

Glu Lys Val Pro Leu Glu Lys Glu Glu Thr Ser His Ile Glu Glu Leu
 65                  70                  75                  80

Gln Ser Glu Glu Thr Ala Ile Ser Asp Phe Ser Thr Gly Glu Asn Val
                 85                  90                  95

Gly Pro Leu Ala Leu Pro Val Gly Lys Ala Arg Gln Leu Ile Gly Leu
```

-continued

```
            100                 105                 110

Tyr Thr Met Ala His Asn Pro Asn Met Thr His Leu Lys Ile Asn Leu
        115                 120                 125

Pro Val Thr Ala Leu Pro Pro Leu Trp Val Arg Cys Asp Ser Ser Asp
    130                 135                 140

Pro Glu Gly Thr Cys Trp Leu Gly Ala Glu Leu Ile Thr Thr Asn Asn
145                 150                 155                 160

Ser Ile Thr Gly Ile Val Leu Tyr Val Val Ser Cys Lys Ala Asp Lys
                165                 170                 175

Asn Tyr Ser Val Asn Leu Glu Asn Leu Lys Asn Leu His Lys Lys Arg
            180                 185                 190

His His Leu Ser Thr Val Thr Ser Lys Gly Phe Ala Gln Tyr Glu Leu
        195                 200                 205

Phe Lys Ser Ser Ala Leu Asp Asp Thr Ile Thr Ala Ser Gln Thr Ala
    210                 215                 220

Ile Ala Leu Asp Ile Ser Trp Ser Pro Val Asp Glu Ile Leu Gln Ile
225                 230                 235                 240

Pro Pro Leu Ser Ser Thr Ala Thr Leu Asn Ile Lys Val Glu Ser Gly
                245                 250                 255

Glu Pro Arg Gly Pro Leu Asn His Leu Tyr Arg Glu Leu Lys Phe Leu
            260                 265                 270

Leu Val Leu Ala Asp Gly Leu Arg Thr Gly Val Thr Glu Trp Leu Glu
        275                 280                 285

Pro Leu Glu Ala Lys Ser Ala Val Glu Leu Val Gln Glu Phe Leu Asn
    290                 295                 300

Asp Leu Asn Lys Leu Asp Gly Phe Gly Asp Ser Thr Lys Lys Asp Thr
305                 310                 315                 320

Glu Val Glu Thr Leu Lys His Asp Thr Ala Ala Val Asp Arg Ser Val
                325                 330                 335

Lys Arg Leu Phe Lys Val Arg Ser Asp Leu Asp Phe Ala Glu Gln Leu
            340                 345                 350

Trp Cys Lys Met Ser Ser Ser Val Ile Ser Tyr Gln Asp Leu Val Lys
        355                 360                 365

Cys Phe Thr Leu Ile Ile Gln Ser Leu Gln Arg Gly Asp Ile Gln Pro
    370                 375                 380

Trp Leu His Ser Gly Ser Asn Ser Leu Leu Ser Lys Leu Ile His Gln
385                 390                 395                 400

Ser Tyr His Gly Thr Met Asp Thr Val Ser Leu Ser Gly Thr Ile Pro
                405                 410                 415

Val Gln Met Leu Leu Glu Ile Gly Leu Asp Lys Leu Lys Lys Asp Tyr
            420                 425                 430

Ile Ser Phe Phe Ile Gly Gln Glu Leu Ala Ser Leu Asn His Leu Glu
        435                 440                 445

Tyr Phe Ile Ala Pro Ser Val Asp Ile Gln Glu Gln Val Tyr Arg Val
    450                 455                 460

Gln Lys Leu His His Ile Leu Glu Ile Leu Val Ser Cys Met Pro Phe
465                 470                 475                 480

Ile Lys Ser Gln His Glu Leu Leu Phe Ser Leu Thr Gln Ile Cys Ile
                485                 490                 495

Lys Tyr Tyr Lys Gln Asn Pro Leu Asp Glu Gln His Ile Phe Gln Leu
            500                 505                 510

Pro Val Arg Pro Thr Ala Val Lys Asn Leu Tyr Gln Ser Glu Lys Pro
        515                 520                 525
```

-continued

```
Gln Lys Trp Arg Val Glu Ile Tyr Ser Gly Gln Lys Lys Ile Lys Thr
    530                 535                 540

Val Trp Gln Leu Ser Asp Ser Ser Pro Ile Asp His Leu Asn Phe His
545                 550                 555                 560

Lys Pro Asp Phe Ser Glu Leu Thr Leu Asn Gly Ser Leu Glu Glu Arg
                565                 570                 575

Ile Phe Phe Thr Asn Met Val Thr Cys Ser Gln Val His Phe Lys
            580                 585                 590


<210> SEQ ID NO 53
<211> LENGTH: 2941
<212> TYPE: DNA
<213> ORGANISM: Homo sapiens
<220> FEATURE:
<223> OTHER INFORMATION: pelota homolog (Drosophila) (PELO) cDNA
<220> FEATURE:
<221> NAME/KEY: CDS
<222> LOCATION: (986)..(2143)
<223> OTHER INFORMATION: PELO

<400> SEQUENCE: 53

gatttggccc ggagaacgag atcaccctct caatgaaagg cagatgtccc tttaaggttt      60

gcttctacag cccgtggact ttagcctaaa cacggacccg cgaagctggc tttatttgtc     120

catgtctcgg acagagcctg ggaagctgcc agtgagattt cagagaccaa gagcgcgaag     180

gggcgggcga tgtggcaatc cgtctgggat gtgaaaagcg tggagcgcat ttagaggaat     240

tcgacgaaaa cacaggaaat cactcctctc ccgctcctgg gcgccgctgc cactggggca     300

gaggactggg aaccgcggca gcgggataag tggcccagcc agagagcgca gctcccgcgc     360

ccggtcctgc cctgcgaacc agcgcggccc cctggcgctg aggctgctcc ggccatggcc     420

cctcggcccc gcgcccgccc aggggtcgct gtcgcctgct gctggctcct cactgacagg     480

gatggaagag aaaacttagg aagttgaagt ttggcattaa aataaaggac tcgccaccac     540

tctgtgcacc ttcttgaggg agttcattcg tccggagcgc ctcacagctt agtgcgcctg     600

cgcacgcgcg aactgcggcc ccgcctctcc tttggggacg ggagacgtgc gtcgggtcgc     660

gggacggggg ctgcgcatgc gccttcattt cgtcagcccg ctgttgcgtg ctgccagcgg     720

gaactgtgta ggggtagatt ttcgctgcag tgttccccga gcctgttaga cgcagcgcgc     780

cgggagactg agagaggaaa ggatagagga agtgctgccc taggctgcat gagtcgaagc     840

aagcgtgttt ccttcccgcc aggcaagtgc ccttagaaac cgggccccgc cccctcctg      900

gcctgcattc ccatcccctc tcccggggcg gaggtgagga cctccttggt tcctttggtt     960

ctgtcagtga gccccttcct tggccatgaa gctcgtgagg aagaacatcg agaaggacaa    1020

tgcgggccag gtgaccctgg tccccgagga gcctgaggac atgtggcaca cttacaacct    1080

cgtgcaggtg ggcgacagcc tgcgcgcctc caccatccgc aaggtacaga cagagtcctc    1140

cacgggcagc gtgggcagca accgggtccg cactaccctc actctctgcg tggaggccat    1200

cgacttcgac tctcaagcct gccagctgcg ggttaagggg accaacatcc aagagaatga    1260

gtatgtcaag atgggggctt accacaccat cgagctggag cccaaccgcc agttcaccct    1320

ggccaagaag cagtgggata gtgtggtact ggagcgcatc gagcaggcct gtgacccagc    1380

ctggagcgct gatgtggcgg ctgtggtcat gcaggaaggc ctcgcccata tctgcttagt    1440

cactcccagc atgaccctca ctcgggccaa ggtggaggtg aacatcccta ggaaaaggaa    1500

aggcaattgc tctcagcatg accgggcctt ggagcggttc tatgaacagg tggtccaggc    1560

tatccagcgc cacatacact ttgatgttgt aaagtgcatc ctggtggcca gcccaggatt    1620
```

```
tgtgagggag cagttctgcg actacctgtt tcaacaagca gtgaagaccg acaacaaact   1680

gctcctggaa aaccggtcca aatttcttca ggtacatgcc tcctccggac acaagtactc   1740

cctgaaagag gccctttgtg accctactgt ggctagccgc ctttcagaca ctaaagctgc   1800

tggggaagtc aaagccttgg atgacttcta taaaatgtta cagcatgaac cggatcgagc   1860

tttctatgga ctcaagcagg tggagaaggc caatgaagcc atggcaattg acacattgct   1920

catcagcgat gagctcttca ggcatcagga tgtagccaca cggagccggt atgtgaggct   1980

ggtggacagt gtgaaagaga atgcaggcac cgttaggata ttctctagtc ttcacgtttc   2040

tggggaacag ctcagccagt tgactggggt agctgccatt ctccgcttcc ctgttcccga   2100

actttctgac caagagggtg attccagttc tgaagaggat taatgattga aacttaaaat   2160

tgagacaatc ttgtgtttcc taaactgtta cagtacattt ctcagcatcc ttgtgacaga   2220

aagctgcaag aatggcactt tttgattcat acagggattt cttatgtctt tggctacact   2280

agatattttg tgattggcaa gacatgtatt taaacaataa actaaaagga aataatctcc   2340

acgtactacc atcttgatta aattgtgtaa tttttatag gaattatgag ttatctgtag    2400

tacttggaaa cagaaaatgt gtgtatttaa agacgatgcc tatgcagtat attgtttggg   2460

atagattgca aaatttcaca ctgcatgctt tgaaacagtt ttccttagaa aaagcttttg   2520

ctatcttatc ctgtttacat tatttcttta ttttaattct gcttggtgtt cttgcattgc   2580

atttaatgat ccctttctc cccacctcca cacactacat ttttttaga tttaaatagt     2640

tttactattt taaatgattg ccgtacaatt agtagacttg aagacaagtt ttaaatattt   2700

ttcttcaaag gcttgttaaa ccaatcatgt taaaaggaaa ttcttggttt tggtttgttg   2760

ttgttagcat tagtcatatt tgatttagag ggtaacttaa atcagttatt tttagctttt   2820

tagaactttg atctgctagg gattgtcaaa ataatctcct tgaggcatct ttatttttaa   2880

aatgagatta aagtatgtga tttgcttgtt atgtggctaa aaaaaaaaaa aaaaaaaaaa   2940

a                                                                   2941
```

<210> SEQ ID NO 54
<211> LENGTH: 385
<212> TYPE: PRT
<213> ORGANISM: Homo sapiens
<220> FEATURE:
<223> OTHER INFORMATION: pelota homolog (Drosophila) (PELO)

<400> SEQUENCE: 54

```
Met Lys Leu Val Arg Lys Asn Ile Glu Lys Asp Asn Ala Gly Gln Val
  1               5                  10                  15

Thr Leu Val Pro Glu Glu Pro Glu Asp Met Trp His Thr Tyr Asn Leu
             20                  25                  30

Val Gln Val Gly Asp Ser Leu Arg Ala Ser Thr Ile Arg Lys Val Gln
         35                  40                  45

Thr Glu Ser Ser Thr Gly Ser Val Gly Ser Asn Arg Val Arg Thr Thr
     50                  55                  60

Leu Thr Leu Cys Val Glu Ala Ile Asp Phe Asp Ser Gln Ala Cys Gln
 65                  70                  75                  80

Leu Arg Val Lys Gly Thr Asn Ile Gln Glu Asn Glu Tyr Val Lys Met
                 85                  90                  95

Gly Ala Tyr His Thr Ile Glu Leu Glu Pro Asn Arg Gln Phe Thr Leu
            100                 105                 110

Ala Lys Lys Gln Trp Asp Ser Val Val Leu Glu Arg Ile Glu Gln Ala
        115                 120                 125
```

```
Cys Asp Pro Ala Trp Ser Ala Asp Val Ala Ala Val Val Met Gln Glu
    130                 135                 140

Gly Leu Ala His Ile Cys Leu Val Thr Pro Ser Met Thr Leu Thr Arg
145                 150                 155                 160

Ala Lys Val Glu Val Asn Ile Pro Arg Lys Arg Lys Gly Asn Cys Ser
                165                 170                 175

Gln His Asp Arg Ala Leu Glu Arg Phe Tyr Glu Gln Val Val Gln Ala
            180                 185                 190

Ile Gln Arg His Ile His Phe Asp Val Val Lys Cys Ile Leu Val Ala
        195                 200                 205

Ser Pro Gly Phe Val Arg Glu Gln Phe Cys Asp Tyr Leu Phe Gln Gln
    210                 215                 220

Ala Val Lys Thr Asp Asn Lys Leu Leu Leu Glu Asn Arg Ser Lys Phe
225                 230                 235                 240

Leu Gln Val His Ala Ser Ser Gly His Lys Tyr Ser Leu Lys Glu Ala
                245                 250                 255

Leu Cys Asp Pro Thr Val Ala Ser Arg Leu Ser Asp Thr Lys Ala Ala
            260                 265                 270

Gly Glu Val Lys Ala Leu Asp Asp Phe Tyr Lys Met Leu Gln His Glu
        275                 280                 285

Pro Asp Arg Ala Phe Tyr Gly Leu Lys Gln Val Glu Lys Ala Asn Glu
    290                 295                 300

Ala Met Ala Ile Asp Thr Leu Leu Ile Ser Asp Glu Leu Phe Arg His
305                 310                 315                 320

Gln Asp Val Ala Thr Arg Ser Arg Tyr Val Arg Leu Val Asp Ser Val
                325                 330                 335

Lys Glu Asn Ala Gly Thr Val Arg Ile Phe Ser Ser Leu His Val Ser
            340                 345                 350

Gly Glu Gln Leu Ser Gln Leu Thr Gly Val Ala Ala Ile Leu Arg Phe
        355                 360                 365

Pro Val Pro Glu Leu Ser Asp Gln Glu Gly Asp Ser Ser Ser Glu Glu
    370                 375                 380

Asp
385
```

<210> SEQ ID NO 55
<211> LENGTH: 4182
<212> TYPE: DNA
<213> ORGANISM: Homo sapiens
<220> FEATURE:
<223> OTHER INFORMATION: zinc finger protein 711 (ZNF711), zinc finger protein 6 (ZNF6, CMPX1) cDNA
<220> FEATURE:
<221> NAME/KEY: CDS
<222> LOCATION: (348)..(2633)
<223> OTHER INFORMATION: ZNF711

<400> SEQUENCE: 55

```
agacgcagag tagattgtga ttggctcggg ctgcggaacc tcggaaaccc gaatgtgagg     60

accttaaggg atccacagct gccgcccccc gcagccatcc agagcgcggt cacagtccga    120

ctggcggcac ggaggcggcg gcggcggcgg cggcggcagc ggcggcggca gcggcggcgg    180

cagctgtagc tgcagcagca ggtaaagaga gcgttttccc aaagaaaata acatagcaca    240

gaaggaaaaa taaaaagaaa ttgctgcaga ttttacttta tgtgagaaaa tctacaattt    300

cttcgagaca ctcatataaa gatattggtg aatgaacttt gctaagtatg gattcaggcg    360

gtggaagtct tggattgcac acgccagact ctagaatggc ccataccatg attatgcaag    420
```

-continued

```
atttgtggc tggaatggct ggtactgcac atatcgatgg agaccatatt gttgtttcag    480
ttcctgaagc tgttttagtt tctgatgttg tcacagatga tgggataact cttgatcatg    540
gccttgcagc tgaagttgtc catggacctg atatcatcac agagactgat gtagtaacag    600
aaggtgtgat tgttcctgaa gcggtacttg aagctgatgt tgccattgaa gaggatttag    660
aggaagatga tggtgatcac atcttgactt ctgaactaat tacagaaacc gttagggtac    720
cagagcaggt tttcgtggct gaccttgtta ctggtcctaa tggacactta gaacatgtgg    780
tccaagattg tgtttcagga gtcgactctc ccacaatggt atcagaggag gttcttgtaa    840
ctaattcaga tacagaaact gtgattcaag cagctggagg tgttcctggt tctacagtta    900
ctataaaaac cgaagatgat gatgatgatg atgtcaagag cacttctgaa gactacttaa    960
tgatatcttt ggatgatgtt ggagaaaaat tagagcatat ggggaataca ccattaaaaa   1020
ttggcagtga tggttcacaa gaagatgcta aagaagatgg gtttggttct gaagttataa   1080
aagtgtatat atttaaagcg gaggctgaag atgatgttga aataggtgga acagaaattg   1140
tcacagagag tgagtacacc agtggacatt cagtagctgg agtgcttgac cagagccgaa   1200
tgcagcggga gaagatggtt tacatggcag ttaaagattc ttctcaagaa gaagatgata   1260
tcagagatga aagaagagtt tcccgaaggt atgaagattg tcaagcatca ggaaatactt   1320
tggactcagc attagaaagc agaagtagta cagcagcaca gtaccttcaa atttgtgacg   1380
gcattaatac aaataaagta cttaaacaaa aagccaaaaa gaggagaagg ggagaaacca   1440
ggcagtggca aacagctgtt ataataggtc ctgatggaca gcccctcaca gtgtaccctt   1500
gccatatttg cacaaaaaag tttaaatcca ggggattctt aaaaagacac atgaagaatc   1560
atcctgatca tttaatgaga aaaaaatatc agtgtacaga ttgtgacttt acaactaaca   1620
agaaagtgag tttccataac cacttagaaa gccataagct cataaacaaa gtcgacaaaa   1680
cccatgaatt tacagaatac acacgaagat acagagaggc tagtccactg agttccaata   1740
aacttatttt aagagacaag gagccgaaga tgcacaagtg caaatactgt gactatgaaa   1800
ctgcagaaca aggactgtta aacaggcatt tgttggccgt tcacagcaag aattttcctc   1860
atgtttgtgt tgagtgtggg aagggttttc gacatccttc tgaactcaag aaacatatga   1920
gaacccatac tggtgagaag ccatatcagt gtcagtattg tattttcagg tgtgcagatc   1980
aatcaaatct gaaaactcac attaagtcta aacatggtaa caatttgcca tataaatgtg   2040
agcattgtcc ccaagcattt ggtgatgaga gggagcttca acgccatctg gatttgtttc   2100
aaggacataa gacacaccag tgtcctcatt gtgaccataa gagcaccaat tcaagtgacc   2160
ttaagcggca catcatatct gtccatacta aggattttcc tcacaaatgt gaggtctgtg   2220
ataaaggttt tcatcgtcct tctgagctca aaaagcatag tgatatccat aagggtagga   2280
agattcatca gtgcaggcac tgtgacttta aaacatccga tccatttatt cttagtggcc   2340
atatcctttc agttcatact aaagatcagc cattgaaatg taaaaggtgc aagagaggat   2400
tcagacaaca aaatgagcta aaaaaacata tgaagaccca tactggaagg aagatttacc   2460
aatgtgagta ttgtgaatac agcactacag atgcatctgg ctttaaacga catgtgatat   2520
caatacatac aaaagactat ccacacaggt gtgaattctg caagaaggga ttccgaagac   2580
catcagaaaa aaatcagcat attatgaggc accacaaaga ggctcttatg taataagatc   2640
aatataaaga aagaagctat ttaggagata tgatatgcta cttgggagaa aactctcact   2700
aactgtctca ccgggtttca aagcttgata ctaaaccatg actttacatt ctttgtatta   2760
aagatcttaa aatatttgaa ttcacagggg atcccatagc cctttgaaaa ttacttaaag   2820
```

```
aatttaagaa gcactataga atggttacag aaaaacttct taagtatctg tgtaatagta   2880

ttatatgcat acttaaacta cagaggggaa aagcaaagac aaatacttta tttggctgat   2940

tatgttagat acaaatgttt ctgagaagag aatacataat tgagtttagt gatgctttgc   3000

tatagcaagc aaacccactt ttatgcaatt ttagaaatgg ggcagggaaa caaaatgtgg   3060

tcattcatca gtcacttagt cattgagcct tttatattgt acctggaaat taaattccag   3120

caatgacaaa agttttgtgt attcattaaa agaaaactaa ctggaaaaca ggttagatta   3180

attcagtact attaaaaaag aattcagagc tgttaatatt ttatcacagg ataggatact   3240

taaaatatag cattctgtgc tgagatctaa ggtgaagtct ataaagatta aagttccctt   3300

ttttctgatg ttcaagttga ttgttgttca gtatggcata tatgacaaaa gtatatttga   3360

gtcaaatgtg gctttctaaa atggatgcaa cattagcgtt gcaaacaaaa tcagcactat   3420

atttcttaat gatctaaaga ttaatttgag agaacacagt tttcttaaat attataatgt   3480

ctagagtttt tttaggacag tcttagcaag tatgattgtt ctagtcttac ttgctctaat   3540

gtttaaaggt gcaattttat gccattattg aaattgattt ttaaaatcta tataccatat   3600

gattaacatg cattttcaat atgaggcagt gtttatgcag tatttaacag agcaatctgc   3660

tgccaataga gtttggaggt ggatatttag tttacagtgt ataaacttaa aatatgcatc   3720

cctttaacaa cgctttgtgt tagcatgctg caaatcaaaa tggcacttaa tattaaaagc   3780

tggtttaggg aaattttatg aaaatcctgt tcataaatgt aatgcatatg atatgtactt   3840

ttaagtttta gttgcttcat gtttacattc agctgttcaa cataattaaa atgtaatttt   3900

acttcatgct atattgtggc tttgtgtttc aaataatgtt cacctttctg tttttgcacc   3960

agataagaat cagttccttg agaataaatt ttttatcttt cttaacttca gaatattaaa   4020

tttggaatat ctactaaaat tgtgtgttat gtggctgtaa atgatgtaca cgctgtaaaa   4080

taagatcgct actgttatgt gggattatta tttctaaatg ttactcattg aaatgagcat   4140

acaataaaaa gcatttattg cacttaaaaa aaaaaaaaaa aa                      4182


<210> SEQ ID NO 56
<211> LENGTH: 761
<212> TYPE: PRT
<213> ORGANISM: Homo sapiens
<220> FEATURE:
<223> OTHER INFORMATION: zinc finger protein 711 (ZNF711), zinc finger
      protein 6 (ZNF6, CMPX1)

<400> SEQUENCE: 56

Met Asp Ser Gly Gly Gly Ser Leu Gly Leu His Thr Pro Asp Ser Arg
  1               5                  10                  15

Met Ala His Thr Met Ile Met Gln Asp Phe Val Ala Gly Met Ala Gly
             20                  25                  30

Thr Ala His Ile Asp Gly Asp His Ile Val Val Ser Val Pro Glu Ala
         35                  40                  45

Val Leu Val Ser Asp Val Val Thr Asp Asp Gly Ile Thr Leu Asp His
     50                  55                  60

Gly Leu Ala Ala Glu Val Val His Gly Pro Asp Ile Ile Thr Glu Thr
 65                  70                  75                  80

Asp Val Val Thr Glu Gly Val Ile Val Pro Glu Ala Val Leu Glu Ala
                 85                  90                  95

Asp Val Ala Ile Glu Glu Asp Leu Glu Glu Asp Asp Gly Asp His Ile
            100                 105                 110

Leu Thr Ser Glu Leu Ile Thr Glu Thr Val Arg Val Pro Glu Gln Val
        115                 120                 125
```

```
Phe Val Ala Asp Leu Val Thr Gly Pro Asn Gly His Leu Glu His Val
    130                 135                 140

Val Gln Asp Cys Val Ser Gly Val Asp Ser Pro Thr Met Val Ser Glu
145                 150                 155                 160

Glu Val Leu Val Thr Asn Ser Asp Thr Glu Thr Val Ile Gln Ala Ala
                165                 170                 175

Gly Gly Val Pro Gly Ser Thr Val Thr Ile Lys Thr Glu Asp Asp Asp
            180                 185                 190

Asp Asp Asp Val Lys Ser Thr Ser Glu Asp Tyr Leu Met Ile Ser Leu
        195                 200                 205

Asp Asp Val Gly Glu Lys Leu Glu His Met Gly Asn Thr Pro Leu Lys
    210                 215                 220

Ile Gly Ser Asp Gly Ser Gln Glu Asp Ala Lys Glu Asp Gly Phe Gly
225                 230                 235                 240

Ser Glu Val Ile Lys Val Tyr Ile Phe Lys Ala Glu Ala Glu Asp Asp
                245                 250                 255

Val Glu Ile Gly Gly Thr Glu Ile Val Thr Glu Ser Glu Tyr Thr Ser
            260                 265                 270

Gly His Ser Val Ala Gly Val Leu Asp Gln Ser Arg Met Gln Arg Glu
        275                 280                 285

Lys Met Val Tyr Met Ala Val Lys Asp Ser Ser Gln Glu Glu Asp Asp
    290                 295                 300

Ile Arg Asp Glu Arg Arg Val Ser Arg Arg Tyr Glu Asp Cys Gln Ala
305                 310                 315                 320

Ser Gly Asn Thr Leu Asp Ser Ala Leu Glu Ser Arg Ser Ser Thr Ala
                325                 330                 335

Ala Gln Tyr Leu Gln Ile Cys Asp Gly Ile Asn Thr Asn Lys Val Leu
            340                 345                 350

Lys Gln Lys Ala Lys Lys Arg Arg Arg Gly Glu Thr Arg Gln Trp Gln
        355                 360                 365

Thr Ala Val Ile Ile Gly Pro Asp Gly Gln Pro Leu Thr Val Tyr Pro
    370                 375                 380

Cys His Ile Cys Thr Lys Lys Phe Lys Ser Arg Gly Phe Leu Lys Arg
385                 390                 395                 400

His Met Lys Asn His Pro Asp His Leu Met Arg Lys Lys Tyr Gln Cys
                405                 410                 415

Thr Asp Cys Asp Phe Thr Thr Asn Lys Lys Val Ser Phe His Asn His
            420                 425                 430

Leu Glu Ser His Lys Leu Ile Asn Lys Val Asp Lys Thr His Glu Phe
        435                 440                 445

Thr Glu Tyr Thr Arg Arg Tyr Arg Glu Ala Ser Pro Leu Ser Ser Asn
    450                 455                 460

Lys Leu Ile Leu Arg Asp Lys Glu Pro Lys Met His Lys Cys Lys Tyr
465                 470                 475                 480

Cys Asp Tyr Glu Thr Ala Glu Gln Gly Leu Leu Asn Arg His Leu Leu
                485                 490                 495

Ala Val His Ser Lys Asn Phe Pro His Val Cys Val Glu Cys Gly Lys
            500                 505                 510

Gly Phe Arg His Pro Ser Glu Leu Lys Lys His Met Arg Thr His Thr
        515                 520                 525

Gly Glu Lys Pro Tyr Gln Cys Gln Tyr Cys Ile Phe Arg Cys Ala Asp
    530                 535                 540

Gln Ser Asn Leu Lys Thr His Ile Lys Ser Lys His Gly Asn Asn Leu
```

-continued

```
545                 550                 555                 560

Pro Tyr Lys Cys Glu His Cys Pro Gln Ala Phe Gly Asp Glu Arg Glu
                565                 570                 575

Leu Gln Arg His Leu Asp Leu Phe Gln Gly His Lys Thr His Gln Cys
            580                 585                 590

Pro His Cys Asp His Lys Ser Thr Asn Ser Ser Asp Leu Lys Arg His
        595                 600                 605

Ile Ile Ser Val His Thr Lys Asp Phe Pro His Lys Cys Glu Val Cys
    610                 615                 620

Asp Lys Gly Phe His Arg Pro Ser Glu Leu Lys Lys His Ser Asp Ile
625                 630                 635                 640

His Lys Gly Arg Lys Ile His Gln Cys Arg His Cys Asp Phe Lys Thr
                645                 650                 655

Ser Asp Pro Phe Ile Leu Ser Gly His Ile Leu Ser Val His Thr Lys
            660                 665                 670

Asp Gln Pro Leu Lys Cys Lys Arg Cys Lys Arg Gly Phe Arg Gln Gln
        675                 680                 685

Asn Glu Leu Lys Lys His Met Lys Thr His Thr Gly Arg Lys Ile Tyr
    690                 695                 700

Gln Cys Glu Tyr Cys Glu Tyr Ser Thr Thr Asp Ala Ser Gly Phe Lys
705                 710                 715                 720

Arg His Val Ile Ser Ile His Thr Lys Asp Tyr Pro His Arg Cys Glu
                725                 730                 735

Phe Cys Lys Lys Gly Phe Arg Arg Pro Ser Glu Lys Asn Gln His Ile
            740                 745                 750

Met Arg His His Lys Glu Ala Leu Met
        755                 760


<210> SEQ ID NO 57
<211> LENGTH: 6439
<212> TYPE: DNA
<213> ORGANISM: Homo sapiens
<220> FEATURE:
<223> OTHER INFORMATION: intersectin 1 (SH3 domain protein) (ITSN1)
      cDNA
<220> FEATURE:
<221> NAME/KEY: CDS
<222> LOCATION: (269)..(5434)
<223> OTHER INFORMATION: ITSN1

<400> SEQUENCE: 57

gagcgaggga gggagcgaag gaggtagaga agagtggagg cgccagggga gggagcgtag     60

cttggttgct ccgtagtacg gcggctcgcg aggaagaatc ccgagcgggc tccgggacgg    120

acagagaggc gggcggggat ggtgtgcggg gctgcggctc ctgcgtccct cccagcggcg    180

cgtgagcggc actgatttgt ccctggggcg gcagcgcgga cccgcccgga gatgaggcgt    240

cgattagcaa ggtaaaagta acagaaccat ggctcagttt ccaacacctt ttggtggcag    300

cctggatatc tgggccataa ctgtagagga aagagcgaag catgatcagc agttccatag    360

tttaaagcca atatctggat tcattactgg tgatcaagct agaaactttt tttttcaatc    420

tgggttacct caacctgttt tagcacagat atgggcacta gctgacatga ataatgatgg    480

aagaatggat caagtggagt tttccatagc tatgaaactt atcaaactga agctacaagg    540

atatcagcta ccctctgcac ttccccctgt catgaaacag caaccagttg ctatttctag    600

cgcaccagca tttggtatgg gaggtatcgc cagcatgcca ccgcttacag ctgttgctcc    660

agtgccaatg ggatccattc cagttgttgg aatgtctcca accctagtat cttctgttcc    720
```

-continued

```
cacagcagct gtgccccccc tggctaacgg ggctccccct gttatacaac ctctgcctgc    780
atttgctcat cctgcagcca cattgccaaa gagttcttcc tttagtagat ctggtccagg    840
gtcacaacta aacactaaat tacaaaaggc acagtcattt gatgtggcca gtgtcccacc    900
agtggcagag tgggctgttc ctcagtcatc aagactgaaa tacaggcaat tattcaatag    960
tcatgacaaa actatgagtg gacacttaac aggtccccaa gcaagaacta ttcttatgca   1020
gtcaagttta ccacaggctc agctggcttc aatatggaat ctttctgaca ttgatcaaga   1080
tggaaaactt acagcagagg aatttatcct ggcaatgcac ctcattgatg tagctatgtc   1140
tggccaacca ctgccacctg tcctgcctcc agaatacatt ccaccttctt ttagaagagt   1200
tcgatctggc agtggtatat ctgtcataag ctcaacatct gtagatcaga ggctaccaga   1260
ggaaccagtt ttagaagatg aacaacaaca attagaaaag aaattacctg taacgtttga   1320
agataagaag cgggagaact ttgaacgtgg caacctggaa ctggagaaac gaaggcaagc   1380
tctcctggaa cagcagcgca aggagcagga gcgcctggcc cagctggagc gggcggagca   1440
ggagaggaag gagcgtgagc gccaggagca agagcgcaaa agacaactgg aactggagaa   1500
gcaactggaa aagcagcggg agctagaacg gcagagagag gaggagagga ggaaagaaat   1560
tgagaggcga gaggctgcaa aacgggaact tgaaaggcaa cgacaacttg agtgggaacg   1620
gaatcgaagg caagaactac taaatcaaag aaacaaagaa caagaggaca tagttgtact   1680
gaaagcaaag aaaaagactt tggaatttga attagaagct ctaaatgata aaaagcatca   1740
actagaaggg aaacttcaag atatcagatg tcgattgacc acccaaaggc aagaaattga   1800
gagcacaaac aaatctagag agttgagaat tgccgaaatc acccatctac agcaacaatt   1860
acaggaatct cagcaaatgc ttggaagact tattccagaa aaacagatac tcaatgacca   1920
attaaaacaa gttcagcaga acagtttgca cagagattca cttgttacac ttaaaagagc   1980
cttagaagca aaagaactag ctcggcagca cctacgagac caactggatg aagtggagaa   2040
agaaactaga tcaaaactac aggagattga tattttcaat aatcagctga aggaactaag   2100
agaaatacac aataagcaac aactccagaa gcaaaagtcc atggaggctg aacgactgaa   2160
acagaaagaa caagaacgaa agatcataga attagaaaaa caaaaagaag aagcccaaag   2220
acgagctcag gaaagggaca agcagtggct ggagcatgtg cagcaggagg acgagcatca   2280
gagaccaaga aaactccacg aagaggaaaa actgaaaagg gaggagagtg tcaaaaagaa   2340
ggatggcgag gaaaaaggca aacaggaagc acaagacaag ctgggtcggc ttttccatca   2400
acaccaagaa ccagctaagc cagctgtcca ggcaccctgg tccactgcag aaaaaggtcc   2460
acttaccatt tctgcacagg aaaatgtaaa agtggtgtat taccgggcac tgtacccctt   2520
tgaatccaga agccatgatg aaatcactat ccagccagga gacatagtca tggttaaagg   2580
ggaatgggtg gatgaaagcc aaactggaga acccggctgg cttggaggag aattaaaagg   2640
aaagacaggg tggttccctg caaactatgc agagaaaatc ccagaaaatg aggttcccgc   2700
tccagtgaaa ccagtgactg attcaacatc tgcccctgcc cccaaactgg ccttgcgtga   2760
gacccccgcc cctttggcag taacctcttc agagccctcc acgaccccta ataactgggc   2820
cgacttcagc tccacgtggc ccaccagcac gaatgagaaa ccagaaacgg ataactggga   2880
tgcatgggca gcccagccct ctctcaccgt tccaagtgcc ggccagttaa ggcagaggtc   2940
cgcctttact ccagccacgg ccactggctc ctccccgtct cctgtgctag gccagggtga   3000
aaaggtggag gggctacaag ctcaagccct atatccttgg agagccaaaa aagacaacca   3060
cttaaatttt aacaaaaatg atgtcatcac cgtcctggaa cagcaagaca tgtggtggtt   3120
```

-continued

```
tggagaagtt caaggtcaga agggttggtt ccccaagtct tacgtgaaac tcatttcagg   3180
gcccataagg aagtctacaa gcatggattc tggttcttca gagagtcctg ctagtctaaa   3240
gcgagtagcc tctccagcag ccaagccggt cgtttcggga gaagaattta ttgccatgta   3300
cacttacgag agttctgagc aaggagattt aacctttcag caaggggatg tgattttggt   3360
taccaagaaa gatggtgact ggtggacagg aacagtgggc gacaaggccg gagtcttccc   3420
ttctaactat gtgaggctta aagattcaga gggctctgga actgctggga aaacagggag   3480
tttaggaaaa aaacctgaaa ttgcccaggt tattgcctca tacaccgcca ccggccccga   3540
gcagctcact ctcgcccctg gtcagctgat tttgatccga aaaaagaacc caggtggatg   3600
gtgggaagga gagctgcaag cacgtgggaa aaagcgccag ataggctggt tcccagctaa   3660
ttatgtaaag cttctaagcc ctgggacgag caaaatcact ccaacagagc cacctaagtc   3720
aacagcatta gcggcagtgt gccaggtgat tgggatgtac gactacaccg cgcagaatga   3780
cgatgagctg gccttcaaca agggccagat catcaacgtc ctcaacaagg aggaccctga   3840
ctggtggaaa ggagaagtca atggacaagt ggggctcttc ccatccaatt atgtgaagct   3900
gaccacagac atggacccaa gccagcaatg gtgttcagac ttacatctct tggatatgtt   3960
gaccccaact gaaagaaagc gacaaggata catccacgag ctcattgtca ccgaggagaa   4020
ctatgtgaat gacctgcagc tggtcacaga gatttttcaa aaacccctga tggagtctga   4080
gctgctgaca gaaaaagagg ttgctatgat tttgtgaac tggaaggagc tgattatgtg   4140
taatatcaaa ctactaaaag cgctgagagt ccgcaagaag atgtccgggg agaagatgcc   4200
tgtgaagatg attggagaca tcctgagcgc acagctgccg cacatgcagc cctacatccg   4260
cttctgcagc cgccagctca acggggctgc cctgatccag cagaagacgg atgaggcccc   4320
agacttcaag gagttcgtca aaagattggc aatggatcct cggtgtaaag ggatgccact   4380
ctctagtttt atactgaagc ctatgcaacg ggtaacaaga tacccactga tcattaaaaa   4440
tatcctggaa aacacccctg aaaaccaccc ggaccacagc cacttgaagc acgccctgga   4500
gaaggcggaa gagctctgtt cccaggtgaa cgaaggggtg cgggagaagg agaactctga   4560
ccggctggag tggatccagg cccacgtgca gtgtgaaggc ctgtctgagc aacttgtgtt   4620
caattcagtg accaattgct tggggccgcg caaatttctg cacagtggga agctctacaa   4680
ggccaagagc aacaaggagc tgtatggctt ccttttcaac gacttcctcc tgctgactca   4740
gatcacgaag cctttggggt cttctggcac cgacaaagtc ttcagcccca aatcaaacct   4800
gcagtataaa atgtataaaa cacctatttt cctaaatgag gttctagtaa aattacccac   4860
cgacccttct ggagacgagc ccatcttcca catctcccac attgaccgcg tctatactct   4920
ccgagcagaa agcataaatg aaaggactgc ctgggtgcag aaaatcaaag ctgcttctga   4980
actctacata gagactgaga aaaagaagcg cgagaaagcg tacctggtcc gttcccaaag   5040
ggcaacaggc attggaaggt tgatggtgaa cgtggttgaa ggcatcgagt tgaaaccctg   5100
tcggtcacat ggaaagagca acccgtactg tgaggtgacc atgggttccc agtgccacat   5160
caccaagacg atccaggaca ctctgaaccc caagtggaat tccaactgcc agttcttcat   5220
ccgagacctg gagcaggaag tcctctgcat cactgtgttc gagagggacc agttctcacc   5280
agatgatttt ttgggtcgga cggagatccg tgtggcggac atcaagaaag accagggctc   5340
caaaggtcca gttacgaagt gtcttctgct gcacgaagtc cccacgggag agattgtggt   5400
ccgcttggac ctgcagttgt ttgatgagcc gtaggcagcg ggctcagggt gtgctcagca   5460
gggtcccagc ccacggccac acatgctgtc tggaaattgt attccttttc taagaaacca   5520
```

-continued

```
ccatttggta ttcagtcaca gggatatggg atggcaaaga caggccccctc aaagctccta   5580

ggaatcattc tcgacaatcc tccctgcccc gaaacaattt cctgtttcat gaaacaaagc   5640

tgtgttttcc tttgtcctca ctacaggtct cattatggct tctagggtcg ctgaaatccc   5700

atagccctca acagggtgca gctgggagtc tagccccttc ccgggcttga gggatgggtc   5760

tggttactat aaaatagatt tataaatgca atgtctatat ttttggagaa ctcatgtaac   5820

cctcctgttt cttacatcca ccagtcccca agtagacttc ttggcctaca atgcccagtc   5880

cttggtgtga gtttagaaac aattatgacg gtcctgtcat tgcttcagaa tcccatctct   5940

cctgcaggga aatgctgcct agagctgatc actcggtgag acggtctgat caggccctgg   6000

cttagctctt tgaagagctg gtctatggaa gtttccagca tgtgcaccgt tatagccgtt   6060

ccttccccct ctaggccttg tattaatata tgtcaatgaa aacacactgg tgtattgttg   6120

cgtggattca gttctgattc ccagcatgct tagaatatgg tcacagaaag tcattatcta   6180

gaaagtcacc cctctgctgg atcagatcac tacaggtcac tggaaaggca actttacaat   6240

gttgggtcac tgggtctcgg ttggcagcca tgttggaaaa atctcttttg gctcggaggc   6300

ctgtgatatt tcatagcagc agtcgttgct ggtgacctgt tctgtgcttg aatgtgctga   6360

atcctgattg ttgtaggaca tttcaacagc tctttttggt acgttcccca aaaagccatg   6420

tcctagatcc ccaaggcgt                                                 6439
```

<210> SEQ ID NO 58
<211> LENGTH: 1721
<212> TYPE: PRT
<213> ORGANISM: Homo sapiens
<220> FEATURE:
<223> OTHER INFORMATION: intersectin 1 (SH3 domain protein) (ITSN1)

<400> SEQUENCE: 58

```
Met Ala Gln Phe Pro Thr Pro Phe Gly Gly Ser Leu Asp Ile Trp Ala
  1               5                  10                  15

Ile Thr Val Glu Glu Arg Ala Lys His Asp Gln Gln Phe His Ser Leu
             20                  25                  30

Lys Pro Ile Ser Gly Phe Ile Thr Gly Asp Gln Ala Arg Asn Phe Phe
         35                  40                  45

Phe Gln Ser Gly Leu Pro Gln Pro Val Leu Ala Gln Ile Trp Ala Leu
     50                  55                  60

Ala Asp Met Asn Asn Asp Gly Arg Met Asp Gln Val Glu Phe Ser Ile
 65                  70                  75                  80

Ala Met Lys Leu Ile Lys Leu Lys Leu Gln Gly Tyr Gln Leu Pro Ser
                 85                  90                  95

Ala Leu Pro Pro Val Met Lys Gln Gln Pro Val Ala Ile Ser Ser Ala
            100                 105                 110

Pro Ala Phe Gly Met Gly Gly Ile Ala Ser Met Pro Pro Leu Thr Ala
        115                 120                 125

Val Ala Pro Val Pro Met Gly Ser Ile Pro Val Val Gly Met Ser Pro
    130                 135                 140

Thr Leu Val Ser Ser Val Pro Thr Ala Ala Val Pro Pro Leu Ala Asn
145                 150                 155                 160

Gly Ala Pro Pro Val Ile Gln Pro Leu Pro Ala Phe Ala His Pro Ala
                165                 170                 175

Ala Thr Leu Pro Lys Ser Ser Ser Phe Ser Arg Ser Gly Pro Gly Ser
            180                 185                 190

Gln Leu Asn Thr Lys Leu Gln Lys Ala Gln Ser Phe Asp Val Ala Ser
        195                 200                 205
```

```
Val Pro Pro Val Ala Glu Trp Ala Val Pro Gln Ser Ser Arg Leu Lys
    210                 215                 220

Tyr Arg Gln Leu Phe Asn Ser His Asp Lys Thr Met Ser Gly His Leu
225                 230                 235                 240

Thr Gly Pro Gln Ala Arg Thr Ile Leu Met Gln Ser Ser Leu Pro Gln
                245                 250                 255

Ala Gln Leu Ala Ser Ile Trp Asn Leu Ser Asp Ile Asp Gln Asp Gly
            260                 265                 270

Lys Leu Thr Ala Glu Glu Phe Ile Leu Ala Met His Leu Ile Asp Val
        275                 280                 285

Ala Met Ser Gly Gln Pro Leu Pro Pro Val Leu Pro Pro Glu Tyr Ile
    290                 295                 300

Pro Pro Ser Phe Arg Arg Val Arg Ser Gly Ser Gly Ile Ser Val Ile
305                 310                 315                 320

Ser Ser Thr Ser Val Asp Gln Arg Leu Pro Glu Glu Pro Val Leu Glu
                325                 330                 335

Asp Glu Gln Gln Gln Leu Glu Lys Lys Leu Pro Val Thr Phe Glu Asp
            340                 345                 350

Lys Lys Arg Glu Asn Phe Glu Arg Gly Asn Leu Glu Leu Glu Lys Arg
        355                 360                 365

Arg Gln Ala Leu Leu Glu Gln Gln Arg Lys Glu Gln Glu Arg Leu Ala
    370                 375                 380

Gln Leu Glu Arg Ala Glu Gln Glu Arg Lys Glu Arg Glu Arg Gln Glu
385                 390                 395                 400

Gln Glu Arg Lys Arg Gln Leu Glu Leu Glu Lys Gln Leu Glu Lys Gln
                405                 410                 415

Arg Glu Leu Glu Arg Gln Arg Glu Glu Glu Arg Arg Lys Glu Ile Glu
            420                 425                 430

Arg Arg Glu Ala Ala Lys Arg Glu Leu Glu Arg Gln Arg Gln Leu Glu
        435                 440                 445

Trp Glu Arg Asn Arg Arg Gln Glu Leu Leu Asn Gln Arg Asn Lys Glu
    450                 455                 460

Gln Glu Asp Ile Val Val Leu Lys Ala Lys Lys Lys Thr Leu Glu Phe
465                 470                 475                 480

Glu Leu Glu Ala Leu Asn Asp Lys Lys His Gln Leu Glu Gly Lys Leu
                485                 490                 495

Gln Asp Ile Arg Cys Arg Leu Thr Thr Gln Arg Gln Glu Ile Glu Ser
            500                 505                 510

Thr Asn Lys Ser Arg Glu Leu Arg Ile Ala Glu Ile Thr His Leu Gln
        515                 520                 525

Gln Gln Leu Gln Glu Ser Gln Gln Met Leu Gly Arg Leu Ile Pro Glu
    530                 535                 540

Lys Gln Ile Leu Asn Asp Gln Leu Lys Gln Val Gln Gln Asn Ser Leu
545                 550                 555                 560

His Arg Asp Ser Leu Val Thr Leu Lys Arg Ala Leu Glu Ala Lys Glu
                565                 570                 575

Leu Ala Arg Gln His Leu Arg Asp Gln Leu Asp Glu Val Glu Lys Glu
            580                 585                 590

Thr Arg Ser Lys Leu Gln Glu Ile Asp Ile Phe Asn Asn Gln Leu Lys
        595                 600                 605

Glu Leu Arg Glu Ile His Asn Lys Gln Gln Leu Gln Lys Gln Lys Ser
    610                 615                 620

Met Glu Ala Glu Arg Leu Lys Gln Lys Glu Gln Glu Arg Lys Ile Ile
```

-continued

```
625                 630                 635                 640

Glu Leu Glu Lys Gln Lys Glu Glu Ala Gln Arg Arg Ala Gln Glu Arg
                645                 650                 655

Asp Lys Gln Trp Leu Glu His Val Gln Gln Glu Asp Glu His Gln Arg
            660                 665                 670

Pro Arg Lys Leu His Glu Glu Glu Lys Leu Lys Arg Glu Glu Ser Val
        675                 680                 685

Lys Lys Lys Asp Gly Glu Glu Lys Gly Lys Gln Glu Ala Gln Asp Lys
    690                 695                 700

Leu Gly Arg Leu Phe His Gln His Gln Glu Pro Ala Lys Pro Ala Val
705                 710                 715                 720

Gln Ala Pro Trp Ser Thr Ala Glu Lys Gly Pro Leu Thr Ile Ser Ala
                725                 730                 735

Gln Glu Asn Val Lys Val Val Tyr Tyr Arg Ala Leu Tyr Pro Phe Glu
            740                 745                 750

Ser Arg Ser His Asp Glu Ile Thr Ile Gln Pro Gly Asp Ile Val Met
        755                 760                 765

Val Lys Gly Glu Trp Val Asp Glu Ser Gln Thr Gly Glu Pro Gly Trp
    770                 775                 780

Leu Gly Gly Glu Leu Lys Gly Lys Thr Gly Trp Phe Pro Ala Asn Tyr
785                 790                 795                 800

Ala Glu Lys Ile Pro Glu Asn Glu Val Pro Ala Pro Val Lys Pro Val
                805                 810                 815

Thr Asp Ser Thr Ser Ala Pro Ala Pro Lys Leu Ala Leu Arg Glu Thr
            820                 825                 830

Pro Ala Pro Leu Ala Val Thr Ser Ser Glu Pro Ser Thr Thr Pro Asn
        835                 840                 845

Asn Trp Ala Asp Phe Ser Ser Thr Trp Pro Thr Ser Thr Asn Glu Lys
    850                 855                 860

Pro Glu Thr Asp Asn Trp Asp Ala Trp Ala Ala Gln Pro Ser Leu Thr
865                 870                 875                 880

Val Pro Ser Ala Gly Gln Leu Arg Gln Arg Ser Ala Phe Thr Pro Ala
                885                 890                 895

Thr Ala Thr Gly Ser Ser Pro Ser Pro Val Leu Gly Gln Gly Glu Lys
            900                 905                 910

Val Glu Gly Leu Gln Ala Gln Ala Leu Tyr Pro Trp Arg Ala Lys Lys
        915                 920                 925

Asp Asn His Leu Asn Phe Asn Lys Asn Asp Val Ile Thr Val Leu Glu
    930                 935                 940

Gln Gln Asp Met Trp Trp Phe Gly Glu Val Gln Gly Gln Lys Gly Trp
945                 950                 955                 960

Phe Pro Lys Ser Tyr Val Lys Leu Ile Ser Gly Pro Ile Arg Lys Ser
                965                 970                 975

Thr Ser Met Asp Ser Gly Ser Ser Glu Ser Pro Ala Ser Leu Lys Arg
            980                 985                 990

Val Ala Ser Pro Ala Ala Lys Pro Val Val Ser Gly Glu Glu Phe Ile
        995                 1000                1005

Ala Met Tyr Thr Tyr Glu Ser Ser Glu Gln Gly Asp Leu Thr Phe Gln
   1010                 1015                1020

Gln Gly Asp Val Ile Leu Val Thr Lys Lys Asp Gly Asp Trp Trp Thr
1025                1030                1035                1040

Gly Thr Val Gly Asp Lys Ala Gly Val Phe Pro Ser Asn Tyr Val Arg
               1045                1050                1055
```

```
Leu Lys Asp Ser Glu Gly Ser Gly Thr Ala Gly Lys Thr Gly Ser Leu
            1060                1065                1070

Gly Lys Lys Pro Glu Ile Ala Gln Val Ile Ala Ser Tyr Thr Ala Thr
        1075                1080                1085

Gly Pro Glu Gln Leu Thr Leu Ala Pro Gly Gln Leu Ile Leu Ile Arg
    1090                1095                1100

Lys Lys Asn Pro Gly Gly Trp Trp Glu Gly Glu Leu Gln Ala Arg Gly
1105                1110                1115                1120

Lys Lys Arg Gln Ile Gly Trp Phe Pro Ala Asn Tyr Val Lys Leu Leu
                1125                1130                1135

Ser Pro Gly Thr Ser Lys Ile Thr Pro Thr Glu Pro Pro Lys Ser Thr
            1140                1145                1150

Ala Leu Ala Ala Val Cys Gln Val Ile Gly Met Tyr Asp Tyr Thr Ala
        1155                1160                1165

Gln Asn Asp Asp Glu Leu Ala Phe Asn Lys Gly Gln Ile Ile Asn Val
    1170                1175                1180

Leu Asn Lys Glu Asp Pro Asp Trp Trp Lys Gly Glu Val Asn Gly Gln
1185                1190                1195                1200

Val Gly Leu Phe Pro Ser Asn Tyr Val Lys Leu Thr Thr Asp Met Asp
                1205                1210                1215

Pro Ser Gln Gln Trp Cys Ser Asp Leu His Leu Leu Asp Met Leu Thr
            1220                1225                1230

Pro Thr Glu Arg Lys Arg Gln Gly Tyr Ile His Glu Leu Ile Val Thr
        1235                1240                1245

Glu Glu Asn Tyr Val Asn Asp Leu Gln Leu Val Thr Glu Ile Phe Gln
    1250                1255                1260

Lys Pro Leu Met Glu Ser Glu Leu Leu Thr Glu Lys Glu Val Ala Met
1265                1270                1275                1280

Ile Phe Val Asn Trp Lys Glu Leu Ile Met Cys Asn Ile Lys Leu Leu
                1285                1290                1295

Lys Ala Leu Arg Val Arg Lys Lys Met Ser Gly Glu Lys Met Pro Val
            1300                1305                1310

Lys Met Ile Gly Asp Ile Leu Ser Ala Gln Leu Pro His Met Gln Pro
        1315                1320                1325

Tyr Ile Arg Phe Cys Ser Arg Gln Leu Asn Gly Ala Ala Leu Ile Gln
    1330                1335                1340

Gln Lys Thr Asp Glu Ala Pro Asp Phe Lys Glu Phe Val Lys Arg Leu
1345                1350                1355                1360

Ala Met Asp Pro Arg Cys Lys Gly Met Pro Leu Ser Ser Phe Ile Leu
                1365                1370                1375

Lys Pro Met Gln Arg Val Thr Arg Tyr Pro Leu Ile Ile Lys Asn Ile
            1380                1385                1390

Leu Glu Asn Thr Pro Glu Asn His Pro Asp His Ser His Leu Lys His
        1395                1400                1405

Ala Leu Glu Lys Ala Glu Glu Leu Cys Ser Gln Val Asn Glu Gly Val
    1410                1415                1420

Arg Glu Lys Glu Asn Ser Asp Arg Leu Glu Trp Ile Gln Ala His Val
1425                1430                1435                1440

Gln Cys Glu Gly Leu Ser Glu Gln Leu Val Phe Asn Ser Val Thr Asn
                1445                1450                1455

Cys Leu Gly Pro Arg Lys Phe Leu His Ser Gly Lys Leu Tyr Lys Ala
            1460                1465                1470

Lys Ser Asn Lys Glu Leu Tyr Gly Phe Leu Phe Asn Asp Phe Leu Leu
        1475                1480                1485
```

```
Leu Thr Gln Ile Thr Lys Pro Leu Gly Ser Ser Gly Thr Asp Lys Val
   1490                1495                1500

Phe Ser Pro Lys Ser Asn Leu Gln Tyr Lys Met Tyr Lys Thr Pro Ile
1505                1510                1515                1520

Phe Leu Asn Glu Val Leu Val Lys Leu Pro Thr Asp Pro Ser Gly Asp
                1525                1530                1535

Glu Pro Ile Phe His Ile Ser His Ile Asp Arg Val Tyr Thr Leu Arg
            1540                1545                1550

Ala Glu Ser Ile Asn Glu Arg Thr Ala Trp Val Gln Lys Ile Lys Ala
       1555                1560                1565

Ala Ser Glu Leu Tyr Ile Glu Thr Glu Lys Lys Lys Arg Glu Lys Ala
   1570                1575                1580

Tyr Leu Val Arg Ser Gln Arg Ala Thr Gly Ile Gly Arg Leu Met Val
1585                1590                1595                1600

Asn Val Val Glu Gly Ile Glu Leu Lys Pro Cys Arg Ser His Gly Lys
                1605                1610                1615

Ser Asn Pro Tyr Cys Glu Val Thr Met Gly Ser Gln Cys His Ile Thr
            1620                1625                1630

Lys Thr Ile Gln Asp Thr Leu Asn Pro Lys Trp Asn Ser Asn Cys Gln
       1635                1640                1645

Phe Phe Ile Arg Asp Leu Glu Gln Glu Val Leu Cys Ile Thr Val Phe
   1650                1655                1660

Glu Arg Asp Gln Phe Ser Pro Asp Asp Phe Leu Gly Arg Thr Glu Ile
1665                1670                1675                1680

Arg Val Ala Asp Ile Lys Lys Asp Gln Gly Ser Lys Gly Pro Val Thr
                1685                1690                1695

Lys Cys Leu Leu Leu His Glu Val Pro Thr Gly Glu Ile Val Val Arg
            1700                1705                1710

Leu Asp Leu Gln Leu Phe Asp Glu Pro
       1715                1720
```

<210> SEQ ID NO 59
<211> LENGTH: 1954
<212> TYPE: DNA
<213> ORGANISM: Homo sapiens
<220> FEATURE:
<223> OTHER INFORMATION: phorbol-12-myristate-13-acetate-induced
      protein 1 (PMAIP1) cDNA
<220> FEATURE:
<221> NAME/KEY: CDS
<222> LOCATION: (219)..(383)
<223> OTHER INFORMATION: PMAIP1

<400> SEQUENCE: 59

```
actggacaaa agcgtggtct ctggcgcggg gatctcagag tttcccgggc actcaccgtg     60

tgtagttggc atctccgcgc gtccggacac ccgatcccag catccctgcc tgcaggactg    120

ttcgtgttca gctcgcgtcc tgcagctgtc cgaggtgctc cagttggagg ctgaggttcc    180

cgggctctgt agctgagtgg gcggcggcac cggcggagat gcctgggaag aaggcgcgca    240

agaacgctca accgagcccc gcgcgggctc cagcagagct ggaagtcgag tgtgctactc    300

aactcaggag atttggagac aaactgaact tccggcagaa acttctgaat ctgatatcca    360

aactcttctg ctcaggaacc tgactgcatc aaaaacttgc atgaggggac tccttcaaaa    420

gagttttctc aggaggtgca cgtttcatca atttgaagaa agactgcatt gtaattgaga    480

ggaatgtgaa ggtgcattca tgggtgccct tggaaacgga agatggaata catcaaagtg    540

aatttctgtt caagttttcc cagattatca ttctttggga tgagagaaca ttataaaacc    600
```

actttgttta ttttaaagca agaatggaag acccttgaaa ataaagaagt aattattgac 660
acatttcttt tttacttaga gaatcgttct agtgtttttg ccgaagatta ccgctggcct 720
actgtgaagg gagatgacct gtgattagac tgggcggctg gggagaaaca gttcagtgca 780
ttgttgttgt tgctgttttt ggtgttttgc ttttcagtgc caactcagca cattgtatat 840
gattcggttt atacatatta ccttgttata atgaaaaaac tcattctgag aacactgaaa 900
tgttatactc agtgttgatt tcttcggtca ctacacaacg taaaatcatt tgtttctttt 960
gactcaaatt gtattgcttc tgttcagatg atctttcatt caatgtgttc ctgttgggcg 1020
ttactagaaa ctatggaaaa ctggaaaata actttgaaaa aattggataa agtataggag 1080
ggttacttgg ggccagtaaa tcagtagact gaacattcaa tataataaaa gaacatgggg 1140
attttgtata accagggata ataaaaagaa aaaagaagtt aatttttaat tgatgttttt 1200
gaaacttagt agaacaaata ttcagaagta acttgataag atatgaatgt ttctaaagaa 1260
gtttctaaag gttcggaaaa tgctccttgt cacattagtg tgcatcctac aaaaagtgat 1320
ctcttaatgt aaattaagaa tattttcata attggaatat acttttctta aaaaaaagga 1380
acagttagtt ctcatctaga atgaaagttc catatatgca ttggtgaata tatatgtata 1440
cacatactta catacttata tgggtatctg tatagataat ttgtattaga gtattatata 1500
gcttcttagt agggtctcaa gtaagtttca tttttttat ctgggctata tacagtcctc 1560
aaataaataa tgtcttgatt ttatttcagc aggaataatt ttatttattt tgcctattta 1620
taattaaagt atttttcttt agtttgaaaa tgtgtattaa agttacattt ttgagttaca 1680
agagtcttat aactacttga atttttagtt aaaatgtctt aatgtaggtt gtagtcactt 1740
tagatggaaa attacctcac atctgttttc ttcagtatta cttaagattg tttatttagt 1800
ggtagagagt ttttttttc agcctagagg cagctatttt accatctggt atttatggtc 1860
taatttgtat ttaaacatat gcacacatat aaaagttgat actgtggcag taaactatta 1920
aaagttttca ctgttcaaaa aaaaaaaaaa aaaa 1954

<210> SEQ ID NO 60
<211> LENGTH: 54
<212> TYPE: PRT
<213> ORGANISM: Homo sapiens
<220> FEATURE:
<223> OTHER INFORMATION: phorbol-12-myristate-13-acetate-induced
protein 1 (PMAIP1)

<400> SEQUENCE: 60

Met Pro Gly Lys Lys Ala Arg Lys Asn Ala Gln Pro Ser Pro Ala Arg
1 5 10 15

Ala Pro Ala Glu Leu Glu Val Glu Cys Ala Thr Gln Leu Arg Arg Phe
20 25 30

Gly Asp Lys Leu Asn Phe Arg Gln Lys Leu Leu Asn Leu Ile Ser Lys
35 40 45

Leu Phe Cys Ser Gly Thr
50

<210> SEQ ID NO 61
<211> LENGTH: 4068
<212> TYPE: DNA
<213> ORGANISM: Homo sapiens
<220> FEATURE:
<223> OTHER INFORMATION: transmembrane protein 47 (TMEM47) cDNA
<220> FEATURE:
<221> NAME/KEY: CDS
<222> LOCATION: (260)..(805)

<223> OTHER INFORMATION: TMEM47

<400> SEQUENCE: 61
ggcagagcgc ggcgcggggc cggcggcgaa ggtccggggt ggaatcgacg tcgctgcggc 60
tgccgacgac ccacacccgg ccggccgcct ccgcagaccc accttggccg cgcggcaggg 120
ggcgcgcaga gccccgaggg agcgagtccc cgcgcgtggc agctcggcgg cttctccctt 180
cgggaggtcc ggctcccggc tctccggacc cgcctggcgt cctcgcctgc ggcggggcgg 240
acgacagcgg cgcccaggaa tggcttcggc gggcagcggc atggaggagg tgcgcgtgtc 300
ggtgctgacc cccttgaagc tggtcgggct ggtgtgcatc ttcctggcgc tgtgtctgga 360
cctgggggcg gtgctgagcc cggcctgggt cacagctgac caccagtact acctgtcgtt 420
gtgggagtcc tgccgcaaac ccgccagctt ggacatctgg cactgcgagt ccacgctcag 480
cagcgattgg cagattgcta ctctggcttt actcctgggc ggcgctgcca tcattctcat 540
tgcattcctg gtgggtttga tttctatctg cgtgggatct cgaaggcgtt tctatagacc 600
tgttgcggtc atgcttttg cagcagttgt tttacaggtt tgcagcctgg tcctttaccc 660
aatcaagttc attgaaactg tgagcttgaa aatttaccat gagttcaact ggggttatgg 720
cctggcctgg ggtgcaacta tattttcgtt tgggggtgcc atcctttatt gcctgaaccc 780
taagaactat gaagactact actagaacca atagtctcaa agtaaaaaca accaccacca 840
tccaacaaaa ggattacgtc tgcatctttt ctaacttact attttctaaa acacttgtgg 900
agcatcaagc agtttgctca gttgatttaa tctttttgc cttttggctg tcaacatcat 960
aaccagcttt tacatccatt ttagaaatct gcacaaatta agagagctga ttagacatag 1020
gcaaatgctg caaacttcca atatgttcat atcgttttc ttgacaaatg aagggtctat 1080
atgacagcaa ccattgtgag aaactagttg gaatgagatt tgcctcaatc tcctattgcc 1140
tgcaggggag cagttggcat aagcaacatt tagaagttcc tttgcgctga caaggattcc 1200
actgttagag cccttaccgc ctgcttatcc tacccaatga ctacattggc tgttggttat 1260
ttgcttgagt gagcccttga aaaatgaact gcccttcagc atctaatggg agttgtgaat 1320
gtaactggtt aatgatacac attccacctt caggaacact ctttttaatg ggaggttatg 1380
ctttggcaat cagcgtctcc ctgggaagag agtcaagact tggagacatg tgcttctcat 1440
tatgtggtta gaaattggtg cctcagccct atctagactg gggaaaaatt gaggatctct 1500
gtttttcctg gggcaaacag aaagaaatct gcatgagttg cttttgtacc ctttaaatca 1560
tttgccaaac attgcagcaa acaagtgtgc gtatgtaaca agcttcactg tttttataga 1620
aggtgaacca ttagtataaa tggtaataag ttgttcccta accctccaca tacatttgcc 1680
tatcacacgt aaaattaata tttactctag tgaagtggtt tgagcactaa ccttgtacac 1740
attgttaaga ggcttagatt ggtattcata cttatttacc atacaaaagt atggtacctt 1800
aaagcttttg ctctatgttc tttactgttt cactggaaag tgtcaataga gttgcctaag 1860
aataaaaatt gaaatggtgt taatctgaaa attaatgatt ctctgtaagc actgtagttg 1920
aaaagagagt agcaattagg atgatcattt tgtgtaaaat tcattaaaat agaaggctgc 1980
tattttttgc aagtatttta aatgtcttca tttttttaag aaaggaatag cgatagattt 2040
atataaatat ctaaatgtct cagtagagga gtagaattca tctggttatc acctggtcct 2100
ctgaagttaa ctgatgggct aaccgatttg tgcacacact taggatggat ttatgttaag 2160
ggaattactt actgactgtt caatggaagg aagtattaat aatagggaat aagtttgcaa 2220
ctaatctcat gctgcaaact tgtgttaatt ctgtttaata tacaaatttg gatagcttaa 2280

-continued

```
ttataaacat atttttatat caaatataca gttctaatat aaaagttata aataattatt   2340

tttgttaaca aagacactaa aacagtatgt tctggttttg gccctcttgc agaaagaagc   2400

attagaaaaa ttactttaaa agtagctata tgttactgta ttgcaaaatc tgttaagagc   2460

aggaccacat cgatagtatt taataatttg ttttacctcc caaaacacag ttcttctttc   2520

agcttgtctt aagaatggtt gccaaaaaca acagccaaaa aaaaaaaacc tattttatta   2580

tccaaatgct agaaaacaca catgaatttt ctataaaatc acgaatatga agtaccaggt   2640

ttagtcttac tttagcaatg atagacaaaa gcgaataaat acatcacaga cagaaacctt   2700

tataaaaata tatgattcta taaagaatca ttagaaatta tgagtggaaa ttctccagaa   2760

agatagtatt atagagtctt ttgaagcaat tttttgagaa atagtaaaat ctggggcaga   2820

gtgtcttgca gttaattgca tattgtcaga gcagcatgag aaatatgata tttggatagg   2880

gatttcagca actaaacatt ctctgttctg agatctcttt attcctgaat aatgaaagaa   2940

tagtactttg gtgctgacac caatgaggca cttctcttgg tcctagtaga ggatgcagtg   3000

tactgttaaa ccaatatcat cacatctcga gtcttatcaa gttttcattc tctgtcaata   3060

tgacaagctc aaagtgacag aatatgttat aggttgaagc acacatattt gcagtttact   3120

gaaaagtaga tttcttatgt gactttttc ccttctcagc aaagagccct acactagatt   3180

tctaccatca ctaatatttg gaagtatttc attactaaca atctcagtac aacatgaaaa   3240

ttgttgcttc tcatctaaaa tacaattttg tctatcagaa taaacacaag tgaaattttc   3300

acctacatta acattatgtc tttgcagctt taggtttgtt agatgtgttc ttaagcataa   3360

tttttagcca caaacccatt gttagataga tatctatgga tatagatcta catctataga   3420

tatagatata cacacatata tatactcaca cacatatagc ataaaatact cagcagggct   3480

agttattccg atttcttgca caattattta gctttttgta agttcaacat gtaaatttta   3540

aagacataaa tatagagaga cttatgtgtt tgaatataaa tgatatatat ggattagcat   3600

gtacctgtat attattaaac atgcaatgaa ctgactggta agtgacgtct aattgtatgg   3660

ctagcaatgt aatttattca gactgtattt ttgtacagag cagtgcactc taacctatgc   3720

ctctgtgtcc tctttaatgc ctaaagctgt gcctagaaat ttcatctgtc ttaaaagtaa   3780

aatatacttc atgctgttta tgctattagt ttctgtactg ctattctata tttattattt   3840

ttaaatatat gacatgttta ctacttaaac atgaattcat ggtatcctgg ttattttttt   3900

taagtcatct gggggaaaac ctgtttatca ctccagtgat tttgagtttg cagtttcaca   3960

atcagttctt catttcatga tttttgtagt tgacatgaag tcatctatgt ggaaaaaaat   4020

aaaaataaaa gtgatttcac ggatgtggtt tgaaaaaaaa aaaaaaaa                4068
```

<210> SEQ ID NO 62
<211> LENGTH: 181
<212> TYPE: PRT
<213> ORGANISM: Homo sapiens
<220> FEATURE:
<223> OTHER INFORMATION: transmembrane protein 47 (TMEM47)

<400> SEQUENCE: 62

```
Met Ala Ser Ala Gly Ser Gly Met Glu Glu Val Arg Val Ser Val Leu
  1               5                  10                  15

Thr Pro Leu Lys Leu Val Gly Leu Val Cys Ile Phe Leu Ala Leu Cys
             20                  25                  30

Leu Asp Leu Gly Ala Val Leu Ser Pro Ala Trp Val Thr Ala Asp His
         35                  40                  45

Gln Tyr Tyr Leu Ser Leu Trp Glu Ser Cys Arg Lys Pro Ala Ser Leu
```

```
    50                  55                  60

Asp Ile Trp His Cys Glu Ser Thr Leu Ser Ser Asp Trp Gln Ile Ala
 65                  70                  75                  80

Thr Leu Ala Leu Leu Leu Gly Gly Ala Ala Ile Ile Leu Ile Ala Phe
                85                  90                  95

Leu Val Gly Leu Ile Ser Ile Cys Val Gly Ser Arg Arg Arg Phe Tyr
            100                 105                 110

Arg Pro Val Ala Val Met Leu Phe Ala Ala Val Val Leu Gln Val Cys
        115                 120                 125

Ser Leu Val Leu Tyr Pro Ile Lys Phe Ile Glu Thr Val Ser Leu Lys
    130                 135                 140

Ile Tyr His Glu Phe Asn Trp Gly Tyr Gly Leu Ala Trp Gly Ala Thr
145                 150                 155                 160

Ile Phe Ser Phe Gly Gly Ala Ile Leu Tyr Cys Leu Asn Pro Lys Asn
                165                 170                 175

Tyr Glu Asp Tyr Tyr
            180


<210> SEQ ID NO 63
<211> LENGTH: 2354
<212> TYPE: DNA
<213> ORGANISM: Homo sapiens
<220> FEATURE:
<223> OTHER INFORMATION: interleukin 11 (IL11) cDNA
<220> FEATURE:
<221> NAME/KEY: CDS
<222> LOCATION: (137)..(736)
<223> OTHER INFORMATION: IL11

<400> SEQUENCE: 63

gctcagggca catgcctccc ctccccaggc cgcggcccag ctgaccctcg ggctccccc      60

ggcagcggac agggaagggt taaaggcccc cggctccctg ccccctgccc tggggaaccc    120

ctggccctgt ggggacatga actgtgtttg ccgcctggtc ctggtcgtgc tgagcctgtg    180

gccagataca gctgtcgccc ctgggccacc acctggcccc cctcgagttt ccccagaccc    240

tcgggccgag ctggacagca ccgtgctcct gacccgctct ctcctggcgg acacgcggca    300

gctggctgca cagctgaggg acaaattccc agctgacggg gaccacaacc tggattccct    360

gcccaccctg gccatgagtg cgggggcact gggagctcta cagctcccag gtgtgctgac    420

aaggctgcga gcggacctac tgtcctacct gcggcacgtg cagtggctgc gccgggcagg    480

tggctcttcc ctgaagaccc tggagcccga gctgggcacc ctgcaggccc gactggaccg    540

gctgctgcgc cggctgcagc tcctgatgtc ccgcctggcc ctgccccagc cacccccgga    600

cccgccggcg cccccgctgg cgcccccctc ctcagcctgg gggggcatca gggccgccca    660

cgccatcctg ggggggctgc acctgacact tgactgggcc gtgaggggac tgctgctgct    720

gaagactcgg ctgtgacccg gggcccaaag ccaccaccgt ccttccaaag ccagatctta    780

tttatttatt tatttcagta ctgggggcga aacagccagg tgatcccccc gccattatct    840

ccccctagtt agagacagtc cttccgtgag gcctgggggg catctgtgcc ttatttatac    900

ttatttattt caggagcagg ggtgggaggc aggtggactc ctgggtcccc gaggaggagg    960

ggactggggt cccggattct tgggtctcca agaagtctgt ccacagactt ctgccctggc   1020

tcttccccat ctaggcctgg gcaggaacat atattattta tttaagcaat tacttttcat   1080

gttggggtgg ggacggaggg gaaagggaag cctgggtttt tgtacaaaaa tgtgagaaac   1140

ctttgtgaga cagagaacag ggaattaaat gtgtcataca tatccacttg agggcgattt   1200
```

```
gtctgagagc tggggctgga tgcttgggta actggggcag ggcaggtgga ggggagacct   1260

ccattcaggt ggaggtcccg agtgggcggg gcagcgactg ggagatgggt cggtcaccca   1320

gacagctctg tggaggcagg gtctgagcct tgcctggggc cccgcactgc atagggcctt   1380

ttgtttgttt tttgagatgg agtctcgctc tgttgcctag gctggagtgc agtgaggcaa   1440

tctgaggtca ctgcaacctc cacctcccgg gttcaagcaa ttctcctgcc tcagcctccc   1500

gattagctgg gatcacaggt gtgcaccacc atgcccagct aattatttat ttcttttgta   1560

tttttagtag agacagggtt tcaccatgtt ggccaggctg gtttcgaact cctgacctca   1620

ggtgatcctc ctgcctcggc ctcccaaagt gctgggatta caggtgtgag ccaccacacc   1680

tgacccatag gtcttcaata aatatttaat ggaaggttcc acaagtcacc ctgtgatcaa   1740

cagtacccgt atgggacaaa gctgcaaggt caagatggtt cattatggct gtgttcacca   1800

tagcaaactg gaaacaatct agatatccaa cagtgagggt taagcaacat ggtgcatctg   1860

tggatagaac gccacccagc cgcccggagc agggactgtc attcagggag gctaaggaga   1920

gaggcttgct tgggatatag aaagatatcc tgacattggc caggcatggt ggctcacgcc   1980

tgtaatcctg gcactttggg aggacgaagc gagtggatca ctgaagtcca agagttcgag   2040

accggcctgc gagacatggc aaaaccctgt ctcaaaaaag aaagaatgat gtcctgacat   2100

gaaacagcag gctacaaaac cactgcatgc tgtgatccca attttgtgtt tttctttcta   2160

tatatggatt aaaacaaaaa tcctaaaggg aaatacgcca aaatgttgac aatgactgtc   2220

tccaggtcaa aggagagagg tgggattgtg ggtgactttt aatgtgtatg attgtctgta   2280

ttttacagaa tttctgccat gactgtgtat tttgcatgac acattttaaa aataataaac   2340

actattttta gaat                                                     2354
```

<210> SEQ ID NO 64
<211> LENGTH: 199
<212> TYPE: PRT
<213> ORGANISM: Homo sapiens
<220> FEATURE:
<223> OTHER INFORMATION: interleukin 11 (IL11)

<400> SEQUENCE: 64

```
Met Asn Cys Val Cys Arg Leu Val Leu Val Val Leu Ser Leu Trp Pro
1               5                   10                  15

Asp Thr Ala Val Ala Pro Gly Pro Pro Pro Gly Pro Pro Arg Val Ser
            20                  25                  30

Pro Asp Pro Arg Ala Glu Leu Asp Ser Thr Val Leu Leu Thr Arg Ser
        35                  40                  45

Leu Leu Ala Asp Thr Arg Gln Leu Ala Ala Gln Leu Arg Asp Lys Phe
    50                  55                  60

Pro Ala Asp Gly Asp His Asn Leu Asp Ser Leu Pro Thr Leu Ala Met
65                  70                  75                  80

Ser Ala Gly Ala Leu Gly Ala Leu Gln Leu Pro Gly Val Leu Thr Arg
                85                  90                  95

Leu Arg Ala Asp Leu Leu Ser Tyr Leu Arg His Val Gln Trp Leu Arg
            100                 105                 110

Arg Ala Gly Gly Ser Ser Leu Lys Thr Leu Glu Pro Glu Leu Gly Thr
        115                 120                 125

Leu Gln Ala Arg Leu Asp Arg Leu Leu Arg Arg Leu Gln Leu Leu Met
    130                 135                 140

Ser Arg Leu Ala Leu Pro Gln Pro Pro Pro Asp Pro Pro Ala Pro Pro
145                 150                 155                 160
```

```
Leu Ala Pro Pro Ser Ser Ala Trp Gly Gly Ile Arg Ala Ala His Ala
                165                 170                 175

Ile Leu Gly Gly Leu His Leu Thr Leu Asp Trp Ala Val Arg Gly Leu
            180                 185                 190

Leu Leu Leu Lys Thr Arg Leu
        195


<210> SEQ ID NO 65
<211> LENGTH: 552
<212> TYPE: DNA
<213> ORGANISM: Homo sapiens
<220> FEATURE:
<223> OTHER INFORMATION: chemokine (C motif) ligand 2 (XCL2) cDNA
<220> FEATURE:
<221> NAME/KEY: CDS
<222> LOCATION: (21)..(365)
<223> OTHER INFORMATION: XCL2

<400> SEQUENCE: 65

agctcagcgg gacctcagcc atgagacttc tcatcctggc cctccttggc atctgctctc     60

tcactgcata cattgtggaa ggtgtaggga gtgaagtctc acataggagg acctgtgtga    120

gcctcactac ccagcgactg ccagttagca gaatcaagac ctacaccatc acggaaggct    180

ccttgagagc agtaattttt attaccaaac gtggcctaaa agtctgtgct gatccacaag    240

ccacgtgggt gagagacgtg gtcaggagca tggacaggaa atccaacacc agaaataaca    300

tgatccagac caagccaaca ggaacccagc aatcgaccaa tacagctgtg accctgactg    360

gctagtagtc tctggcaccc tgtccgtctc cagccagcca gctcatttca ctttacaccc    420

tcatggactg agattatact caccttttat gaaagcactg catgaataaa attattcctt    480

tgtattttta cttttaaatg tcttctgtat tcacttatat gttctaatta ataaattatt    540

tattattaag aa                                                        552


<210> SEQ ID NO 66
<211> LENGTH: 114
<212> TYPE: PRT
<213> ORGANISM: Homo sapiens
<220> FEATURE:
<223> OTHER INFORMATION: chemokine (C motif) ligand 2 (XCL2)

<400> SEQUENCE: 66

Met Arg Leu Leu Ile Leu Ala Leu Leu Gly Ile Cys Ser Leu Thr Ala
1               5                   10                  15

Tyr Ile Val Glu Gly Val Gly Ser Glu Val Ser His Arg Arg Thr Cys
            20                  25                  30

Val Ser Leu Thr Thr Gln Arg Leu Pro Val Ser Arg Ile Lys Thr Tyr
        35                  40                  45

Thr Ile Thr Glu Gly Ser Leu Arg Ala Val Ile Phe Ile Thr Lys Arg
    50                  55                  60

Gly Leu Lys Val Cys Ala Asp Pro Gln Ala Thr Trp Val Arg Asp Val
65                  70                  75                  80

Val Arg Ser Met Asp Arg Lys Ser Asn Thr Arg Asn Asn Met Ile Gln
                85                  90                  95

Thr Lys Pro Thr Gly Thr Gln Gln Ser Thr Asn Thr Ala Val Thr Leu
            100                 105                 110

Thr Gly


<210> SEQ ID NO 67
<211> LENGTH: 3432
<212> TYPE: DNA
```

```
<213> ORGANISM: Homo sapiens
<220> FEATURE:
<223> OTHER INFORMATION: prostaglandin E receptor 4 (subtype EP4)
      (PTGER4) cDNA
<220> FEATURE:
<221> NAME/KEY: CDS
<222> LOCATION: (593)..(2059)
<223> OTHER INFORMATION: PTGER4

<400> SEQUENCE: 67

gcgagagcgg agctccaagc ccggcagccc gagaggaaga tgaacagccc caggccagag     60

cctctggcag agtggacccc gagccgcccc caggtagcca ggagcggcct cagcggcagc    120

cgcaaactcc agtagccgcc cgtgctgccc gtggctgggg cggagggcag ccagagctgg    180

ggaccaaggc tccgcgccac ctgcgcgcac agcctcacac ctgaacgctg tcctcccgca    240

gacgagaccg gcgggcactg caaagctggg actcgtcttt gaaggaaaaa aaatagcgag    300

taagaaatcc agcaccattc ttcactgacc catcccgctg cacctcttgt ttcccaagtt    360

tttgaaagct ggcaactctg acctcggtgt ccaaaaatcg acagccactg agaccggctt    420

tgagaagccg aagatttggc agtttccaga ctgagcagga caaggtgaaa gcaggttgga    480

ggcgggtcca ggacatctga gggctgaccc tgggggctcg tgaggctgcc accgctgctg    540

ccgctacaga cccagccttg cactccaagg ctgcgcaccg ccagccacta tcatgtccac    600

tcccggggtc aattcgtccg cctccttgag ccccgaccgg ctgaacagcc cagtgaccat    660

cccggcggtg atgttcatct tcggggtggt gggcaacctg gtggccatcg tggtgctgtg    720

caagtcgcgc aaggagcaga aggagacgac cttctacacg ctggtatgtg ggctggctgt    780

caccgacctg ttgggcactt tgttggtgag cccggtgacc atcgccacgt acatgaaggg    840

ccaatggccc gggggccagc cgctgtgcga gtacagcacc ttcattctgc tcttcttcag    900

cctgtccggc ctcagcatca tctgcgccat gagtgtcgag cgctacctgg ccatcaacca    960

tgcctatttc tacagccact acgtggacaa gcgattggcg ggcctcacgc tctttgcagt   1020

ctatgcgtcc aacgtgctct tttgcgcgct gcccaacatg ggtctcggta gctcgcggct   1080

gcagtaccca gacacctggt gcttcatcga ctggaccacc aacgtgacgg cgcacgccgc   1140

ctactcctac atgtacgcgg gcttcagctc cttcctcatt ctcgccaccg tcctctgcaa   1200

cgtgcttgtg tgcggcgcgc tgctccgcat gcaccgccag ttcatgcgcc gcacctcgct   1260

gggcaccgag cagcaccacg cggccgcggc cgcctcggtt gcctcccggg gccacccccgc   1320

tgcctcccca gccttgccgc gcctcagcga ctttcggcgc cgccggagct tccgccgcat   1380

cgcgggcgcc gagatccaga tggtcatctt actcattgcc acctccctgg tggtgctcat   1440

ctgctccatc ccgctcgtgg tgcgagtatt cgtcaaccag ttatatcagc caagtttgga   1500

gcgagaagtc agtaaaaatc cagatttgca ggccatccga attgcttctg tgaaccccat   1560

cctagacccc tggatatata tcctcctgag aaagacagtg ctcagtaaag caatagagaa   1620

gatcaaatgc ctcttctgcc gcattggcgg gtcccgcagg gagcgctccg gacagcactg   1680

ctcagacagt caaaggacat cttctgccat gtcaggccac tctcgctcct tcatctcccg   1740

ggagctgaag gagatcagca gtacatctca gaccctcctg ccagacctct cactgccaga   1800

cctcagtgaa aatggccttg gaggcaggaa tttgcttcca ggtgtgcctg gcatgggcct   1860

ggcccaggaa gacaccacct cactgaggac tttgcgaata tcagagacct cagactcttc   1920

acagggtcag gactcagaga gtgtcttact ggtggatgag gctggtggga gcggcagggc   1980

tgggcctgcc cctaagggga gctccctgca agtcacattt cccagtgaaa cactgaactt   2040

atcagaaaaa tgtatataat aggcaaggaa agaaatacag tactgtttct ggacccttat   2100
```

```
aaaatcctgt gcaatagaca catacatgtc acatttagct gtgctcagaa gggctatcat   2160
catcctacaa ctcacattag agaacatcct ggcttttgag cacttttcaa acaatcaagt   2220
tgactcacgt gggtcctgag gcctgcagca cgtcggatgc taccccacta tgacagagga   2280
ttgtggtcac aacttgatgg ctgcgaagac ctaccctccg tttttctact agataggagg   2340
atggtagaag tttggctgct gtcataacat ccagagcttt gtcgtatttg gcacacagca   2400
gaggcccaga tattagaaag gctctattcc aataaactat gaggactgcc ttatggatga   2460
tttaagtgtc tcactaaagc atgaaatgtg aatttttatt gttgtacata cgatttaagg   2520
tatttaaagt atttcttct ctgtgagaag gtttattgtt aatacaaggt ataataaaat   2580
tatcgcaacc cctctccttc cagtataacc agctgaagtt gcagatgtta gatatttttc   2640
ataaacaagt tcgagtcaaa gttgaaaatt catagtaaga ttgatatcta taaaatagat   2700
ataaattttt aagagaaaga atttagtatt atcaaaggga taaagaaaaa aatactattt   2760
aagatgtgaa aattacagtc caaaatactg ttctttccag gctatgtata aaatacatag   2820
tgaaaattgt ttagtgatat tacatttatt tatccagaaa actgtgattt caggagaacc   2880
taacatgctg gtgaatattt tcaacttttt ccctcactaa ttggtacttt taaaaacata   2940
acataaattt tttgaagtct ttaataaata acccataatt gaagtgtata atataaaaaa   3000
ttttaaaaat ctaagcagct tattgtttct ctgaaagtgt gtgtagtttt actttcctaa   3060
ggaattacca agaatatcct ttaaaattta aaaggatggc aagttgcatc agaaagcttt   3120
atttgagat gtaaaaagat tcccaaacgt ggttacatta gccattcatg tatgtcagaa   3180
gtgcagaatt ggggcactta atggtcacct tgtaacagtt ttgtgtaact cccagtgatg   3240
ctgtacacat atttgaaggg tctttctcaa agaaatatta agcatgtttt gttgctcagt   3300
gtttttgtga attgcttggt tgtaattaaa ttctgagcct gatattgata tggttttaag   3360
aagcagttgt accaagtgaa attattttgg agattataat aaatatatac attcaaaaaa   3420
aaaaaaaaaa aa                                                        3432
```

<210> SEQ ID NO 68
<211> LENGTH: 488
<212> TYPE: PRT
<213> ORGANISM: Homo sapiens
<220> FEATURE:
<223> OTHER INFORMATION: prostaglandin E receptor 4 (subtype EP4) (PTGER4)

<400> SEQUENCE: 68

```
Met Ser Thr Pro Gly Val Asn Ser Ser Ala Ser Leu Ser Pro Asp Arg
  1               5                  10                  15

Leu Asn Ser Pro Val Thr Ile Pro Ala Val Met Phe Ile Phe Gly Val
             20                  25                  30

Val Gly Asn Leu Val Ala Ile Val Val Leu Cys Lys Ser Arg Lys Glu
         35                  40                  45

Gln Lys Glu Thr Thr Phe Tyr Thr Leu Val Cys Gly Leu Ala Val Thr
     50                  55                  60

Asp Leu Leu Gly Thr Leu Leu Val Ser Pro Val Thr Ile Ala Thr Tyr
 65                  70                  75                  80

Met Lys Gly Gln Trp Pro Gly Gly Gln Pro Leu Cys Glu Tyr Ser Thr
                 85                  90                  95

Phe Ile Leu Leu Phe Phe Ser Leu Ser Gly Leu Ser Ile Ile Cys Ala
            100                 105                 110

Met Ser Val Glu Arg Tyr Leu Ala Ile Asn His Ala Tyr Phe Tyr Ser
```

-continued

```
        115                 120                 125

His Tyr Val Asp Lys Arg Leu Ala Gly Leu Thr Leu Phe Ala Val Tyr
    130                 135                 140

Ala Ser Asn Val Leu Phe Cys Ala Leu Pro Asn Met Gly Leu Gly Ser
145                 150                 155                 160

Ser Arg Leu Gln Tyr Pro Asp Thr Trp Cys Phe Ile Asp Trp Thr Thr
                165                 170                 175

Asn Val Thr Ala His Ala Ala Tyr Ser Tyr Met Tyr Ala Gly Phe Ser
            180                 185                 190

Ser Phe Leu Ile Leu Ala Thr Val Leu Cys Asn Val Leu Val Cys Gly
        195                 200                 205

Ala Leu Leu Arg Met His Arg Gln Phe Met Arg Arg Thr Ser Leu Gly
    210                 215                 220

Thr Glu Gln His His Ala Ala Ala Ala Ala Ser Val Ala Ser Arg Gly
225                 230                 235                 240

His Pro Ala Ala Ser Pro Ala Leu Pro Arg Leu Ser Asp Phe Arg Arg
                245                 250                 255

Arg Arg Ser Phe Arg Arg Ile Ala Gly Ala Glu Ile Gln Met Val Ile
            260                 265                 270

Leu Leu Ile Ala Thr Ser Leu Val Val Leu Ile Cys Ser Ile Pro Leu
        275                 280                 285

Val Val Arg Val Phe Val Asn Gln Leu Tyr Gln Pro Ser Leu Glu Arg
    290                 295                 300

Glu Val Ser Lys Asn Pro Asp Leu Gln Ala Ile Arg Ile Ala Ser Val
305                 310                 315                 320

Asn Pro Ile Leu Asp Pro Trp Ile Tyr Ile Leu Leu Arg Lys Thr Val
                325                 330                 335

Leu Ser Lys Ala Ile Glu Lys Ile Lys Cys Leu Phe Cys Arg Ile Gly
            340                 345                 350

Gly Ser Arg Arg Glu Arg Ser Gly Gln His Cys Ser Asp Ser Gln Arg
        355                 360                 365

Thr Ser Ser Ala Met Ser Gly His Ser Arg Ser Phe Ile Ser Arg Glu
    370                 375                 380

Leu Lys Glu Ile Ser Ser Thr Ser Gln Thr Leu Leu Pro Asp Leu Ser
385                 390                 395                 400

Leu Pro Asp Leu Ser Glu Asn Gly Leu Gly Gly Arg Asn Leu Leu Pro
                405                 410                 415

Gly Val Pro Gly Met Gly Leu Ala Gln Glu Asp Thr Thr Ser Leu Arg
            420                 425                 430

Thr Leu Arg Ile Ser Glu Thr Ser Asp Ser Ser Gln Gly Gln Asp Ser
        435                 440                 445

Glu Ser Val Leu Leu Val Asp Glu Ala Gly Gly Ser Gly Arg Ala Gly
    450                 455                 460

Pro Ala Pro Lys Gly Ser Ser Leu Gln Val Thr Phe Pro Ser Glu Thr
465                 470                 475                 480

Leu Asn Leu Ser Glu Lys Cys Ile
                485
```

<210> SEQ ID NO 69
<211> LENGTH: 4145
<212> TYPE: DNA
<213> ORGANISM: Homo sapiens
<220> FEATURE:
<223> OTHER INFORMATION: caspase 2, apoptosis-related cysteine
      peptidase (neural precursor cell expressed, developmentally
      down-regulated 2) (CASP2) cDNA -continued <220> FEATURE:
<221> NAME/KEY: CDS
<222> LOCATION: (148)..(1506)
<223> OTHER INFORMATION: CASP2

<400> SEQUENCE: 69

```
gggtggcctg gtgtgtgggc gcggcagggc gcaggcgcag gcgcagtgtg cgtccgcgtc     60
tgaggggagg gatgtggggg aagcgacggc ccccggtttg tttgggctgt gggcggtgcg    120
cagcggagag cccgggaaaa gcgggaaatg gcggcgccga gcgcggggtc ttggtccacc    180
ttccagcaca aggagctgat ggccgctgac aggggacgca ggatattggg agtgtgtggc    240
atgcatcctc atcatcagga aactctaaaa aagaaccgag tggtgctagc caaacagctg    300
ttgttgagcg aattgttaga acatcttctg gagaaggaca tcatcacctt ggaaatgagg    360
gagctcatcc aggccaaagt gggcagtttc agccagaatg tggaactcct caacttgctg    420
cctaagaggg gtccccaagc ttttgatgcc ttctgtgaag cactgaggga gaccaagcaa    480
ggccacctgg aggatatgtt gctcaccacc ctttctgggc ttcagcatgt actcccaccg    540
ttgagctgtg actacgactt gagtctccct ttccggtgt gtgagtcctg tcccctttac    600
aagaagctcc gcctgtcgac agatactgtg gaacactccc tagacaataa agatggtcct    660
gtctgccttc aggtgaagcc ttgcactcct gaattttatc aaacacactt ccagctggca    720
tataggttgc agtctcggcc tcgtggccta gcactggtgt tgagcaatgt gcacttcact    780
ggagagaaag aactggaatt tcgctctgga ggggatgtgg accacagtac tctagtcacc    840
ctcttcaagc ttttgggcta tgacgtccat gttctatgtg accagactgc acaggaaatg    900
caagagaaac tgcagaattt tgcacagtta cctgcacacc gagtcacgga ctcctgcatc    960
gtggcactcc tctcgcatgg tgtggagggc gccatctatg gtgtggatgg gaaactgctc   1020
cagctccaag aggtttttca gctctttgac aacgccaact gcccaagcct acagaacaaa   1080
ccaaaaatgt tcttcatcca ggcctgccgt ggagatgaga ctgatcgtgg ggttgaccaa   1140
caagatggaa agaaccacgc aggatcccct gggtgcgagg agagtgatgc cggtaaagaa   1200
aagttgccga agatgagact gcccacgcgc tcagacatga tatgcggcta tgcctgcctc   1260
aaagggactg ccgccatgcg gaacaccaaa cgaggttcct ggtacatcga ggctcttgct   1320
caagtgtttt ctgagcgggc ttgtgatatg cacgtggccg acatgctggt taaggtgaac   1380
gcacttatca aggatcggga aggttatgct cctggcacag aattccaccg gtgcaaggag   1440
atgtctgaat actgcagcac tctgtgccgc cacctctacc tgttcccagg acaccctccc   1500
acatgatgtc acctccccat catccacgcc aagtggaagc cactggacca caggaggtgt   1560
gatagagcct ttgatcttca ggatgcacgg tttctgttct gccccctcag ggatgtggga   1620
atctcccaga cttgtttcct gtgcccatca tctctgcctt tgagtgtggg actccaggcc   1680
agctcctttt ctgtgaagcc ctttgcctgt agagccagcc ttggttggac ctattgccag   1740
gaatgtttca gctgcagttg aagagcctga caagtgaagt tgtaaacaca gtgtggttat   1800
ggggagaggg catataaatt ccccatattt gtgttcagtt ccagcttttg tagatggcac   1860
tttagtgatt gcttttatta cattagttaa gatgtctgag agaccatctc ctatctttta   1920
tttcattcat atcctccgcc ctttttgtcc tagagtgaga gtttggaagg tgtccaaatt   1980
taatgtagac attatctttt ggctctgaag aagcaaacat gactagagac gcaccttgct   2040
gcagtgtcca gaagcggcct gtgcgttccc ttcagtactg cagcgccacc cagtggaagg   2100
acactcttgg ctcgtttggg ctcaaggcac cgcagcctgt cagccaacat tgccttgcat   2160
ttgtacctta ttgatctttg cccatggaag tctcaaagat ctttcgttgg ttgtttctct   2220
```

-continued

```
gagctttgtt actgaaatga gcctcgtggg gagcatcaga gaaggccagg aagaatggtg   2280

tgtttcccta gactctgtaa ccacctctct gtctttttcc ttcctgagaa acgtccatct   2340

ctctccctta ctattcccac tttcattcaa tcaacctgca cttcatatct agatttctag   2400

aaaagcttcc tagcttatct ccctgcttca tatctctccc ttctttacct tcatttcatc   2460

ctgttggctg ctgccaccaa atctgtctag aatcctgctt tacaggatca tgtaaatgct   2520

caaagatgta atgtagttct ttgttcctgc tttctctttc agtattaaac tctcctttga   2580

tattatgtgg cttttatttc agtgccatac atgttattgt tttcaaccta gaaaccttta   2640

tccctgctta tctgaaactt cccaacttcc ctgttcttta agactttttt tttttttttt   2700

tttttttttg agacagagtc tcgctctgtc gcccaggctg gagggcagtg gcacgatctc   2760

agctcactgc aagctccaac tcccgggttc acgccattct cctgcctcag ccttccaagt   2820

agctgggact acaggtgccc gccaccgtgc ccggctaatt tttttgtatt tttagtagag   2880

acagggtttc accatgttag ccgggatggt cttgatctcc tgacctcatg atccacccac   2940

ctcagcctcc caaagtgttg ggattacagg cgtgagccac tgcgcccggg caagaccttt   3000

ttttaaaaaa aaaaaaaaaa aaacttccat tctttcttcc tccagtctgt tctcacataa   3060

cagagtagtt ttggttttta attttttttg gttgtttgct gtttttttgtt ttttaaggtg   3120

agttctcact atgtttctca gactggtctc gaactcctgg cctcaagcca tcttcccgcc   3180

tcagcctctc aaatagctgg gcttacaggc atgagccacc acacctggcc aggatttggt   3240

tgtttaaata taaatctgat cacccccctg cttagaaccc ttctgctttc tattacccct   3300

catttaaaat gtaaactctt caccttggtt tatgagaact ggttcttgcc ttccccttga   3360

acctcattaa atggtgattt cttgctaagc tccagcccga gtggtctcct ctcagcttct   3420

aattttgtgc tctttcctgc ccttttcctg ggccttctca gctctccacc cccaccactc   3480

ttgactcagg tggtgtcctt cttcctcaag tcttgacaat tcccgggccc ttcagtccct   3540

gagcagtcta cttctgtgtc tgtcaccaca tcttgtcttt tcccctcatt gcatttattg   3600

cagtttatat atatgctact tttacttgtt catttctgtc tcccctacca ggctgtaaat   3660

gagggcagaa accttgtttg ttttattcac catcatgtac caagtgcttg gcacatagtg   3720

ggccttcatt aaatgtttgt tgaataaaag agggaagaag gcaagccaac cttagctaca   3780

atcctacctt ttgataaaat gttccttttg acaatataca cggattatta tttgtacttt   3840

gtttttccat gtgttttgct tttatccact ggcattttta gctccttgaa gacatatcat   3900

gtgtgagata acttccttca catctcccat ggtccctagc aaaatgctag gcctgtagta   3960

gtcaaggtgc tcaataaata tttgtttggg tggtttgtga gccttgctgc caagtcctgc   4020

ctttgggtcg acatagtatg gaagtatttg agagagagaa cctttccact cccactgcca   4080

ggattttgta ttgccatcgg gtgccaaata aatgctcata tttattaaaa aaaaaaaaaa   4140

aaaaa                                                                4145
```

<210> SEQ ID NO 70
<211> LENGTH: 452
<212> TYPE: PRT
<213> ORGANISM: Homo sapiens
<220> FEATURE:
<223> OTHER INFORMATION: caspase 2, apoptosis-related cysteine peptidase (neural precursor cell expressed, developmentally down-regulated 2) (CASP2)

<400> SEQUENCE: 70

Met Ala Ala Pro Ser Ala Gly Ser Trp Ser Thr Phe Gln His Lys Glu

-continued

```
 1               5                  10                  15

Leu Met Ala Ala Asp Arg Gly Arg Arg Ile Leu Gly Val Cys Gly Met
             20                  25                  30

His Pro His His Gln Glu Thr Leu Lys Lys Asn Arg Val Val Leu Ala
         35                  40                  45

Lys Gln Leu Leu Leu Ser Glu Leu Leu Glu His Leu Leu Glu Lys Asp
     50                  55                  60

Ile Ile Thr Leu Glu Met Arg Glu Leu Ile Gln Ala Lys Val Gly Ser
 65                  70                  75                  80

Phe Ser Gln Asn Val Glu Leu Leu Asn Leu Leu Pro Lys Arg Gly Pro
                 85                  90                  95

Gln Ala Phe Asp Ala Phe Cys Glu Ala Leu Arg Glu Thr Lys Gln Gly
            100                 105                 110

His Leu Glu Asp Met Leu Leu Thr Thr Leu Ser Gly Leu Gln His Val
        115                 120                 125

Leu Pro Pro Leu Ser Cys Asp Tyr Asp Leu Ser Leu Pro Phe Pro Val
    130                 135                 140

Cys Glu Ser Cys Pro Leu Tyr Lys Lys Leu Arg Leu Ser Thr Asp Thr
145                 150                 155                 160

Val Glu His Ser Leu Asp Asn Lys Asp Gly Pro Val Cys Leu Gln Val
                165                 170                 175

Lys Pro Cys Thr Pro Glu Phe Tyr Gln Thr His Phe Gln Leu Ala Tyr
            180                 185                 190

Arg Leu Gln Ser Arg Pro Arg Gly Leu Ala Leu Val Leu Ser Asn Val
        195                 200                 205

His Phe Thr Gly Glu Lys Glu Leu Glu Phe Arg Ser Gly Gly Asp Val
    210                 215                 220

Asp His Ser Thr Leu Val Thr Leu Phe Lys Leu Leu Gly Tyr Asp Val
225                 230                 235                 240

His Val Leu Cys Asp Gln Thr Ala Gln Glu Met Gln Glu Lys Leu Gln
                245                 250                 255

Asn Phe Ala Gln Leu Pro Ala His Arg Val Thr Asp Ser Cys Ile Val
            260                 265                 270

Ala Leu Leu Ser His Gly Val Glu Gly Ala Ile Tyr Gly Val Asp Gly
        275                 280                 285

Lys Leu Leu Gln Leu Gln Glu Val Phe Gln Leu Phe Asp Asn Ala Asn
    290                 295                 300

Cys Pro Ser Leu Gln Asn Lys Pro Lys Met Phe Phe Ile Gln Ala Cys
305                 310                 315                 320

Arg Gly Asp Glu Thr Asp Arg Gly Val Asp Gln Gln Asp Gly Lys Asn
                325                 330                 335

His Ala Gly Ser Pro Gly Cys Glu Glu Ser Asp Ala Gly Lys Glu Lys
            340                 345                 350

Leu Pro Lys Met Arg Leu Pro Thr Arg Ser Asp Met Ile Cys Gly Tyr
        355                 360                 365

Ala Cys Leu Lys Gly Thr Ala Ala Met Arg Asn Thr Lys Arg Gly Ser
    370                 375                 380

Trp Tyr Ile Glu Ala Leu Ala Gln Val Phe Ser Glu Arg Ala Cys Asp
385                 390                 395                 400

Met His Val Ala Asp Met Leu Val Lys Val Asn Ala Leu Ile Lys Asp
                405                 410                 415

Arg Glu Gly Tyr Ala Pro Gly Thr Glu Phe His Arg Cys Lys Glu Met
            420                 425                 430
```

```
Ser Glu Tyr Cys Ser Thr Leu Cys Arg His Leu Tyr Leu Phe Pro Gly
        435                 440                 445

His Pro Pro Thr
    450


<210> SEQ ID NO 71
<211> LENGTH: 1101
<212> TYPE: DNA
<213> ORGANISM: Homo sapiens
<220> FEATURE:
<223> OTHER INFORMATION: killer cell immunoglobulin-like receptor, two
      domains, short cytoplasmic tail, 1 (KIR2DS1) cDNA
<220> FEATURE:
<221> NAME/KEY: CDS
<222> LOCATION: (14)..(928)
<223> OTHER INFORMATION: KIR2DS1

<400> SEQUENCE: 71

caccggcagc accatgtcgc tcacggtcgt cagcatggcg tgtgttgggt tcttcttgct      60

gcagggggcc tggccacatg agggagtcca cagaaaacct tccctcctgg cccacccagg     120

tcgcctggtg aaatcagaag agacagtcat cctgcaatgt tggtcagatg tcatgtttga     180

acacttcctt ctgcacagag aggggatgtt taacgacact ttgcgcctca ttggagaaca     240

ccatgatggg gtctccaagg ccaacttctc catcagtcgc atgaagcaag acctggcagg     300

gacctacaga tgctacggtt ctgttactca ctccccctat cagttgtcag ctcccagtga     360

ccctctggac atcgtgatca taggtctata tgagaaacct tctctctcag cccagccggg     420

ccccacggtt ctggcaggag agaatgtgac cttgtcctgc agctcccgga gctcctatga     480

catgtaccat ctatccaggg aaggggaggc ccatgaacgt aggctccctg cagggaccaa     540

ggtcaacgga acattccagg ccaactttcc tctgggccct gccacccatg gagggaccta     600

cagatgcttc ggctctttcc gtgactctcc atacgagtgg tcaaagtcaa gtgacccact     660

gcttgtttct gtcacaggaa acccttcaaa tagttggcct tcacccactg aaccaagctc     720

cgaaaccggt aaccccagac acctacatgt tctgattggg acctcagtgg tcaaaatccc     780

tttcaccatc ctcctcttct ttctccttca tcgctggtgc tccgacaaaa aaaatgctgc     840

tgtaatggac caagagcctg cagggaacag aacagtgaac agcgaggatt ctgatgaaca     900

agaccatcag gaggtgtcat acgcataatt ggatcactgt gttttcacac agagaaaaat     960

cactcgccct tctgagaggc ccaagacacc cccaacagat accagcatgt acatagaact    1020

tccaaatgct gagcccagat ccaaagttgt cttctgtcca cgagcaccac agtcaggcct    1080

tgaggggatc ttctagggag a                                              1101


<210> SEQ ID NO 72
<211> LENGTH: 304
<212> TYPE: PRT
<213> ORGANISM: Homo sapiens
<220> FEATURE:
<223> OTHER INFORMATION: killer cell immunoglobulin-like receptor, two
      domains, short cytoplasmic tail, 1 (KIR2DS1)

<400> SEQUENCE: 72

Met Ser Leu Thr Val Val Ser Met Ala Cys Val Gly Phe Phe Leu Leu
  1               5                  10                  15

Gln Gly Ala Trp Pro His Glu Gly Val His Arg Lys Pro Ser Leu Leu
             20                  25                  30

Ala His Pro Gly Arg Leu Val Lys Ser Glu Glu Thr Val Ile Leu Gln
         35                  40                  45

Cys Trp Ser Asp Val Met Phe Glu His Phe Leu Leu His Arg Glu Gly
```

```
     50                  55                  60

Met Phe Asn Asp Thr Leu Arg Leu Ile Gly Glu His His Asp Gly Val
 65                  70                  75                  80

Ser Lys Ala Asn Phe Ser Ile Ser Arg Met Lys Gln Asp Leu Ala Gly
                85                  90                  95

Thr Tyr Arg Cys Tyr Gly Ser Val Thr His Ser Pro Tyr Gln Leu Ser
          100                 105                 110

Ala Pro Ser Asp Pro Leu Asp Ile Val Ile Ile Gly Leu Tyr Glu Lys
      115                 120                 125

Pro Ser Leu Ser Ala Gln Pro Gly Pro Thr Val Leu Ala Gly Glu Asn
  130                 135                 140

Val Thr Leu Ser Cys Ser Ser Arg Ser Ser Tyr Asp Met Tyr His Leu
145                 150                 155                 160

Ser Arg Glu Gly Glu Ala His Glu Arg Arg Leu Pro Ala Gly Thr Lys
                165                 170                 175

Val Asn Gly Thr Phe Gln Ala Asn Phe Pro Leu Gly Pro Ala Thr His
            180                 185                 190

Gly Gly Thr Tyr Arg Cys Phe Gly Ser Phe Arg Asp Ser Pro Tyr Glu
        195                 200                 205

Trp Ser Lys Ser Ser Asp Pro Leu Leu Val Ser Val Thr Gly Asn Pro
    210                 215                 220

Ser Asn Ser Trp Pro Ser Pro Thr Glu Pro Ser Ser Glu Thr Gly Asn
225                 230                 235                 240

Pro Arg His Leu His Val Leu Ile Gly Thr Ser Val Val Lys Ile Pro
                245                 250                 255

Phe Thr Ile Leu Leu Phe Phe Leu Leu His Arg Trp Cys Ser Asp Lys
            260                 265                 270

Lys Asn Ala Ala Val Met Asp Gln Glu Pro Ala Gly Asn Arg Thr Val
        275                 280                 285

Asn Ser Glu Asp Ser Asp Glu Gln Asp His Gln Glu Val Ser Tyr Ala
    290                 295                 300


<210> SEQ ID NO 73
<211> LENGTH: 2964
<212> TYPE: DNA
<213> ORGANISM: Homo sapiens
<220> FEATURE:
<223> OTHER INFORMATION: mitogen-activated protein kinase kinase
      kinase kinase 2 (MAP4K2) cDNA
<220> FEATURE:
<221> NAME/KEY: CDS
<222> LOCATION: (93)..(2555)
<223> OTHER INFORMATION: MAP4K2

<400> SEQUENCE: 73

cagagccacg ggcgcccgcc ccgccccgcg ccgccccgcg ccggctccgc agctcgcgcc     60

cgcccgcctg ccggcccgcc cggcgccggg ccatggcgct gctgcgggat gtgtcgctgc    120

aggacccgcg ggaccgcttc gagctgctgc agcgcgtggg ggccgggacc tatggcgacg    180

tctacaaggc ccgcgacacg gtcacgtccg aactggccgc cgtgaagata gtcaagctag    240

acccagggga cgacatcagc tccctccagc aggaaatcac catcctgcgt gagtgccgcc    300

accccaatgt ggtggcctac attggcagct acctcaggaa tgaccgcttg tggatctgca    360

tggagttctg cggagggggc tccctgcagg agatttacca tgccactggg cccctggagg    420

agcggcagat tgcctacgtc tgccgagagg cactgaaggg gctccaccac ctgcattctc    480

aggggaagat ccacagagac atcaagggag ccaaccttct cctcactctc cagggagatg    540
```

-continued

```
tcaaactggc tgactttggg gtgtcaggcg agctgacagc gtctgtggcc aagaggaggt    600
ctttcattgg gactccctac tggatggctc ccgaggtggc tgctgtggag cgcaaaggtg    660
gctacaatga gctatgtgac gtctgggccc tgggcatcac tgccattgag ctgggcgagc    720
tgcagccccc tctgttccac ctgcacccca tgagggccct gatgctcatg tcgaagagca    780
gcttccagcc gcccaaactg agagataaga ctcgctggac ccagaatttc caccactttc    840
tcaaactggc cctgaccaag aatcctaaga agaggccgac agcagagaag ctcctgcagc    900
acccgttcac gactcagcag ctccctcggg ccctcctcac acagctgctg gacaaagcca    960
gtgaccctca tctggggacc ccctcccctg aggactgtga gctggagacc tatgacatgt   1020
ttccagacac cattcactcc cgggggcagc acggcccagc cgagaggacc ccctcggaga   1080
tccagtttca ccaggtgaaa tttggcgccc cacgcaggaa ggaaactgac ccactgaatg   1140
agccgtggga ggaagagtgg acactactgg gaaaggaaga gttgagtggg agcctgctgc   1200
agtcggtcca ggaggccctg gaggaaagga gtctgactat tcggtcagcc tcagaattcc   1260
aggagctgga ctccccagac gataccatgg gaaccatcaa gcgggccccg ttcctagggc   1320
cactccccac tgaccctcca gcagaggagc ctctgtccag tcccccagga accctgcccc   1380
cacctccttc aggccccaac agctccccac tgctgcccac ggcctgggcc accatgaagc   1440
agcgggagga tcctgagagg tcatcctgcc acgggctccc cccaactccc aaggtgcata   1500
tgggcgcctg cttctccaag gtcttcaatg gctgccccct gcggatccac gctgctgtca   1560
cctggattca ccctgttact cgggaccagt tcctggtggt aggggccgag gaaggcatct   1620
acacactcaa cctgcatgaa ctgcatgagg atacgctgga gaagctgatt tcacatcgct   1680
gctcctggct ctactgcgtg aacaacgtgc tgctgtcact ctcagggaaa tccacgcaca   1740
tctgggccca tgacctccca ggcctgtttg agcagcggag gctacagcaa caggttcccc   1800
tctccatccc caccaaccgc ctcacccagc gcatcatccc caggcgcttt gctctgtcca   1860
ccaagattcc tgacaccaaa ggctgcttgc agtgtcgtgt ggtgcggaac ccctacacgg   1920
gtgccacctt cctgctggcc gccctgccca ccagcctgct cctgctgcag tggtatgagc   1980
cgctgcagaa gtttctgctg ctgaagaact tctccagccc tctgcccagc ccagctggga   2040
tgctggagcc gctggtgctg gatgggaagg agctgccgca ggtgtgtgtt ggggccgagg   2100
ggcctgaggg gcccggctgc cgcgtcctgt tccatgtcct gcccctggag gctggcctga   2160
cgcccgacat cctcatccca cctgagggga tcccaggctc ggcccagcag gtgatccagg   2220
tggacaggga cacaatccta gtcagctttg aacgctgtgt gaggattgtc aacatgcagg   2280
gcgagcccac ggccacactg gcacctgagc tgacctttga tttccccatc gagactgtgg   2340
tgtgcctgca ggacagtgtg ctggccttct ggagccatgg gatgcaaggc cgaagcctgg   2400
ataccaatga ggtgacccag gagatcacag atgaaacaag gatcttccga gtgcttgggg   2460
cccacagaga catcatcctg gagagcattc ccactgacaa cccagaggcg cacagcaacc   2520
tctacatcct cacgggccac cagagcacct actaagagca gcgggcctgt ccaggggctc   2580
cccgccccac cccacgcctt agctgcaggc ccttttgggc aaaggggccc atcctagacc   2640
agaggagccc aggccctggc cctgctgggg ctgaaggtca gaagtaatcc tgagaaatgt   2700
ttcaggcctg gggagggagg ggagccccccg acgcctctgc aataactgga ccagggggag   2760
ctgctgtcac tcccccatcc ccgaggcagc ccagtcccta gtgcccaagg cagggaccct   2820
gggcctgggc catccattcc attttgttcc acatttcctt tctactcttt ctgccaagag   2880
cctgcccctg catttgtcct gggaaacacg gtatttaaga gagaactata ttggtattaa   2940
```

agctggtttg ttttaaaaaa aaaa 2964

<210> SEQ ID NO 74
<211> LENGTH: 820
<212> TYPE: PRT
<213> ORGANISM: Homo sapiens
<220> FEATURE:
<223> OTHER INFORMATION: mitogen-activated protein kinase kinase kinase kinase 2 (MAP4K2)

<400> SEQUENCE: 74

```
Met Ala Leu Leu Arg Asp Val Ser Leu Gln Asp Pro Arg Asp Arg Phe
  1               5                  10                  15

Glu Leu Leu Gln Arg Val Gly Ala Gly Thr Tyr Gly Asp Val Tyr Lys
             20                  25                  30

Ala Arg Asp Thr Val Thr Ser Glu Leu Ala Ala Val Lys Ile Val Lys
         35                  40                  45

Leu Asp Pro Gly Asp Asp Ile Ser Ser Leu Gln Gln Glu Ile Thr Ile
     50                  55                  60

Leu Arg Glu Cys Arg His Pro Asn Val Val Ala Tyr Ile Gly Ser Tyr
 65                  70                  75                  80

Leu Arg Asn Asp Arg Leu Trp Ile Cys Met Glu Phe Cys Gly Gly Gly
                 85                  90                  95

Ser Leu Gln Glu Ile Tyr His Ala Thr Gly Pro Leu Glu Glu Arg Gln
            100                 105                 110

Ile Ala Tyr Val Cys Arg Glu Ala Leu Lys Gly Leu His His Leu His
        115                 120                 125

Ser Gln Gly Lys Ile His Arg Asp Ile Lys Gly Ala Asn Leu Leu Leu
    130                 135                 140

Thr Leu Gln Gly Asp Val Lys Leu Ala Asp Phe Gly Val Ser Gly Glu
145                 150                 155                 160

Leu Thr Ala Ser Val Ala Lys Arg Arg Ser Phe Ile Gly Thr Pro Tyr
                165                 170                 175

Trp Met Ala Pro Glu Val Ala Ala Val Glu Arg Lys Gly Gly Tyr Asn
            180                 185                 190

Glu Leu Cys Asp Val Trp Ala Leu Gly Ile Thr Ala Ile Glu Leu Gly
        195                 200                 205

Glu Leu Gln Pro Pro Leu Phe His Leu His Pro Met Arg Ala Leu Met
    210                 215                 220

Leu Met Ser Lys Ser Ser Phe Gln Pro Pro Lys Leu Arg Asp Lys Thr
225                 230                 235                 240

Arg Trp Thr Gln Asn Phe His His Phe Leu Lys Leu Ala Leu Thr Lys
                245                 250                 255

Asn Pro Lys Lys Arg Pro Thr Ala Glu Lys Leu Leu Gln His Pro Phe
            260                 265                 270

Thr Thr Gln Gln Leu Pro Arg Ala Leu Leu Thr Gln Leu Leu Asp Lys
        275                 280                 285

Ala Ser Asp Pro His Leu Gly Thr Pro Ser Pro Glu Asp Cys Glu Leu
    290                 295                 300

Glu Thr Tyr Asp Met Phe Pro Asp Thr Ile His Ser Arg Gly Gln His
305                 310                 315                 320

Gly Pro Ala Glu Arg Thr Pro Ser Glu Ile Gln Phe His Gln Val Lys
                325                 330                 335

Phe Gly Ala Pro Arg Arg Lys Glu Thr Asp Pro Leu Asn Glu Pro Trp
            340                 345                 350

Glu Glu Glu Trp Thr Leu Leu Gly Lys Glu Glu Leu Ser Gly Ser Leu
```

```
        355                 360                 365

Leu Gln Ser Val Gln Glu Ala Leu Glu Glu Arg Ser Leu Thr Ile Arg
    370                 375                 380

Ser Ala Ser Glu Phe Gln Glu Leu Asp Ser Pro Asp Asp Thr Met Gly
385                 390                 395                 400

Thr Ile Lys Arg Ala Pro Phe Leu Gly Pro Leu Pro Thr Asp Pro Pro
                405                 410                 415

Ala Glu Glu Pro Leu Ser Ser Pro Pro Gly Thr Leu Pro Pro Pro Pro
            420                 425                 430

Ser Gly Pro Asn Ser Ser Pro Leu Leu Pro Thr Ala Trp Ala Thr Met
        435                 440                 445

Lys Gln Arg Glu Asp Pro Glu Arg Ser Ser Cys His Gly Leu Pro Pro
    450                 455                 460

Thr Pro Lys Val His Met Gly Ala Cys Phe Ser Lys Val Phe Asn Gly
465                 470                 475                 480

Cys Pro Leu Arg Ile His Ala Ala Val Thr Trp Ile His Pro Val Thr
                485                 490                 495

Arg Asp Gln Phe Leu Val Val Gly Ala Glu Glu Gly Ile Tyr Thr Leu
            500                 505                 510

Asn Leu His Glu Leu His Glu Asp Thr Leu Glu Lys Leu Ile Ser His
        515                 520                 525

Arg Cys Ser Trp Leu Tyr Cys Val Asn Asn Val Leu Leu Ser Leu Ser
    530                 535                 540

Gly Lys Ser Thr His Ile Trp Ala His Asp Leu Pro Gly Leu Phe Glu
545                 550                 555                 560

Gln Arg Arg Leu Gln Gln Gln Val Pro Leu Ser Ile Pro Thr Asn Arg
                565                 570                 575

Leu Thr Gln Arg Ile Ile Pro Arg Arg Phe Ala Leu Ser Thr Lys Ile
            580                 585                 590

Pro Asp Thr Lys Gly Cys Leu Gln Cys Arg Val Val Arg Asn Pro Tyr
        595                 600                 605

Thr Gly Ala Thr Phe Leu Leu Ala Ala Leu Pro Thr Ser Leu Leu Leu
    610                 615                 620

Leu Gln Trp Tyr Glu Pro Leu Gln Lys Phe Leu Leu Leu Lys Asn Phe
625                 630                 635                 640

Ser Ser Pro Leu Pro Ser Pro Ala Gly Met Leu Glu Pro Leu Val Leu
                645                 650                 655

Asp Gly Lys Glu Leu Pro Gln Val Cys Val Gly Ala Glu Gly Pro Glu
            660                 665                 670

Gly Pro Gly Cys Arg Val Leu Phe His Val Leu Pro Leu Glu Ala Gly
        675                 680                 685

Leu Thr Pro Asp Ile Leu Ile Pro Pro Glu Gly Ile Pro Gly Ser Ala
    690                 695                 700

Gln Gln Val Ile Gln Val Asp Arg Asp Thr Ile Leu Val Ser Phe Glu
705                 710                 715                 720

Arg Cys Val Arg Ile Val Asn Met Gln Gly Glu Pro Thr Ala Thr Leu
                725                 730                 735

Ala Pro Glu Leu Thr Phe Asp Phe Pro Ile Glu Thr Val Val Cys Leu
            740                 745                 750

Gln Asp Ser Val Leu Ala Phe Trp Ser His Gly Met Gln Gly Arg Ser
        755                 760                 765

Leu Asp Thr Asn Glu Val Thr Gln Glu Ile Thr Asp Glu Thr Arg Ile
    770                 775                 780
```

```
Phe Arg Val Leu Gly Ala His Arg Asp Ile Ile Leu Glu Ser Ile Pro
785                 790                 795                 800

Thr Asp Asn Pro Glu Ala His Ser Asn Leu Tyr Ile Leu Thr Gly His
                805                 810                 815

Gln Ser Thr Tyr
            820


<210> SEQ ID NO 75
<211> LENGTH: 2475
<212> TYPE: DNA
<213> ORGANISM: Homo sapiens
<220> FEATURE:
<223> OTHER INFORMATION: chemokine (C-X-C motif) ligand 5 (CXCL5)
      cDNA
<220> FEATURE:
<221> NAME/KEY: CDS
<222> LOCATION: (119)..(463)
<223> OTHER INFORMATION: CXCL5

<400> SEQUENCE: 75

gtgcagaagg cacgaggaag ccacagtgct ccggatcctc caatcttcgc tcctccaatc     60

tccgctcctc cacccagttc aggaacccgc gaccgctcgc agcgctctct tgaccactat    120

gagcctcctg tccagccgcg cggcccgtgt ccccggtcct tcgagctcct tgtgcgcgct    180

gttggtgctg ctgctgctgc tgacgcagcc agggcccatc gccagcgctg gtcctgccgc    240

tgctgtgttg agagagctgc gttgcgtttg tttacagacc acgcaaggag ttcatcccaa    300

aatgatcagt aatctgcaag tgttcgccat aggcccacag tgctccaagg tggaagtggt    360

agcctccctg aagaacggga aggaaatttg tcttgatcca gaagcccctt ttctaaagaa    420

agtcatccag aaaattttgg acggtggaaa caaggaaaac tgattaagag aaatgagcac    480

gcatggaaaa gtttcccagt cttcagcaga gaagttttct ggaggtctct gaacccaggg    540

aagacaagaa ggaaagattt tgttgttgtt tgtttatttg tttttccagt agttagcttt    600

cttcctggat tcctcacttt gaagagtgtg aggaaaacct atgtttgccg cttaagcttt    660

cagctcagct aatgaagtgt ttagcatagt acctctgcta tttgctgtta ttttatctgc    720

tatgctattg aagttttggc aattgactat agtgtgagcc aggaatcact ggctgttaat    780

ctttcaaagt gtcttgaatt gtaggtgact attatatttc caagaaatat tccttaagat    840

attaactgag aaggctgtgg atttaatgtg gaaatgatgt ttcataagaa ttctgttgat    900

ggaaatacac tgttatcttc acttttataa gaaataggaa atattttaat gtttcttggg    960

gaatatgtta gagaatttcc ttactcttga ttgtgggata ctatttaatt atttcacttt   1020

agaaagctga gtgtttcaca ccttatctat gtagaatata tttccttatt cagaatttct   1080

aaaagtttaa gttctatgag ggctaatatc ttatcttcct ataattttag acattcttta   1140

tctttttagt atggcaaact gccatcattt acttttaaac tttgatttta tatgctattt   1200

attaagtatt ttattaggag taccataatt ctggtagcta aatatatatt ttagatagat   1260

gaagaagcta gaaaacaggc aaattcctga ctgctagttt atatagaaat gtattctttt   1320

agtttttaaa gtaaaggcaa acttaacaat gacttgtact ctgaaagttt tggaaacgta   1380

ttcaaacaat ttgaatataa atttatcatt tagttataaa aatatatagc gacatcctcg   1440

aggccctagc atttctcctt ggatagggga ccagagagag cttggaatgt taaaaacaaa   1500

acaaaacaaa aaaaaacaag gagaagttgt ccaagggatg tcaatttttt atccctctgt   1560

atgggttaga ttttccaaaa tcataatttg aagaaggcca gcatttatgg tagaatatat   1620

aattatatat aaggtggcca cgctggggca agttccctcc ccactcacag ctttggcccc   1680
```

-continued

```
tttcacagag tagaacctgg gttagaggat tgcagaagac gagcggcagc ggggagggca   1740

gggaagatgc ctgtcgggtt tttagcacag ttcatttcac tgggattttg aagcatttct   1800

gtctgaatgt aaagcctgtt ctagtcctgg tgggacacac tggggttggg ggtgggggaa   1860

gatgcggtaa tgaaaccggt tagtcagtgt tgtcttaata tccttgataa tgctgtaaag   1920

tttattttta caaatatttc tgtttaagct atttcacctt tgtttggaaa tccttccctt   1980

ttaaagagaa aatgtgacac ttgtgaaaag gcttgtagga aagctcctcc cttttttttct  2040

ttaaaccttt aaatgacaaa cctaggtaat taatggttgt gaatttctat ttttgctttg   2100

tttttaatga acatttgtct ttcagaatag gattctgtga taatatttaa atggcaaaaa   2160

caaaacataa ttttgtgcaa ttaacaaagc tactgcaaga aaaataaaac atttcttggt   2220

aaaaacgtat gtatttatat attatatatt tatatataat atatattata tatttagcat   2280

tgctgagctt tttagatgcc tattgtgtat cttttaaagg ttttgaccat tttgttatga   2340

gtaattacat atatattaca ttcactatat taaaattgta cttttttact atgtgtctca   2400

ttggttcata gtctttattt tgtcctttga ataaacatta aaagatttct aaacttcaaa   2460

aaaaaaaaaa aaaaa                                                    2475
```

<210> SEQ ID NO 76
<211> LENGTH: 114
<212> TYPE: PRT
<213> ORGANISM: Homo sapiens
<220> FEATURE:
<223> OTHER INFORMATION: chemokine (C-X-C motif) ligand 5 (CXCL5)

<400> SEQUENCE: 76

```
Met Ser Leu Leu Ser Ser Arg Ala Ala Arg Val Pro Gly Pro Ser Ser
  1               5                  10                  15

Ser Leu Cys Ala Leu Leu Val Leu Leu Leu Leu Leu Thr Gln Pro Gly
             20                  25                  30

Pro Ile Ala Ser Ala Gly Pro Ala Ala Ala Val Leu Arg Glu Leu Arg
         35                  40                  45

Cys Val Cys Leu Gln Thr Thr Gln Gly Val His Pro Lys Met Ile Ser
     50                  55                  60

Asn Leu Gln Val Phe Ala Ile Gly Pro Gln Cys Ser Lys Val Glu Val
 65                  70                  75                  80

Val Ala Ser Leu Lys Asn Gly Lys Glu Ile Cys Leu Asp Pro Glu Ala
                 85                  90                  95

Pro Phe Leu Lys Lys Val Ile Gln Lys Ile Leu Asp Gly Gly Asn Lys
            100                 105                 110

Glu Asn
```

<210> SEQ ID NO 77
<211> LENGTH: 1166
<212> TYPE: DNA
<213> ORGANISM: Homo sapiens
<220> FEATURE:
<223> OTHER INFORMATION: chemokine (C-X-C motif) ligand 3 (CXCL3) cDNA
<220> FEATURE:
<221> NAME/KEY: CDS
<222> LOCATION: (163)..(486)
<223> OTHER INFORMATION: CXCL3

<400> SEQUENCE: 77

```
gctccgggaa tttccctggc ccggccgctc cgggctttcc agtctcaacc atgcataaaa     60

agggttcgcc gatcttgggg agccacacag cccgggtcgc aggcacctcc ccgccagctc    120

tcccgcttct cgcacagctt cccgacgcgt ctgctgagcc ccatggccca cgccacgctc    180
```

-continued

```
tccgccgccc ccagcaatcc ccggctcctg cgggtggcgc tgctgctcct gctcctggtg    240
gccgccagcc ggcgcgcagc aggagcgtcc gtggtcactg aactgcgctg ccagtgcttg    300
cagacactgc agggaattca cctcaagaac atccaaagtg tgaatgtaag gtcccccgga    360
ccccactgcg cccaaaccga agtcatagcc acactcaaga atgggaagaa agcttgtctc    420
aaccccgcat cccccatggt tcagaaaatc atcgaaaaga tactgaacaa ggggagcacc    480
aactgacagg agagaagtaa gaagcttatc agcgtatcat tgacacttcc tgcagggtgg    540
tccctgccct taccagagct gaaaatgaaa aagagaacag cagctttcta gggacagctg    600
gaaaggactt aatgtgtttg actatttctt acgagggttc tacttattta tgtatttatt    660
tttgaaagct tgtattttaa tattttacat gctgttattt aaagatgtga gtgtgtttca    720
tcaaacatag ctcagtcctg attatttaat tggaatatga tgggttttaa atgtgtcatt    780
aaactaatat ttagtgggag accataatgt gtcagccacc ttgataaatg acagggtggg    840
gaactggagg gtggggggat tgaaatgcaa gcaattagtg gatcactgtt agggtaaggg    900
aatgtatgta cacatctatt ttttatactt ttttttttaaa aaaagaatgt cagttgttat    960
ttattcaaat tatctcacat tatgtgttca acatttttat gctgaagttt cccttagaca   1020
ttttatgtct tgcttgtagg gcataatgcc ttgtttaatg tccattctgc agcgtttctc   1080
tttcccttgg aaaagagaat ttatcattac tgttacattt gtacaaatga catgataata   1140
aaagttttat gaaaaaaaaa aaaaaa                                         1166
```

<210> SEQ ID NO 78
<211> LENGTH: 107
<212> TYPE: PRT
<213> ORGANISM: Homo sapiens
<220> FEATURE:
<223> OTHER INFORMATION: chemokine (C-X-C motif) ligand 3 (CXCL3) cDNA

<400> SEQUENCE: 78

```
Met Ala His Ala Thr Leu Ser Ala Ala Pro Ser Asn Pro Arg Leu Leu
  1               5                  10                  15

Arg Val Ala Leu Leu Leu Leu Leu Leu Val Ala Ala Ser Arg Arg Ala
             20                  25                  30

Ala Gly Ala Ser Val Val Thr Glu Leu Arg Cys Gln Cys Leu Gln Thr
         35                  40                  45

Leu Gln Gly Ile His Leu Lys Asn Ile Gln Ser Val Asn Val Arg Ser
     50                  55                  60

Pro Gly Pro His Cys Ala Gln Thr Glu Val Ile Ala Thr Leu Lys Asn
 65                  70                  75                  80

Gly Lys Lys Ala Cys Leu Asn Pro Ala Ser Pro Met Val Gln Lys Ile
                 85                  90                  95

Ile Glu Lys Ile Leu Asn Lys Gly Ser Thr Asn
            100                 105
```

<210> SEQ ID NO 79
<211> LENGTH: 861
<212> TYPE: DNA
<213> ORGANISM: Homo sapiens
<220> FEATURE:
<223> OTHER INFORMATION: chemokine (C-C motif) ligand 13 (CCL13) cDNA
<220> FEATURE:
<221> NAME/KEY: CDS
<222> LOCATION: (73)..(372)
<223> OTHER INFORMATION: CCL13

<400> SEQUENCE: 79

-continued

```
aaaaggccgg cggaacagcc agaggagcag agaggcaaag aaacattgtg aaatctccaa     60

ctcttaacct tcaacatgaa agtctctgca gtgcttctgt gcctgctgct catgacagca    120

gctttcaacc cccagggact tgctcagcca gatgcactca acgtcccatc tacttgctgc    180

ttcacattta gcagtaagaa gatctccttg cagaggctga agagctatgt gatcaccacc    240

agcaggtgtc cccagaaggc tgtcatcttc agaaccaaac tgggcaagga gatctgtgct    300

gacccaaagg agaagtgggt ccagaattat atgaaacacc tgggccggaa agctcacacc    360

ctgaagactt gaactctgct acccctactg aaatcaagct ggagtacgtg aaatgacttt    420

tccattctcc tctggcctcc tcttctatgc tttggaatac ttctaccata attttcaaat    480

aggatgcatt cggttttgtg attcaaaatg tactatgtgt taagtaatat tggctattat    540

ttgacttgtt gctggtttgg agtttatttg agtattgctg atctttttcta aagcaaggcc   600

ttgagcaagt aggttgctgt ctctaagccc ccttcccttc cactatgagc tgctggcagt    660

gggtttgtat tcggttccca ggggttgaga gcatgcctgt gggagtcatg gacatgaagg    720

gatgctgcaa tgtaggaagg agagctcttt gtgaatgtga ggtgttgcta aatatgttat    780

tgtggaaaga tgaatgcaat agtaggactg ctgacatttt gcagaaaata cattttattt    840

aaaatctcct aaaaaaaaaa a                                              861


<210> SEQ ID NO 80
<211> LENGTH: 98
<212> TYPE: PRT
<213> ORGANISM: Homo sapiens
<220> FEATURE:
<223> OTHER INFORMATION: chemokine (C-C motif) ligand 13 (CCL13)

<400> SEQUENCE: 80

Met Lys Val Ser Ala Val Leu Leu Cys Leu Leu Leu Met Thr Ala Ala
  1               5                  10                  15

Phe Asn Pro Gln Gly Leu Ala Gln Pro Asp Ala Leu Asn Val Pro Ser
             20                  25                  30

Thr Cys Cys Phe Thr Phe Ser Ser Lys Lys Ile Ser Leu Gln Arg Leu
         35                  40                  45

Lys Ser Tyr Val Ile Thr Thr Ser Arg Cys Pro Gln Lys Ala Val Ile
     50                  55                  60

Phe Arg Thr Lys Leu Gly Lys Glu Ile Cys Ala Asp Pro Lys Glu Lys
 65                  70                  75                  80

Trp Val Gln Asn Tyr Met Lys His Leu Gly Arg Lys Ala His Thr Leu
                 85                  90                  95

Lys Thr


<210> SEQ ID NO 81
<211> LENGTH: 2032
<212> TYPE: DNA
<213> ORGANISM: Homo sapiens
<220> FEATURE:
<223> OTHER INFORMATION: alpha-fetoprotein (AFP) cDNA
<220> FEATURE:
<221> NAME/KEY: CDS
<222> LOCATION: (48)..(1877)
<223> OTHER INFORMATION: AFP

<400> SEQUENCE: 81

tccatattgt gcttccacca ctgccaataa caaaataact agcaaccatg aagtgggtgg     60

aatcaatttt tttaattttc ctactaaatt ttactgaatc cagaacactg catagaaatg    120

aatatggaat agcttccata ttggattctt accaatgtac tgcagagata agtttagctg    180
```

-continued

```
acctggctac catatttttt gcccagtttg ttcaagaagc cacttacaag gaagtaagca    240

aaatggtgaa agatgcattg actgcaattg agaaacccac tggagatgaa cagtcttcag    300

ggtgtttaga aaaccagcta cctgcctttc tggaagaact ttgccatgag aaagaaattt    360

tggagaagta cggacattca gactgctgca gccaaagtga agagggaaga cataactgtt    420

ttcttgcaca caaaaagccc actccagcat cgatcccact tttccaagtt ccagaacctg    480

tcacaagctg tgaagcatat gaagaagaca gggagacatt catgaacaaa ttcatttatg    540

agatagcaag aaggcatccc ttcctgtatg cacctacaat tcttctttgg gctgctcgct    600

atgacaaaat aattccatct tgctgcaaag ctgaaaatgc agttgaatgc ttccaaacaa    660

aggcagcaac agttacaaaa gaattaagag aaagcagctt gttaaatcaa catgcatgtg    720

cagtaatgaa aaattttggg acccgaactt tccaagccat aactgttact aaactgagtc    780

agaagtttac caaagttaat tttactgaaa tccagaaact agtcctggat gtggcccatg    840

tacatgagca ctgttgcaga ggagatgtgc tggattgtct gcaggatggg gaaaaaatca    900

tgtcctacat atgttctcaa caagacactc tgtcaaacaa aataacagaa tgctgcaaac    960

tgaccacgct ggaacgtggt caatgtataa ttcatgcaga aaatgatgaa aaacctgaag   1020

gtctatctcc aaatctaaac aggtttttag gagatagaga ttttaaccaa ttttcttcag   1080

gggaaaaaaa tatcttcttg gcaagttttg ttcatgaata ttcaagaaga catcctcagc   1140

ttgctgtctc agtaattcta agagttgcta aaggatacca ggagttattg gagaagtgtt   1200

tccagactga aaccctcttt gaatgccaag ataaaggaga agaagaatta cagaaataca   1260

tccaggagag ccaagcattg gcaaagcgaa gctgcggcct cttccagaaa ctaggagaat   1320

attacttaca aaatgcgttt ctcgttgctt acacaaagaa agccccccag ctgacctcgt   1380

cggagctgat ggccatcacc agaaaaatgg cagccacagc agccacttgt tgccaactca   1440

gtgaggacaa actattggcc tgtggcgagg gagcggctga cattattatc ggacacttat   1500

gtatcagaca tgaaatgact ccagtaaacc ctggtgttgg ccagtgctgc acttcttcat   1560

atgccaacag gaggccatgc ttcagcagct tggtggtgga tgaaacatat gtccctcctg   1620

cattctctga tgacaagttc attttccata aggatctgtg ccaagctcag ggtgtagcgc   1680

tgcaaacgat gaagcaagag tttctcatta accttgtgaa gcaaaagcca caaataacag   1740

aggaacaact tgaggctgtc attgcagatt tctcaggcct gttggagaaa tgctgccaag   1800

gccaggaaca ggaagtctgc tttgctgaag agggacaaaa actgatttca aaaactcgtg   1860

ctgctttggg agtttaaatt acttcagggg aagagaagac aaaacgagtc tttcattcgg   1920

tgtgaacttt tctctttaat tttaactgat ttaacacttt ttgtgaatta atgaaatgat   1980

aaagactttt atgtgagatt tccttatcac agaaataaaa tatctccaaa tg           2032
```

```
<210> SEQ ID NO 82
<211> LENGTH: 609
<212> TYPE: PRT
<213> ORGANISM: Homo sapiens
<220> FEATURE:
<223> OTHER INFORMATION: alpha-fetoprotein (AFP)

<400> SEQUENCE: 82

Met Lys Trp Val Glu Ser Ile Phe Leu Ile Phe Leu Leu Asn Phe Thr
  1               5                  10                  15

Glu Ser Arg Thr Leu His Arg Asn Glu Tyr Gly Ile Ala Ser Ile Leu
             20                  25                  30

Asp Ser Tyr Gln Cys Thr Ala Glu Ile Ser Leu Ala Asp Leu Ala Thr
         35                  40                  45
```

```
Ile Phe Phe Ala Gln Phe Val Gln Glu Ala Thr Tyr Lys Glu Val Ser
     50                  55                  60

Lys Met Val Lys Asp Ala Leu Thr Ala Ile Glu Lys Pro Thr Gly Asp
 65                  70                  75                  80

Glu Gln Ser Ser Gly Cys Leu Glu Asn Gln Leu Pro Ala Phe Leu Glu
                 85                  90                  95

Glu Leu Cys His Glu Lys Glu Ile Leu Glu Lys Tyr Gly His Ser Asp
            100                 105                 110

Cys Cys Ser Gln Ser Glu Glu Gly Arg His Asn Cys Phe Leu Ala His
        115                 120                 125

Lys Lys Pro Thr Pro Ala Ser Ile Pro Leu Phe Gln Val Pro Glu Pro
    130                 135                 140

Val Thr Ser Cys Glu Ala Tyr Glu Glu Asp Arg Glu Thr Phe Met Asn
145                 150                 155                 160

Lys Phe Ile Tyr Glu Ile Ala Arg Arg His Pro Phe Leu Tyr Ala Pro
                165                 170                 175

Thr Ile Leu Leu Trp Ala Ala Arg Tyr Asp Lys Ile Ile Pro Ser Cys
            180                 185                 190

Cys Lys Ala Glu Asn Ala Val Glu Cys Phe Gln Thr Lys Ala Ala Thr
        195                 200                 205

Val Thr Lys Glu Leu Arg Glu Ser Ser Leu Leu Asn Gln His Ala Cys
    210                 215                 220

Ala Val Met Lys Asn Phe Gly Thr Arg Thr Phe Gln Ala Ile Thr Val
225                 230                 235                 240

Thr Lys Leu Ser Gln Lys Phe Thr Lys Val Asn Phe Thr Glu Ile Gln
                245                 250                 255

Lys Leu Val Leu Asp Val Ala His Val His Glu His Cys Cys Arg Gly
            260                 265                 270

Asp Val Leu Asp Cys Leu Gln Asp Gly Glu Lys Ile Met Ser Tyr Ile
        275                 280                 285

Cys Ser Gln Gln Asp Thr Leu Ser Asn Lys Ile Thr Glu Cys Cys Lys
    290                 295                 300

Leu Thr Thr Leu Glu Arg Gly Gln Cys Ile Ile His Ala Glu Asn Asp
305                 310                 315                 320

Glu Lys Pro Glu Gly Leu Ser Pro Asn Leu Asn Arg Phe Leu Gly Asp
                325                 330                 335

Arg Asp Phe Asn Gln Phe Ser Ser Gly Glu Lys Asn Ile Phe Leu Ala
            340                 345                 350

Ser Phe Val His Glu Tyr Ser Arg Arg His Pro Gln Leu Ala Val Ser
        355                 360                 365

Val Ile Leu Arg Val Ala Lys Gly Tyr Gln Glu Leu Leu Glu Lys Cys
    370                 375                 380

Phe Gln Thr Glu Asn Pro Leu Glu Cys Gln Asp Lys Gly Glu Glu Glu
385                 390                 395                 400

Leu Gln Lys Tyr Ile Gln Glu Ser Gln Ala Leu Ala Lys Arg Ser Cys
                405                 410                 415

Gly Leu Phe Gln Lys Leu Gly Glu Tyr Tyr Leu Gln Asn Ala Phe Leu
            420                 425                 430

Val Ala Tyr Thr Lys Lys Ala Pro Gln Leu Thr Ser Ser Glu Leu Met
        435                 440                 445

Ala Ile Thr Arg Lys Met Ala Ala Thr Ala Ala Thr Cys Cys Gln Leu
    450                 455                 460

Ser Glu Asp Lys Leu Leu Ala Cys Gly Glu Gly Ala Ala Asp Ile Ile
```

-continued

```
465                 470                 475                 480

Ile Gly His Leu Cys Ile Arg His Glu Met Thr Pro Val Asn Pro Gly
                485                 490                 495

Val Gly Gln Cys Cys Thr Ser Ser Tyr Ala Asn Arg Arg Pro Cys Phe
            500                 505                 510

Ser Ser Leu Val Val Asp Glu Thr Tyr Val Pro Pro Ala Phe Ser Asp
        515                 520                 525

Asp Lys Phe Ile Phe His Lys Asp Leu Cys Gln Ala Gln Gly Val Ala
    530                 535                 540

Leu Gln Thr Met Lys Gln Glu Phe Leu Ile Asn Leu Val Lys Gln Lys
545                 550                 555                 560

Pro Gln Ile Thr Glu Glu Gln Leu Glu Ala Val Ile Ala Asp Phe Ser
                565                 570                 575

Gly Leu Leu Glu Lys Cys Cys Gln Gly Gln Glu Gln Glu Val Cys Phe
            580                 585                 590

Ala Glu Glu Gly Gln Lys Leu Ile Ser Lys Thr Arg Ala Ala Leu Gly
        595                 600                 605

Val


<210> SEQ ID NO 83
<211> LENGTH: 2158
<212> TYPE: DNA
<213> ORGANISM: Homo sapiens
<220> FEATURE:
<223> OTHER INFORMATION: C-type lectin domain 4, member E (CLEC4E)
      cDNA
<220> FEATURE:
<221> NAME/KEY: CDS
<222> LOCATION: (166)..(825)
<223> OTHER INFORMATION: CLEC4E

<400> SEQUENCE: 83

atattctaca tctatcggag ctgaacttcc taaaagacaa agtgtttatc tttcaagatt     60

cattctccct gaatcttacc aacaaaacac tcctgaggag aaagaaagag agggagggag    120

agaaaaagag agagagagaa acaaaaaacc aaagagagag aaaaaatgaa ttcatctaaa    180

tcatctgaaa cacaatgcac agagagagga tgcttctctt cccaaatgtt cttatggact    240

gttgctggga tccccatcct atttctcagt gcctgtttca tcaccagatg tgttgtgaca    300

tttcgcatct ttcaaacctg tgatgagaaa aagtttcagc tacctgagaa tttcacagag    360

ctctcctgct acaattatgg atcaggttca gtcaagaatt gttgtccatt gaactgggaa    420

tattttcaat ccagctgcta cttcttttct actgacacca tttcctgggc gttaagttta    480

aagaactgct cagccatggg ggctcacctg gtggttatca actcacagga ggagcaggaa    540

ttcctttcct acaagaaacc taaaatgaga gagtttttta ttggactgtc agaccaggtt    600

gtcgagggtc agtggcaatg ggtggacggc acacctttga caaagtctct gagcttctgg    660

gatgtagggg agcccaacaa catagctacc ctggaggact gtgccaccat gagagactct    720

tcaaacccaa ggcaaaattg gaatgatgta acctgtttcc tcaattattt tcggatttgt    780

gaaatggtag gaataaatcc tttgaacaaa ggaaaatctc tttaagaaca gaaggcacaa    840

ctcaaatgtg taaagaagga agagcaagaa catggccaca cccaccgccc cacacgagaa    900

atttgtgcgc tgaacttcaa aggacttcat aagtatttgt tactctgata taaataaaaa    960

taagtagttt taaatgttat aattcatgtt actggctgaa gtgcattttc tctctacgtt   1020

agtctcaggt cctcttccca gaatttacaa agcaattcac taccttttgc tacatttgcc   1080

tcatttttta gtgttcgtat gaaagtacag ggacacggag ccaagacaga gtctagcaaa   1140
```

```
gaaggggatt ttggaaggtg ccttccaaaa atctcctgaa tccgggctct gtagcaggtc   1200

ctcttctttc tagcttctga caagtctgtc ttctcttctt ggtttcatac cgttcttatc   1260

tcctgcccaa gcatatatcg tctctttact cccctgtata atgagtaaga agcttcttca   1320

agtcatgaaa cttattcctg ctcagaatac cggtgtggcc tttctggcta caggcctcca   1380

ctgcaccttc ttagggaagg gcatgccagc catcagctcc aaacaggctg taaccaagtc   1440

cacccatccc tggggcttcc tttgctctgc cttattttca attgactgaa tggatctcac   1500

cagattttgt atctattgct cagctaggac ccgagtccaa tagtcaattt attctaagcg   1560

aacattcatc tccacacttt cctgtctcaa gcccatccat tatttcttaa cttttatttt   1620

agctttcggg ggtacatgtt aaaggctttt tatataggta aactcatgtc gtggaggttt   1680

gttgtacaga ttatttcatc acccaggtat taagcccagt gcctaatatt gttttttttcg  1740

gctcctctcc ctcctcctac cttccgccct caagtagact ccagtgtctg ttattccctt   1800

ctttgtgttt atgaattctc atcatttagc tcccacttat aagtgaggac atgcagtatt   1860

tggttttctg ttcccatgtt tgctaaggat aatggtttcc agttctaccg atgttcccac   1920

aaaagacata attttctttt ttaaggctgc ttagtattcc atggtatcta tgtatcacat   1980

tttctctatc caatctattg ttgactcaca tttagattga ttccatgttt ttgctattgt   2040

gaatagtgct gcaatgaaca ttcgtgtgca tgtgtcttta tggtagaaag atttatattt   2100

ctctgagtat gtatccagta atagcccatt catttattgc ataaaattct accaatac     2158
```

```
<210> SEQ ID NO 84
<211> LENGTH: 218
<212> TYPE: PRT
<213> ORGANISM: Homo sapiens
<220> FEATURE:
<223> OTHER INFORMATION: C-type lectin domain 4, member E (CLEC4E)

<400> SEQUENCE: 84

Met Asn Ser Ser Lys Ser Ser Glu Thr Gln Cys Thr Glu Arg Gly Cys
  1               5                  10                  15

Phe Ser Ser Gln Met Phe Leu Trp Thr Val Ala Gly Ile Pro Ile Leu
             20                  25                  30

Phe Leu Ser Ala Cys Phe Ile Thr Arg Cys Val Val Phe Arg Ile Phe
         35                  40                  45

Gln Thr Cys Asp Glu Lys Lys Phe Gln Leu Pro Glu Asn Phe Thr Glu
     50                  55                  60

Leu Ser Cys Tyr Asn Tyr Gly Ser Gly Ser Val Lys Asn Cys Cys Pro
 65                  70                  75                  80

Leu Asn Trp Glu Tyr Phe Gln Ser Ser Cys Tyr Phe Phe Ser Thr Asp
                 85                  90                  95

Thr Ile Ser Trp Ala Leu Ser Leu Lys Asn Cys Ser Ala Met Gly Ala
            100                 105                 110

His Leu Val Val Ile Asn Ser Gln Glu Glu Gln Glu Phe Leu Ser Tyr
        115                 120                 125

Lys Lys Pro Lys Met Arg Glu Phe Phe Ile Gly Leu Ser Asp Gln Val
    130                 135                 140

Val Glu Gly Gln Trp Gln Trp Val Asp Gly Thr Pro Leu Thr Lys Ser
145                 150                 155                 160

Leu Ser Phe Trp Asp Val Gly Glu Pro Asn Asn Ile Ala Thr Leu Glu
                165                 170                 175

Asp Cys Ala Thr Met Arg Asp Ser Ser Asn Pro Arg Gln Asn Trp Asn
            180                 185                 190
```

-continued

```
Asp Val Thr Cys Phe Leu Asn Tyr Phe Arg Ile Cys Glu Met Val Gly
        195                 200                 205

Ile Asn Pro Leu Asn Lys Gly Lys Ser Leu
    210                 215
```

IVIG MODULATION OF CHEMOKINES FOR TREATMENT OF MULTIPLE SCLEROSIS, ALZHEIMER'S DISEASE, AND PARKINSON'S DISEASE

CROSS-REFERENCES TO RELATED APPLICATIONS

The present application claims priority to U.S. Ser. No. 60/955,610, filed Aug. 13, 2007, herein incorporated by reference in its entirety.

STATEMENT AS TO RIGHTS TO INVENTIONS MADE UNDER FEDERALLY SPONSORED RESEARCH AND DEVELOPMENT

Not Applicable

REFERENCE TO A "SEQUENCE LISTING," A TABLE, OR A COMPUTER PROGRAM LISTING APPENDIX SUBMITTED ON A COMPACT DISK

Not Applicable

BACKGROUND OF THE INVENTION

Multiple sclerosis (MS) is the most common autoimmune inflammatory disease of the central nervous system. It is characterized by demyelinating lesions in the white matter of the central nervous system that lead to neurological deficits (Sospedra M. and Martin R., *Immunology of Multiple Sclerosis. Annu Rev Immunol.,* 23:683-747 (2005)). The pathogenesis of the disease is associated with the infiltration of immune cells, mainly activated T cells, into the brain (Sospedra M. and Martin R., *Annu Rev Immunol.,* 23:683-747 (2005)). This infiltration is accompanied by a disruption of the blood-brain barrier (van Horssen J. et al., *J Neuropathol Exp Neurol.,* 66:321-8 (2007)).

Intravenous immunoglobulins (IVIG) have been shown to be effective in the treatment of a number of autoimmune diseases including MS (Sospedra M. and Martin R., *Immunology of Multiple Sclerosis. Annu Rev Immunol.,* 23:683-747 (2005)), but the exact mechanisms of action underlying the immunomodulatory activities of IVIG have not been fully explained. There are several models that try to explain the immunomodulatory efficacy of IVIG in patients suffering from autoimmune and inflammatory diseases (Kazatchkine M. D. et al., *Mult Scler,* 2:24-6; 33:24-26 (2000); Trebst C. and Stangel M., *Curr. Pharm. Design,* 12:241-2493 (2006)). These models include Fcγ-receptor-mediated immunomodulation (Sorensen P. S., *Neurol Sci,* 4:227-230 (2003)), modulation of idiotype/anti-idiotype networks (Samuelsson A. et al., *Science,* 291:484-6 (2001)), elimination of immunostimulating microbial products (Dalakas M. C., *Ann Intern Med,* 126:721-30 (1997)) and neutralizing antibodies against cytokines and chemokines (Bayry J. et al., *Transfus Clin Biol.,* 10:165-9 (2003)). IVIG's potential to modify the balance between Th1 and Th2 cell immunoreactivity and to inhibit the formation of antibody/complement complexes have also been demonstrated (Andersson U. et al., *Immunol Rev,* 139:21-42 (1994); Bayry J. et al., *Intravenous immunoglobulin in autoimmune disorders: An insight into the immunregulatory mechanisms*).

The beneficial effects of IVIG in patients with MS were shown by a number of open clinical trials (Basta M. et al., *Blood,* 77:376-80 (1991)) and by four randomized double-blind clinical studies (Sorensen P. S. et al., *Eur J Neurol,* 9:557-563 (2002); Strasser-Fuchs S. et al., *Mult Scler,* 2:9-13 (2000); Sorensen P. S. et al., *Neurology,* 50:1273-1281 (1998); Lewanska M. et al., *Eur J Neurol,* 9:565-572 (2002)). IVIG decreased the relapse rate in MS patients and the number of gadolinium-enhancing lesions seen on brain magnetic resonance imaging (MRI) (Dudesek A. and Zettl U. K., *J Neurol,* 253; V/50-V/58)). Furthermore, IVIG was shown to suppress proliferation of activated peripheral T cells (Bayry J. et al., *Neurol Sci,* 4:217-221 (2003); Stangel M. and Gold R., *Nervenarzt,* (2005)). Auto-reactive peripheral T cells can cross the blood-brain barrier and are believed to be the main effector cells responsible for brain inflammation (Sospedra M. and Martin R., *Annu Rev Immunol.,* 23:683-747 (2005); Helling N. et al., *Immunol Res.,* 1:27-51 (2002)). Therefore, a modulation of T cell function by IVIG could explain the beneficial therapeutic effect of IVIG seen in MS patients.

Recently, we showed that IVIG is an effective alternative treatment for patients with acute exacerbations in relapsing-remitting multiple sclerosis (RRMS) (Elovaara I. et al., *Intravenous Immunoglobulin is effective and well tolerated in the treatment of MS Relapse*, manuscript submitted). Because peripheral auto-reactive T cells are believed to be responsible for brain inflammation in MS, we undertook to identify genes that are differentially regulated in peripheral T cells of patients with MS in acute exacerbation that are treated with IVIG. We reasoned that differences in gene expression profiles could provide important information about the potential mechanisms of action of IVIG treatment. Furthermore, changes in gene expression profiles could provide prognostic markers to predict treatment success. Such markers could also help to identify targets for developing new therapeutic agents.

Furthermore, increasing evidence has suggested a role for brain inflammation not only in MS but also in the pathogenesis of Alzheimers' disease and Parkinsons' disease (see, e.g., Wilms et al., *Curr. Pharm. Des.* 13:1925 (2007)). In particular microglia, the resident innate immune cells, play a major role in inflammatory processes of the brain and are known to be associated not only with MS but also with Alzheimers' disease and in Parkinsons' disease (see, e.g., Yamamoto et al., *Am. J. Pathology* 166:1475 (2006); Huang et al., *FASEB* 19:761 (2005); Kim et al., *Exp. And Mol. Med.* 38:333 (2006)). Thus, the present invention provides new prognostic markers to predict treatment success associated with the administration of intravenous immunoglobulin treatment as well as new therapeutic targets that may be exploited in the treatment of MS, e.g., relapsing-remitting multiple sclerosis (RRMS), Parkinsons' disease or Alzheimers disease.'

BRIEF SUMMARY OF THE INVENTION

The present invention provides methods for providing a prognosis of treatment of multiple sclerosis, Parkinson's disease and Alzheimer's disease using molecular markers that are overexpressed or underexpressed in patients treated with intravenous immunoglobulins (IVIG). Also provided are methods to identify compounds that are useful for the treatment or prevention of multiple sclerosis. In some aspects, the subtype of multiple sclerosis is relapsing-remitting multiple sclerosis (RRMS).

Accordingly, in one embodiment the present invention provides method of providing a prognosis of multiple sclerosis, Parkinson's disease and Alzheimer's disease in a subject treated with intravenous immunoglobulin (IVIG) by contacting a biological sample from the subject treated with IVIG with a reagent that specifically binds to at least one marker selected from any of the nucleic acids and corresponding protein sequences shown in Table 3a, Table 3b, and Table 4, and then determining whether or not the marker is overexpressed or underexpressed in the sample, thus providing a prognosis for MS, Parkinson's disease and Alzheimer's disease in a subject treated with IVIG. In an aspect of this embodiment, the multiple sclerosis is of the relapsing-remitting multiple sclerosis (RRMS) subtype.

In various aspects of this embodiment, the reagent is an antibody, such as a monoclonal antibody. Alternatively, the reagent can be a nucleic acid, including an oligonucleotide or an RT PCR primer set. In other aspects, the sample is a blood sample, which can contain T cells. The sample can also be cerebrospinal fluid. In some aspects of this embodiment, one of the markers is a chemokine. Examples of chemokines include: CXCL3, CXCL5, CCL13, and XCL2.

Another embodiment of the invention provides a method of identifying a compound that prevents or treats multiple sclerosis, Parkinson's disease and Alzheimer's disease by contacting a compound with a sample comprising a cell that expresses a marker selected from any of the nucleic acid and corresponding protein sequences shown in Table 3a, Table 3b, Table 3c, Table 3d, and Table 4, and then determining the functional effect of the compound on the marker, thus identifying a compound that prevents or treats MS, Parkinson's disease and Alzheimer's disease. In an aspect of this embodiment, the multiple sclerosis is of the relapsing-remitting multiple sclerosis (RRMS) subtype.

In various aspects of this embodiment, the functional effect is an increase or decrease in expression of the marker. In other aspects, the functional effect is an increase or decrease in activity of the marker. Examples of compounds used in various aspects of this embodiment include: a small molecule, a siRNA, a ribozyme, an antibody, which can be a monoclonal antibody.

A further embodiment of the invention provides a method of treating or preventing multiple sclerosis, Parkinson's disease and Alzheimer's disease in a subject by administering to the subject an effective amount of an antibody which binds a chemokine, including CXCL5, CXCL3, and CCL13, in which the effective amount is sufficient to inactivate the chemokine or chemokine cell signaling, thus treating or preventing multiple sclerosis, Parkinson's disease and Alzheimer's disease. In an aspect of this embodiment, the multiple sclerosis is of the relapsing-remitting multiple sclerosis (RRMS) subtype.

A yet further embodiment of the invention provides a method of treating or preventing multiple sclerosis, Parkinson's disease and Alzheimer's disease in a subject by administering to the subject an effective amount of an antibody which binds a chemokine receptor, including receptors for CXCL5, CXCL3, and CCL13, in which the effective amount is sufficient to inactivate the function of the chemokine receptor, thus treating or preventing multiple sclerosis, Parkinson's disease and Alzheimer's disease. In an aspect of this embodiment, the multiple sclerosis is of the relapsing-remitting multiple sclerosis (RRMS) subtype.

Another embodiment of this invention provides a method of treating or preventing multiple sclerosis, Parkinson's disease and Alzheimer's disease in a subject by administering to the subject an effective amount of an antibody which binds to a XCL2 chemokine receptor, in which the effective amount is sufficient to activate the XCL2 chemokine receptor, thus treating or preventing multiple sclerosis, Parkinson's disease and Alzheimer's disease. In an aspect of this embodiment, the multiple sclerosis is of the relapsing-remitting multiple sclerosis (RRMS) subtype.

BRIEF DESCRIPTION OF THE DRAWINGS

FIG. 2 shows that treatment with IVIG does not alter the cellular composition of cells obtained for isolation of RNA. Relative gene expression data obtained from microarray analysis are presented for CD3, CD4, CD8 and CD14. Gene expression on day 0 was set as 1 and compared with gene expression on day 6 (A) and day 26 (B). Each point represents an individual patient.

FIG. 3 shows real-time PCR demonstrating the expression of representative genes. Box plots containing the median, 25% and 75% percentile, minimum and maximum, demonstrate the relative expression of the indicated genes. Expression of genes was normalized to an endogenous control (glyceraldhyde-3-phosphate dehydrogenase). Real-time PCR experiments were done in triplets and confirmed at least two times on different days.

DETAILED DESCRIPTION OF THE INVENTION

Figure 1:
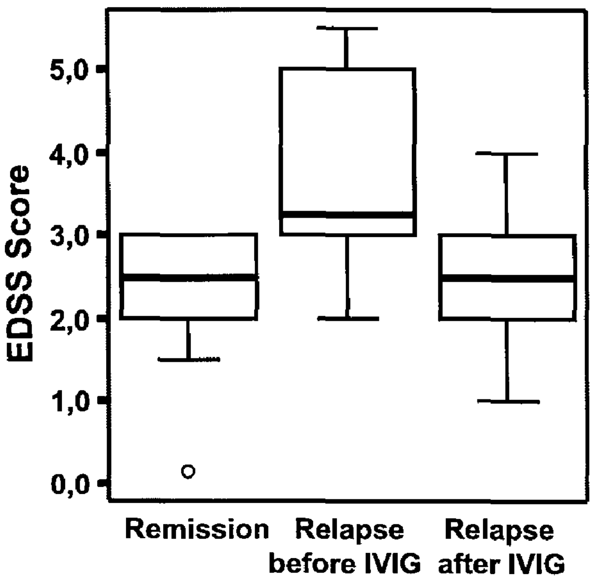
FIG. 1 shows development of EDSS scores in 10 RRMS patients during treatment with IVIG. Box plots containing the median, 25% and 75% percentile, minimum and maximum, demonstrate the EDSS scores of patients during remission, as well as before and after treatment with IVIG during relapse.

Multiple sclerosis (MS) refers generally to an inflammatory, demyelinating disease that affects the central nervous system (CNS). During the progression of MS, the myelin surrounding the axons of neurons degenerates, resulting in subsequent axonal degeneration. The pathogenesis of MS is believed to involve an autoimmune response in which T cells attack parts of the central nervous system, triggering inflammatory responses, which results in the stimulation of other immune cells and the secretion of soluble factors such as cytokines and antibodies. The inflammatory processes triggered by T cells create leaks in the blood-brain barrier formed by endothelial cells. The leaks in the blood-brain barrier, in turn, cause a number of other damaging effects such as brain swelling, activation of macrophages, and further secretion of cytokines and other proteolytic proteins such as matrix metalloproteinases. The final outcome of these pathological processes is neuronal demyelination. See, e.g., Calabresi, P. A., *American Family Physician,* 70: 1935-1944 (2004), for review.

As MS progresses, gradual demyelination and transection of neuron axons in patches throughout the brain and spinal cord occur. Thus, the term multiple sclerosis refers to the multiple scars (or scleroses) found on myelin sheaths in affected individuals. This scarring causes symptoms which may vary widely depending upon the extent of scarring and which neuronal pathways are disrupted.

Among the symptoms and manifestations of MS include changes in sensation (hypoesthesia), muscle weakness, abnormal muscle spasms, difficulties in movement; difficulties with coordination and balance (ataxia); problems in speech (dysarthria) or swallowing (dysphagia), visual problems (nystagmus, optic neuritis, or diplopia), fatigue and acute or chronic pain syndromes, bladder and bowel difficulties, cognitive impairment, or emotional symptomatology (e.g., depression).

The most common initial symptoms reported are: changes in sensation in the arms, legs or face (33%), complete or partial vision loss (optic neuritis) (16%), weakness (13%), double vision (7%), unsteadiness when walking (5%), and balance problems (3%). See Navarro et al., *Rev Neurol* 41: 601-3 (2005); Jongen P., *J Neurol Sci* 245: 59-62 (2006). In some individuals, the initial MS attack is preceded by infection, trauma, or strenuous physical effort.

A number of diagnostic tests are currently in use for the diagnosis of MS. These include the clinical presentation of two separate episodes of neurologic symptoms characteristic of MS, along with the finding of consistent abnormalities on physical examination. Alternatively, magnetic resonance imaging (MRI) of the brain and spine is often used to evaluate individuals with suspected MS. MRI reveals areas of demyelination as bright lesions on T2-weighted images or FLAIR (fluid attenuated inversion recovery) sequences. Gadolinium contrast can be used to demonstrate active plaques on T1-weighted images.

The testing of cerebrospinal fluid (CSF) can provide evidence of chronic inflammation of the central nervous system, a characteristic of MS. In such a test, the CSF is tested for oligoclonal bands, which are immunoglobulins found in 85% to 95% of people with definite MS. When combined with MRI and clinical data, the presence of oligoclonal bands can help make a definite diagnosis of MS.

Because the brains MS-affected individuals often respond less actively to stimulation of the optic nerve and sensory nerves, the measurement of such brain responses can also be used as a diagnostic tool. These brain responses can be examined using visual evoked potentials (VEPs) and somatosensory evoked potentials (SEPs). Decreased activity on either test can reveal demyelination which may be otherwise asymptomatic. Along with other data, these exams can help uncover the widespread nerve involvement required for a definite diagnosis of MS.

Several subtypes, or patterns of progression, of MS have been described. In 1996, the United States National Multiple Sclerosis Society standardized the following four subtype definitions, as described below.

Relapsing-remitting MS (RRMS) refers to a subtype characterized by unpredictable attacks (relapses) followed by periods of months to years of relative quiet (remission) with no new signs of disease activity. Deficits suffered during the attacks may either resolve or may be permanent. Relapsing-remitting describes the initial course of 85% to 90% of individuals with MS.

Secondary progressive describes around 80% of those with initial relapsing-remitting MS, who then begin to have neurologic decline between their acute attacks without any definite periods of remission. This decline may include new neurologic symptoms, worsening cognitive function, or other deficits. Secondary progressive is the most common type of MS and causes the greatest amount of disability.

Primary progressive describes the approximately 10% of individuals who never have remission after their initial MS symptoms. Decline occurs continuously without clear attacks. The primary progressive subtype tends to affect people who are older at disease onset.

Progressive relapsing describes those individuals who, from the onset of their MS, have a steady neurologic decline but also suffer superimposed attacks; and is the least common of all subtypes.

While there is currently no definitive cure for MS, a number of therapies have been developed that are directed toward returning function after an attack, preventing new attacks, or preventing disability. Thus, different therapies are used for patients experiencing acute attacks; those who have the relapsing-remitting subtype; those who have the progressive subtypes; those without a diagnosis of MS who have a demyelinating event; and for managing the various consequences of MS attacks.

The pharmacological agents currently in use for MS include interferons, which have been approved for use in relapsing forms of secondary progressive MS; glatiramer acetate, a synthetic medication made of four amino acids that are found in myelin, which stimulates T cells to secrete anti-inflammatory agents that reduce inflammation at lesion sites; mitoxantrone, an agent used to treat progressive, progressive-relapsing, and worsening relapsing-remitting MS; and Natalizumab, a monoclonal antibody that recognizes α4-integrin.

High doses of intravenous corticosteroids, such as methylprednisolone, are frequently administered in the treatment of RRMS and have been shown to be effective at shortening the length of relapsing-remitting symptomatic attacks. As described in greater detail herein, intravenous IgG immunoglobulins have also been used to treat MS.

Similarly to MS, other disease states are associated with brain inflammation, such as Parkinson's disease and Alzheimer's disease, as described above. For example, chemokine CCL13, described herein, activates the chemokine receptor CCR2, which is expressed in microglia and astrocytes. Both of these cell types are associated with Parkinson's disease and Alzheimer's disease. This and other markers described herein are therefore useful for drug assays, diagnostic and prognostic assays, and for therapeutic siRNA and antibody treatment for Alzheimer's disease and Parkinson's disease.

Intravenous immunoglobulins (IVIG) have been successfully used to treat a number of autoimmune diseases of the central nervous system, including multiple sclerosis (MS). However, the underlying mechanisms of action of IVIG have not been fully explained. Accordingly, we have undertaken the identification of gene expression profiles that are associated with the immunomodulatory activity of IVIG in patients with acute exacerbations in relapsing-remitting MS (RRMS). As described below, HU-133 microarrays from Affymetrix were used to study gene expression profiles of peripheral T cells in 10 RRMS patients before and after treatment with IVIG. Patients treated with intravenous methylprednisolone were included as controls. The differential expression of representative genes was confirmed by real-time polymerase chain reaction. All patients were analyzed neurologically and by brain and spinal cord magnetic resonance imaging before and after IVIG therapy.

As shown below in the Examples, 360 genes that were differentially expressed during IVIG treatment were identified. Some encode chemokines such as CXCL3 and CXCL5 that are known to bind to CXCR2, a receptor essential for the regulation of oligodendrocyte migration in the brain. Others encode proteins that are involved in signal transduction, proliferation or apoptosis.

The studies disclosed herein indicate that among the differentially expressed genes the regulation of chemokine expression in peripheral T cells is an important new mechanism of action of IVIG in patients with acute exacerbations in MS. Thus, the genes disclosed herein may serve as diagnostic markers for predicting treatment success in IVIG therapy and provide new molecular targets for drug development.

DEFINITIONS

The term "intravenous IgG" or "IVIG" treatment refers generally to a composition of IgG immunoglobulins administered intravenously to treat a number of conditions such as immune deficiencies, inflammatory diseases, and autoimmune diseases. The IgG immunoglobulins are typically pooled and prepared from serum. Whole antibodies or fragments can be used.

The term “chemokine” refers generally to a family of small cytokines which are secreted by various cells that promote chemotaxis in responsive cells. Chemokines have also gone by the nomenclature of SIS family of cytokines, SIG family of cytokines, SCY family of cytokines, Platelet factor-4 superfamily or intercrines. Cells that are attracted by chemokines follow a signal of increasing chemokine concentration towards the source of the chemokine.

Some members of the chemokine family control cells of the immune system during the process of immune surveillance, such as by directing lymphocytes to the lymph nodes to allow lymphocyte surveillance invasion of pathogens through interaction with antigen-presenting cells residing in these tissues. Such chemokines are known as homeostatic chemokines and are produced and secreted without any need to stimulate their source cell(s). Some chemokines have roles in development by, e.g., promoting angiogenesis or guiding cells to tissues that provide specific signals critical for cellular maturation. Other chemokines are inflammatory and are released from a wide variety of cells in response to bacterial infection, viruses and agents that cause physical damage. The release of inflammatory chemokines is often stimulated by pro-inflammatory cytokines such as interleukin 1. Inflammatory chemokines function mainly as chemoattractants for leukocytes, recruiting monocytes, neutrophils and other effector cells from the blood to sites of infection or tissue damage. Certain inflammatory chemokines activate cells to initiate an immune response or promote wound healing. They are released by many different cell types and serve to guide cells of both innate immune system and adaptive immune system.

Structurally, chemokines are small proteins, with molecular masses of between 8 and 10 kDa. Chemokines also possess conserved amino acids that are important for creating their 3-dimensional or tertiary structure, such as (in most cases) four cysteines that interact with each other in pairs to create a greek key shape that is a characteristic of this class of proteins; intramolecular disulphide bonds typically join the first to third, and the second to fourth cysteine residues, numbered as they appear in the protein sequence of the chemokine.

Members of the chemokine family are categorized into four groups depending on the spacing of their first two cysteine residues. The CC chemokines (or β-chemokines) have two adjacent cysteines near their amino terminus. There have been at least 27 distinct members of this subgroup reported for mammals, called CC chemokine ligands (CCL)-1 to -28. The first two cysteine residues in CXC chemokines (or α-chemokines) are separated by one amino acid, represented by “X”. There have been 17 different CXC chemokines described in mammals, that are subdivided into two categories, those with a specific amino acid sequence (or motif) of Glutamic acid-Leucine-Arginine (ELR) immediately before the first cysteine of the CXC motif (ELR-positive), and those without an ELR motif (ELR-negative). The third group of chemokines is known as the C chemokines (or γ chemokines), and is unlike all other chemokines in that it has only two cysteines; one N-terminal cysteine and one cysteine downstream. A fourth group has three amino acids between the two cysteines and is termed $CX_3C$ chemokine (or δ-chemokines).

Chemokine receptors are G protein-coupled receptors containing 7 transmembrane domains that are found on the surface of leukocytes. Approximately 19 different chemokine receptors have been characterized to date, which are divided into four families depending on the type of chemokine they bind; CXCR that bind CXC chemokines, CCR that bind CC chemokines, CX3CR1 that binds the sole CX3C chemokine (CX3CL1), and XCR1 that binds the two XC chemokines (XCL1 and XCL2).

“Chemokine cell signaling” refers generally to the ability of chemokine receptors to associate with G-proteins to transmit cell signals following ligand binding. Activation of G proteins, by chemokine receptors, causes the subsequent activation of phospholipase C (PLC). PLC cleaves a phosphatidylinositol (4,5)-bisphosphate (PIP2) into two second messenger molecules, inositol triphosphate (IP3) and diacylglycerol (DAG) that trigger intracellular signaling events; DAG activates another enzyme called protein kinase C (PKC), and IP3 triggers the release of calcium from intracellular stores. These events promote signaling cascades such as the MAP kinase pathway that generate responses including chemotaxis, degranulation, release of superoxide anions and changes in the avidity of cell adhesion molecules such as integrins within the cell harboring the chemokine receptor.

The term “marker” or “biomarker” refers to a molecule (typically protein, nucleic acid, carbohydrate, or lipid) that is expressed in a cell, expressed on the surface of a cell or secreted by a cell and which is useful for providing a prognosis of relapsing-remitting multiple sclerosis (RRMS) in a subject treated with IVIG. Some of the biomarkers disclosed herein are molecules that are overexpressed in individuals with relapsing-remitting multiple sclerosis (RRMS) treated with IVIG, in comparison to individuals not treated IVIG or in RRMS patients prior to treatment with IVIG, for instance, 1-fold overexpression, 2-fold overexpression, 3-fold overexpression, or more. Alternatively, other biomarkers are molecules that are underexpressed in individuals with relapsing-remitting multiple sclerosis (RRMS) treated with IVIG, in comparison to individuals not treated IVIG or in RRMS patients prior to treatment with IVIG, for instance, 1-fold underexpression, 2-fold underexpression, 3-fold underexpression, or more. Further, a marker can be a molecule that is inappropriately synthesized in individuals with relapsing-remitting multiple sclerosis (RRMS) treated with IVIG, in comparison to individuals not treated IVIG or in RRMS patients prior to treatment with IVIG, for instance, a molecule that contains deletions, additions or mutations in comparison to the molecule expressed on a normal cell.

It will be understood by the skilled artisan that markers may be used singly or in combination with other markers for any of the uses, e.g., prognosis of IVIG treatment of relapsing-remitting multiple sclerosis (RRMS), disclosed herein.

“Biological sample” includes biological fluid samples, such as blood and cerebrospinal fluid, sections of tissues such as biopsy and autopsy samples, and frozen sections taken for histologic purposes. Such samples include blood and blood fractions or products (e.g., serum, plasma, platelets, red blood cells, and the like), cerebrospinal fluid, sputum, cervicovaginal fluid, lymph and tongue tissue, cultured cells, e.g., primary cultures, explants, and transformed cells, stool, urine, etc. A biological sample is typically obtained from a eukaryotic organism, most preferably a mammal such as a primate e.g., chimpanzee or human; cow; dog; cat; a rodent, e.g., guinea pig, rat, Mouse; rabbit; or a bird; reptile; or fish.

The terms “overexpress,” “overexpression” or “overexpressed” or “upregulated” interchangeably refer to a protein or nucleic acid (RNA) that is transcribed or translated at a detectably greater level, usually in an IVIG-treated relapsing-remitting multiple sclerosis (RRMS) patient, in comparison to a patient not undergoing IVIG treatment. The term includes overexpression due to transcription, post transcriptional processing, translation, post-translational processing, cellular localization (e.g., organelle, cytoplasm, nucleus, cell surface), and RNA and protein stability, as compared to a control. Overexpression can be detected using conventional techniques for detecting mRNA (i.e., RT-PCR, PCR, hybridization) or proteins (i.e., ELISA, immunohistochemical techniques). Overexpression can be 10%, 20%, 30%, 40%, 50%, 60%, 70%, 80%, 90% or more in comparison to a normal cell. In certain instances, overexpression is 1-fold, 2-fold, 3-fold, 4-fold or more higher levels of transcription or translation in comparison to a control.

The terms "underexpress," "underexpression" or "underexpressed" or "downregulated" interchangeably refer to a protein or nucleic acid that is transcribed or translated at a detectably lower level, usually in an IVIG-treated relapsing-remitting multiple sclerosis (RRMS) patient, in comparison to a patient not undergoing IVIG treatment. The term includes underexpression due to transcription, post transcriptional processing, translation, post-translational processing, cellular localization (e.g., organelle, cytoplasm, nucleus, cell surface), and RNA and protein stability, as compared to a control. Underexpression can be detected using conventional techniques for detecting mRNA (i.e., RT-PCR, PCR, hybridization) or proteins (i.e., ELISA, immunohistochemical techniques). Underexpression can be 10%, 20%, 30%, 40%, 50%, 60%, 70%, 80%, 90% or less in comparison to a control. In certain instances, underexpression is 1-fold, 2-fold, 3-fold, 4-fold or more lower levels of transcription or translation in comparison to a control.

The term "differentially expressed" or "differentially regulated" refers generally to a protein or nucleic acid that is overexpressed (upregulated) or underexpressed (downregulated) in one sample compared to at least one other sample, generally in an IVIG-treated relapsing-remitting multiple sclerosis (RRMS) patient, in comparison to a patient not undergoing IVIG treatment, in the context of the present invention.

"Therapeutic treatment" refers to drug therapy, hormonal therapy, immunotherapy, and biologic (targeted) therapy.

By "therapeutically effective amount or dose" or "sufficient amount or dose" herein is meant a dose that produces effects for which it is administered. The exact dose will depend on the purpose of the treatment, and will be ascertainable by one skilled in the art using known techniques (see, e.g., Lieberman, *Pharmaceutical Dosage Forms* (vols. 1-3, 1992); Lloyd, *The Art, Science and Technology of Pharmaceutical Compounding* (1999); Pickar, *Dosage Calculations* (1999); and *Remington: The Science and Practice of Pharmacy,* 20th Edition, 2003, Gennaro, Ed., Lippincott, Williams & Wilkins).

The terms "identical" or percent "identity," in the context of two or more nucleic acids or polypeptide sequences, refer to two or more sequences or subsequences that are the same or have a specified percentage of amino acid residues or nucleotides that are the same (i.e., about 60% identity, preferably 65%, 70%, 75%, 80%, 85%, 90%, 91%, 92%, 93%, 94%, 95%, 96%, 97%, 98%, 99%, or higher identity over a specified region, when compared and aligned for maximum correspondence over a comparison window or designated region) as measured using a BLAST or BLAST 2.0 sequence comparison algorithms with default parameters described below, or by manual alignment and visual inspection (see, e.g., NCBI web site http://www.ncbi.nlm.nih.gov/BLAST/ or the like). Such sequences are then said to be "substantially identical." This definition also refers to, or may be applied to, the compliment of a test sequence. The definition also includes sequences that have deletions and/or additions, as well as those that have substitutions. As described below, the preferred algorithms can account for gaps and the like. Preferably, identity exists over a region that is at least about 25 amino acids or nucleotides in length, or more preferably over a region that is 50-100 amino acids or nucleotides in length.

For sequence comparison, typically one sequence acts as a reference sequence, to which test sequences are compared. When using a sequence comparison algorithm, test and reference sequences are entered into a computer, subsequence coordinates are designated, if necessary, and sequence algorithm program parameters are designated. Preferably, default program parameters can be used, or alternative parameters can be designated. The sequence comparison algorithm then calculates the percent sequence identities for the test sequences relative to the reference sequence, based on the program parameters.

A "comparison window," as used herein, includes reference to a segment of any one of the number of contiguous positions selected from the group consisting of from 20 to 600, usually about 50 to about 200, more usually about 100 to about 150 in which a sequence may be compared to a reference sequence of the same number of contiguous positions after the two sequences are optimally aligned. Methods of alignment of sequences for comparison are well-known in the art. Optimal alignment of sequences for comparison can be conducted, e.g., by the local homology algorithm of Smith & Waterman, *Adv. Appl. Math.* 2:482 (1981), by the homology alignment algorithm of Needleman & Wunsch, *J. Mol. Biol.* 48:443 (1970), by the search for similarity method of Pearson & Lipman, *Proc. Nat'l. Acad. Sci. USA* 85:2444 (1988), by computerized implementations of these algorithms (GAP, BESTFIT, FASTA, and TFASTA in the Wisconsin Genetics Software Package, Genetics Computer Group, 575 Science Dr., Madison, Wis.), or by manual alignment and visual inspection (see, e.g., *Current Protocols in Molecular Biology* (Ausubel et al., eds. 1987-2005, Wiley Interscience)).

A preferred example of algorithm that is suitable for determining percent sequence identity and sequence similarity are the BLAST and BLAST 2.0 algorithms, which are described in Altschul et al., *Nuc. Acids Res.* 25:3389-3402 (1977) and Altschul et al., *J. Mol. Biol.* 215:403-410 (1990), respectively. BLAST and BLAST 2.0 are used, with the parameters described herein, to determine percent sequence identity for the nucleic acids and proteins of the invention. Software for performing BLAST analyses is publicly available through the National Center for Biotechnology Information (http://www.ncbi.nlm.nih.gov/). This algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold (Altschul et al, supra). These initial neighborhood word hits act as seeds for initiating searches to find longer HSPs containing them. The word hits are extended in both directions along each sequence for as far as the cumulative alignment score can be increased. Cumulative scores are calculated using, for nucleotide sequences, the parameters M (reward score for a pair of matching residues; always >0) and N (penalty score for mismatching residues; always <0). For amino acid sequences, a scoring matrix is used to calculate the cumulative score. Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T, and X determine the sensitivity and speed of the alignment. The BLASTN program (for nucleotide sequences) uses as defaults a wordlength (W) of 11, an expectation (E) of 10, M=5, N=−4 and a comparison of both strands. For amino acid sequences, the BLASTP program uses as defaults a wordlength of 3, and expectation (E) of 10, and the BLOSUM62 scoring matrix (see Henikoff & Henikoff, *Proc. Natl. Acad. Sci. USA* 89:10915 (1989)) alignments (B) of 50, expectation (E) of 10, M=5, N=−4, and a comparison of both strands.

"Nucleic acid" refers to deoxyribonucleotides or ribonucleotides and polymers thereof in either single- or double-stranded form, and complements thereof. The term encompasses nucleic acids containing known nucleotide analogs or modified backbone residues or linkages, which are synthetic, naturally occurring, and non-naturally occurring, which have similar binding properties as the reference nucleic acid, and which are metabolized in a manner similar to the reference nucleotides. Examples of such analogs include, without limitation, phosphorothioates, phosphoramidates, methyl phosphonates, chiral-methyl phosphonates, 2-O-methyl ribonucleotides, peptide-nucleic acids (PNAs).

"RNAi molecule" or an "siRNA" refers to a nucleic acid that forms a double stranded RNA, which double stranded RNA has the ability to reduce or inhibit expression of a gene or target gene when the siRNA expressed in the same cell as the gene or target gene. "siRNA" thus refers to the double stranded RNA formed by the complementary strands. The complementary portions of the siRNA that hybridize to form the double stranded molecule typically have substantial or complete identity. In one embodiment, an siRNA refers to a nucleic acid that has substantial or complete identity to a target gene and forms a double stranded siRNA. The sequence of the siRNA can correspond to the full length target gene, or a subsequence thereof. Typically, the siRNA is at least about 15-50 nucleotides in length (e.g., each complementary sequence of the double stranded siRNA is 15-50 nucleotides in length, and the double stranded siRNA is about 15-50 base pairs in length, preferable about preferably about 20-30 base nucleotides, preferably about 20-25 nucleotides in length, e.g., 20, 21, 22, 23, 24, 25, 26, 27, 28, 29, or 30 nucleotides in length.

An "antisense" polynucleotide is a polynucleotide that is substantially complementary to a target polynucleotide and has the ability to specifically hybridize to the target polynucleotide.

Ribozymes are enzymatic RNA molecules capable of catalyzing specific cleavage of RNA. The composition of ribozyme molecules preferably includes one or more sequences complementary to a target mRNA, and the well known catalytic sequence responsible for mRNA cleavage or a functionally equivalent sequence (see, e.g., U.S. Pat. No. 5,093,246, which is incorporated herein by reference in its entirety). Ribozyme molecules designed to catalytically cleave target mRNA transcripts can also be used to prevent translation of subject target mRNAs.

Unless otherwise indicated, a particular nucleic acid sequence also implicitly encompasses conservatively modified variants thereof (e.g., degenerate codon substitutions) and complementary sequences, as well as the sequence explicitly indicated. Specifically, degenerate codon substitutions may be achieved by generating sequences in which the third position of one or more selected (or all) codons is substituted with mixed-base and/or deoxyinosine residues (Batzer et al., *Nucleic Acid Res.* 19:5081 (1991); Ohtsuka et al., *J. Biol. Chem.* 260:2605-2608 (1985); Rossolini et al., *Mol. Cell. Probes* 8:91-98 (1994)). The term nucleic acid is used interchangeably with gene, cDNA, mRNA, oligonucleotide, and polynucleotide.

A particular nucleic acid sequence also implicitly encompasses "splice variants" and nucleic acid sequences encoding truncated forms of a protein. Similarly, a particular protein encoded by a nucleic acid implicitly encompasses any protein encoded by a splice variant or truncated form of that nucleic acid. "Splice variants," as the name suggests, are products of alternative splicing of a gene. After transcription, an initial nucleic acid transcript may be spliced such that different (alternate) nucleic acid splice products encode different polypeptides. Mechanisms for the production of splice variants vary, but include alternate splicing of exons. Alternate polypeptides derived from the same nucleic acid by read-through transcription are also encompassed by this definition. Any products of a splicing reaction, including recombinant forms of the splice products, are included in this definition. Nucleic acids can be truncated at the 5' end or at the 3' end. Polypeptides can be truncated at the N-terminal end or the C-terminal end. Truncated versions of nucleic acid or polypeptide sequences can be naturally occurring or recombinantly created.

The terms "polypeptide," "peptide" and "protein" are used interchangeably herein to refer to a polymer of amino acid residues. The terms apply to amino acid polymers in which one or more amino acid residue is an artificial chemical mimetic of a corresponding naturally occurring amino acid, as well as to naturally occurring amino acid polymers and non-naturally occurring amino acid polymer.

The term "amino acid" refers to naturally occurring and synthetic amino acids, as well as amino acid analogs and amino acid mimetics that function in a manner similar to the naturally occurring amino acids. Naturally occurring amino acids are those encoded by the genetic code, as well as those amino acids that are later modified, e.g., hydroxyproline, γ-carboxyglutamate, and O-phosphoserine. Amino acid analogs refers to compounds that have the same basic chemical structure as a naturally occurring amino acid, i.e., an a carbon that is bound to a hydrogen, a carboxyl group, an amino group, and an R group, e.g., homoserine, norleucine, methionine sulfoxide, methionine methyl sulfonium. Such analogs have modified R groups (e.g., norleucine) or modified peptide backbones, but retain the same basic chemical structure as a naturally occurring amino acid. Amino acid mimetics refers to chemical compounds that have a structure that is different from the general chemical structure of an amino acid, but that functions in a manner similar to a naturally occurring amino acid.

Amino acids may be referred to herein by either their commonly known three letter symbols or by the one-letter symbols recommended by the IUPAC-IUB Biochemical Nomenclature Commission. Nucleotides, likewise, may be referred to by their commonly accepted single-letter codes.

"Conservatively modified variants" applies to both amino acid and nucleic acid sequences. With respect to particular nucleic acid sequences, conservatively modified variants refers to those nucleic acids which encode identical or essentially identical amino acid sequences, or where the nucleic acid does not encode an amino acid sequence, to essentially identical sequences. Because of the degeneracy of the genetic code, a large number of functionally identical nucleic acids encode any given protein. For instance, the codons GCA, GCC, GCG and GCU all encode the amino acid alanine. Thus, at every position where an alanine is specified by a codon, the codon can be altered to any of the corresponding codons described without altering the encoded polypeptide. Such nucleic acid variations are "silent variations," which are one species of conservatively modified variations. Every nucleic acid sequence herein which encodes a polypeptide also describes every possible silent variation of the nucleic acid. One of skill will recognize that each codon in a nucleic acid (except AUG, which is ordinarily the only codon for methionine, and TGG, which is ordinarily the only codon for tryptophan) can be modified to yield a functionally identical molecule. Accordingly, each silent variation of a nucleic acid which encodes a polypeptide is implicit in each described sequence with respect to the expression product, but not with respect to actual probe sequences.

As to amino acid sequences, one of skill will recognize that individual substitutions, deletions or additions to a nucleic acid, peptide, polypeptide, or protein sequence which alters, adds or deletes a single amino acid or a small percentage of amino acids in the encoded sequence is a "conservatively modified variant" where the alteration results in the substitution of an amino acid with a chemically similar amino acid. Conservative substitution tables providing functionally similar amino acids are well known in the art. Such conservatively modified variants are in addition to and do not exclude polymorphic variants, interspecies homologs, and alleles of the invention.

The following eight groups each contain amino acids that are conservative substitutions for one another: 1) Alanine (A), Glycine (G); 2) Aspartic acid (D), Glutamic acid (E); 3) Asparagine (N), Glutamine (Q); 4) Arginine (R), Lysine (K); 5) Isoleucine (I), Leucine (L), Methionine (M), Valine (V); 6) Phenylalanine (F), Tyrosine (Y), Tryptophan (W); 7) Serine (S), Threonine (T); and 8) Cysteine (C), Methionine (M). See, e.g., Creighton, Proteins (1984).

A "label" or a "detectable moiety" is a composition detectable by spectroscopic, photochemical, biochemical, immunochemical, chemical, or other physical means. For example, useful labels include $^{32}P$, fluorescent dyes, electron-dense reagents, enzymes (e.g., as commonly used in an ELISA), biotin, digoxigenin, or haptens and proteins which can be made detectable, e.g., by incorporating a radiolabel into the peptide or used to detect antibodies specifically reactive with the peptide.

The term "recombinant" when used with reference, e.g., to a cell, or nucleic acid, protein, or vector, indicates that the cell, nucleic acid, protein or vector, has been modified by the introduction of a heterologous nucleic acid or protein or the alteration of a native nucleic acid or protein, or that the cell is derived from a cell so modified. Thus, for example, recombinant cells express genes that are not found within the native (non-recombinant) form of the cell or express native genes that are otherwise abnormally expressed, under expressed or not expressed at all.

The phrase "stringent hybridization conditions" refers to conditions under which a probe will hybridize to its target subsequence, typically in a complex mixture of nucleic acids, but to no other sequences. Stringent conditions are sequence-dependent and will be different in different circumstances. Longer sequences hybridize specifically at higher temperatures. An extensive guide to the hybridization of nucleic acids is found in Tijssen, *Techniques in Biochemistry and Molecular Biology—Hybridization with Nucleic Probes*, "Overview of principles of hybridization and the strategy of nucleic acid assays" (1993). Generally, stringent conditions are selected to be about 5-10° C. lower than the thermal melting point ($T_m$) for the specific sequence at a defined ionic strength pH. The $T_m$ is the temperature (under defined ionic strength, pH, and nucleic concentration) at which 50% of the probes complementary to the target hybridize to the target sequence at equilibrium (as the target sequences are present in excess, at $T_m$, 50% of the probes are occupied at equilibrium). Stringent conditions may also be achieved with the addition of destabilizing agents such as formamide. For selective or specific hybridization, a positive signal is at least two times background, preferably 10 times background hybridization. Exemplary stringent hybridization conditions can be as following: 50% formamide, 5×SSC, and 1% SDS, incubating at 42° C., or, 5×SSC, 1% SDS, incubating at 65° C., with wash in 0.2×SSC, and 0.1% SDS at 65° C.

Nucleic acids that do not hybridize to each other under stringent conditions are still substantially identical if the polypeptides which they encode are substantially identical. This occurs, for example, when a copy of a nucleic acid is created using the maximum codon degeneracy permitted by the genetic code. In such cases, the nucleic acids typically hybridize under moderately stringent hybridization conditions. Exemplary "moderately stringent hybridization conditions" include a hybridization in a buffer of 40% formamide, 1 M NaCl, 1% SDS at 37° C., and a wash in 1×SSC at 45° C. A positive hybridization is at least twice background. Those of ordinary skill will readily recognize that alternative hybridization and wash conditions can be utilized to provide conditions of similar stringency. Additional guidelines for determining hybridization parameters are provided in numerous reference, e.g., and *Current Protocols in Molecular Biology*, ed. Ausubel, et al., supra.

For PCR, a temperature of about 36° C. is typical for low stringency amplification, although annealing temperatures may vary between about 32° C. and 48° C. depending on primer length. For high stringency PCR amplification, a temperature of about 62° C. is typical, although high stringency annealing temperatures can range from about 50° C. to about 65° C., depending on the primer length and specificity. Typical cycle conditions for both high and low stringency amplifications include a denaturation phase of 90° C.-95° C. for 30 sec-2 min., an annealing phase lasting 30 sec.-2 min., and an extension phase of about 72° C. for 1-2 min. Protocols and guidelines for low and high stringency amplification reactions are provided, e.g., in Innis et al. (1990) *PCR Protocols, A Guide to Methods and Applications*, Academic Press, Inc. N.Y.).

"Antibody" refers to a polypeptide comprising a framework region from an immunoglobulin gene or fragments thereof that specifically binds and recognizes an antigen. The recognized immunoglobulin genes include the kappa, lambda, alpha, gamma, delta, epsilon, and mu constant region genes, as well as the myriad immunoglobulin variable region genes. Light chains are classified as either kappa or lambda. Heavy chains are classified as gamma, mu, alpha, delta, or epsilon, which in turn define the immunoglobulin classes, IgG, IgM, IgA, IgD and IgE, respectively. Typically, the antigen-binding region of an antibody will be most critical in specificity and affinity of binding. Antibodies can be polyclonal or monoclonal, derived from serum, a hybridoma or recombinantly cloned, and can also be chimeric, primatized, or humanized.

An exemplary immunoglobulin (antibody) structural unit comprises a tetramer. Each tetramer is composed of two identical pairs of polypeptide chains, each pair having one "light" (about 25 kDa) and one "heavy" chain (about 50-70 kDa). The N-terminus of each chain defines a variable region of about 100 to 110 or more amino acids primarily responsible for antigen recognition. The terms variable light chain ($V_L$) and variable heavy chain ($V_H$) refer to these light and heavy chains respectively.

Antibodies exist, e.g., as intact immunoglobulins or as a number of well-characterized fragments produced by digestion with various peptidases. Thus, for example, pepsin digests an antibody below the disulfide linkages in the hinge region to produce $F(ab)'_2$, a dimer of Fab which itself is a light chain joined to $V_H$-$C_H1$ by a disulfide bond. The $F(ab)'_2$ may be reduced under mild conditions to break the disulfide linkage in the hinge region, thereby converting the $F(ab)'_2$ dimer into an Fab' monomer. The Fab' monomer is essentially Fab with part of the hinge region (see *Fundamental Immunology* (Paul ed., 3d ed. 1993). While various antibody fragments are defined in terms of the digestion of an intact antibody, one of skill will appreciate that such fragments may be synthesized de novo either chemically or by using recombinant DNA methodology. Thus, the term antibody, as used herein, also includes antibody fragments either produced by the modification of whole antibodies, or those synthesized de novo using recombinant DNA methodologies (e.g., single chain Fv) or those identified using phage display libraries (see, e.g., McCafferty et al., *Nature* 348:552-554 (1990)).

An antibody immunologically reactive with a particular biomarker protein of the present invention can be generated by recombinant methods such as selection of libraries of recombinant antibodies in phage or similar vectors, see, e.g., Huse et al., *Science,* 246:1275-1281 (1989); Ward et al., *Nature,* 341:544-546 (1989); and Vaughan et al., *Nature Biotech.,* 14:309-314 (1996), or by immunizing an animal with the antigen or with DNA encoding the antigen.

Methods of preparing polyclonal antibodies are known to the skilled artisan (e.g., Harlow & Lane, 1988, Antibodies: A Laboratory Manual. (Cold Spring Harbor Press)). Polyclonal antibodies can be raised in a mammal, e.g., by one or more injections of an immunizing agent and, if desired, an adjuvant. Typically, the immunizing agent and/or adjuvant will be injected in the mammal by multiple subcutaneous or intraperitoneal injections. The immunizing agent may include a protein encoded by a nucleic acid of the figures or fragment thereof or a fusion protein thereof. It may be useful to conjugate the immunizing agent to a protein known to be immunogenic in the mammal being immunized. Examples of such immunogenic proteins include but are not limited to keyhole limpet hemocyanin, serum albumin, bovine thyroglobulin, and soybean trypsin inhibitor. Examples of adjuvants which may be employed include Freund's complete adjuvant and MPL-TDM adjuvant (monophosphoryl Lipid A, synthetic trehalose dicorynomycolate). The immunization protocol may be selected by one skilled in the art without undue experimentation.

The antibodies can, alternatively, be monoclonal antibodies. Monoclonal antibodies may be prepared using hybridoma methods, such as those described by Kohler & Milstein, *Nature,* 256:495 (1975). In a hybridoma method, a mouse, hamster, or other appropriate host animal, is typically immunized with an immunizing agent to elicit lymphocytes that produce or are capable of producing antibodies that will specifically bind to the immunizing agent. Alternatively, the lymphocytes may be immunized in vitro. Generally, either peripheral blood lymphocytes ("PBLs") are used if cells of human origin are desired, or spleen cells or lymph node cells are used if nonhuman mammalian sources are desired. The lymphocytes are then fused with an immortalized cell line using a suitable fusing agent, such as polyethylene glycol, to form a hybridoma cell (Goding, *Monoclonal Antibodies: Principles and Practice*, pp. 59-103 (1986)). Immortalized cell lines are usually transformed mammalian cells, particularly myeloma cells of rodent, bovine and human origin. Usually, rat or mouse myeloma cell lines are employed. The hybridoma cells may be cultured in a suitable culture medium that preferably contains one or more substances that inhibit the growth or survival of the unfused, immortalized cells. For example, if the parental cells lack the enzyme hypoxanthine guanine phosphoribosyl transferase (HGPRT or HPRT), the culture medium for the hybridomas typically will include hypoxanthine, aminopterin, and thymidine ("HAT medium"), which substances prevent the growth of HGPRT-deficient cells.

Human antibodies can be produced using various techniques known in the art, including phage display libraries (Hoogenboom & Winter, *J. Mol. Biol.,* 227:381 (1991); Marks et al., *J. Mol. Biol.,* 222:581 (1991)). The techniques of Cole et al. and Boerner et al. are also available for the preparation of human monoclonal antibodies (Cole et al., *Monoclonal Antibodies and Cancer Therapy*, p. 77 (1985) and Boerner et al., *J. Immunol.,* 147(1):86-95 (1991)). Similarly, human antibodies can be made by introducing of human immunoglobulin loci into transgenic animals, e.g., mice in which the endogenous immunoglobulin genes have been partially or completely inactivated. Upon challenge, human antibody production is observed, which closely resembles that seen in humans in all respects, including gene rearrangement, assembly, and antibody repertoire. This approach is described, e.g., in U.S. Pat. Nos. 5,545,807; 5,545,806; 5,569,825; 5,625,126; 5,633,425; 5,661,016, and in the following scientific publications: Marks et al., *BioTechnology,* 10:779-783 (1992); Lonberg et al., *Nature,* 368:856-859 (1994); Morrison, Nature, 368:812-13 (1994); Fishwild et al., *Nature Biotechnology,* 14:845-51 (1996); Neuberger, *Nature Biotechnology,* 14:826 (1996); Lonberg & Huszar, *Inter. Rev. Immunol.,* 13:65-93 (1995).

In one embodiment, the antibody is conjugated to an "effector" moiety. The effector moiety can be any number of molecules, including labeling moieties such as radioactive labels or fluorescent labels, or can be a therapeutic moiety. In one aspect the antibody modulates the activity of the protein.

The nucleic acids of the differentially expressed genes of this invention or their encoded polypeptides refer to all forms of nucleic acids (e.g., gene, pre-mRNA, mRNA) or proteins, their polymorphic variants, alleles, mutants, and interspecies homologs that (as applicable to nucleic acid or protein): (1) have an amino acid sequence that has greater than about 60% amino acid sequence identity, 65%, 70%, 75%, 80%, 85%, 90%, preferably 91%, 92%, 93%, 94%, 95%, 96%, 97%, 98% or 99% or greater amino acid sequence identity, preferably over a region of at least about 25, 50, 100, 200, 500, 1000, or more amino acids, to a polypeptide encoded by a referenced nucleic acid or an amino acid sequence described herein; (2) specifically bind to antibodies, e.g., polyclonal antibodies, raised against an immunogen comprising a referenced amino acid sequence, immunogenic fragments thereof, and conservatively modified variants thereof; (3) specifically hybridize under stringent hybridization conditions to a nucleic acid encoding a referenced amino acid sequence, and conservatively modified variants thereof; (4) have a nucleic acid sequence that has greater than about 95%, preferably greater than about 96%, 97%, 98%, 99%, or higher nucleotide sequence identity, preferably over a region of at least about 25, 50, 100, 200, 500, 1000, or more nucleotides, to a reference nucleic acid sequence. A polynucleotide or polypeptide sequence is typically from a mammal including, but not limited to, primate, e.g., human; rodent, e.g., rat, mouse, hamster; cow, pig, horse, sheep, or any mammal. The nucleic acids and proteins of the invention include both naturally occurring or recombinant molecules. Truncated and alternatively spliced forms of these antigens are included in the definition.

The phrase "specifically (or selectively) binds" when referring to a protein, nucleic acid, antibody, or small molecule compound refers to a binding reaction that is determinative of the presence of the protein or nucleic acid, such as the differentially expressed genes of the present invention, often in a heterogeneous population of proteins or nucleic acids and other biologics. In the case of antibodies, under designated immunoassay conditions, a specified antibody may bind to a particular protein at least two times the background and more typically more than 10 to 100 times background. Specific binding to an antibody under such conditions requires an antibody that is selected for its specificity for a particular protein. For example, polyclonal antibodies can be selected to obtain only those polyclonal antibodies that are specifically immunoreactive with the selected antigen and not with other proteins. This selection may be achieved by subtracting out antibodies that cross-react with other molecules. A variety of immunoassay formats may be used to select antibodies specifically immunoreactive with a particular protein. For example, solid-phase ELISA immunoassays are routinely used to select antibodies specifically immunoreactive with a protein (see, e.g., Harlow & Lane, *Antibodies, A Laboratory Manual* (1988) for a description of immunoassay formats and conditions that can be used to determine specific immunoreactivity).

The phrase "functional effects" in the context of assays for testing compounds that modulate a marker protein includes the determination of a parameter that is indirectly or directly under the influence of a biomarker of the invention, e.g., a chemical or phenotypic effect such as altered chemokine cell signaling. A functional effect therefore includes ligand binding activity, transcriptional activation or repression, the ability of cells to proliferate, the ability to migrate, among others. "Functional effects" include in vitro, in vivo, and ex vivo activities.

By "determining the functional effect" is meant assaying for a compound that increases or decreases a parameter that is indirectly or directly under the influence of a biomarker of the invention, e.g., measuring physical and chemical or phenotypic effects. Such functional effects can be measured by any means known to those skilled in the art, e.g., changes in spectroscopic characteristics (e.g., fluorescence, absorbance, refractive index); hydrodynamic (e.g., shape), chromatographic; or solubility properties for the protein; ligand binding assays, e.g., binding to antibodies; measuring inducible markers or transcriptional activation of the marker; measuring changes in enzymatic activity; the ability to increase or decrease cellular proliferation, apoptosis, cell cycle arrest, measuring changes in cell surface markers. The functional effects can be evaluated by many means known to those skilled in the art, e.g., microscopy for quantitative or qualitative measures of alterations in morphological features, measurement of changes in RNA or protein levels for other genes expressed in chemokine-responsive cells, measurement of RNA stability, identification of downstream or reporter gene expression (CAT, luciferase, β-gal, GFP and the like), e.g., via chemiluminescence, fluorescence, colorimetric reactions, antibody binding, inducible markers, etc.

"Inhibitors," "activators," and "modulators" of the markers are used to refer to activating, inhibitory, or modulating molecules identified using in vitro and in vivo assays of biomarkers responsive to IVIG treatment of relapsing-remitting multiple sclerosis (RRMS). Inhibitors are compounds that, e.g., bind to, partially or totally block activity, decrease, prevent, delay activation, inactivate, desensitize, or down regulate the activity or expression of biomarkers responsive to IVIG treatment of relapsing-remitting multiple sclerosis (RRMS). "Activators" are compounds that increase, open, activate, facilitate, enhance activation, sensitize, agonize, or up regulate activity of biomarkers responsive to IVIG treatment of relapsing-remitting multiple sclerosis (RRMS), e.g., agonists. Inhibitors, activators, or modulators also include genetically modified versions of biomarkers responsive to IVIG treatment of relapsing-remitting multiple sclerosis (RRMS), e.g., versions with altered activity, as well as naturally occurring and synthetic ligands, antagonists, agonists, antibodies, peptides, cyclic peptides, nucleic acids, antisense molecules, ribozymes, RNAi molecules, small organic molecules and the like. Such assays for inhibitors and activators include, e.g., expressing biomarkers responsive to IVIG treatment of relapsing-remitting multiple sclerosis (RRMS) in vitro, in cells, or cell extracts, applying putative modulator compounds, and then determining the functional effects on activity, as described above.

Samples or assays comprising biomarkers responsive to IVIG treatment of relapsing-remitting multiple sclerosis (RRMS) that are treated with a potential activator, inhibitor, or modulator are compared to control samples without the inhibitor, activator, or modulator to examine the extent of inhibition. Control samples (untreated with inhibitors) are assigned a relative protein activity value of 100%. Inhibition of biomarkers responsive to IVIG treatment of relapsing-remitting multiple sclerosis (RRMS) is achieved when the activity value relative to the control is about 80%, preferably 50%, more preferably 25-0%. Activation of biomarkers responsive to IVIG treatment of relapsing-remitting multiple sclerosis (RRMS) is achieved when the activity value relative to the control (untreated with activators) is 110%, more preferably 150%, more preferably 200-500% (i.e., two to five fold higher relative to the control), more preferably 1000-3000% higher.

The term "test compound" or "drug candidate" or "modulator" or grammatical equivalents as used herein describes any molecule, either naturally occurring or synthetic, e.g., protein, oligopeptide (e.g., from about 5 to about 25 amino acids in length, preferably from about 10 to 20 or 12 to 18 amino acids in length, preferably 12, 15, or 18 amino acids in length), small organic molecule, polysaccharide, peptide, circular peptide, lipid, fatty acid, siRNA, polynucleotide, oligonucleotide, etc., to be tested for the capacity to directly or indirectly modulate biomarkers responsive to IVIG treatment of relapsing-remitting multiple sclerosis (RRMS). The test compound can be in the form of a library of test compounds, such as a combinatorial or randomized library that provides a sufficient range of diversity. Test compounds are optionally linked to a fusion partner, e.g., targeting compounds, rescue compounds, dimerization compounds, stabilizing compounds, addressable compounds, and other functional moieties. Conventionally, new chemical entities with useful properties are generated by identifying a test compound (called a "lead compound") with some desirable property or activity, e.g., inhibiting activity, creating variants of the lead compound, and evaluating the property and activity of those variant compounds. Often, high throughput screening (HTS) methods are employed for such an analysis.

A "small organic molecule" refers to an organic molecule, either naturally occurring or synthetic, that has a molecular weight of more than about 50 daltons and less than about 2500 daltons, preferably less than about 2000 daltons, preferably between about 100 to about 1000 daltons, more preferably between about 200 to about 500 daltons.

Prognostic Methods

The present invention provides methods of providing a prognosis of IVIG treatment of multiple sclerosis, including relapsing-remitting multiple sclerosis (RRMS), Alzheimer's disease, or Parkinson's disease by detecting the expression of markers overexpressed or underexpressed in patients treated with IVIG. Providing a prognosis involves determining the level of one or more IVIG responsive biomarker polynucleotides or the corresponding polypeptides in a patient or patient sample and then comparing the level to a baseline or range. Typically, the baseline value is representative of levels of the polynucleotide or nucleic acid in a relapsing-remitting multiple sclerosis (RRMS) patient prior to IVIG treatment, as measured using a biological sample such as a sample of a bodily fluid (e.g., blood or cerebrospinal fluid). Variation of levels of a polynucleotide or corresponding polypeptides of the invention from the baseline range (either up or down) indicates that the patient is benefiting from IVIG treatment of relapsing-remitting multiple sclerosis (RRMS).

As used herein, the term "providing a prognosis" refers to providing a prediction of the probable course and outcome of treatment of a patient suffering from multiple sclerosis, including relapsing-remitting multiple sclerosis (RRMS), Alzheimer's disease, or Parkinson's disease with IVIG. The methods can also be used to devise a suitable alternative or additional therapy for multiple sclerosis, including relapsing-remitting multiple sclerosis (RRMS) treatment, Alzheimer's disease, or Parkinson's disease, e.g., by indicating the failure of IVIG treatment to alleviate multiple sclerosis, including relapsing-remitting multiple sclerosis (RRMS), Alzheimer's disease, or Parkinson's disease. The prognosis can be used to adjust dose or frequency of IVIG administration as well.

Antibody reagents can be used in assays to detect expression levels of the biomarkers of the invention in patient samples using any of a number of immunoassays known to those skilled in the art. Immunoassay techniques and protocols are generally described in Price and Newman, "Principles and Practice of Immunoassay," 2nd Edition, Grove's Dictionaries, 1997; and Gosling, "Immunoassays: A Practical Approach," Oxford University Press, 2000. A variety of immunoassay techniques, including competitive and non-competitive immunoassays, can be used. See, e.g., Self et al., *Curr. Opin. Biotechnol.,* 7:60-65 (1996). The term immunoassay encompasses techniques including, without limitation, enzyme immunoassays (EIA) such as enzyme multiplied immunoassay technique (EMIT), enzyme-linked immunosorbent assay (ELISA), IgM antibody capture ELISA (MAC ELISA), and microparticle enzyme immunoassay (MEIA); capillary electrophoresis immunoassays (CEIA); radioimmunoassays (RIA); immunoradiometric assays (IRMA); fluorescence polarization immunoassays (FPIA); and chemiluminescence assays (CL). If desired, such immunoassays can be automated. Immunoassays can also be used in conjunction with laser induced fluorescence. See, e.g., Schmalzing et al., *Electrophoresis,* 18:2184-93 (1997); Bao, *J. Chromatogr. B. Biomed. Sci.,* 699:463-80 (1997). Liposome immunoassays, such as flow-injection liposome immunoassays and liposome immunosensors, are also suitable for use in the present invention. See, e.g., Rongen et al., *J. Immunol. Methods,* 204:105-133 (1997). In addition, nephelometry assays, in which the formation of protein/antibody complexes results in increased light scatter that is converted to a peak rate signal as a function of the marker concentration, are suitable for use in the methods of the present invention. Nephelometry assays are commercially available from Beckman Coulter (Brea, Calif.; Kit #449-430) and can be performed using a Behring Nephelometer Analyzer (Fink et al., *J. Clin. Chem. Clin. Biochem.,* 27:261-276 (1989)).

Specific immunological binding of antibodies can be detected directly or indirectly. Direct labels include fluorescent or luminescent tags, metals, dyes, radionuclides, and the like, attached to the antibody. An antibody labeled with iodine-125 ($^{125}I$) can be used. A chemiluminescence assay using a chemiluminescent antibody specific for the nucleic acid is suitable for sensitive, non-radioactive detection of protein levels. An antibody labeled with fluorochrome is also suitable. Examples of fluorochromes include, without limitation, DAPI, fluorescein, Hoechst 33258, R-phycocyanin, B-phycoerythrin, R-phycoerythrin, rhodamine, Texas red, and lissamine. Indirect labels include various enzymes well known in the art, such as horseradish peroxidase (HRP), alkaline phosphatase (AP), β-galactosidase, urease, and the like. A horseradish-peroxidase detection system can be used, for example, with the chromogenic substrate tetramethylbenzidine (TMB), which yields a soluble product in the presence of hydrogen peroxide that is detectable at 450 nm. An alkaline phosphatase detection system can be used with the chromogenic substrate p-nitrophenyl phosphate, for example, which yields a soluble product readily detectable at 405 nm. Similarly, a β-galactosidase detection system can be used with the chromogenic substrate o-nitrophenyl-β-D-galactopyranoside (ONPG), which yields a soluble product detectable at 410 nm. An urease detection system can be used with a substrate such as urea-bromocresol purple (Sigma Immunochemicals; St. Louis, Mo.).

A signal from the direct or indirect label can be analyzed, for example, using a spectrophotometer to detect color from a chromogenic substrate; a radiation counter to detect radiation such as a gamma counter for detection of $^{125}I$; or a fluorometer to detect fluorescence in the presence of light of a certain wavelength. For detection of enzyme-linked antibodies, a quantitative analysis can be made using a spectrophotometer such as an EMAX Microplate Reader (Molecular Devices; Menlo Park, Calif.) in accordance with the manufacturer's instructions. If desired, the assays of the present invention can be automated or performed robotically, and the signal from multiple samples can be detected simultaneously.

The antibodies can be immobilized onto a variety of solid supports, such as magnetic or chromatographic matrix particles, the surface of an assay plate (e.g., microtiter wells), pieces of a solid substrate material or membrane (e.g., plastic, nylon, paper), and the like. An assay strip can be prepared by coating the antibody or a plurality of antibodies in an array on a solid support. This strip can then be dipped into the test sample and processed quickly through washes and detection steps to generate a measurable signal, such as a colored spot.

Alternatively, nucleic acid binding molecules such as probes, oligonucleotides, oligonucleotide arrays, and primers can be used in assays to detect differential RNA expression in patient samples, e.g., RT-PCR. In one embodiment, RT-PCR is used according to standard methods known in the art. In another embodiment, PCR assays such as Taqman® assays available from, e.g., Applied Biosystems, can be used to detect nucleic acids and variants thereof. In other embodiments, qPCR and nucleic acid microarrays can be used to detect nucleic acids. Reagents that bind to selected biomarkers can be prepared according to methods known to those of skill in the art or purchased commercially.

Analysis of nucleic acids can be achieved using routine techniques such as Southern analysis, reverse-transcriptase polymerase chain reaction (RT-PCR), or any other methods based on hybridization to a nucleic acid sequence that is complementary to a portion of the marker coding sequence (e.g., slot blot hybridization) are also within the scope of the present invention. Applicable PCR amplification techniques are described in, e.g., Ausubel et al. and Innis et al., supra. General nucleic acid hybridization methods are described in Anderson, "Nucleic Acid Hybridization," BIOS Scientific Publishers, 1999. Amplification or hybridization of a plurality of nucleic acid sequences (e.g., genomic DNA, mRNA or cDNA) can also be performed from mRNA or cDNA sequences arranged in a microarray. Microarray methods are generally described in Hardiman, "Microarrays Methods and Applications: Nuts & Bolts," DNA Press, 2003; and Baldi et al., "DNA Microarrays and Gene Expression From Experiments to Data Analysis and Modeling," Cambridge University Press, 2002.

Analysis of nucleic acid markers and their variants can be performed using techniques known in the art including, without limitation, microarrays, polymerase chain reaction (PCR)-based analysis, sequence analysis, and electrophoretic analysis. A non-limiting example of a PCR-based analysis includes a Taqman® allelic discrimination assay available from Applied Biosystems. Non-limiting examples of sequence analysis include Maxam-Gilbert sequencing, Sanger sequencing, capillary array DNA sequencing, thermal cycle sequencing (Sears et al., *Biotechniques,* 13:626-633 (1992)), solid-phase sequencing (Zimmerman et al., *Methods Mol. Cell. Biol.,* 3:39-42 (1992)), sequencing with mass spectrometry such as matrix-assisted laser desorption/ionization time-of-flight mass spectrometry (MALDI-TOF/MS; Fu et al., *Nat. Biotechnol.,* 16:381-384 (1998)), and sequencing by hybridization. Chee et al., *Science,* 274:610-614 (1996); Drmanac et al., *Science,* 260:1649-1652 (1993); Drmanac et al., *Nat. Biotechnol.,* 16:54-58 (1998). Non-limiting examples of electrophoretic analysis include slab gel electrophoresis such as agarose or polyacrylamide gel electrophoresis, capillary electrophoresis, and denaturing gradient gel electrophoresis. Other methods for detecting nucleic acid variants include, e.g., the INVADER® assay from Third Wave Technologies, Inc., restriction fragment length polymorphism (RFLP) analysis, allele-specific oligonucleotide hybridization, a heteroduplex mobility assay, single strand conformational polymorphism (SSCP) analysis, single-nucleotide primer extension (SNUPE) and pyrosequencing.

A detectable moiety can be used in the assays described herein. A wide variety of detectable moieties can be used, with the choice of label depending on the sensitivity required, ease of conjugation with the antibody, stability requirements, and available instrumentation and disposal provisions. Suitable detectable moieties include, but are not limited to, radionuclides, fluorescent dyes (e.g., fluorescein, fluorescein isothiocyanate (FITC), Oregon Green™, rhodamine, Texas red, tetrarhodimine isothiocynate (TRITC), Cy3, Cy5, etc.), fluorescent markers (e.g., green fluorescent protein (GFP), phycoerythrin, etc.), autoquenched fluorescent compounds that are activated by tumor-associated proteases, enzymes (e.g., luciferase, horseradish peroxidase, alkaline phosphatase, etc.), nanoparticles, biotin, digoxigenin, and the like.

Useful physical formats comprise surfaces having a plurality of discrete, addressable locations for the detection of a plurality of different markers. Such formats include microarrays and certain capillary devices. See, e.g., Ng et al., *J. Cell Mol. Med.,* 6:329-340 (2002); U.S. Pat. No. 6,019,944. In these embodiments, each discrete surface location may comprise antibodies to immobilize one or more markers for detection at each location. Surfaces may alternatively comprise one or more discrete particles (e.g., microparticles or nanoparticles) immobilized at discrete locations of a surface, where the microparticles comprise antibodies to immobilize one or more markers for detection.

Analysis can be carried out in a variety of physical formats. For example, the use of microtiter plates or automation could be used to facilitate the processing of large numbers of test samples. Alternatively, single sample formats could be developed to facilitate a prognosis in a timely fashion.

Alternatively, the antibodies or nucleic acid probes of the invention can be applied to sections of patient biopsies immobilized on microscope slides. The resulting antibody staining or in situ hybridization pattern can be visualized using any one of a variety of light or fluorescent microscopic methods known in the art.

In another format, the various markers of the invention also provide reagents for in vivo imaging such as, for instance, the imaging of labeled regents that detect the nucleic acids or encoded proteins of the biomarkers of the invention. For in vivo imaging purposes, reagents that detect the presence of proteins encoded by IVIG-responsive relapsing-remitting multiple sclerosis (RRMS) biomarkers, such as antibodies, may be labeled using an appropriate marker, such as a fluorescent marker.

Preparations and Administration of IVIG

IVIG compositions comprising whole antibodies have been described for the treatment of certain autoimmune conditions. (See, e.g., U.S. Patent Publication US 2002/0114802, US 2003/0099635, and US 2002/0098182.) The IVIG compositions disclosed in these references include polyclonal antibodies.

Immunoglobulin preparations according to the present invention can be prepared from any suitable starting materials. For example, immunoglobulin preparations can be prepared from donor serum or monoclonal or recombinant immunoglobulins. In a typical example, blood is collected from healthy donors. Usually, the blood is collected from the same species of animal as the subject to which the immunoglobulin preparation will be administered (typically referred to as "homologous" immunoglobulins). The immunoglobulins are isolated from the blood by suitable procedures, such as, for example, Cohn fractionation, ultracentrifugation, electrophoretic preparation, ion exchange chromatography, affinity chromatography, immunoaffinity chromatography, polyethylene glycol fractionation, or the like. (See, e.g., Cohn et al., *J. Am. Chem. Soc.* 68:459-75 (1946); Oncley et al., *J. Am. Chem. Soc.* 71:541-50 (1949); Barundern et al., *Vox Sang.* 7:157-74 (1962); Koblet et al., *Vox Sang.* 13:93-102 (1967); U.S. Pat. Nos. 5,122,373 and 5,177,194; the disclosures of which are incorporated by reference herein.)

In certain embodiments, immunoglobulin is prepared from gamma globulin-containing products produced by the alcohol fractionation and/or ion exchange and affinity chromatography methods well known to those skilled in the art. Purified Cohn Fraction II is commonly used. The starting Cohn Fraction II paste is typically about 95 percent IgG and is comprised of the four IgG subtypes. The different subtypes are present in Fraction II in approximately the same ratio as they are found in the pooled human plasma from which they are obtained. The Fraction II is further purified before formulation into an administrable product. For example, the Fraction II paste can be dissolved in a cold purified aqueous alcohol solution and impurities removed via precipitation and filtration. Following the final filtration, the immunoglobulin suspension can be dialyzed or diafiltered (e.g., using ultrafiltration membranes having a nominal molecular weight limit of less than or equal to 100,000 daltons) to remove the alcohol. The solution can be concentrated or diluted to obtain the desired protein concentration and can be further purified by techniques well known to those skilled in the art.

Preparative steps can be used to enrich a particular isotype or subtype of immunoglobulin. For example, protein A, protein G or protein H sepharose chromatography can be used to enrich a mixture of immunoglobulins for IgG, or for specific IgG subtypes. (See generally Harlow and Lane, *Using Antibodies*, Cold Spring Harbor Laboratory Press (1999); Harlow and Lane, *Antibodies, A Laboratory Manual*, Cold Spring Harbor Laboratory Press (1988); U.S. Pat. No. 5,180,810.)

Commercial sources of immunoglobulins can also be used. Such sources include but are not limited to: Gammagard S/D® (Baxter Healthcare); BayRho-D® products (Bayer Biological); Gamimune N®, 5% (Bayer Biological); Gamimune N®, 5% Solvent/Detergent Treated (Bayer Biological); Gamimune N®, 10% (Bayer Biological); Sandoglobulin I.V.® (Novartis); Polygam S/D® (American Red Cross); Venoglobulin-S® 5% Solution Solvent Detergent Treated (Alpha Therapeutic); Venoglobulin-S® 10% Solution Solvent Detergent/Treated (Alpha Therapeutic); and VZIG® (American Red Cross). The commercial source of immunoglobulin preparation for use in the methods of the present invention is not critical.

An alternative approach is to use fragments of antibodies, such as Fc fragments of immunoglobulins. An Fc preparation comprises Fc fragments of immunoglobulins. The term "Fc fragment" refers to a portion of an immunoglobulin heavy chain constant region containing at least one heavy chain constant region domain (e.g., $C_H2$, $C_H3$ and/or $C_H4$) or an antigenic portion thereof, but excluding the variable regions of the immunoglobulin. (As used herein, a variable region refers to region of the immunoglobulin that binds to an antigen, but excludes the $C_H1$ and $C_L$ domains.) The Fc preparation can contain entire Fc fragments and/or portions thereof (e.g., one or more heavy chain constant region domains or portions thereof containing an epitope(s) bound by the rheumatoid factors). An Fc fragment optionally can include an immunoglobulin hinge region, a heavy chain $C_H1$ domain, and/or a heavy chain $C_H1$ domain joined to a light chain $C_L$ domain.

An Fc preparation includes Fc fragments of at least one Fc isotype and can contain a mixture of immunoglobulin Fc fragments of different isotypes (e.g., IgA, IgD, IgE, IgG and/or IgM). The Fc preparation also can contain predominantly (at least 60%, at least 75%, at least 90%, at least 95%, or at least 99%) Fc fragments from one immunoglobulin isotype, and can contain minor amounts of the other subtypes. For example, an Fc preparation can contain at least at least about 75%, at least about 90%, at least about 95%, or at least about 99% IgG Fc fragments. In addition, the Fc preparation can comprise a single IgG subtype or a mixture two or more of IgG Fc subtypes. Suitable IgG subtypes include IgG1, IgG2, IgG3, and IgG4. In a specific embodiment, the Fc preparation comprises IgG1 Fc fragments.

An Fc preparation is substantially free of $F(ab')_2$ fragments (i.e., heavy and light chain variable and first constant regions and a portion of the hinge region, which can be produced by pepsin digestion of the antibody molecule), Fab' fragments (i.e., Fab' fragments which can be generated by reducing the disulfide bridges of the $F(ab')_2$ fragment), or Fab fragments (i.e., which can be generated by treating the antibody molecule with papain and a reducing agent). In this context, "substantially free" means the Fc preparation contains less than about 30%, less than about 20%, less than about 10%, less than about 5%, or less than about 1% $F(ab')_2$, Fab' or Fab fragments. In another embodiment, the Fc preparation contains Fc fragments which are essentially free of $F(ab')_2$, Fab' or Fab fragments. The Fc preparations are typically substantially free of whole (i.e., full length) immunoglobulins. In this context, "substantially free" means less than about 25%, or less than about 10%, or less than about 5%, or less than about 2%, less than about 1% or are free of full length immunoglobulins.

Immunoglobulins can be cleaved at any suitable time during preparation to separate the Fc fragments from the Fab, F(ab') and/or $F(ab')_2$ fragments, as applicable. A suitable enzyme for cleavage is, for example, papain, pepsin or plasmin. (See, e.g., Harlow and Lane, *Using Antibodies*, Cold Spring Harbor Laboratory Press (1999); Plan and Makula, *Vox Sanguinis* 28:157-75 (1975).) After cleavage, the Fc portions can be separated from the Fab F(ab') and/or $F(ab')_2$ fragments by, for example, affinity chromatography, ion exchange chromatography, gel filtration, or the like. In a specific example, immunoglobulins are digested with papain to separate the Fc fragment from the Fab fragments. The digestion mixture is then subjected to cationic exchange chromatography to separate the Fc fragments from the Fab fragments.

Immunoglobulin or Fc fragments can also be prepared from hybridomas or other culture system which express monoclonal antibody. (See, e.g., Kohler and Milstein, *Nature* 256:495-97 (1975); Hagiwara and Yuasa, Hum. *Antibodies Hybridomas* 4:15-19 (1993); Kozbor et al., *Immunology Today* 4:72 (1983); Cole et al., in *Monoclonal Antibodies and Cancer Therapy*, Alan R. Liss, Inc., pp. 77-96 (1985).) Human monoclonal antibodies can be obtained, for example, from human hybridomas (see, e.g., Cote et al., *Proc. Natl. Acad. Sci. USA* 80:2026-30 (1983)) or by transforming human B cells with EBV virus in vitro (see, e.g., Cole et al., supra). Monoclonal antibodies produced from hybridomas can be purified and the Fc fragments separated from the Fab, F(ab') and/or $F(ab')_2$ fragments as described herein or as known to the skilled artisan.

Immunoglobulin or Fc fragments also can be produced recombinantly, such as from eukaryotic cell culture systems. For example, an Fc fragment of an immunoglobulin can be recombinantly produced by Chinese hamster ovary (CHO) cells transfected with a vector containing a DNA sequence encoding the Fc fragment. Methods for creating such recombinant mammalian cells are described in, for example, Sambrook and Russell, *Molecular Cloning, A Laboratory Manual,* 3rd ed. (Cold Spring Harbor Laboratory Press (New York) 2001) and Ausubel et al., *Short Protocols in Molecular Biology,* 4th ed. (John Wiley & Sons, Inc. (New York) 1999) and are known to the skilled artisan. Recombinant Fc can also be produced in other mammalian cell lines, such as baby hamster kidney (BHK) cells. Methods of culturing recombinant cells to produce recombinant proteins are also known to the art.

A variety of other expression systems can be utilized to express recombinant immunoglobulins or Fc fragments. These include, but are not limited to, insect cell systems and microorganisms such as yeast or bacteria which have been transfected or transformed with an expression cassette encoding the desired Fc fragment. In certain embodiments, the microorganism optionally can be engineered to reproduce glycosylation patterns of mammalian or human Fc fragments.

In certain embodiments, further preparative steps can be used in order to render an immunoglobulin or Fc preparation safe for use in the methods according to the present invention. Such steps can include, for example, treatment with solvent/detergent, pasteurization and sterilization. Additional preparative steps may be used in order to ensure the safety of an Fc preparation. Such preparative steps can include, for example, enzymatic hydrolysis, chemical modification via reduction and alkylation, sulfonation, treatment with B-propiolactone, treatment at low pH, or the like. Descriptions of suitable methods can also be found in, for example, U.S. Pat. Nos. 4,608,254; 4,687,664; 4,640,834; 4,814,277; 5,864,016; 5,639,730 and 5,770,199; Romer et al., *Vox Sang.* 42:62-73 (1982); Romer et al., *Vox Sang.* 42:74-80 (1990); and Rutter, *J. Neurosurg. Psychiat.* 57 (Suppl.):2-5 (1994) (the disclosures of which are incorporated by reference herein).

An effective amount of an immunoglobulin or Fc preparation is administered to the subject generally by intravenous means. The term "effective amount" refers to an amount of an immunoglobulin or Fc preparation that results in an improvement or remediation of RRMS in the subject. An effective amount to be administered to the subject can be determined by a physician with consideration of individual differences in age, weight, disease severity and response to the therapy. In certain embodiments, an immunoglobulin or Fc preparation can be administered to a subject at about 5 mg/kilogram to about 500 mg/kilogram each day. In additional embodiments, an immunoglobulin or Fc preparation can be administered in amounts of at least about 10 mg/kilogram, at last 15 mg/kilogram, at least 20 mg/kilogram, at least 25 mg/kilogram, at least 30 mg/kilogram or at least 50 mg/kilogram. In additional embodiments, an immunoglobulin or Fc preparation can be administered to a subject at doses up to about 100 mg/kilogram, to about 150 mg/kilogram, to about 200 mg/kilogram, to about 250 mg/kilogram, to about 300 mg/kilogram, to about 400 mg/kilogram each day. In other embodiments, the doses of the immunoglobulin or Fc preparation can be greater or less. Immunoglobulin or Fc preparations can be administered in one or more doses per day.

In accordance with the present invention, the time needed to complete a course of the treatment can be determined by a physician and may range from as short as one day to more than a month. In certain embodiments, a course of treatment can be from 1 to 6 months.

Compositions, Kits and Integrated Systems

The invention provides compositions, kits and integrated systems for practicing the assays described herein using antibodies specific for the polypeptides or nucleic acids specific for the polynucleotides of the invention.

Kits for carrying out the diagnostic assays of the invention typically include a probe that comprises an antibody or nucleic acid sequence that specifically binds to polypeptides or polynucleotides of the invention, and a label for detecting the presence of the probe. The kits may include several antibodies or polynucleotide sequences encoding polypeptides of the invention, e.g., a cocktail of antibodies that recognize the proteins encoded by the biomarkers of the invention.

Methods to Identify Compounds

A variety of methods may be used to identify compounds that prevent or treat multiple sclerosis, including relapsing-remitting multiple sclerosis (RRMS), Alzheimer's disease, or Parkinson's disease. Typically, an assay that provides a readily measured parameter is adapted to be performed in the wells of multi-well plates in order to facilitate the screening of members of a library of test compounds as described herein. Thus, in one embodiment, an appropriate number of cells, e.g., T cells, can be plated into the cells of a multi-well plate, and the effect of a test compound on the expression of an IVIG-responsive relapsing-remitting multiple sclerosis (RRMS) biomarker can be determined.

The compounds to be tested can be any small chemical compound, or a macromolecule, such as a protein, sugar, nucleic acid or lipid. Typically, test compounds will be small chemical molecules and peptides. Essentially any chemical compound can be used as a test compound in this aspect of the invention, although most often compounds that can be dissolved in aqueous or organic (especially DMSO-based) solutions are used. The assays are designed to screen large chemical libraries by automating the assay steps and providing compounds from any convenient source to assays, which are typically run in parallel (e.g., in microtiter formats on microtiter plates in robotic assays). It will be appreciated that there are many suppliers of chemical compounds, including Sigma (St. Louis, Mo.), Aldrich (St. Louis, Mo.), Sigma-Aldrich (St. Louis, Mo.), Fluka Chemika-Biochemica Analytika (Buchs Switzerland) and the like.

In one preferred embodiment, high throughput screening methods are used which involve providing a combinatorial chemical or peptide library containing a large number of potential therapeutic compounds. Such "combinatorial chemical libraries" or "ligand libraries" are then screened in one or more assays, as described herein, to identify those library members (particular chemical species or subclasses) that display a desired characteristic activity. In this instance, such compounds are screened for their ability to reduce or increase the expression of the relapsing-remitting multiple sclerosis (RRMS) biomarkers of the invention.

A combinatorial chemical library is a collection of diverse chemical compounds generated by either chemical synthesis or biological synthesis, by combining a number of chemical "building blocks" such as reagents. For example, a linear combinatorial chemical library such as a polypeptide library is formed by combining a set of chemical building blocks (amino acids) in every possible way for a given compound length (i.e., the number of amino acids in a polypeptide compound). Millions of chemical compounds can be synthesized through such combinatorial mixing of chemical building blocks.

Preparation and screening of combinatorial chemical libraries are well known to those of skill in the art. Such combinatorial chemical libraries include, but are not limited to, peptide libraries (see, e.g., U.S. Pat. No. 5,010,175, Furka, *Int. J. Pept. Prot. Res.,* 37:487-493 (1991) and Houghton et al., *Nature,* 354:84-88 (1991)). Other chemistries for generating chemical diversity libraries can also be used. Such chemistries include, but are not limited to: peptoids (e.g., PCT Publication No. WO 91/19735), encoded peptides (e.g., PCT Publication No. WO 93/20242), random bio-oligomers (e.g., PCT Publication No. WO 92/00091), benzodiazepines (e.g., U.S. Pat. No. 5,288,514), diversomers such as hydantoins, benzodiazepines and dipeptides (Hobbs et al., *PNAS USA,* 90:6909-6913 (1993)), vinylogous polypeptides (Hagihara et al., *J. Amer. Chem. Soc.,* 114:6568 (1992)), nonpeptidal peptidomimetics with glucose scaffolding (Hirschmann et al., *J. Amer. Chem. Soc.,* 114:9217-9218 (1992)), analogous organic syntheses of small compound libraries (Chen et al., *J. Amer. Chem. Soc.,* 116:2661 (1994)), oligocarbamates (Cho et al, *Science,* 261:1303 (1993)), and/or peptidyl phosphonates (Campbell et al., *J. Org. Chem.,* 59:658 (1994)), nucleic acid libraries (see Ausubel, Berger and Sambrook, all supra), peptide nucleic acid libraries (see, e.g., U.S. Pat. No. 5,539,083), antibody libraries (see, e.g., Vaughn et al., *Nature Biotechnology,* 14(3):309-314 (1996) and PCT/US96/10287), carbohydrate libraries (see, e.g., Liang et al., *Science,* 274:1520-1522 (1996) and U.S. Pat. No. 5,593,853), small organic molecule libraries (see, e.g., benzodiazepines, Baum C&EN, Jan. 18, page 33 (1993); isoprenoids, U.S. Pat. No. 5,569,588; thiazolidinones and metathiazanones, U.S. Pat. No. 5,549,974; pyrrolidines, U.S. Pat. Nos. 5,525,735 and 5,519,134; morpholino compounds, U.S. Pat. No. 5,506,337; benzodiazepines, U.S. Pat. No. 5,288,514, and the like).

Devices for the preparation of combinatorial libraries are commercially available (see, e.g., 357 MPS, 390 MPS, Advanced Chem Tech, Louisville Ky., Symphony, Rainin, Woburn, Mass., 433A Applied Biosystems, Foster City, Calif., 9050 Plus, Millipore, Bedford, Mass.). In addition, numerous combinatorial libraries are themselves commercially available (see, e.g., ComGenex, Princeton, N.J., Asinex, Moscow, Ru, Tripos, Inc., St. Louis, Mo., ChemStar, Ltd, Moscow, RU, 3D Pharmaceuticals, Exton, Pa., Martek Biosciences, Columbia, Md., etc.).

In the high throughput assays of the invention, it is possible to screen up to several thousand different modulators or ligands in a single day. In particular, each well of a microtiter plate can be used to run a separate assay against a selected potential modulator, or, if concentration or incubation time effects are to be observed, every 5-10 wells can test a single modulator. Thus, a single standard microtiter plate can assay about 96 modulators. If 1536 well plates are used, then a single plate can easily assay from about 100-about 1500 different compounds. It is possible to assay many plates per day; assay screens for up to about 6,000, 20,000, 50,000, or 100,000 or more different compounds is possible using the integrated systems of the invention.

Methods to Inhibit or Activate Biomarker Proteins or Biomarker Receptor Function using Antibodies Because the biomarkers of the present invention are overexpressed or underexpressed in response to IVIG treatment of multiple sclerosis, Alzheimer's disease, or Parkinson's disease, the biomarker proteins or their cellular receptors, may serve as targets for multiple sclerosis therapy using antibodies. In the case of, for instance, of chemokines, such as CXCL5, CXCL3, and CCL13, whose expression is decreased upon treatment of RRMS with IVIG, antibodies that bind to and inactivate these chemokines or their receptors can be used in the treatment of multiple sclerosis, Alzheimer's disease, or Parkinson's disease. Alternatively, in the case of chemokines, such as XCL2, whose expression is increased upon IVIG treatment, antibodies may be generated which bind to and activate XCL2 receptors, thus mimicking the effect of XCL2 binding.

The antibodies described above may be formulated into pharmaceutical compositions comprising a carrier suitable for the desired delivery method. Suitable carriers include any material which when combined with the antibody does not interfere with function of the antibody and is non-reactive with the subject's immune systems. Examples include, but are not limited to, any of a number of standard pharmaceutical carriers such as sterile phosphate buffered saline solutions, bacteriostatic water, and the like (see, generally, *Remington's Pharmaceutical Sciences,* $20^{th}$ ed., 2003).

Antibody formulations may be administered via any route capable of delivering the antibodies to an individual suffering from multiple sclerosis. Potentially effective routes of administration include, but are not limited to, intravenous, intraperitoneal, intramuscular, intradermal, and the like. One preferred route of administration is by intravenous injection. A preferred formulation for intravenous injection comprises the antibodies in a solution of preserved bacteriostatic water, sterile unpreserved water, and/or diluted in polyvinylchloride or polyethylene bags containing 0.9% sterile Sodium Chloride for Injection, USP. The antibody preparation may be lyophilized and stored as a sterile powder, preferably under vacuum, and then reconstituted in bacteriostatic water containing, for example, benzyl alcohol preservative, or in sterile water prior to injection.

Treatment will generally involve the repeated administration of antibody preparations via an acceptable route of administration such as intravenous injection (IV), at an effective dose. Dosages will depend upon various factors generally appreciated by those of skill in the art, including without limitation the type, stage, the severity, grade, or stage of multiple sclerosis, the binding affinity and half life of the antibody used, the degree of biomarker or receptor expression in the patient, the desired steady-state antibody concentration level, frequency of treatment, and the influence of any other agents used in combination with the treatment method of the invention. Typical daily doses may range from about 0.1 to 100 mg/kg. Doses in the range of 10-500 mg mAb per week may be effective and well tolerated, although even higher weekly doses may be appropriate and/or well tolerated. The principal determining factor in defining the appropriate dose is the amount of a particular antibody necessary to be therapeutically effective in a particular context. Repeated administrations may be required in order to achieve longer lasting remission in RRMS. Initial loading doses may be higher. The initial loading dose may be administered as an infusion. Periodic maintenance doses may be administered similarly, provided the initial dose is well tolerated.

Methods to Inhibit Marker Protein Expression Using Nucleic Acids

A variety of nucleic acids, such as antisense nucleic acids, siRNAs or ribozymes, may be used to inhibit the function of the markers of this invention. Ribozymes that cleave mRNA at site-specific recognition sequences can be used to destroy target mRNAs, particularly through the use of hammerhead ribozymes. Hammerhead ribozymes cleave mRNAs at locations dictated by flanking regions that form complementary base pairs with the target mRNA. Preferably, the target mRNA has the following sequence of two bases: 5'-UG-3'. The construction and production of hammerhead ribozymes is well known in the art.

Gene targeting ribozymes necessarily contain a hybridizing region complementary to two regions, each of at least 5 and preferably each 6, 7, 8, 9, 10, 11, 12, 13, 14, 15, 16, 17, 18, 19 or 20 contiguous nucleotides in length of a target mRNA. In addition, ribozymes possess highly specific endoribonuclease activity, which autocatalytically cleaves the target sense mRNA.

With regard to antisense, siRNA or ribozyme oligonucleotides, phosphorothioate oligonucleotides can be used. Modifications of the phosphodiester linkage as well as of the heterocycle or the sugar may provide an increase in efficiency. Phosphorothioate is used to modify the phosphodiester linkage. An N3'-P5' phosphoramidate linkage has been described as stabilizing oligonucleotides to nucleases and increasing the binding to RNA. Peptide nucleic acid (PNA) linkage is a complete replacement of the ribose and phosphodiester backbone and is stable to nucleases, increases the binding affinity to RNA, and does not allow cleavage by RNAse H. Its basic structure is also amenable to modifications that may allow its optimization as an antisense component. With respect to modifications of the heterocycle, certain heterocycle modifications have proven to augment antisense effects without interfering with RNAse H activity. An example of such modification is C-5 thiazole modification. Finally, modification of the sugar may also be considered. 2'-O-propyl and 2'-methoxyethoxy ribose modifications stabilize oligonucleotides to nucleases in cell culture and in vivo.

Inhibitory oligonucleotides can be delivered to a cell by direct transfection or transfection and expression via an expression vector. Appropriate expression vectors include mammalian expression vectors and viral vectors, into which has been cloned an inhibitory oligonucleotide with the appropriate regulatory sequences including a promoter to result in expression of the antisense RNA in a host cell. Suitable promoters can be constitutive or development-specific promoters. Transfection delivery can be achieved by liposomal transfection reagents, known in the art (e.g., Xtreme transfection reagent, Roche, Alameda, Calif.; Lipofectamine formulations, Invitrogen, Carlsbad, Calif.). Delivery mediated by cationic liposomes, by retroviral vectors and direct delivery are efficient. Another possible delivery mode is targeting using antibody to cell surface markers for the target cells.

For transfection, a composition comprising one or more nucleic acid molecules (within or without vectors) can comprise a delivery vehicle, including liposomes, for administration to a subject, carriers and diluents and their salts, and/or can be present in pharmaceutically acceptable formulations. Methods for the delivery of nucleic acid molecules are described, for example, in Gilmore, et al., *Curr Drug Delivery* (2006) 3:147-5 and Patil, et al., *AAPS Journal* (2005) 7:E61-E77, each of which are incorporated herein by reference. Delivery of siRNA molecules is also described in several U.S. Patent Publications, including for example, 2006/0019912; 2006/0014289; 2005/0239687; 2005/0222064; and 2004/0204377, the disclosures of each of which are hereby incorporated herein by reference. Nucleic acid molecules can be administered to cells by a variety of methods known to those of skill in the art, including, but not restricted to, encapsulation in liposomes, by iontophoresis, by electroporation, or by incorporation into other vehicles, including biodegradable polymers, hydrogels, cyclodextrins (see, for example Gonzalez et al., 1999, *Bioconjugate Chem.,* 10, 1068-1074; Wang et al., International PCT publication Nos. WO 03/47518 and WO 03/46185), poly(lactic-co-glycolic)acid (PLGA) and PLCA microspheres (see for example U.S. Pat. No. 6,447,796 and US Patent Application Publication No. 2002/130430), biodegradable nanocapsules, and bioadhesive microspheres, or by proteinaceous vectors (O'Hare and Normand, International PCT Publication No. WO 00/53722). In another embodiment, the nucleic acid molecules of the invention can also be formulated or complexed with polyethyleneimine and derivatives thereof, such as polyethyleneimine-polyethyleneglycol-N-acetylgalactosamine (PEI-PEG-GAL) or polyethyleneimine-polyethyleneglycol-tri-N-acetylgalactosamine (PEI-PEG-triGAL) derivatives.

Examples of liposomal transfection reagents of use with this invention include, for example: CellFectin, 1:1.5 (M/M) liposome formulation of the cationic lipid N,NI,NII,NIII-tetramethyl-N,NI,NII,NIII-tetrapalmit-y-spermine and dioleoyl phosphatidylethanolamine (DOPE) (GIBCO BRL); Cytofectin GSV, 2:1 (M/M) liposome formulation of a cationic lipid and DOPE (Glen Research); DOTAP (N-[1-(2,3-dioleoyloxy)-N,N,N-tri-methyl-ammoniummethylsulfate) (Boehringer Manheim); Lipofectamine, 3:1 (M/M) liposome formulation of the polycationic lipid DOSPA and the neutral lipid DOPE (GIBCO BRL); and (5) siPORT (Ambion); HiPerfect (Qiagen); X-treme GENE (Roche); RNAicarrier (Epoch Biolabs) and TransPass (New England Biolabs).

In some embodiments, antisense, siRNA, or ribozyme sequences are delivered into the cell via a mammalian expression vector. For example, mammalian expression vectors suitable for siRNA expression are commercially available, for example, from Ambion (e.g., pSilencer vectors), Austin, Tex.; Promega (e.g., GeneClip, siSTRIKE, SiLentGene), Madison, Wis.; Invitrogen, Carlsbad, Calif.; InvivoGen, San Diego, Calif.; and Imgenex, San Diego, Calif. Typically, expression vectors for transcribing siRNA molecules will have a U6 promoter.

In some embodiments, antisense, siRNA, or ribozyme sequences are delivered into cells via a viral expression vector. Viral vectors suitable for delivering such molecules to cells include adenoviral vectors, adeno-associated vectors, and retroviral vectors (including lentiviral vectors). For example, viral vectors developed for delivering and expressing siRNA oligonucleotides are commercially available from, for example, GeneDetect, Bradenton, Fla.; Ambion, Austin, Tex.; Invitrogen, Carlsbad, Calif.; Open BioSystems, Huntsville, Ala.; and Imgenex, San Diego, Calif.

EXAMPLES

The following examples are offered to illustrate, but not to limit the claimed invention.

Example 1

Methods and Materials

Patients Involved in the Study 10 consecutive patients with acute MS relapse as rated on McDonald's criteria (McDonald W. I. et al., *Ann Neurol,* 50:121-27 (2001)) were included. The diagnosis of definite MS was based on McDonald's criteria (Kurtzke J. F., *Neurology,* 33:1444-1452 (1983)). The EDSS (Dastidar P. et al., *Med Biol Eng Comput,* 37:104-7 (1999)) and volumetric brain MRI were evaluated at baseline (at relapse immediately before treatment) and 3 weeks after completion of IVIG therapy (Elovaara I. et al., *Intravenous Immunoglobulin is effective and well tolerated in the treatment of MS Relapse*, Manuscript submitted). The primary outcome measure of the study was a change in the EDSS score from baseline to week 3 after the start of IVIG therapy on day 21. Secondary outcome measures were changes in the volumes of T1-, T2-, Flair- and gadolinium (Gd)-enhanced lesions, the number of Gd-enhanced lesions, and brain volumes (Elovaara I. et al., *Intravenous Immunoglobulin is effective and well tolerated in the treatment of MS Relapse*, Manuscript submitted; Dastidar P. et al., *Med Biol Eng Comput,* 37:104-7 (1999)). Patients' characteristics are listed in Table 1. Before entry into the study each patient signed a form of consent. The study was approved by the Ethics Committee of Tampere University, Tampere, Finland.

Patients who received treatment with immunosuppressants in the preceding nine months or patients who received corticosteroids in the preceding 8 weeks were excluded. All patients received 0.4 g/kg/day Endobulin (Baxter AG, Vienna, Austria) for 5 days. Clinical evaluation of the patients was done before treatment with IVIG, 1 day after completion of therapy on day 6 as well as 3 weeks after the beginning of therapy on day 21. Clinical evaluation included neurological examination, determination of the EDSS score, arm index and ambulation index. A control group of five patients received standard treatment of IVMP 100 mg/day for 3 days.

TABLE 1

Characteristics of patients included in the study

| Characteristics | IVIG Patients | IVMP Patients (controls) |
|---|---|---|
| Number of patients | 10 | 5 |
| Age (years, average ± SD) | 40 ± 10.6 | 35.3 ± 8.8 |
| Sex (male vs female) | 3 vs 7 | 0 vs 5 |
| Disease duration (years, average ± SD) | 5.6 ± 3.5 | 5.2 ± 3.6 |
| Time current vs previous relapse (months, average ± SD) | 17.6 ± 21.0 | 5 ± 3.2 |
| EDSS score during remission (average ± SD) | 2.3 ± 0.95 | 3.2 ± 2.4 |
| EDSS score at acute relapse (average ± SD) | 3.7 ± 1.1 | 4.2 ± 2.0 |

MRI Analysis

Brain MRI examinations were done using a 1.5 Tesla MRI unit (Philips Gyroscan ACS NT Intera, Best, Netherlands) as described (Kurtzke J. F., *Neurology,* 33:1444-1452 (1983)). The MRI protocol included sagittal T1 localizer, axial fluid attenuated inversion recovery (FLAIR), T1 magnetization transfer contrast (MTC), T1 spin echo (SE), T2 turbo spin echo (TSE) (3 mm thick and 0 mm gap) and gadolinium-enhanced T1 MTC sequences. T1 axial SE (3 mm thick and 0 mm gap) and axial FLAIR (5 mm thick and 1 mm gap) sequences were used for volumetric analyses of plaques. Computerized semiautomatic segmentation and volumetric analyses were done using Anatomatic software operating in a Windows environment. The inter- and intra-observer variability of the volumetric results has been reported elsewhere (Dastidar P. et al., *Med Biol Eng Comput,* 37:104-7 (1999); Heinonen T. et al., *J Med Eng Technol,* 22:173-8 (1998)). The volumetric accuracy of the Anatomatic program was analyzed as described (Dastidar P. et al., *Med Biol Eng Comput,* 37:104-7 (1999)). Good head repositioning was controlled using the same head coil, the same anatomic locations and the same pack of images in different MRI sequences. Whole spinal cords were scanned separating into upper and lower parts. The same scanner was used for all MRI examinations.

Preparation of RNA Samples

Blood samples were obtained using Vacutainer CPTTM Cell Preparation Tubes (Becton Dickinson, Franklin Lakes, N.J.). Peripheral blood mononuclear cells (PBMC) were separated from peripheral blood within 60 min after blood sampling using density gradient (Lymphoprep, Nycomed, Roskilde, DK) centrifugation according to the manufacturer's protocol. The cells were separated into T cells and non-T cells using a mixture of non-stimulating anti-CD4+ and anti-CD8+ magnetic Dynabeads (Dynal Biotech, Oslo, N) at 4° C. Cell pellets obtained from $5\times10^6$ cells were thoroughly mixed with 1 ml TRIzol (Invitrogen, Carlsbad, Calif.). Aliquots were frozen and stored at −80° C. until further processing. Total RNA was isolated according to the manufacturer's protocol. RNA pellets were dissolved in nuclease-free water (Invitrogen, Carlsbad, Calif.) and stored at −80° C.

Microarray Analysis

The HU-133A Genechip (Affymetrix, Santa Clara, Calif.) containing approximately 33,000 human genes was used. 51 g of total RNA were transcribed, labelled and hybridized in vitro on the array according to the manufacturer's protocol (see Affymetrix.com). The quality of the RNA was checked before in vitro processing using a Bioanalyzer (Agilent Technologies, Palo Alto, Calif.).

Statistical Analysis of Gene Expression Data

Statistical analysis of gene expression data was done at the Microarray Facility Tübingen, Eberhard-Karls-University Tübingen, Germany. The Affymetrix CHP files were imported into Genespring 7.1 for statistical data analysis. The signals of each array were divided by the median of all signals of the arrays from time point zero. Subsequently, a "per-gene" normalization was done by dividing all signals of a gene by the median signal of this gene. Thus the signals of each gene start at time point zero around 1 and display values greater than 1 upon increase and vice versa. The signals were log-transformed, and fold change and p-values (Welch's t-test) (Han T. et al., *BMC bioinformatics,* 7:9 (2006)) were calculated for each gene in pair-wise comparisons. Probe sets with a fold change of more than 2 and a p-value of less than 0.05 were identified in volcano plots and called statistically significant.

Real Time Polymerase Chain Reaction

The gene expression data obtained by microarray analysis for four representative genes were confirmed by quantitative real-time polymerase chain reaction (PCR). For this purpose, 1 μg of total T cell RNA was used for reverse transcription into cDNA according to the manufacturer's protocol (MBI Fermentas, Burlington, Canada). For each sample to be analyzed, 100 mg cDNA were dissolved in 5 μl nuclease-free water (Invitrogen, Carlsbad, Calif.) and quantitatively analyzed using different TaqMan Assays-on-Demand and the ABPrism 7000 (both from Applied Biosystems, Foster City, Calif.). Data were analyzed using the ^^CT-method, which is commonly used for relative quantification (Livak K. J. and Schmittgen T. D., *Methods,* 25:402-40 (2001)). For normalization of expression data human glyceraldhyde-3 phosphate dehydrogenase was included as a housekeeping gene. For verification of normalization, a second housekeeping gene, β-2 microglobulin, was used as a control (data not shown).

Example 2

Clinical Outcome of Treatment of Subjects with IVIG

Analysis of the clinical outcome of the study showed that a 5-day course of IVIG therapy resulted in a significant reduction of the EDSS score in all 10 patients (FIG. 1). The effectiveness of the IVIG therapy was supported by an improvement of most MRI variables (Table 2). Although similar effects were observed in the control group that received standard treatment with IVMP (Table 2), the changes in MRI variables in the control group did not reach statistical significance. Treatment with IVIG was safe and well-tolerated.

TABLE 2

MRI analysis of brain abnormalities before and after treatment with IVIG and IVMP

| Parameter | Before IVIG Lesion vol $cm^3$ mean ± SE | After IVIG Lesion vol $cm^3$ mean ± SE |
|---|---|---|
| T1 | 1.76 ± 0.55 | 1.73 ± 0.59 |
| T2 | 5.49 ± 1.09 | 5.08 ± 1.03* |
| Flair | 15.76 ± 2.23 | 14.09 ± 1.94** |
| Gd-enhanced | 0.32 ± 0.27 | 0.21 ± 0.24** |
| Brain volume | 1124.94 ± 40.61 | 1120.31 ± 40.72 |
| Gd + lesion N | 2.83 ± 0.71 | 2.00 ± 0.60** |
| EDSS score | 3.8 ± 0.3 | 2.6 ± 0.2** |
| **Parameter** | **Before IVMP Lesion vol $cm^3$ mean ± SE** | **After IVMP Lesion vol $cm^3$ mean ± SE** |
| T1 | 1.41 ± 0.60 | 1.64 ± 0.84 |
| T2 | 11.15 ± 4.59 | 9.83 ± 4.17 |
| Flair | 24.37 ± 8.19 | 23.18 ± 8.05 |
| Gd-enhanced | 0.70 ± 0.39 | 0.63 ± 0.37 |
| Brain volume | 1056.32 ± 47.78 | 1045.07 ± 52.53 |
| Gd + lesion N | 3.0 ± 1.5 | 2.7 ± 1.4 |
| EDSS score | 4.2 ± 2.0 | 3.3 ± 2.4 |

*$p < 0.05$;
**$p < 0.01$
EDSS = Kurtzke's Expanded Disability Status Scale
Gd = Gadolinium-enhanced lesion volumes

Example 3

Treatment With IVIG does not Significantly Alter the Cellular Composition of Cells Obtained for Isolation of RNA PBMCs obtained from peripheral blood were separated into T cells and non-T cells using a mixture of non-stimulating anti-CD4+ and anti-CD8+ magnetic Dynabeads at 4° C. This procedure was chosen to prevent stimulation of T cells during cell separation. To ensure that potential differences in gene expression profiles are not due to differences in the cellular composition of the different samples, we compared the expression of genes that encode CD3, CD4, CD8 and CD14 between samples obtained at different time points for each patient. Our results show that the cellular composition of the samples obtained from each patient on different days is similar (FIGS. 2A, 2B). No statistically significant differences were observed.

Example 4

Analysis of Gene Expression Data Obtained from Patients Treated With IVIG

Statistic analysis of gene expression data included all results obtained from microarray analysis done at three different time points (before treatment, 1 day and 21 days after beginning of treatment) and included all 10 patients treated with IVIG. The analysis revealed that 360 genes in peripheral T cells were significantly changed in expression during the course of IVIG treatment. The expression of 91 of these genes changed between day 0 and day 6, the expression of 147 genes changed between day 0 and day 21, and the expression of 122 genes changed between day 6 and day 21.

Statistical analysis of the control-patient group treated with IVMP showed differential expression of 583 genes, with the majority (218 genes) being changed between day 0 and day 6.

Tables 3a-3d present the 20 most significant changes in gene expression observed in patients treated with IVIG and IVMP.

TABLE 3a 10 genes that were most extensively up-regulated in peripheral T cells of patients during IVIG therapy

| Fold Change | Time Point | Gene Title | Gene Symbol | Ref Seq ID |
|---|---|---|---|---|
| 4.37 | 21 vs 6 | Transcriptional regulating factor 1 | TRERF1 | NM_018415 |
| 4.26 | 21 vs 0 | chromosome 19 open reading frame 28 | C19orf28 | NM_174983 |
| 4 | 6 vs 0 | cyclin-dependent kinase inhibitor 1C (p57, Kip2) | CDKN1C | NM_000076 |
| 3.86 | 21 vs 6 | breast cancer 1, early onset | BRCA1 | NM_007294 |
| 3.83 | 6 vs 0 | Clone 23555 mRNA sequence | — | — |
| 3.54 | 21 vs 6 | — | — | — |
| 3.52 | 21 vs 6 | SH3-domain binding protein 4 | SH3BP4 | NM_014521 |
| 3.5 | 6 vs 0 | collagen, type III, alpha 1 (Ehlers-Danlos syndrome type IV, autosomal dominant) | COL3A1 | NM_000090 |
| 3.41 | 21 vs 0 | UDP-Gal:betaGlcNAc beta 1,3-galactosyltransferase, polypeptide 2 | B3GALT2 | NM_003783 |
| 3.36 | 21 vs 6 | glycosylphosphatidylinositol specific phospholipase D1 | GPLD1 | NM_001503 |

TABLE 3b 10 genes that were most extensively down-regulated in peripheral T cells of patients during IVIG therapy

| Fold Change | Time Point | Gene Title | Gene Symbol | Ref Seq ID |
|---|---|---|---|---|
| −4.82 | 6 vs 0 | myotubularin related protein 7 | MTMR7 | NM_004686 |
| −3.96 | 6 vs 0 | transmembrane protein with EGF-like and two follistatin-like domains 1 | TMEFF1 | NM_003692 |
| −3.9 | 21 vs 0 | NADH dehydrogenase (ubiquinone) 1 alpha subcomplex, 5, 13 kDa | NDUFA5 | NM_005000 |
| −3.89 | 21 vs 6 | collagen, type III, alpha 1 (Ehlers-Danlos syndrome type IV, autosomal dominant) | COL3A1 | NM_000090 |
| −3.59 | 21 vs 6 | FAT tumor suppressor homolog 2 (*Drosophila*) | FAT2 | NM_001447 |
| −3.57 | 21 vs 6 | DNA damage repair and recombination protein RAD52 pseudogene | — | — |
| −3.34 | 21 vs 0 | chemokine (C—X—C motif) ligand 5 | CXCL5 | NM_002994 |
| −3.34 | 21 vs 0 | mesenchymal stem cell protein DSC43 | LOC51333 | NM_016643 |
| −3.26 | 21 vs 6 | natriuretic peptide receptor C/guanylate cyclase C (atrionatriuretic peptide receptor C) | NPR3 | NM_000908 |
| −3.22 | 21 vs 6 | early growth response 2 (Krox-20 homolog, *Drosophila*) | EGR2 | NM_000399 |

Table 3a/b:
Timepoints:
6 vs ) represents genes with a different expression between day 0 and day 6;
21 vs 0 represents genes with a differential expression between day 21 and day 0; and
21 vs 6 refers to genes with a change in expression between day 6 and day 21.

TABLE 3c 10 genes that were most extensively up-regulated in peripheral T cells of patients during IVMP therapy

| Fold Change | Time Point | Gene Title | Gene Symbol | Ref Seq ID |
|---|---|---|---|---|
| 15.94 | 21 vs 6 | leukocyte immunoglobulin-like receptor, subfamily A (without TM domain), member 4 | ILT7 | NM_012276 |
| 9.26 | 21 vs 6 | prostaglandin D2 synthase 21 kDa (brain) | PTGDS | NM_000954 |
| 8.91 | 21 vs 6 | Periostin, osteoblast specific factor | POSTN | NM_006475 |
| 8.64 | 21 vs 6 | wingless-type MMTV integration site family, member 5A | WNT5A | NM_003392 |
| 8.31 | 21 vs 6 | prostaglandin D2 synthase 21 kDa (brain) /// prostaglandin D2 synthase 21 kDa (brain) | PTGDS | NM_000954 |

TABLE 3c-continued

| 10 genes that were most extensively up-regulated in peripheral T cells of patients during IVMP therapy | | | | |
|---|---|---|---|---|
| Fold Change | Time Point | Gene Title | Gene Symbol | Ref Seq ID |
| 7.94 | 21 vs 6 | cyclin-dependent kinase inhibitor 1C (p57, Kip2) | CDKN1C | NM_000076 |
| 7.41 | 21 vs 6 | cyclin-dependent kinase inhibitor 1C (p57, Kip2) | CDKN1C | NM_000076 |
| 7.33 | 6 vs 0 | defensin, alpha 1, myeloid-related sequence /// defensin, alpha 3, neutrophil-specific | DEFA1 /// | NM_005217 |
| 6.48 | 6 vs 0 | POU domain, class 1, transcription factor 1 (Pit1, growth hormone factor 1) | POU1F1 | NM_000306 |
| 6 | 6 vs 0 | cadherin 13, H-cadherin (heart) | CDH13 | NM_001257 |

TABLE 3d

| 10 genes that were most extensively down-regulated in peripheral blood cells of patients during IVMP therapy | | | | |
|---|---|---|---|---|
| Fold Change | Time Point | Gene Title | Gene Symbol | Ref Seq ID |
| −11.52 | 6 vs 0 | leukocyte immunoglobulin-like receptor, subfamily A (without TM domain), member 4 | ILT7 | NM_012276 |
| −9.73 | 6 vs 0 | tripartite motif-containing 58 | TRIM58 | NM_015431 |
| −9.11 | 21 vs 6 | Zwilch | FLJ10036 | NM_017975 |
| −8.24 | 21 vs 0 | Integrin, alpha 1 | PELO | NM_015946 |
| −7.86 | 21 vs 0 | zinc finger protein 6 (CMPX1) | ZNF6 | NM_021998 |
| −7.36 | 21 vs 6 | intersectin 1 (SH3 domain protein) | ITSN1 | NM_003024 |
| −7.3 | 21 vs 6 | phorbol-12-myristate-13-acetate-induced protein 1 | PMAIP1 | NM_021127 |
| −7.28 | 21 vs 0 | transmembrane protein 47 | TMEM47 | NM_031442 |
| −6.84 | 6 vs 0 | — | — | — |
| −6.82 | 6 vs 0 | prostaglandin D2 synthase 21 kDa (brain) | PTGDS | NM_000954 |

Table 3c/d:
Timepoints:
6 vs 0 represents genes with a differential expression between day 0 and day 6;
21 vs 0 represents genes with a differential expression between day 21 and day 0; and
21 vs 6 refers to genes with a change in expression between day 6 and day 21.

Genes mostly affected in expression by IVIG treatment include genes that encode proteins that regulate cell cycle (transcriptional regulating factor 1, TRERF1; cyclin-dependent kinase inhibitor 1C, CDKN1C; breast cancer 1, BRCA1; SH3-domain binding protein 4, SH3BP4); but also proteins that regulate inflammation [chemokine (C-X-C motif) ligand 5, CXCL5], cell adhesion (FAT tumor suppressor homolog 2, FAT2) or cell differentiation (early growth response, EGR2). Other genes included in the list encode proteins that are involved in electron transport, phosphorylation, glycosylation, skeletal development or proteins that have not yet been defined in function.

Other genes of interest that were differentially regulated upon IVIG treatment encoded proteins involved in immune regulation such as interleukin 11 (IL 11), chemokine (C motif) ligand 2 (XCL2), prostaglandin E receptor 4 (PTGER4), caspase 2 (CASP2), killer cell immunoglobin-like receptor, two domains, short cytoplasmic tail 1 (KIR2DS1), mitogen-activated protein kinase kinase kinase kinase 2 ($MAP4K_2$), chemokine (C-X-C motif) ligand 5 (CXCL5), chemokine (C-X-C motif) ligand 3 (CXCL3), C-type lectin domain family 4, member E (CLEC4E), chemokine (C-C motif) ligand 13 (CCL13) and alpha-fetoprotein (AFP) (see Table 4).

TABLE 4

| Genes differentially expressed under IVIG treatment that encode proteins involved in immune regulation. | | | | |
|---|---|---|---|---|
| Fold Change | Time Point | Gene Title | Gene Symbol | Ref Seq ID |
| 2.00 | 6 vs 0 | interleukin 11 | IL11 | NM_000641 |
| 2.38 | 21 vs 0 | chemokine (C motif) ligand 2 | XCL2 | NM_003175 |
| 2.28 | 21 vs 0 | prostaglandin E receptor 4 (subtype EP4) | PTGER4 | NM_000958 |
| 2.02 | 21 vs 0 | caspase 2, apoptosis-related cysteine protease (neural precursor cell expressed) | CASP2 | NM_032982 |
| 2.37 | 21 vs 6 | killer cell immunoglobulin-like receptor, two domains, short cytoplasmic tail, 1 | KIR2DS1 | NM_014512 |
| 2.35 | 21 vs 0 | mitogen-activated protein kinase kinase kinase kinase 2 | MAP4K2 | NM_004579 |
| −3.34 | 21 vs 0 | chemokine (C—X—C motif) ligand 5 | CXCL5 | NM_002994 |
| −2.46 | 21 vs 0 | chemokine (C—X—C motif) ligand 3 | CXCL3 | NM_002090 |
| −2.26 | 21 vs 0 | C-type lectin domain family 4, member E | CLEC4E | NM_014358 |
| −3.06 | 21 vs 6 | chemokine (C-C motif) ligand 13 | CCL13 | NM_005408 |
| −2.53 | 21 vs 6 | alpha-fetoprotein | AFP | NM_001134 |

Table 4:
Timepoints
6 vs 0 represents genes with a differential expression between day 0 and day 6;
21 vs 0 represents genes with a differential expression between day 21 and day 0; and
21 vs 6 refers to genes with a change in expression between day 6 and day 21.

Example 5

Comparison of Gene Expression Data Obtained From Patients Treated With IVIG and Patients Treated With IVMP When gene expression data obtained from patients treated with IVIG were compared with gene expression data obtained from patients treated with IVMP, 17 genes were identified that significantly changed in expression in both groups of patients (Table 5). Most of the proteins that are encoded by these 17 genes regulate cell cycle (HABP4, STAT1, CDKN1, SH3BP4 and ORC1L). These results indicate that cell cycle regulation might be a mechanism of therapeutic effectiveness that both drugs have in common. The other genes that were found to be differentially regulated were only found in one of the two treatment groups and, therefore, reflect mechanisms of action that are specific for only one of the two drugs.

TABLE 5

Intersection of genes differentially expressed under both IVIG treatment and IVMP treatment

| Gene Title | Gene Symbol | GO Biological Process Description | Ref Seq ID |
|---|---|---|---|
| cadherin 5, type 2, VE-cadherin (vascular epithelium) | CDH5 | cell adhesion /// homophilic cell adhesion | NM_001795 |
| hyaluronan binding protein 4 | HABP4 | — | NM_014282 |
| signal transducer and activator of transcription 1, 91 kDa | STAT1 | regulation of cell cycle /// transcription /// regulation of transcription, DNA-dependent /// transcription from RNA polymerase II promoter /// caspase activation /// intracellular signaling cascade /// I-kappaB kinase/NF-kappaB cascade /// tyrosine phosp | NM_007315 |
| cyclin-dependent kinase inhibitor 1C(p57, Kip2) | CDKN1C | regulation of cyclin dependent protein kinase activity /// G1 phase of mitotic cell cycle /// cell cycle /// cell cycle arrest /// negative regulation of cell proliferation /// negative regulation of cell cycle | NM_000076 |
| actinin, alpha 2 | ACTN2 | — | NM_001103 |
| histone 1, H2bh | HIST1H2BH | nucleosome assembly /// nucleosome assembly /// chromosome organization and biogenesis (sensu Eukaryota) | NM_003524 |
| SH3-domain binding protein 4 | SH3BP4 | endocytosis /// cell cycle | NM_014521 |
| origin recognition complex, subunit 1-like (yeast) | ORC1L | DNA replication /// DNA replication initiation | NM_004153 |
| KIAA0644 gene product | KIAA0644 | — | NM_014817 |
| Heparan sulfate (glucosamine) 3-O-sulfotransferase 1 | HS3ST1 | — | NM_005114 |
| ropporin, rhophilin associated protein 1B | ROPN1B | cytokinesis /// signal transduction /// Rho protein signal transduction /// spermatogenesis /// acrosome reaction /// fusion of sperm to egg plasma membrane /// cell-cell adhesion /// sperm motility | NM_001012337 |
| outer dense fiber of sperm tails 2 | ODF2 | — | NM_002540 |
| — | — | — | |
| unknown protein | — | — | |
| 1-acylglycerol-3-phosphate O-acetyltransferase 7 | AGPAT7 | metabolism | NM_153613 |
| zinc finger protein 804A | ZNF804A | — | NM_194250 |
| TRAF-type zinc finger domain containing 1 | TRAFD1 | — | NM_006700 |

Example 6

Confirmation of Gene Expression Data Obtained with Microarray Analysis by Real-Time PCR Data obtained with microarray analysis were confirmed by quantitative real-time PCR. For this purpose, 4 genes were selected that encoded proteins known to regulate immune regulation (see Table 4): PTGER4, CXCL5, IL11 and CASP2. Results of real-time PCR are shown in FIG. 3A-D. Results obtained with real-time PCR confirm the data obtained with microarray analysis (FIG. 3A-D, and Tables 3 and 4).

Discussion

The present study was designed to identify genes that are differentially expressed in peripheral T cells of patients with RRMS in acute exacerbation after treatment with IVIG. Peripheral T cells (CD4+ and CD8+ T cells) have been shown to be involved in the disease pathogenesis, in particular in the process of demyelination and axonal damage (Stinissen P. et al., *Mult Scler.,* 4:203-11 (1998)). This is supported by a recent study in which a number of genes in peripheral blood cells of MS patients were shown to be differentially expressed compared with those in healthy twins (Särkijärvi S. et al., *BMC Medical Genetics,* 7:11 (2006)).

Statistical data analysis revealed 360 genes that were at least 2-fold up- or down-regulated in all patients following IVIG treatment. The effect of IVIG treatment was most prominent at 21 days after the beginning of IVIG treatment. Genes mostly affected in expression by IVIG treatment included genes that encode proteins that regulate cell cycle, signal transduction, transcription, inflammation, cell-cell interactions and apoptosis. These processes are likely to be involved in the pathogenesis of MS. When we compared the effects on gene expression caused by IVIG treatment with the effects caused by IVMP treatment, we found 583 genes to be differentially regulated upon IVMP treatment. The majority of these genes was altered in expression at day 6 compared to day 0 after the beginning of therapy. These results indicate that IVMP might be a faster acting drug than IVIG.

We identified 17 genes that were significantly changed in expression in both groups of patients. Most of the proteins that are encoded by these 17 genes regulate cell cycle. These results strongly suggest that the regulation of cell proliferation, in particular the regulation of T cell proliferation, is a mechanism of action that both drugs have in common. These results agree with published data that indicate that IVIG suppresses the proliferation of activated T cells when given to patients with MS (Andersson U. et al., *Immunol Rev,* 139:21-

42 (1994); Bayry J. et al., *Intravenous immunoglobulin in autoimmune disorders: An insight into the immunregulatory mechanisms*).

An important mechanism of action of IVIG in MS seems to be the modulation of chemokine expression. This conclusion is based on our findings that a number of genes that encode chemokines (CXCL3, CXCL5, CCL13 and XCL2) are differentially expressed upon IVIG treatment. These changes in gene expression were not found in patients treated with IVMP. Therefore, we believe that the modulation of chemokine expression in peripheral T cells might be a specific mechanism of action of IVIG in MS. Several studies have shown that chemokines and chemokine receptors are involved in the pathogenesis of MS (Trebst C. and Ransohoff R. M., *Arch Neurol,* 58:1975-80 (2001)). Chemokines have been shown to mediate trafficking of immune cells across the blood-brain barrier and to direct migration of immune cells towards sites of active lesions (Szczucinski A. and Losy J., *Acta Neurol Scand,* 115:137-146 (2007)). Moreover, chemokines were detected in active lesions and were found to be elevated in the cerebrospinal fluid of patients with MS during relapse (Sindern E. et al., *J Neuroimmunol,* 131:186-90 (2002)). Two of the chemokines (CXCL3 and CXCL5) that were significantly down-regulated in our study are known to specifically interact with the chemokine receptor CXCR2 (Omari K. et al., *Brain,* 128:1003-1015 (2005)). Previous studies have shown that CXCR2 is not only expressed on peripheral blood cells such as granulocytes, monocytes or lymphocytes (Murdoch C. et al., *Brain,* 128:1003-1015 (2005(?)); Murphy P. M. et al., *Pharmacol Rev.,* 52:145-76 (2000)) but also on oligodendrocytes in the brain. Oligodendrocytes are most essential for the myelination of axons in the white matter of the Central Nervous System and for remyelination after demyelination of axons during inflammation in MS (Blakemore W. F., *J Neurol Sci*., (2007)). Recently it was shown that CXCR2 expressed on oligodendrocytes is essential for the development and maintenance of the oligodendrocyte lineage, myelination and white matter in the vertebrate CNS (Tsai H. H. et al., *Cell,* 110:373-83 (2002); Padovani-Claudio D. et al., *Glia,* 54:471-483 (2006)). The regulation of oligodendrocyte development and migration depends on the localized expression of the chemokine CXCL1 and its interaction with CXCR2 expressed on oligodendrocyte precursor cells and oligodendrocytes (Padovani-Claudio D. et al., *Glia,* 54:471-483 (2006)). Any event that disrupts the interaction between CXCL1 and CXCR2 expressed on oligodendrocytes or the signalling induced by this interaction could therefore cause a disruption of the remyelination processes in MS patients. Based on these findings we propose the following hypothesis for a new mechanism of action of IVIG in RRMS patients during relapse. Peripheral T cells and monocytes enter the CNS in response to chemokines produced by the inflammation in the brain. The disrupted blood-brain barrier (Man S. et al., *Brain Pathol.,* 17:243-50 (2007)) facilitates this process. Both T cells and monocytes produce chemokines in the brain that interfere with the tightly regulated activity of oligodendrocyte precursor cells and oligodendrocytes. This interference could be caused by either a desensitization of the CXCR2 receptor expressed on oligodendrocytes or by interference with the interaction between locally expressed CXCL1 and CXCR2 on oligodendrocytes. IVIG down-regulates the expression of chemokines in peripheral T cells, monocytes or both. Consequently, the interference of chemokines produced by these cells with the function of oligodendrocytes would be prevented and the natural process of remyelination induced by oligodendrocytes would be re-established. It remains to be shown whether IVIG might not only modulate the expression of chemokines in peripheral T cells but also the expression of chemokines in cells of the CNS, e.g., in astrocytes.

The aim of our study was to identify genes that are likely to be associated with T cell responses in MS. The strategy that we used for positive cell selection does not exclude the possibility that some of the identified genes are associated with peripheral monocytes rather than T cells. This has to be taken into consideration when interpreting the above data. The genes that we found to be differentially expressed under IVIG treatment will be confirmed in a second clinical trial with a larger study group. Differentially expressed genes can be used as diagnostic markers for the therapeutic efficacy of IVIG treatment. Furthermore, some of the proteins encoded by the genes of interest will provide suitable targets for future drug development.

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference in their entirety for all purposes.

What is claimed is:

1. A method of monitoring the efficacy of intravenous immunoglobulin (IVIG) treatment of multiple sclerosis in a subject, the method comprising the steps of:

(a) contacting a biological sample from the subject treated with IVIG with a reagent that specifically binds to at least one marker selected from the group consisting of TRERF1 (SEQ ID NOs: 1 and 2), C19orf28 (SEQ ID NOs: 3 and 4), CDKN1C (SEQ ID NOs: 5 and 6), SH3BP4 (SEQ ID NOs: 9 and 10), COL3A1 (SEQ ID NOs: 11 and 12), B3GALT2 (SEQ ID NOs: 13 and 14), MTMR7 (SEQ ID NOs: 17 and 18), TMEFF1 (SEQ ID NOs: 19 and 20), NDUFA5 (SEQ ID NOs: 21 and 22), FAT2 (SEQ ID NOs: 23 and 24), LOC51333 (SEQ ID NOs: 27 and 28), NPR3 (SEQ ID NOs: 29 and 30), EGR2 (SEQ ID NOs: 31 and 32), IL11 (SEQ ID NOs: 71 and 72), XCL2 (SEQ ID NOs: 73 and 74), CASP2 (SEQ ID NOs: 77 and 78), KIR2DS1 (SEQ ID NOs: 79 and 80), MAP4K2 (SEQ ID NOs: 81 and 82), CCL13 (SEQ ID NOs: 87 and 88), AFP (SEQ ID NOs: 89 and 90), and CLEC4E (SEQ ID NOs: 91 and 92);

(b) measuring the expression of the marker;

(c) comparing the expression of the marker in the sample from the subject treated with IVIG to the expression of said at least one marker in a baseline sample from the subject obtained at an earlier timepoint; and (d) determining whether or not the marker is overexpressed or underexpressed in the sample from the subject treated with IVIG as compared to the expression of the marker in the baseline sample; thereby monitoring the efficacy of IVIG treatment of multiple sclerosis in the subject.

2. The method of claim 1, wherein the multiple sclerosis is relapsing-remitting multiple sclerosis (RRMS).

3. The method of claim 1, wherein the reagent is a nucleic acid.

4. The method of claim 1, wherein the reagent is an oligonucleotide.

5. The method of claim 1, wherein the reagent is an RT PCR primer set.

6. The method of claim 1, wherein the sample is a blood sample.

7. The method of claim 6, wherein the blood sample comprises T cells.

8. The method of claim 1, wherein the sample is cerebrospinal fluid.

9. The method of claim 1, wherein said at least one marker is a chemokine.

10. The method according to claim 9, wherein said chemokine is selected from the group consisting of CCL13 and XCL2.

11. The method of claim 1, wherein said at least one marker is TRERF1 (SEQ ID NOs:1 and 2).

12. The method of claim 1, wherein said at least one marker is C19orf28 (SEQ ID NOs: 3 and 4), CDKN1C (SEQ ID NOs: 5 and 6), SH3BP4 (SEQ ID NOs: 9 and 10), MTMR7 (SEQ ID NOs: 17 and 18), TMEFF1 (SEQ ID NOs: 19 and 20), NDUFA5 (SEQ ID NOs: 21 and 22), or FAT2 (SEQ ID NOs: 23 and 24).

13. The method of claim 1, wherein the baseline sample is obtained from the subject prior to IVIG treatment.

* * * * *